US012415788B2

(12) United States Patent
Glenn et al.

(10) Patent No.: US 12,415,788 B2
(45) Date of Patent: Sep. 16, 2025

(54) PI4-KINASE INHIBITORS AND METHODS OF USING THE SAME

(71) Applicant: The Board of Trustees of the Leland Stanford Junior University, Stanford, CA (US)

(72) Inventors: Jeffrey S. Glenn, Palo Alto, CA (US); Mark Smith, San Francisco, CA (US); Edward A. Pham, Palo Alto, CA (US); Kaustabh Basu, Redwood City, CA (US); Stephen Stabler, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 994 days.

(21) Appl. No.: 17/439,085

(22) PCT Filed: Mar. 19, 2020

(86) PCT No.: PCT/US2020/023654
§ 371 (c)(1),
(2) Date: Sep. 14, 2021

(87) PCT Pub. No.: WO2020/191205
PCT Pub. Date: Sep. 24, 2020

(65) Prior Publication Data
US 2022/0153711 A1    May 19, 2022

Related U.S. Application Data

(60) Provisional application No. 62/821,853, filed on Mar. 21, 2019.

(51) Int. Cl.
| | |
|---|---|
| C07D 263/48 | (2006.01) |
| A61K 45/06 | (2006.01) |
| A61P 31/12 | (2006.01) |
| A61P 35/00 | (2006.01) |
| C07D 233/88 | (2006.01) |
| C07D 277/42 | (2006.01) |
| C07D 401/12 | (2006.01) |
| C07D 401/14 | (2006.01) |
| C07D 405/12 | (2006.01) |
| C07D 413/12 | (2006.01) |
| C07D 417/12 | (2006.01) |
| C07D 417/14 | (2006.01) |

(52) U.S. Cl.
CPC ............ C07D 263/48 (2013.01); A61K 45/06 (2013.01); A61P 31/12 (2018.01); A61P 35/00 (2018.01); C07D 233/88 (2013.01); C07D 277/42 (2013.01); C07D 401/12 (2013.01); C07D 401/14 (2013.01); C07D 405/12 (2013.01); C07D 413/12 (2013.01); C07D 417/12 (2013.01); C07D 417/14 (2013.01)

(58) Field of Classification Search
CPC .. C07D 263/48; C07D 233/88; C07D 277/42; C07D 401/12; C07D 401/14; C07D 405/12; C07D 413/12; C07D 417/12; C07D 417/14; A61P 31/12; A61P 35/00; A61K 45/06
See application file for complete search history.

(56) References Cited

U.S. PATENT DOCUMENTS

| | | | |
|---|---|---|---|
| 7,361,669 B2 | 4/2008 | Scarborough et al. | |
| 7,687,637 B2 | 3/2010 | Bruce et al. | |
| 7,868,188 B2 | 1/2011 | Bengtsson et al. | |
| 8,088,806 B2 | 1/2012 | Zhang et al. | |
| 8,106,209 B2 | 1/2012 | Liu et al. | |

(Continued)

FOREIGN PATENT DOCUMENTS

| | | |
|---|---|---|
| CN | 105326831 A | 2/2016 |
| KR | 10-2010-0085912 A | 7/2010 |

(Continued)

OTHER PUBLICATIONS

Borden, K. L. B., & Culjkovic-Kraljacic, B. (2010). Ribavirin as an anti-cancer therapy: acute myeloid leukemia and beyond? Leukemia & Lymphoma, 51(10), 1805-1815. https://doi.org/10.3109/10428194.2010.496506 (Year: 2010).*

Anonymous: "CDDI—Genes & Targets Record: PI4Kb", Jan. 1, 2022, XP55890650, Retrieved from the Internet: URL:https://www.cortellis.com/drugdiscovery/entity/genestargets/G5298/generecord?ent=bTrxiA2T [retrieved on Feb. 11, 2022].

(Continued)

Primary Examiner — Kortney L. Klinkel
Assistant Examiner — Sophia Reilly
(74) Attorney, Agent, or Firm — Todd Esker; Bret E. Field; Bozicevic, Field & Francis LLP

(57) ABSTRACT

Compounds and methods are provided for inhibiting a PI4-kinase. Methods of treating a pathogen infection and methods of treating cancer are also provided. The PI4-kinase inhibitor can be a compound that is a 5-aryl or heteroaryl-thiazole, e.g., as described herein. In certain embodiments, the PI4-kinase inhibitor is a substituted 2-amino-5-phenylthiazole or substituted 2-amino-5-pyridylthiazole compound. In some embodiments, the compounds have broad spectrum anti-infective activity against a variety of infective diseases, where the diseases are caused by pathogens containing a basic amino acid PIP-2 pincer (BAAPP) domain that interacts with phosphatidylinositol 4,5-bisphosphate (PIP-2) to mediate pathogen replication. Also provided are methods of treating a subject for cancer using a PI4-kinase inhibitor. Aspects of the methods include inhibiting PI4-kinase in a cancer cell to reduce cellular proliferation.

21 Claims, 11 Drawing Sheets

(56) References Cited

U.S. PATENT DOCUMENTS

| | | |
|---|---|---|
| 8,404,684 B2 | 3/2013 | Bruce et al. |
| 9,309,236 B2 | 4/2016 | Glenn et al. |
| 9,447,158 B2 | 9/2016 | Panitch et al. |
| 9,926,309 B2 | 3/2018 | Glenn et al. |
| 10,428,060 B2 | 10/2019 | Glenn et al. |
| 11,091,472 B2 | 8/2021 | Glenn et al. |
| 2004/0186148 A1 | 9/2004 | Shankar et al. |
| 2005/0119320 A1 | 6/2005 | Bruce et al. |
| 2005/0228020 A1 | 10/2005 | Miyamoto et al. |
| 2006/0052416 A1 | 3/2006 | Dickson, Jr. et al. |
| 2006/0148822 A1 | 7/2006 | Bloomfield et al. |
| 2007/0032487 A1 | 2/2007 | Bruce et al. |
| 2007/0212717 A1 | 9/2007 | Kukolj et al. |
| 2008/0132502 A1 | 6/2008 | Bengtsson et al. |
| 2009/0029997 A1 | 1/2009 | Quattropani et al. |
| 2009/0076009 A1 | 3/2009 | Arnould et al. |
| 2009/0163469 A1 | 6/2009 | Caravatti et al. |
| 2010/0010057 A1 | 1/2010 | Moffat et al. |
| 2010/0093690 A1 | 4/2010 | Bruce et al. |
| 2011/0124693 A1 | 5/2011 | Bloomfield et al. |
| 2012/0135997 A1 | 5/2012 | Kato et al. |
| 2015/0051193 A1 | 2/2015 | Glenn et al. |
| 2015/0175562 A1 | 6/2015 | Gege et al. |
| 2016/0194314 A1 | 7/2016 | Glenn et al. |
| 2018/0170924 A1 | 6/2018 | Glenn et al. |
| 2019/0062323 A1 | 2/2019 | Glenn et al. |

FOREIGN PATENT DOCUMENTS

| | | |
|---|---|---|
| WO | WO 96/23783 A1 | 8/1996 |
| WO | WO 03/018536 A1 | 3/2003 |
| WO | WO 2003/072557 A1 | 9/2003 |
| WO | WO 2004/080377 A2 | 9/2004 |
| WO | WO 2005/044797 A1 | 5/2005 |
| WO | WO 2006/051270 A1 | 5/2006 |
| WO | WO 2007/070600 A2 | 6/2007 |
| WO | WO 2007/073497 A2 | 6/2007 |
| WO | WO 2007/129048 A1 | 11/2007 |
| WO | WO 2008/020227 A2 | 2/2008 |
| WO | WO 2008/154601 A1 | 12/2008 |
| WO | WO 2009/148541 A1 | 12/2009 |
| WO | WO 2010/008739 A2 | 1/2010 |
| WO | WO 2010/066324 A1 | 6/2010 |
| WO | WO 2011/007819 A1 | 1/2011 |
| WO | WO 2013/052845 A1 | 4/2013 |
| WO | WO2015193168 A1 | 12/2015 |
| WO | WO2015193169 A1 | 12/2015 |
| WO | WO 2016/123054 A2 | 8/2016 |
| WO | WO2016206999 A1 | 12/2016 |
| WO | WO 2017/147526 A1 | 8/2017 |
| WO | WO 2018/022868 A1 | 2/2018 |
| WO | WO2018029126 A1 | 2/2018 |
| WO | WO2018185120 A1 | 10/2018 |
| WO | WO 2020/146657 A1 | 7/2020 |

OTHER PUBLICATIONS

Delang et al., The role of phosphatidylinositol 4-kinases and phosphatidylinositol 4-phosphate during viral replication, Biochem Pharmacol. Dec. 1, 2012; 84(11): 1400-1408.

Chemical Abstracts Registry No. 329792-54-3, indexed in the Registry file on STN CAS Online Apr. 3, 2001.

Jamieson et al., A Drug Targeting only p110α can Block Phosphoinositide 3-Kinase Signalling and Tumour Growth in Certain Cell Types, Biochemical Journal, Aug. 15, 2011, pp. 53-62, 438(1). Portland Press Limited, London.

Miller et al., Shaping Development of Autophagy Inhibitors with the Structure of the Lipid Kinase Vps34, Science, Mar. 26, 2010, 327(5973):1638-1642, and the supporting online material (33 pages) including materials, methods, figs. S1 to S11, Table S1 and references, http:/science.sciencemag.org/content/sci/suppl/2010/03/23/327.5973.1638.DC1/Miller.SOM.pdf., American Association for the Advancement of Science, Washington, D.C.

Schickli et al., Challenges in Developing a Pediatric RSV Vaccine, Human Vaccines, vol. 5, Issue 9, pp. 582-591, Sep. 2009.

Tassini et al., Discovery of Multitarget Agents Active as Broad-Spectrum Antivirals and Correctors of Cystic Fibrosis Transmembrane Conductance Regulator for Associated Pulmonary Diseases, Journal of Medicinal Chemistry, 2017, 17 pages.

Morrow et al., The Lipid Kinase PI4KIIIB Is Highly Expressed in Breast Tumors and Activates Akt in Cooperation With Rab11a, Mal Cancer Res,. Oct. 2014; 12(10):1492-508.

Pubchem, Substance Record for SID 344338623, Oct. 7, 2017, Retrieved on Jun. 23, 2020 from the Internet: <URL:https://pubchem.ncbi.nlm.nih.gov/substance/344338623>.

Rutaganira et al., Design and structural characterization of potent and selective inhibitors of phosphatidylinositol 4 Kinase IIIβ, J Med Chem. Mar. 10, 2016; 59(5): 1830-1839.

Cardile et al., Will There Be a Cure for Ebola?, Annu Rev Pharmacol Toxicol, Jan. 6, 2017; 57:329-348.

Du et al., Vaccines for the prevention against the threat of MERS-CoV, Expert Rev Vaccines, Sep. 2016; 15(9):1123-34.

\* cited by examiner

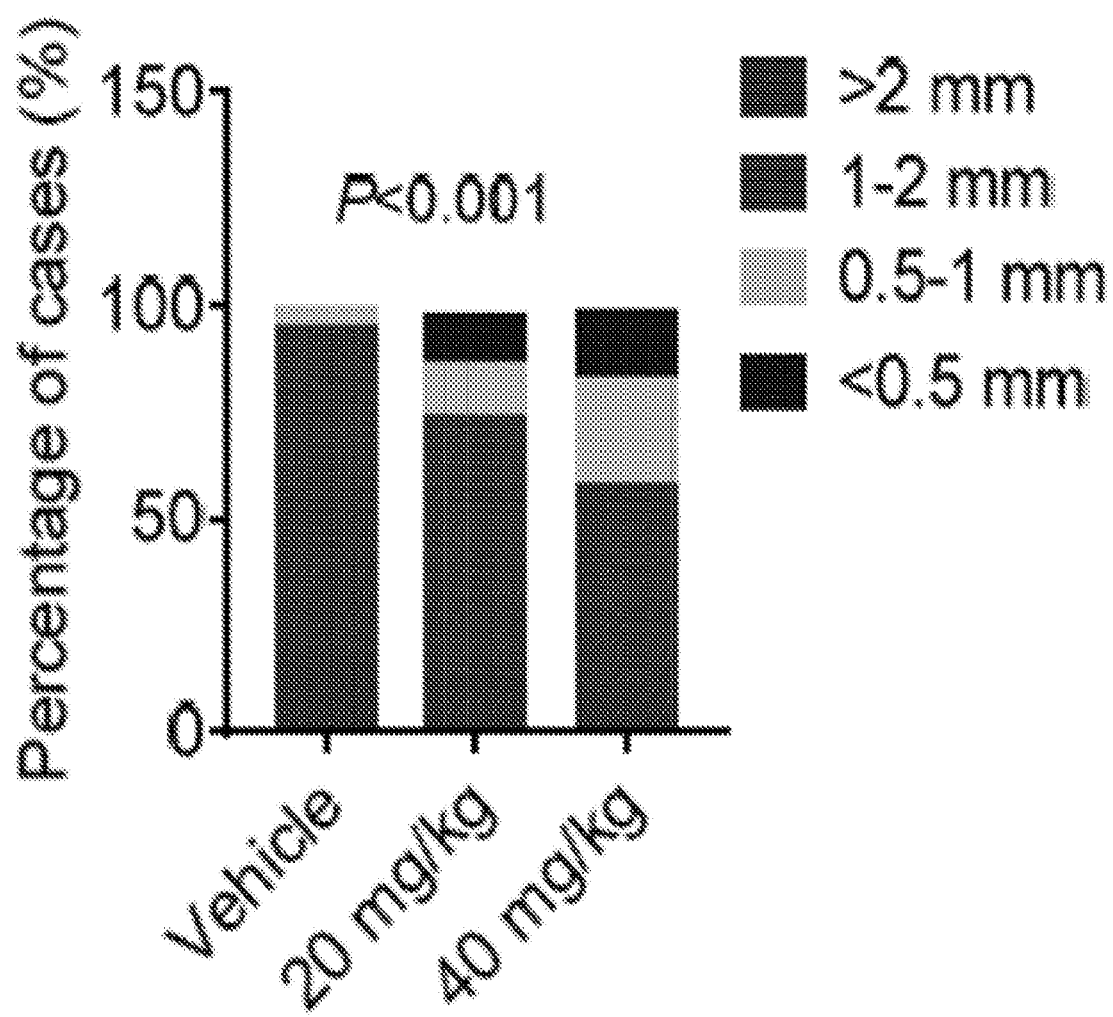

PI4-KINASE INHIBITORS AND METHODS OF USING THE SAME

CROSS-REFERENCE TO RELATED APPLICATION

This application is a U.S. National Stage Application of PCT Application No. PCT/US2020/023654 filed Mar. 19, 2020, which application, pursuant to 35 U.S.C. § 119 (e), claims priority to the filing date of U.S. Provisional Patent Application Ser. No. 62/821,853 filed Mar. 21, 2019, the disclosures of which applications are incorporated herein by reference in its entirety.

GOVERNMENT RIGHTS

This invention was made with Government support under contract AT109662 awarded by the National Institute of Allergy and Infectious Diseases. The Government has certain rights in the invention.

INTRODUCTION

Many infectious diseases are without adequate therapies. The rapid rise in the number of emerging pathogens in the world's population represents a serious global health problem and underscores the need to develop broad spectrum anti-infectives that target common components of large classes of pathogens. Human rhinoviruses (HRVs) are responsible for more than one-half of cold-like illnesses and cost billions of dollars annually in medical visits and missed days of work. Hepatitis C virus (HCV) is a member of the family Flaviviridae and is the cause of hepatitis C and some cancers such as liver cancer (hepatocellular carcinoma, abbreviated HCC) and lymphomas in humans. It is estimated that more than 2% of the world's population is currently infected with the Hepatitis C Virus (HCV). Enteroviruses are members of the picornavirus family, a large and diverse group of small RNA viruses. Enteroviral infections range in presentation and seriousness, and can cause a wide range of symptoms, including anything from rashes in small children, to summer colds, encephalitis, blurred vision, pericarditis, etc. Non polio enteroviruses cause 10-15 million infections and tens of thousands of hospitalizations in the US each year.

Many cancers are dependent on PI4-kinase for growth and metastasis. In many cases this reflects a tumor "addiction" for PI4-kinase activity. Among the ways that this can be readily identified is the presence of increased PI4-kinase activity in target cancer cells. This increased activity can be directly measured, or reliably predicted by the presence of increased levels of factors known to enhance PI4-kinase activity (e.g. Eukaryotic protein translation elongation factor 1 alpha 2 (eEF1A2)), or chromosomal amplifications that increase the PI4-kinase gene copy number. For example, high levels of eEF1A2 protein and mRNA can be detected in 30-60% of ovarian, breast, and lung tumors among others. Similarly, amplification of PI4-kinase is readily detected in a significant percentage of most human tumor types (see e.g., Cancer Genome Atlas (TCGA) available through cbioportal.org). Other cancer cells are also more sensitive to selective PI-4 kinase inhibition as compared to normal cells. Thus, pharmacologic inhibitors of PI-4 kinase useful for treating cancer, including human cancers and/or their metastases, are of interest.

SUMMARY

Compounds and methods are provided for inhibiting a PI4-kinase. Methods of treating a pathogen infection and methods of treating cancer are also provided. The PI4-kinase inhibitor can be a compound that is a particular 5-aryl or heteroaryl-thiazole, e.g., as described herein. In certain embodiments, the PI4-kinase inhibitor is a substituted 2-amino-5-phenylthiazole or substituted 2-amino-5-pyridylthiazole compound.

Aspects of the methods include the treatment of pathogen infections, which include, without limitation, viruses and other pathogens that utilize intracellular replication mechanisms, e.g. hepatitis C virus (HCV), *Plasmodium falciparum*, rhinovirus, and the like. The anti-infective compounds can have broad spectrum activity against a variety of infective diseases, where the diseases are caused by pathogens containing a basic amino acid PIP2 pincer (BAAPP) domain that interacts with phosphatidylinositol 4,5-bisphosphate ($PI(4,5)P_2$) to mediate replication, or are otherwise dependent on PI4-phosphate.

Aspects of the methods also include inhibiting a PI4-kinase and methods of inhibiting viral infection in a subject. The subject compounds may be formulated or provided to a subject in combination with one or more additional anti-infective agents, e.g. interferon, ribavirin, and the like. The subject compounds find use in the treatment of a variety of viruses such as a virus from the Picomaviridae, Flaviviridae, Caliciviridae, Filoviridae, Hepeviridae or Coronavirinae families. For treatment of viruses such as HCV, the compounds may be formulated to specifically target the liver, e.g. by conjugation with polyarginine or a bile acid, or as pro-drugs designed to be activated by enzymes resident in the liver.

Also provided are methods of treating a subject for cancer using a PI4-kinase inhibitor. Aspects of the methods include inhibiting PI4-kinase in a cancer cell to reduce cellular proliferation. The subject compounds may be formulated or provided to a subject in combination with one or more additional anti-cancer agents. Use of PI4-kinase inhibitors in methods of reducing cellular proliferation and methods of treatment is provided in a variety of cancer cells and cancer subjects.

These and other advantages and features of the disclosure will become apparent to those persons skilled in the art upon reading the details of the compositions and methods of use, which are more fully described below.

BRIEF DESCRIPTION OF THE DRAWINGS

FIGS. 1F and 1G. Schema of compound B treatment; Day 0, H2122 human lung cancer cell injection; day 7-27 compound B treatment; tumor imaging day 26 and necropsy day 27. (FIG. 1F) Mice subjected to micro-computed tomography after 19 days of treatment to determine tumor areas (left dot plot). Tumor diameters determined at necropsy (right dot plot). (FIG. 1G) Mice grouped on the basis of lung tumor measurements determined at necropsy, which showed a shift toward smaller tumor diameters in compound B-treated mice.

(FIG. 2A) Mouse body weight changes after 8 days treatment with vehicle (left panel) or vehicle plus 100 mg/kg/b.i.d. IP compound A (right panel). (FIG. 2B) Mice subjected to micro-computed tomography before and after treatment to determine tumor areas after 7 days treatment with vehicle or vehicle plus 100 mg/kg/b.i.d. IP compound A. Left panel: tumor area as measured before and after treatment. Right panel: tumor area expressed as percent of baseline measurement. (FIG. 2C) Tumor diameters determined at necropsy (left panel), and number of tumor metastases (right panel).

DETAILED DESCRIPTION OF THE EMBODIMENTS

Figure 1A:
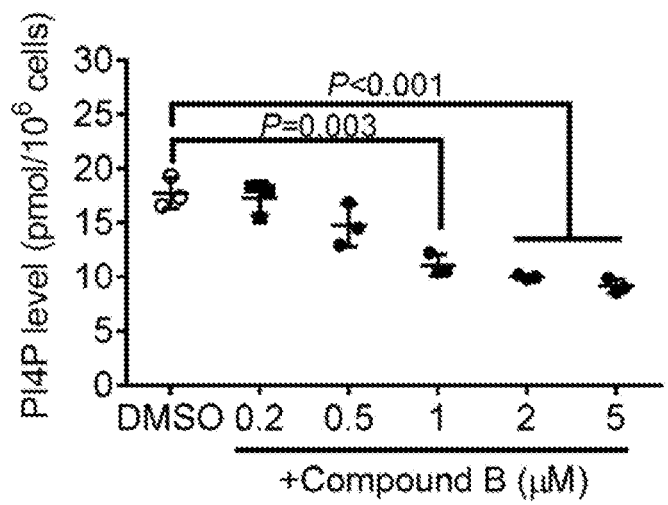
FIG. 1A. Intracellular PI4P concentrations in H2122 lung cancer cells treated with compound B (PI4-kinase inhibitor) or vehicle DMSO.

As summarized above, compounds and methods are provided for inhibiting a PI4-kinase. Methods of treating a pathogen infection and methods of treating cancer are also provided. The PI4-kinase inhibitor can be a compound that is a 5-aryl or heteroaryl-thiazole, e.g., as described herein. In certain embodiments, the PI4-kinase inhibitor is a substituted 2-amino-5-phenylthiazole or substituted 2-amino-5-pyridylthiazole compound.

In some embodiments, the PI4-kinase inhibitor compounds have broad spectrum activity against a variety of infective diseases, where the diseases are caused by pathogens containing a basic amino acid PIP-2 pincer (BAAPP) domain that interacts with phosphatidylinositol 4,5-bisphosphate (PIP-2) to mediate replication, or pathogens otherwise dependent on PIP4, and thus sensitive to PI4 kinase. In certain cases, the compounds have activity against one or more viruses selected from the Picornaviridae, Flaviviridae, Caliciviridae, Filoviridae, Hepeviridae, Togaviridae, Papovaviridae, Papillomaviridae, Polyomaviridae, Retroviridae, and Coronavirinae families.

In some embodiments, an PI4-kinase inhibitor compound that is a PI4-kinase inhibiting compound is contacted with a pathogen, in a dose and for a period of time sufficient to inhibit replication. Contacting may be performed in vitro or in vivo. Such PI4-kinase inhibiting compounds may inhibit pathogen replication by inhibiting the production of PIP-2.

In some embodiments, the PI4-kinase inhibitor compounds have broad spectrum activity against a variety of cancers. In some embodiments, the compound is a PI4-kinase inhibiting compound in a cancer cell to reduce cellular proliferation. The subject compounds may be formulated or provided to a subject in combination with one or more additional anti-cancer agents. Use of PI4-kinase inhibitors in methods of reducing cellular proliferation and methods of treatment is provided in a variety of cancer cells and cancer subjects.

In some embodiments a method of inhibiting a PI4-kinase, including but not limited to a class III PI4-kinase, are provided, where a compound of the invention is brought into contact with a PI4-kinase in a dose and for a period of time sufficient to inhibit activity of the enzyme.

Also provided are pharmaceutical compositions that include the subject compounds, where a compound of the present disclosure can be formulated with a pharmaceutically acceptable excipient.

Formulations may be provided in a unit dose, where the dose provides an amount of the compound effective to achieve a desired result, including without limitation inhibition of pathogen replication.

These compounds and methods find use in a variety of applications in which inhibition of a PT-kinase is desired.

Compounds

Aspects of the disclosure include particular PI4-kinase inhibitor compounds. In general, the compounds include a 5-aryl-thiazole or a 5-heteroaryl-thiazole core structure. The 5-aryl or 5-heteroaryl ring may be a 6-membered heteroaryl (e.g., pyridyl) or phenyl ring that includes at least a further substituent meta to the thiazole ring substituent. The thiazole ring of the core structure may include further substituents at the 2- and/or 4-positions of the ring. In some embodiments, the PI4-kinase inhibitor compounds are 2-amino-5-phenylthiazole compounds that include a thiazole ring having an amino substituent at the 2-position of the ring, and a phenyl substituent at the 5-position of the ring. In some embodiments, the PI4-kinase inhibitor compounds are 2-amino-5-pyridyl-thiazole compounds that include a thiazole ring having an amino substituent at the 2-position of the ring, and a pyridyl substituent at the 5-position of the ring. In some embodiments, the amino substituent at the 2-position of the ring may be further substituted with any convenient substituents including but not limited to —C(CH$_3$)$_2$R, —CyR, where R is alkyl, heteroalkyl, heterocycle, or aryl; and Cy is a cyclic group, such as cycloalkyl, heterocycle, aryl, heteroaryl, and any of the groups R or Cy may be optionally substituted. In some embodiments, the compound includes further substituents, such as a substituent at either the 4 or 5-position of the thiazole ring. The aryl ring of the core structure (e.g., 5-phenyl or pyridyl ring) may be further substituted with any convenient substituents including but not limited to alkyl, acyloxy, aminoalkoxy, cyano, halogen, hydroxyl, nitro, —NHCOR, —SO$_2$NHR, —CONHR or —NHSO$_2$R, where R is alkyl, heteroalkyl, heterocycle or aryl. Exemplary compounds are set forth in the following structures and formulae.

In some cases, the subject compound is described by the structure of formula (Ia):

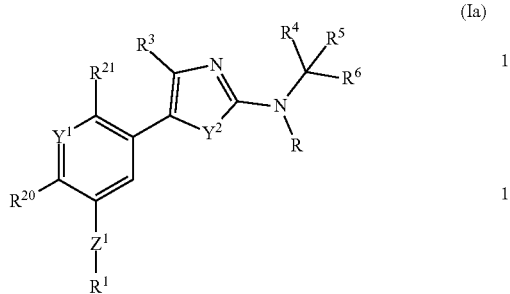

(Ia)

where:

$Z^1$ is a covalent bond or a linking functional group;

R is H, alkyl or alkyl (e.g., lower alkyl, such as methyl), $Y^1$ is $CR^{22}$ or N;

$Y^2$ is selected from S, O or $NR^{19}$, wherein $R^{19}$ is selected from hydrogen, alkyl, and substituted alkyl;

$R^1$ is selected from aryl, substituted aryl, heteroaryl, substituted heteroaryl, alkyl, substituted alkyl, cycloalkyl, substituted cycloalkyl, heterocycle and substituted heterocycle;

$R^3$ is selected from hydrogen, lower alkyl and substituted lower alkyl;

$R^4$ and $R^5$ are each independently selected from lower alkyl and substituted lower alkyl; or $R^4$ and $R^5$ together with the carbon to which they are attached form a cyclic group selected from cycloalkyl, substituted cycloalkyl, heterocycle, substituted heterocycle, aryl, substituted aryl, heteroaryl and substituted heteroaryl; and $R^6$ is selected from substituted alkyl, cycloalkyl, substituted cycloalkyl, aryl, substituted aryl, heterocycle, substituted heterocycle, heteroaryl and substituted heteroaryl; or $R^4$, $R^5$ and $R^6$ together with the carbon to which they are attached provide a bridged cyclic group selected from bridged cycloalkyl, substituted bridged cycloalkyl, bridged heterocycle and substituted bridged heterocycle; and $R^{20}$, $R^{21}$ and $R^{22}$ are independently selected from hydrogen, an alkyl, a substituted alkyl, an aryl, a substituted aryl, a hydroxy, an alkoxy, a substituted alkoxy, an aryloxy, a substituted aryloxy, a heterocycle, a substituted heterocycle, a cyano, a halogen, an amino, a substituted amino, an acyl, an acyloxy, an amido, and a nitro.

In some cases, the subject compound is described by the structure of formula (Ib):

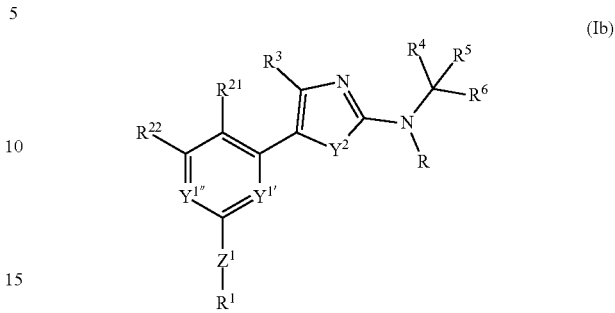

(Ib)

where:

$Z^1$ is a covalent bond or a linking functional group;

R is H, alkyl or alkyl (e.g., lower alkyl, such as methyl), $Y^{1'}$ and $Y^{1''}$ are each independently $CR^{20}$ or N;

$Y^2$ is selected from S, O or $NR^{19}$, wherein $R^{19}$ is selected from hydrogen, alkyl, and substituted alkyl;

$R^1$ is selected from aryl, substituted aryl, heteroaryl, substituted heteroaryl, alkyl, substituted alkyl, cycloalkyl, substituted cycloalkyl, heterocycle and substituted heterocycle;

$R^3$ is selected from hydrogen, lower alkyl and substituted lower alkyl;

$R^4$ and $R^5$ are each independently selected from lower alkyl and substituted lower alkyl; or $R^4$ and $R^5$ together with the carbon to which they are attached form a cyclic group selected from cycloalkyl, substituted cycloalkyl, heterocycle, substituted heterocycle, aryl, substituted aryl, heteroaryl and substituted heteroaryl; and $R^1$ is selected from substituted alkyl, cycloalkyl, substituted cycloalkyl, aryl, substituted aryl, heterocycle, substituted heterocycle, heteroaryl and substituted heteroaryl; or $R^4$, $R^5$ and $R^6$ together with the carbon to which they are attached provide a bridged cyclic group selected from bridged cycloalkyl, substituted bridged cycloalkyl, bridged heterocycle and substituted bridged heterocycle; and $R^{20}$, $R^{21}$ and $R^{22}$ are independently selected from hydrogen, an alkyl, a substituted alkyl, an aryl, a substituted aryl, a hydroxy, an alkoxy, a substituted alkoxy, an aryloxy, a substituted aryloxy, a heterocycle, a substituted heterocycle, a cyano, a halogen, an amino, a substituted amino, an acyl, an acyloxy, an amido, and a nitro.

In certain embodiments, in formula (Ia) or (Ib), R, $R^1$, $R^3$, $R^4$, $R^5$, $R^6$, $R^{19}$, $R^{20}$, $R^{21}$, $R^{22}$ are independently selected from corresponding groups as depicted in any of the structures of Table 1, 2 or 3.

In some embodiments, in formula (Ib), $Y^{1'}$ is CH and $Y^{1''}$ is $CR^{20}$, such that the compound is described by the formula (Ic):

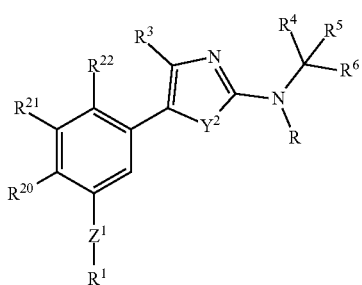

(Ic)

where:
Z¹ is a covalent bond or a linking functional group;
R is H, alkyl or alkyl (e.g., lower alkyl, such as methyl),
$Y^2$ is selected from S, C or $NR^{19}$, wherein $R^{19}$ is selected from hydrogen, alkyl, and substituted alkyl;
$R^{1'}$ is selected from aryl, substituted aryl, heteroaryl, substituted heteroaryl, alkyl, substituted alkyl, cycloalkyl, substituted cycloalkyl, heterocycle and substituted heterocycle;
$R^{20}$ is selected from hydrogen, a halogen, an alkyl, a substituted alkyl, an alkoxy and a substituted alkoxy;
$R^3$ is selected from hydrogen and an alkyl;
$R^4$ and $R^5$ are each independently selected from lower alkyl and substituted lower alkyl; or R and R together with the carbon to which they are attached form a cyclic group selected from cycloalkyl, substituted cycloalkyl, heterocycle, substituted heterocycle, aryl, substituted aryl, heteroaryl and substituted heteroaryl; and
$R^6$ is selected from substituted alkyl, cycloalkyl, substituted cycloalkyl, aryl, substituted aryl, heterocycle, substituted heterocycle, heteroaryl and substituted heteroaryl; or
$R^4$, $R^5$ and $R^6$ together with the carbon to which they are attached provide a bridged cyclic group selected from bridged cycloalkyl, substituted bridged cycloalkyl, bridged heterocycle and substituted bridged heterocycle; and
$R^{21}$ and $R^{22}$ are independently selected from hydrogen, an alkyl, an aryl, a hydroxy, an alkoxy, an aryloxy, a heterocycle, a cyano, a halogen, an amino, an acyl, an acyloxy, an amido and nitro.

In certain embodiments, $R^{20}$ is selected from hydrogen, a halogen and an alkoxy. In certain embodiments, $R^2$ is selected from hydrogen, a halogen, an alkyl, a substituted alkyl and an alkoxy. In certain embodiments, $R^2$ is selected from a lower alkyl, a halogen, a substituted lower alkyl, and a lower alkoxy. In certain embodiments, $R^2$ is selected from Me, Cl, Br, $CHF_2$, $CF_3$, $CH_2F$ and OMe.

In some embodiments, $R^3$ and $R^{22}$ are selected such that they form a 6-membered ring as part of a fused tricyclic aryl-thiazole core structure.

In some embodiments, the subject compound is described by the structure of formula (Id):

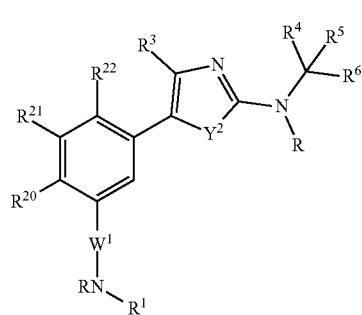

(Id)

where:
$W^1$ is a covalent bond or a linking functional group;
$Y^2$ is selected from S, O or $NR^{19}$, wherein $R^{19}$ is selected from hydrogen, alkyl, and substituted alkyl;
$R^1$ is selected from a substituted alkyl (e.g., an alkyl halide, or a heterocycle-substituted lower alkyl), an aryl (e.g., a phenyl), a substituted aryl, heteroaryl (e.g., a pyridine), substituted heteroaryl, a heterocycle (e.g., a pyridyl, a pyrimidinyl) and a substituted heterocycle;
$R^{20}$ is selected from hydrogen, a halogen, an alkyl, a substituted alkyl, an alkoxy and a substituted alkoxy;
$R^3$ and each R are independently selected from hydrogen and an alkyl (e.g., a lower alkyl such as a methyl);
$R^4$ and $R^5$ are each independently selected from lower alkyl and substituted lower alkyl; or $R^4$ and $R^5$ together with the carbon to which they are attached form a cyclic group selected from cycloalkyl, substituted cycloalkyl, heterocycle, substituted heterocycle, aryl, substituted aryl, heteroaryl and substituted heteroaryl; and
$R^6$ is selected from substituted alkyl, cycloalkyl, substituted cycloalkyl, aryl, substituted aryl, heterocycle, substituted heterocycle, heteroaryl and substituted heteroaryl; or
$R^4$, $R^5$ and $R^6$ together with the carbon to which they are attached provide a bridged cyclic group selected from bridged cycloalkyl, substituted bridged cycloalkyl, bridged heterocycle and substituted bridged heterocycle; and
$R^{21}$ and $R^{22}$ are independently selected from hydrogen, an alkyl, an aryl, a hydroxy, an alkoxy, an aryloxy, a heterocycle, a cyano, a halogen, an amino, an acyl, an acyloxy, an amido and nitro.

In certain embodiments of any one of formulae (Ia), (Ib), (Ic) or (Id), $Y^2$ is S. In certain embodiments, $Y^2$ is O. In certain embodiments, $Y^2$ is $NR^{19}$, wherein $R^{19}$ is selected from hydrogen, alkyl, and substituted alkyl. In certain cases, $R^{19}$ is hydrogen.

In certain embodiments, the subject compound is described by the structure of formula (Ie):

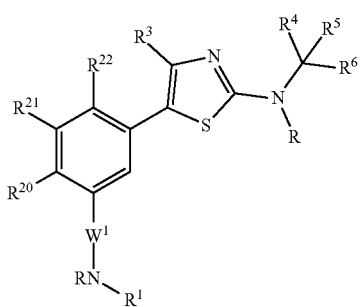

(Ie)

where:
- $W^1$ is a covalent bond or a linking functional group;
- $R^1$ is selected from a substituted alkyl (e.g., an alkyl halide, or a heterocycle-substituted lower alkyl), an aryl (e.g., a phenyl), a substituted aryl, heteroaryl (e.g., a pyridine), substituted heteroaryl, a heterocycle (e.g., a pyridyl, a pyrimidinyl) and a substituted heterocycle;
- $R^{20}$ is selected from hydrogen, a halogen, an alkyl, a substituted alkyl, an alkoxy and a substituted alkoxy;
- $R^3$ and each R are independently selected from hydrogen and an alkyl (e.g., a lower alkyl such as a methyl);
- $R^4$ and $R^5$ are each independently selected from lower alkyl and substituted lower alkyl; or R and $R^5$ together with the carbon to which they are attached form a cyclic group selected from cycloalkyl, substituted cycloalkyl, heterocycle, substituted heterocycle, aryl, substituted aryl, heteroaryl and substituted heteroaryl; and
- $R^6$ is selected from substituted alkyl, cycloalkyl, substituted cycloalkyl, aryl, substituted aryl, heterocycle, substituted heterocycle, heteroaryl and substituted heteroaryl; or
- $R^4$, $R^5$ and $R^6$ together with the carbon to which they are attached provide a bridged cyclic group selected from bridged cycloalkyl, substituted bridged cycloalkyl, bridged heterocycle and substituted bridged heterocycle; and
- $R^{21}$ and $R^{22}$ are independently selected from hydrogen, an alkyl, an aryl, a hydroxy, an alkoxy, an aryloxy, a heterocycle, a cyano, a halogen, an amino, an acyl, an acyloxy, an amido and nitro.

In certain embodiments, of any one of formula (Ia), (Ib), (Ic), (Id) or (Ie), $R^{20}$ is selected from hydrogen, a halogen and an alkoxy. In certain embodiments, $R^{20}$ is selected from hydrogen, a halogen, an alkyl, a substituted alkyl and an alkoxy. In certain embodiments, $R^{20}$ is selected from a lower alkyl, a halogen, a substituted lower alkyl, and a lower alkoxy. In certain embodiments, $R^{20}$ is selected from Me, Cl, Br, $CHF_2$, $CF_3$, $CH_2F$ and OMe.

In certain embodiments of any one of the formulae (Ia), (Ib), (Ic), (Id) or (Ie), $R^{20}$ is methoxy.

In certain embodiments of any one of formulae (Ia), (Ib), (Ic), (Id) or (Ie), $R^3$ is methyl.

In certain embodiments, in formula (Ia), (Ib), (Ic), (Id) or (Ie), $R^1$, $R^3$, $R^4$, $R^5$ $R^6$ and $R^{20}$ are independently selected from corresponding groups as depicted in any of the structures of Table 1, 2 or 3.

In any of the formulae described herein, the linking functional group may be any convenient bivalent group. Linking functional groups of interest include, but are not limited to, an amino, an amido, an ester, a carbonyloxy, an ether, a carbamate, a sulfonamide, a carbonyl, a sulfonyl, a sulfinyl, or the like. In some embodiments, the linking functional group is described by one of the following formulas: —$SO_2NR$—, —NR—, —NRC(=O)—, or —NRC(=O)NR— where each R is independently H, an alkyl, a cycloalkyl, a heterocycle, a heterocycloalkyl, an aryl or a heteroaryl; —O—; —C(=O)—; —C(=O)X— where X is NR, O or S and where R is H or an alkyl; —S(=O)— or —$SO_2$—; where for each of the formulae depicted it is understood that both possible orientations of a functional group are included. In some embodiments, in formula (Ia)-(Ic), $Z^1$ is —$SO_2NH$— or —CONH—. In some embodiments, in formulae (Id) or (Ie), $W^1$ is —$SO_2$—.

In certain embodiments, the subject compound is described by the structure of formula (I):

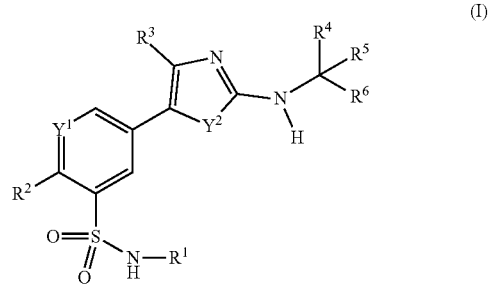

(I)

wherein:
- $Y^1$ is selected from CH or N;
- $Y^2$ is selected from S, O or $NR^{19}$, wherein $R^{19}$ is selected from hydrogen, alkyl, and substituted alkyl;
- $R^1$ is selected from aryl, substituted aryl, heteroaryl, substituted heteroaryl, alkyl, substituted alkyl, cycloalkyl, substituted cycloalkyl, heterocycle and substituted heterocycle; $R^1$ is selected from alkoxy and substituted alkoxy;
- $R^3$ is selected from hydrogen, lower alkyl and substituted lower alkyl;
- $R^4$ and $R^5$ are each independently selected from lower alkyl and substituted lower alkyl; or $R^4$ and $R^5$ together with the carbon to which they are attached form a cyclic group selected from cycloalkyl, substituted cycloalkyl, heterocycle, substituted heterocycle, aryl, substituted aryl, heteroaryl and substituted heteroaryl; and
- $R^6$ is selected from substituted alkyl, cycloalkyl, substituted cycloalkyl, aryl, substituted aryl, heterocycle, substituted heterocycle, heteroaryl and substituted heteroaryl; or
- $R^4$, $R^5$ and $R^6$ together with the carbon to which they are attached provide a bridged cyclic group selected from bridged cycloalkyl, substituted bridged cycloalkyl, bridged heterocycle and substituted bridged heterocycle.

In certain embodiments of formula (I), $Y^2$ is S. In certain embodiments, $Y^2$ is O. In certain embodiments, $Y^2$ is $NR^{19}$, wherein $R^{19}$ is selected from hydrogen, alkyl, and substituted alkyl. In certain cases. $R^{19}$ is hydrogen.

In certain embodiments, formula (I) is of the formula (If):

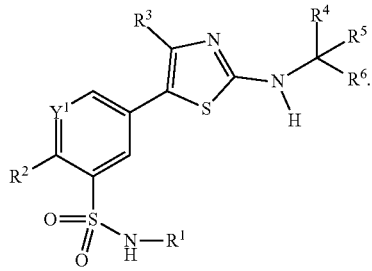
(If)

In certain embodiments, formula (I) is of the formula (Ig):

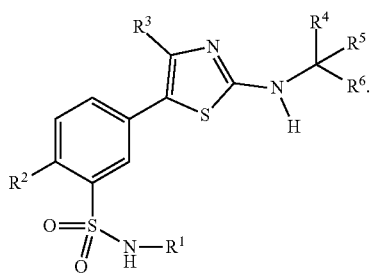
(Ig)

In some embodiments of formula (I), (If) or (Ig), $R^2$ is alkoxy. In some cases, $R^2$ is methoxy.

In other cases, $R^2$ is a substituted alkoxy.

In certain embodiments, in formula (I), (If) or (Ig). $R^1$, $R^2$. $R^3$, $R^4$, $R^5$ and $R^6$ are independently selected from corresponding groups as depicted in any of the structures of Table 1, 2 or 3.

In certain embodiments of formula (I), (If) or (Ig), $R^3$ is lower alkyl, such as methyl, ethyl, propyl, pentyl or hexyl. In some cases, $R^3$ is methyl. In other cases, $R^3$ is substituted lower alkyl (e.g., alkyl halide).

In some embodiments, in formulae (I), (If) or (Ig), $R^2$ is methoxy. In some embodiments, in formulae (I), (If) or (Ig), $R^3$ is methyl.

In some embodiments, $R^1$ is not a hydroxy-substituted alkyl group, such as —(CH$_2$)$_2$—OH.

In some embodiments, $R^1$ is selected from an alkyl, an aryl (e.g., a phenyl), an alkyl-heterocycle and a heterocycle (e.g., pyridyl, pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl). In some embodiments, $R^1$ is selected from a substituted lower alkyl (e.g., a substituted methyl or ethyl), a phenyl, a cycloalkyl, a pyridyl and a pyrimidinyl.

In some embodiments, any of the formulae described herein are not:

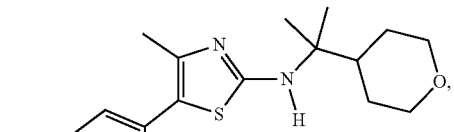

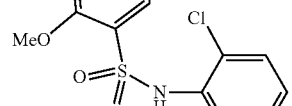

,

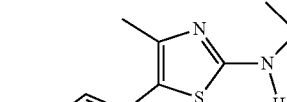

, or

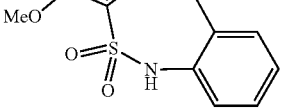

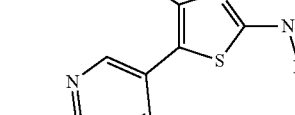

.

In some instances of any one of formulae (I) to (Ig), $R^4$ and $R^5$ each lower alkyl (e.g., methyl, ethyl, propyl, pentyl, hexyl). In some cases, $R^4$ and $R^5$ are each methyl. In certain cases, $R^4$ and $R^5$ together with the carbon to which they are attached form a cyclic group. In certain cases, $R^4$ and $R^5$ together with the carbon to which they are attached form a cyclopropyl group. In certain cases, $R^4$, $R^5$ and $R^6$ can be represented by the following formulae:

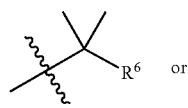
(IA1)

or

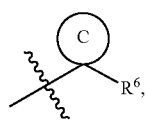
(IA2)

where:
$R^6$ is selected from substituted alkyl, cycloalkyl, substituted cycloalkyl, aryl, substituted aryl, heterocycle, substituted heterocycle, heteroaryl and substituted heteroaryl; and
C ring is selected from cycloalkyl, substituted cycloalkyl, aryl, substituted aryl, heterocycle, substituted heterocycle, heteroaryl and substituted heteroaryl.

In certain cases, $R^4$, $R^5$ and $R^6$ can be represented by the following formulae:

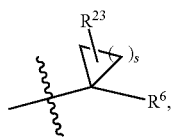

(IA3)

where:
R$^6$ is selected from substituted alkyl, cycloalkyl, substituted cycloalkyl, aryl, substituted aryl, heterocycle, substituted heterocycle, heteroaryl and substituted heteroaryl;
R$^{23}$ is one or more optional substituent selected from a lower alkyl, a halogen, a substituted lower alkyl, and a lower alkoxy (e.g., Me, Cl, Br, CHF$_2$, CF$_3$, CH$_2$F and OMe); and
s is 1, 2, 3 or 4.

In some embodiments of formula (IA3), any of the carbon atoms in the cycle may be replaced by a hetero atom (e.g., N, S or O), provided the structure is synthetically feasible. In certain cases, any number of R$^{23}$ substitutes may be included, provided the structure is sterically practical. In certain embodiments, no R$^2$ substituents are present. In certain cases, the cycle in formula (IA3) is a cyclopropyl group.

In certain cases of any one of formulae (I) to (Ig), R$^4$, R$^5$ and R$^6$ together with the carbon to which they are attached provide a bridged cyclic group selected from bridged cycloalkyl, substituted bridged cycloalkyl, bridged heterocycle and substituted bridged heterocycle. In certain cases, R$^4$, R$^5$ and R$^6$ can be represented by the following formulae:

(IA4)

In some cases of any one of formulae (I) to (Ig), R$^6$ is a substituted alkyl. In some cases, R$^6$ may be represented by the formula —(CH$_2$)$_n$—X$^1$, where n is 1, 2 or 3; and X$^1$ hydroxyl, halogen, alkyl halide (e.g., CF$_3$), an aryl (e.g., a phenyl) or a heterocycle (e.g., pyridyl (e.g., 3-pyridyl), pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl). In some instances. R$^6$ is a cycloalkyl or a heterocycle (e.g., a 5- or 6-membered saturated N-containing heterocycle). In certain cases, R$^6$ is selected from a cyclohexyl, a cyclopentyl, a cyclopropyl, a pyrrolidinyl, a piperidinyl, a tetrahydrofuranyl, a phenyl and a pyridinyl. In certain cases, R$^6$ may be represented by ring A (e.g., as described herein).

In some embodiments of any one of formula (I) to (Ig), R$^1$ is described by the formula —(CH$_2$)$_n$—X$^1$, where n is 0, 1, 2 or 3; and X$^1$ is a lower alkyl (e.g., methyl), hydroxyl, halogen, alkyl halide, an aryl (e.g., a phenyl) or a heterocycle (e.g., pyridyl (e.g., 3-pyridyl), pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl). In some cases, R$^1$ may be represented by ring B (e.g., as described herein).

In some embodiments the subject compound is described by the structure of formula (II):

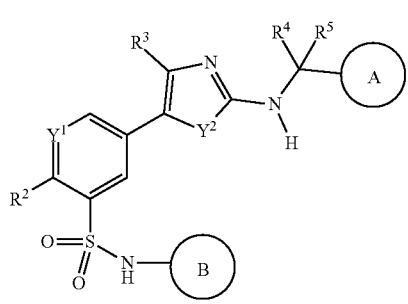

(II)

wherein:
A ring is selected from aryl, substituted aryl, heteroaryl, substituted heteroaryl, cycloalkyl, substituted cycloalkyl, heterocycle and substituted heterocycle; and
B ring is selected from aryl, substituted aryl, heteroaryl, substituted heteroaryl, cycloalkyl, substituted cycloalkyl, heterocycle and substituted heterocycle.

In certain embodiments, formula (II) is of the formula (IV):

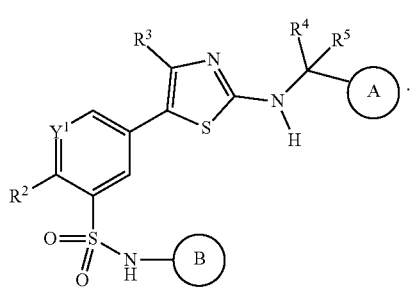

(IV)

In certain embodiments, formula (II) is of the formula (V):

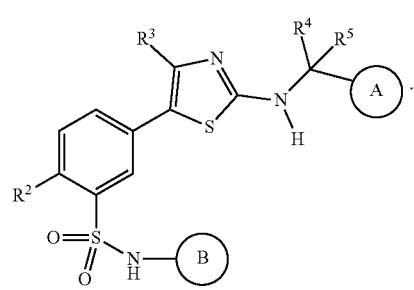

(V)

In certain embodiments, in formula (IT), (IV) or (V), R$^2$, R$^3$, R$^4$, R$^5$, ring A and ring B are independently selected from corresponding groups as depicted in any of the structures of Table 1, 2 or 3.

In certain embodiments of formula (II), (IV) or (V), R$^3$ is lower alkyl, such as methyl, ethyl, propyl, pentyl or hexyl. In some cases, R$^3$ is methyl. In other cases, R$^3$ is substituted lower alkyl (e.g., alkyl halide).

In some embodiments, in formulae (IT), (IV) or (V), R$^2$ is methoxy. In some embodiments, in formulae ((II), (IV) or (V), R$^3$ is methyl.

In some instances of any one of formulae (II), (IV) or (V), $R^4$ and $R^5$ each lower alkyl (e.g., methyl, ethyl, propyl, pentyl, hexyl). In some cases, $R^4$ and $R^5$ are each methyl. In certain cases, $R^4$ and $R^5$ together with the carbon to which they are attached form a cyclic group. In certain cases, $R^4$ and $R^5$ together with the carbon to which they are attached form a cyclopropyl group. In certain cases, $R^4$, $R^5$ and $R^6$ can be represented by the following formulae:

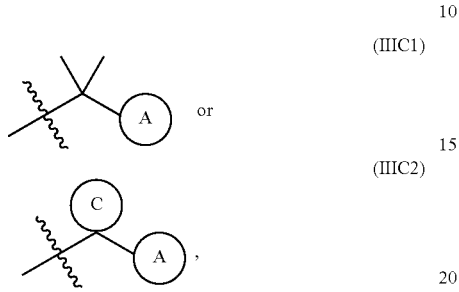

where:
C ring is selected from cycloalkyl, substituted cycloalkyl, aryl, substituted aryl, heterocycle, substituted heterocycle, heteroaryl and substituted heteroaryl.

In certain cases, $R^4$ and $R^5$ can be represented by the following formulae:

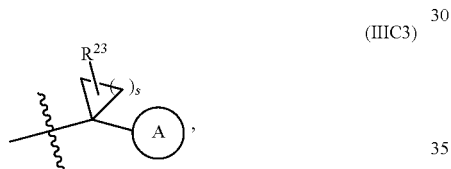

where:
$R^{11}$ is one or more optional substituent selected from a lower alkyl, a halogen, a substituted lower alkyl, and a lower alkoxy (e.g., Me, Cl, Br, $CHF_2$, $CF_3$, $CH_2F$ and OMe); and
s is 1, 2, 3 or 4.

In some embodiments of formula (IIIC3), any of the carbon atoms in the cycle may be replaced by a hetero atom (e.g., N, S or O), provided the structure is synthetically feasible. In certain cases, any number of $R^{23}$ substitutes may be included, provided the structure is sterically practical. In certain embodiments, no $R^{23}$ substituents are present. In certain cases, the cycle in formula (IIIC3) is a cyclopropyl group.

In some embodiments, the A ring is selected from an aryl (e.g., a phenyl), optionally including one or more substituents. In some embodiments, the A ring is selected from a heteroaryl or a heterocycle (e.g., pyridyl, pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl) optionally including one or more substituents. In some embodiments, the A ring is selected from a cycloalkyl (e.g., a cyclohexane, cyclopentane), optionally including one or more substituents. In some embodiments, the A ring is selected from phenyl, substituted phenyl, pyridyl, substituted pyridyl, 2-pyrimidinyl, substituted 2-pyrimidinyl, 3-pyrimidinyl, substituted 3-pyrimidinyl, 6-pyrimidinyl, substituted 6-pyrimidinyl, piperidine, substituted piperidine, piperazine, substituted piperazine, 2-oxopiperidine, 2-oxopiperazine, imidazole, substituted imidazole, thiazole, substituted thiazole, oxazole, substituted oxazole, tetrahydropyran, substituted tetrahydropyran, morpholine, substituted morpholine, cyclic sulfone, substituted cyclic sulfone, cycloalkyl and substituted cycloalkyl.

In other embodiments, the A ring is described by the formula (A1):

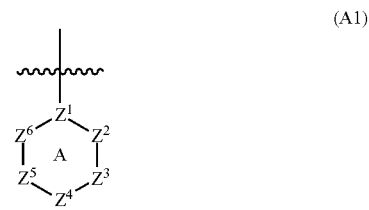

where A1 is a 6-membered aryl, heteroaryl, heterocyclyl, or cycloalkyl, where $Z^1$-$Z^6$ are independently selected from N, O, $CR^{11}$, $NR^{11}$, $CR^{11}_2$, $SO_2$ and CO, provided that valency requirements are fulfilled, where $R^{11}$ are each independently selected from hydrogen, alkyl, substituted alkyl, hydroxy, alkoxy, substituted alkoxy, trifluoromethyl, halogen, acyl, substituted acyl, carboxy, carboxyamide, substituted carboxyamide, sulfonyl, substituted sulfonyl, sulfonamide and substituted sulfonamide. In certain cases, $Z^2$ and $Z^3$, or $Z^3$ and $Z^4$, or $Z^4$ and $Z^5$, or $Z^5$ and $Z^6$ are $CR^{11}$, wherein each $R^{11}$ together with the carbons to which they are attached form a 5-membered or 6-membered cyclic group selected from aryl, substituted aryl, heteroaryl, substituted heteroaryl, heterocycle, substituted heterocycle, cycloalkyl and substituted cycloalkyl. In certain cases, A1 is an indole or a substituted indole. In some cases, A1 is a phenyl, or substituted phenyl. In some cases, A1 is a cycloalkyl, or a substituted cycloalkyl. In some cases, A1 is pyridyl or substituted pyridyl. In some cases, A1 is pyrimidinyl, such as 2-pyrimidinyl, substituted 2-pyrimidinyl, 3-pyrimidinyl, substituted 3-pyrimidinyl, 6-pyrimidinyl or substituted 6-pyrimidinyl. In some cases, A1 is a pyridazine, or a substituted pyridazine. In some cases, A1 is a triazine, or a substituted triazine. In some cases, A1 is piperidine or substituted piperidine. In some cases, A1 is piperazine or substituted piperazine. In some cases, A1 is 2-oxopiperidine or substituted 2-oxopiperidine. In some cases, A1 is 2-oxopiperazine or substituted 2-oxopiperazine. In some cases, A1 is tetrahydropyran or substituted tetrahydropyran. In some cases, A1 is a pyran or a substituted pyran. In some cases, A1 is morpholine or substituted morpholine. In some cases, A1 is a cyclic sulfone or a substituted cyclic sulfone.

In some embodiments the A ring is described by the formula (B2):

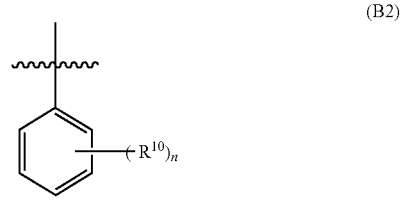

where:
R$^{10}$ is one or more optional substituents independently selected from, alkyl, substituted alkyl, hydroxy, alkoxy, substituted alkoxy, trifluoromethyl and halogen; and
n is an integer from 0 to 5.

In certain cases, B2 is phenyl. In certain cases, B2 is a mono-substituted phenyl. In certain cases, B2 is a di-substituted phenyl. In certain cases, B2 is a tri-substituted phenyl. In certain cases, B2 is a tetra-substituted phenyl. In certain cases, B2 is a penta-substituted aryl. In certain cases, the substitutes are selected from lower alkyl (e.g., methyl, ethyl, propyl, butyl, pentyl and hexyl) and halogen (e.g., F, Cl, I or Br). In certain embodiments, B2 is a 2,6-disubstituted phenyl, wherein the substituents are independently selected from halogen and lower alkyl.

In some embodiments of the A ring, the B2 ring is described by the formula (B2a):

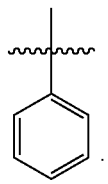

(B2a)

In some embodiments the A ring is described by the formula (B3):

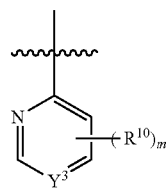

(B3)

where:
R$^{10}$ is one or more optional substituents independently selected from, alkyl, substituted alkyl, hydroxy, alkoxy, substituted alkoxy, trifluoromethyl and halogen;
Y$^3$ is selected from N and CR$^{31}$, wherein R$^{11}$ is selected from hydrogen. R$^{10}$, acyl, substituted acyl, carboxy, carboxyamide, substituted carboxyamide, sulfonyl, substituted sulfonyl, sulfonamide and substituted sulfonamide; and
m is an integer from 0 to 3.

In certain cases, B3 is pyridyl. In certain cases, B3 is a substituted pyridyl. In some cases, the pyridyl is a mono-substituted pyridyl. In other cases, the pyridyl is a di-substituted pyridyl. In other cases, the pyridyl is a tri-substituted pyridyl. In other cases, the pyridyl is a tetra-substituted pyridyl. In certain cases, Y$^1$ is N, such that B3 is a pyrimidyl. In some cases, B3 is a substituted pyrimidyl. In some cases, the pyrimidyl is mono-substituted. In some cases, the pyrimidyl is di-substituted. In other cases, the pyrimidyl is tri-substituted. In certain embodiments of B3, the substitutes are selected from lower alkyl (e.g., methyl, ethyl, propyl, butyl, pentyl and hexyl) and halogen (e.g., F, Cl, I or Br).

In some embodiments the A ring is described by the formula (B4):

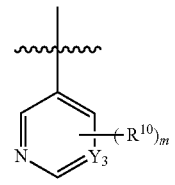

(B4)

where:
R$^{10}$ is one or more optional substituents independently selected from, alkyl, substituted alkyl, hydroxy, alkoxy, substituted alkoxy, trifluoromethyl and halogen;
Y$^3$ is selected from N and CR$^{11}$, wherein R$^{11}$ is selected from hydrogen, R$^{10}$, acyl, substituted acyl, carboxy, carboxyamide, substituted carboxyamide, sulfonyl, substituted sulfonyl, sulfonamide and substituted sulfonamide; and
m is an integer from 0 to 3.

In certain cases, B4 is pyridyl. In certain cases, B4 is a substituted pyridyl. In some cases, the pyridyl is a mono-substituted pyridyl. In other cases, the pyridyl is a di-substituted pyridyl. In other cases, the pyridyl is a tri-substituted pyridyl. In other cases, the pyridyl is a tetra-substituted pyridyl. In certain cases, Y$^3$ is N, such that B4 is a pyrimidyl. In some cases, B4 is a substituted pyrimidyl. In some cases, the pyrimidyl is mono-substituted. In some cases, the pyrimidyl is di-substituted. In other cases, the pyrimidyl is tri-substituted. In certain embodiments of B4, the substitutes are selected from lower alkyl (e.g., methyl, ethyl, propyl, butyl, pentyl and hexyl), trifluoromethyl and halogen (e.g., F, Cl, I or Br). In some cases, B4 is a mono-substituted pyridyl, wherein the substituent is selected from lower alkyl (e.g., methyl) and trifluoromethyl.

In some embodiments the A ring is described b the formula (B5):

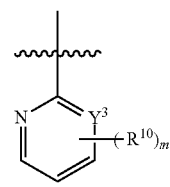

(B5)

where:
R$^{10}$ is one or more optional substituents independently selected from, alkyl, substituted alkyl, hydroxy, alkoxy, substituted alkoxy, trifluoromethyl and halogen;
Y$^3$ is selected from N and CR$^{11}$, wherein R$^{11}$ is selected from hydrogen, R$^{10}$, acyl, substituted acyl, carboxy, carboxyamide, substituted carboxyamide, sulfonyl, substituted sulfonyl, sulfonamide and substituted sulfonamide; and
m is an integer from 0 to 3.

In certain cases of formula B5, when Y3 is CR$^{11}$, the formula B5 may be equivalent to B3. In certain cases, B5 is pyridyl. In certain cases, B5 is a substituted pyridyl. In some cases, the pyridyl is a mono-substituted pyridyl. In other cases, the pyridyl is a di-substituted pyridyl. In other cases, the pyridyl is a tri-substituted pyridyl. In other cases, the pyridyl is a tetra-substituted pyridyl. In certain cases, Y$^3$ is N, such that B5 is a pyrimidyl. In some cases, B5 is a substituted pyrimidyl. In some cases, the pyrimidyl is mono-substituted. In some cases, the pyrimidyl is di-substituted. In other cases, the pyrimidyl is tri-substituted. In certain embodiments of B5, the substitutes are selected from lower alkyl (e.g., methyl, ethyl, propyl, butyl, pentyl and hexyl), trifluoromethyl and halogen (e.g., F, Cl, I or Br).

In some embodiments the A ring is described by the formula (B6):

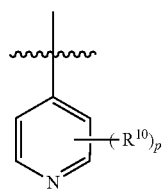

(B6)

where:

R$^{10}$ is one or more optional substituents independently selected from, alkyl, substituted alkyl, hydroxy, alkoxy, substituted alkoxy, trifluoromethyl and halogen; and p is an integer from 0 to 4.

In certain cases, p is 0 and B6 is pyridyl. In certain cases, B6 is a substituted pyridyl. In some cases, the pyridyl is a mono-substituted pyridyl. In other cases, the pyridyl is a di-substituted pyridyl.

In other cases, the pyridyl is a tri-substituted pyridyl. In other cases, the pyridyl is a tetra-substituted pyridyl. In certain embodiments of B6, the substitutes are selected from lower alkyl (e.g., methyl, ethyl, propyl, butyl, pentyl and hexyl), trifluoromethyl and halogen (e.g., F, Cl, I or Br).

In certain embodiments, the A ring has any one of the formulae (B4a), (B6a), (B5a) or (B5b):

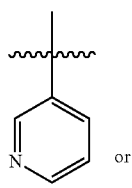

(B4a)

or

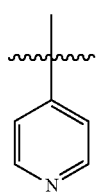

(B6a)

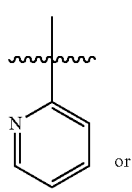

(B5a)

or

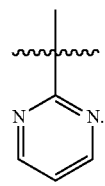

(B5b)

In some embodiments the A ring is described by the formula (B7):

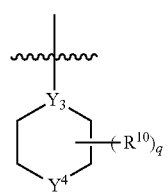

(B7)

where:

R$^{10}$ is one or more optional substituents independently selected from, alkyl, substituted alkyl, hydroxy, alkoxy, substituted alkoxy, trifluoromethyl and halogen;

Y$^3$ is selected from N and CR$^{11}$, wherein R$^{11}$ is selected from hydrogen, R$^{10}$, acyl, substituted acyl, carboxy, carboxyamide, substituted carboxyamide, sulfonyl, substituted sulfonyl, sulfonamide and substituted sulfonamide;

Y$^4$ is selected from CR$^{11}$$_2$, NR$^{11}$, SO$_2$ and O; and q is an integer from 0 to 8.

In certain cases, B7 is piperidine or substituted piperidine. In certain cases, B7 is piperazine or substituted piperazine. In certain cases, B7 is a cycloalkyl or a substituted cycloalkyl. In some cases, B7 is tetrahydropyran or substituted tetrahydropyran. In some cases, B7 is morpholine or substituted morpholine. In some cases, B7 is a cyclic sulfone or a substituted cyclic sulfone. In certain embodiments of B7, q is greater than 0, such as 1, 2, 3, 4, 5, 6, 7 or 8. In some cases, B7 includes one R$^{10}$ group. In some cases, B7 includes two R$^{10}$ groups. In some cases, B7 includes three R$^{10}$ groups. In some cases, B7 includes four R$^{10}$ groups. In certain embodiments, the substitutes are selected from lower alkyl (e.g., methyl, ethyl, propyl, butyl, pentyl and hexyl), trifluoromethyl and halogen (e.g., F, Cl, I or Br).

In certain embodiments, the A ring has the any one of the formulae (B7a) or (B7b):

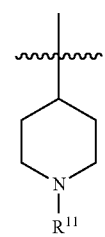

(B7a)

-continued (B7a)

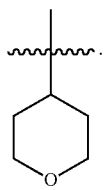

In some embodiments of formula (B7a), $R^{11}$ is hydrogen. In some embodiments of formula (B7a), $R^{11}$ is an acyl group.

In some embodiments, the formula (B7a) has the relative configuration of formula (B7ai) or (B7aii):

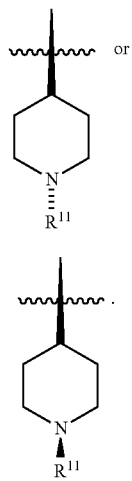

In some embodiments the A ring is described by the formula (B8):

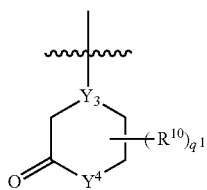

where:
$R^{10}$ is one or more optional substituents independently selected from, alkyl, substituted alkyl, hydroxy, alkoxy, substituted alkoxy, trifluoromethyl and halogen;
$Y^3$ is selected from N and $CR^{11}$, wherein $R^{11}$ is selected from hydrogen, $R^{10}$, acyl, substituted acyl, carboxy, carboxyamide, substituted carboxyamide, sulfonyl, substituted sulfonyl, sulfonamide and substituted sulfonamide;
$Y^4$ is selected from $CR^{11}_2$, $NR^{11}$, $SO_2$ and O; and
$q^1$ is an integer from 0 to 6.

In certain cases, B8 is 2-oxopiperidine or substituted 2-oxopiperadine. In certain cases, B8 is 2-oxopiperazine or substituted 2-oxopiperazine. In certain cases, B8 is a cyclohexanone or a substituted cyclohexanone. In some cases, B8 is a lactone or a substituted lactone. In some cases, B8 is morpholin-2-one or substituted morpholin-2-one. In certain embodiments of B8, q is greater than 0, such as 1, 2, 3, 4, 5 or 6. In some cases, B8 includes one $R^{10}$ group. In some cases, B8 includes two $R^{10}$ groups. In some cases, B8 includes three $B^7$ groups. In some cases, B8 includes four $R^{11}$ groups. In certain embodiments, the substitutes are selected from lower alkyl (e.g., methyl, ethyl, propyl, butyl, pentyl and hexyl), trifluoromethyl and halogen (e.g., F, Cl, I or Br).

In some embodiments, the B ring is selected from an aryl (e.g., a phenyl), optionally including one or more substituents. In some embodiments, the B ring is selected from a heteroaryl or a heterocycle (e.g., pyridyl, pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl) optionally including one or more substituents. In some embodiments, the B ring is selected from phenyl, substituted phenyl, pyridyl, substituted pyridyl, 2-pyrimidinyl, substituted 2-pyrimidinyl, 3-pyrimidinyl, substituted 3-pyrimidinyl, 6-pyrimidinyl, substituted 6-pyrimidinyl, piperidine, substituted piperidine, piperazine, substituted piperazine, 2-oxopiperidine, 2-oxopiperazine, imidazole, substituted imidazole, thiazole, substituted thiazole, oxazole, substituted oxazole, tetrahydropyran, substituted tetrahydropyran, morpholine, substituted morpholine, cyclic sulfone, substituted cyclic sulfone.

In other embodiments, the B ring is described by the formula (B1):

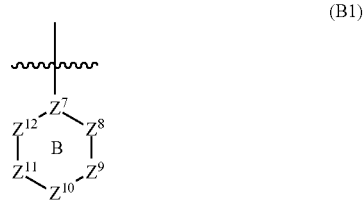

where B1 is a 6-membered aryl, heteroaryl, heterocyclyl, or cycloalkyl, where $Z^3$-$Z^{12}$ are independently selected from N, O, $CR^{11}$, $NR^{11}$, $CR^{11}_2$, $SO_2$ and CO, provided that valency requirements are fulfilled, where $R^{11}$ are each independently selected from hydrogen, alkyl, substituted alkyl, hydroxy, alkoxy, substituted alkoxy, trifluoromethyl, halogen, acyl, substituted acyl, carboxy, carboxyamide, substituted carboxyamide, sulfonyl, substituted sulfonyl, sulfonamide and substituted sulfonamide. In certain cases, $Z^8$ and $Z^9$, or $Z^9$ and $Z^{10}$, or $Z^{10}$ and $Z^{11}$, or $Z^{12}$ and $Z^{12}$ are $CR^{11}$, wherein each $R^{11}$ together with the carbons to which they are attached form a 5-membered or 6-membered cyclic group selected from aryl, substituted aryl, heteroaryl, substituted heteroaryl, heterocycle, substituted heterocycle, cycloalkyl and substituted cycloalkyl. In certain cases, B1 is an indole or a substituted indole. In some cases, B1 is a phenyl, or substituted phenyl. In some cases, B1 is a cycloalkyl, or a substituted cycloalkyl. In some cases, B1 is pyridyl or substituted pyridyl. In some cases, B1 is pyrimidinyl, such as 2-pyrimidinyl, substituted 2-pyrimidinyl, 3-pyrimidinyl, substituted 3-pyrimidinyl, 6-pyrimidinyl or substituted 6-pyrimidinyl. In some cases, B1 is a pyridazine, or a substituted pyridazine. In some cases, B1 is a triazine, or a substituted triazine. In some cases, B1 is piperidine or substituted piperidine. In some cases, $B^1$ is piperazine or substituted piperazine. In some cases, B1 is 2-oxopiperidine or substituted 2-oxopiperidine. In some cases, B1 is 2-oxopiperazine or substituted 2-oxopiperazine. In some cases, B1 is tetrahydropyran or substituted tetrahydropyran. In some cases, B1 is a pyran or a substituted pyran. In some cases, B1 is morpholine or substituted morpholine. In some cases. B1 is a cyclic sulfone or a substituted cyclic sulfone.

In some embodiments the B ring is described by the formula (B2):

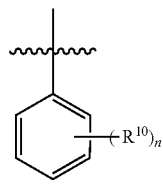

(B2)

where:

$R^{10}$ is one or more optional substituents independently selected from, alkyl, substituted alkyl, hydroxy, alkoxy, substituted alkoxy, trifluoromethyl and halogen; and n is an integer from 0 to 5.

In certain cases, B2 is phenyl. In certain cases, B2 is a di-substituted phenyl. In certain cases, B2 is a tri-substituted phenyl. In certain cases, B2 is a tetra-substituted phenyl. In certain cases, B2 is a penta-substituted aryl. In certain cases, the substitutes are selected from lower alkyl (e.g., methyl, ethyl, propyl, butyl, pentyl and hexyl) and halogen (e.g., F, Cl, I or Br). In certain embodiments, B2 is a 2,6-disubstituted phenyl, wherein the substituents are independently selected from halogen and lower alkyl.

In some embodiments the B2 ring is described by the formula (B2b):

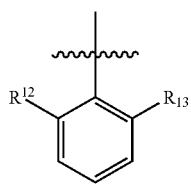

(B2b)

where:

$R^{12}$ and $R^{13}$ each independently selected from, alkyl, substituted alkyl, hydroxy, alkoxy, substituted alkoxy, trifluoromethyl and halogen. In some embodiments, $R^{12}$ and $R^{13}$ are each independently selected from alkyl, substituted alkyl, trifluoromethyl and halogen. In some embodiments, $R^{12}$ is halogen (e.g., fluoro, chloro, bromo, iodo) and $R^{13}$ is a lower alkyl (e.g., methyl, ethyl, propyl, butyl, pentyl, hexyl).

In some embodiments the B ring is described by the formula (B3):

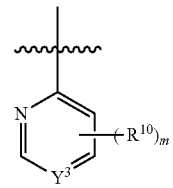

(B3)

where:

$R^{10}$ is one or more optional substituents independently selected from, alkyl, substituted alkyl, hydroxy, alkoxy, substituted alkoxy, trifluoromethyl and halogen;

$Y^3$ is selected from N and $CR^{11}$, wherein $R^{11}$ is selected from hydrogen, $R^{10}$, acyl, substituted acyl, carboxy, carboxyamide, substituted carboxyamide, sulfonyl, substituted sulfonyl, sulfonamide and substituted sulfonamide; and m is an integer from 0 to 3.

In certain cases, B3 is pyridyl. In certain cases, B3 is a substituted pyridyl. In some cases, the pyridyl is a mono-substituted pyridyl. In other cases, the pyridyl is a di-substituted pyridyl. In other cases, the pyridyl is a tri-substituted pyridyl. In other cases, the pyridyl is a tetra-substituted pyridyl. In certain cases, $Y^3$ is N, such that B3 is a pyrimidyl. In some cases, B3 is a substituted pyrimidyl. In some cases, the pyrimidyl is mono-substituted. In some cases, the pyrimidyl is di-substituted. In other cases, the pyrimidyl is tri-substituted. In certain embodiments of B3 the substituents are selected from lower alkyl (e.g., methyl, ethyl, propyl, butyl, pentyl and hexyl) and halogen (e.g., F, Cl, I or Br).

In some embodiments the B ring is described by the formula (B4):

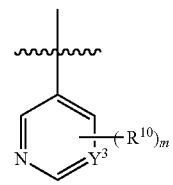

(B4)

where:

$R^{10}$ is one or more optional substituents independently selected from, alkyl, substituted alkyl, hydroxy, alkoxy, substituted alkoxy, trifluoromethyl and halogen:

$Y^3$ is selected from N and $CR^{11}$, wherein $R^{11}$ is selected from hydrogen, $R^{10}$, acyl, substituted acyl, carboxy, carboxyamide, substituted carboxyamide, sulfonyl, substituted sulfonyl, sulfonamide and substituted sulfonamide; and m is an integer from 0 to 3.

In certain cases, B4 is pyridyl. In certain cases. B4 is a substituted pyridyl. In some cases, the pyridyl is a mono-substituted pyridyl. In other cases, the pyridyl is a di-substituted pyridyl. In other cases, the pyridyl is a tri-substituted pyridyl. In other cases, the pyridyl is a tetra-substituted pyridyl. In certain cases, $Y^3$ is N, such that B4 is a pyrimidyl. In some cases, B4 is a substituted pyrimidyl. In some cases, the pyrimidyl is mono-substituted. In some cases, the pyrimidyl is di-substituted. In other cases, the pyrimidyl is tri-substituted. In certain embodiments of B4, the substituents are selected from lower alkyl (e.g., methyl, ethyl, propyl, butyl, pentyl and hexyl), trifluoromethyl and halogen (e.g., F, Cl, I or Br). In some cases, B4 is a mono-substituted pyridyl, wherein the substituent is selected from lower alkyl (e.g., methyl) and trifluoromethyl.

In some embodiments the B ring is described by the formula (B5):

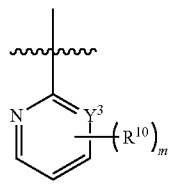

(B5)

where:
R$^{10}$ is one or more optional substituents independently selected from, alkyl, substituted alkyl, hydroxy, alkoxy, substituted alkoxy, trifluoromethyl and halogen;
Y$^3$ is selected from N and CR$^{11}$, wherein R$^{11}$ is selected from hydrogen, R$^{10}$, acyl, substituted acyl, carboxy, carboxyamide, substituted carboxyamide, sulfonyl, substituted sulfonyl, sulfonamide and substituted sulfonamide;
and
m is an integer from 0 to 3.

In certain cases of formula B5, when Y3 is CR$^{11}$, the formula B5 may be equivalent to B3. In certain cases, B5 is pyridyl. In certain cases, B5 is a substituted pyridyl. In some cases, the pyridyl is a mono-substituted pyridyl. In other cases, the pyridyl is a di-substituted pyridyl. In other cases, the pyridyl is a tri-substituted pyridyl. In other cases, the pyridyl is a tetra-substituted pyridyl. In certain cases, Y$^3$ is N, such that B5 is a pyrimidyl. In some cases, B5 is a substituted pyrimidyl. In some cases, the pyrimidyl is mono-substituted. In some cases, the pyrimidyl is di-substituted. In other cases, the pyrimidyl is tri-substituted. In certain embodiments of B5, the substitutes are selected from lower alkyl (e.g., methyl, ethyl, propyl, butyl, pentyl and hexyl), trifluoromethyl and halogen (e.g., F, Cl, I or Br).

In some embodiments the B ring is described by the formula (B6):

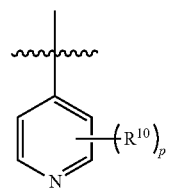

(B6)

where:
R$^{10}$ is one or more optional substituents independently selected from, alkyl, substituted alkyl, hydroxy, alkoxy, substituted alkoxy, trifluoromethyl and halogen; and
p is an integer from 0 to 4.

In certain cases, p is 0 and B6 is pyridyl. In certain cases, B6 is a substituted pyridyl. In some cases, the pyridyl is a mono-substituted pyridyl. In other cases, the pyridyl is a di-substituted pyridyl. In other cases, the pyridyl is a tri-substituted pyridyl. In other cases, the pyridyl is a tetra-substituted pyridyl. In certain embodiments of B6, the substitutes are selected from lower alkyl (e.g., methyl, ethyl, propyl, butyl, pentyl and hexyl), trifluoromethyl and halogen (e.g., F, Cl, I or Br).

In certain embodiments, the B ring has the formula (B4b) or (B6b):

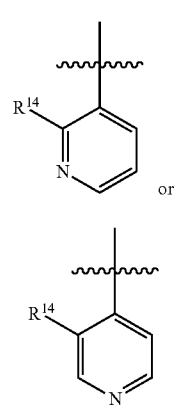

(B4b)

or (B6b)

where:
R$^{14}$ is selected from, alkyl, substituted alkyl, hydroxy, alkoxy, substituted alkoxy, trifluoromethyl and halogen. In some embodiments, R$^{14}$ is selected from alkyl, substituted alkyl, trifluoromethyl and halogen. In some embodiments, R$^{14}$ is a lower alkyl (e.g., methyl, ethyl, propyl, butyl, pentyl, hexyl) or trifluoromethyl.

In some embodiments the B ring is described by the formula (B7):

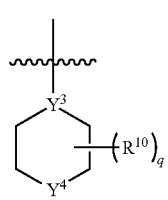

(B7)

where:
R$^{10}$ is one or more optional substituents independently selected from, alkyl, substituted alkyl, hydroxy, alkoxy, substituted alkoxy, trifluoromethyl and halogen;
Y$^3$ is selected from N and CR$^{11}$, wherein R$^{11}$ is selected from hydrogen, R$^{10}$, acyl, substituted acyl, carboxy, carboxyamide, substituted carboxyamide, sulfonyl, substituted sulfonyl, sulfonamide and substituted sulfonamide;
Y$^4$ is selected from CR$^{11}$$_2$, NR$^{11}$, SO$_2$ and O; and
q is an integer from 0 to 8.

In certain cases, B7 is piperidine or substituted piperidine. In certain cases, B7 is piperazine or substituted piperazine. In certain cases, B7 is a cycloalkyl or a substituted cycloalkyl. In some cases, B7 is tetrahydropyran or substituted tetrahydropyran. In some cases, B7 is morpholine or substituted morpholine. In some cases, B7 is a cyclic sulfone or a substituted cyclic sulfone. In certain embodiments of B7, q is greater than 0, such as 1, 2, 3, 4, 5, 6, 7 or 8. In some cases, B7 includes one R$^{10}$ group. In some cases, B7 includes two R$^{10}$ groups. In some cases, B7 includes three $R^{10}$ groups. In some cases, B7 includes four $R^{10}$ groups. In certain embodiments, the substitutes are selected from lower alkyl (e.g., methyl, ethyl, propyl, butyl, pentyl and hexyl), trifluoromethyl and halogen (e.g., F, Cl, I or Br).

In some embodiments the B ring is described by the formula (B8):

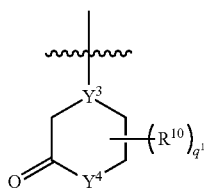
(B8)

where:
$R^{10}$ is one or more optional substituents independently selected from, alkyl, substituted alkyl, hydroxy, alkoxy, substituted alkoxy, trifluoromethyl and halogen;
$Y^3$ is selected from N and $CR^{11}$, wherein $R^{11}$ is selected from hydrogen, $R^{10}$, acyl, substituted acyl, carboxy, carboxyamide, substituted carboxyamide, sulfonyl, substituted sulfonyl, sulfonamide and substituted sulfonamide;
$Y^4$ is selected from $CR^{11}{}_2$, $NR^{11}$, $SO_2$ and O; and
$q^1$ is an integer from 0 to 6.

In certain cases, B8 is 2-oxopiperidine or substituted 2-oxopiperadine. In certain cases, B8 is 2-oxopiperazine or substituted 2-oxopiperazine. In certain cases, B8 is a cyclohexanone or a substituted cyclohexanone. In some cases, B8 is a lactone or a substituted lactone. In some cases, B8 is morpholin-2-one or substituted morpholin-2-one. In certain embodiments of B8, q is greater than 0, such as 1, 2, 3, 4, 5 or 6. In some cases, B8 includes one $R^{10}$ group. In some cases, B8 includes two $R^{10}$ groups. In some cases. B8 includes three $R^{10}$ groups. In some cases, B8 includes four $R^{10}$ groups. In certain embodiments, the substitutes are selected from lower alkyl (e.g., methyl, ethyl, propyl, butyl, pentyl and hexyl), trifluoromethyl and halogen (e.g., F, Cl, I or Br).

In some embodiments, the B ring has the formula (B7b) or (B8a):

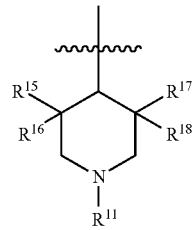
(B7b)

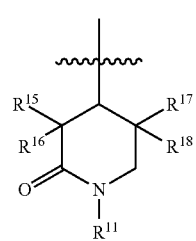
(B8a)

where:
$R^{15}$, $R^{16}$, $R^{17}$ and $R^{18}$ are each independently selected from, hydrogen, alkyl and substituted alkyl. In some cases, $R^{15}$, $R^{16}$, $R^{17}$ and $R^{18}$ are each hydrogen. In some cases, $R^{15}$ is a lower alkyl and each of $R^{16}$, $R^{17}$ and $R^{18}$ are hydrogen. In some cases, $R^{15}$ and $R^{16}$ are each lower alkyl and $R^{17}$ and $R^{18}$ are each hydrogen. In some cases, $R^{15}$ and $R^{17}$ are each lower alkyl and $R^{16}$ and $R^{18}$ are each hydrogen.

In some embodiments, the formula (B7b) has the relative configuration of formula (B7bi) or (B7bii):

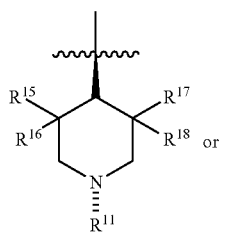
(B7bi)

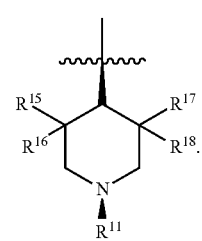
(B7bii)

In some embodiments, the formula (B8a) has the relative configuration of formula B8ai) or (B8aii):

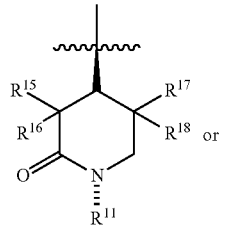
(B8ai)

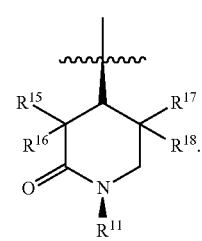
(B8aii)

In some embodiments, the B ring is described the formula (B10)

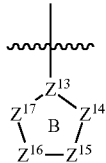
(B10)

where B10 is a 5-membered aryl, heteroaryl, heterocyclyl, or cycloalkyl, where $Z^{13}$-$Z^{17}$ are independently selected from N, O, S. $CR^{11}$, $NR^{11}$, $CR^{11}{}_2$, $SO_2$ and CO, provided that valency requirements are fulfilled, where $R^{11}$ are each independently selected from hydrogen, alkyl, substituted alkyl, hydroxy, alkoxy, substituted alkoxy, trifluoromethyl, halogen, acyl, substituted acyl, carboxy, carboxyamide, substituted carboxyamide, sulfonyl, substituted sulfonyl, sulfonamide and substituted sulfonamide. In certain cases. $Z^{14}$ and $Z^{15}$, or $Z^{15}$ and $Z^{16}$, or $Z^{16}$ and $Z^{17}$ are $CR^{11}$, wherein each $R^{11}$ together with the carbons to which they are attached form a 5-membered or 6-membered cyclic group selected from aryl, substituted aryl, heteroaryl, substituted heteroaryl, heterocycle, substituted heterocycle, cycloalkyl and substituted cycloalkyl. In certain cases. B10 is an imidazole, or substituted imidazole. In certain cases, B10 is a thiazole, or substituted thiazole. In some cases, B10 is an oxazole, or substituted oxazole. In some cases, B10 is a pyrazole, or substituted pyrazole. In some cases, B10 is an isoxazole, or a substituted isoxazole. In some cases, B10 is an isothiazole, or a substituted isothiazole. In some case B10 is a furan, or a substituted furan. In some cases, B10 is a thiophene, or a substituted thiophene. In some cases, B10 is a cyclopentane, or a substituted cyclopentane. In some cases, B10 is a cyclopentane, or a substituted cyclopentane. In some cases, B10 is cyclopentadiene, or a substituted cyclopentadiene. In some cases, B10 is a cyclic sulfone or a substituted cyclic sulfone.

In some embodiments the B ring is described by the formula (B9):

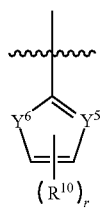
(B9)

where:
$R^{10}$ is one or more optional substituents independently selected from, alkyl, substituted alkyl, hydroxy, alkoxy, substituted alkoxy, trifluoromethyl and halogen;

$Y^5$ is selected from N and $CR^{11}$, wherein $R^{11}$ is selected from hydrogen. $R^{10}$, acyl, substituted acyl, carboxy, carboxyamide, substituted carboxyamide, sulfonyl, substituted sulfonyl, sulfonamide and substituted sulfonamide;

$Y^6$ is selected from $CR^{10}$ and $NR^{11}$; and r is an integer from 0 to 2.

In certain cases, B9 is an imidazole, or a substituted imidazole. In certain cases, B9 is a pyrrole or a substituted pyrrole. In certain cases, the pyrrole is 1H-pyrrole, or substituted 1H-pyrrole. In other cases, the pyrrole is 3H-pyrrole, or substituted 3H-pyrrole. In certain cases, B9 is a cyclopentadiene, or a substituted cyclopentadiene. In certain embodiments of B9, r is greater than 0, such as 1 or 2. In some cases, B9 includes one $R^{10}$ group. In some cases, B9 includes two $R^{10}$ groups. In certain embodiments, the substitutes are selected from lower alkyl (e.g., methyl, ethyl, propyl, butyl, pentyl and hexyl), trifluoromethyl and halogen (e.g., F, Cl, I or Br).

In certain embodiments of formula (II), the compound is described by the formula (IIA):

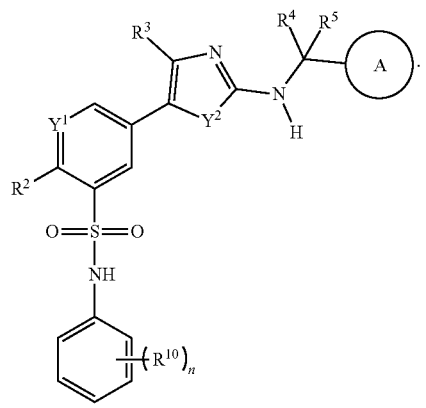
(IIA)

In certain embodiments, the formula (IIA) is of the formula (IIA1) or (IIA2):

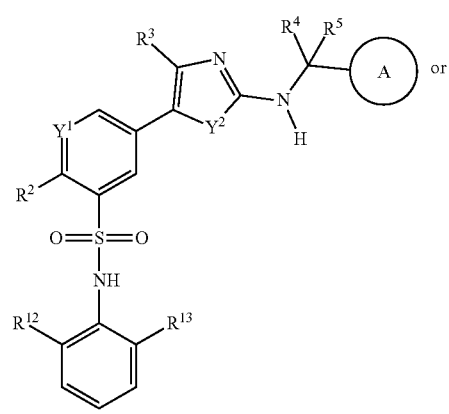
(IIA1)

or

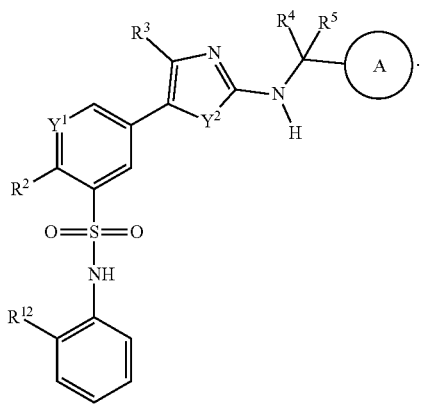
(IIA2)
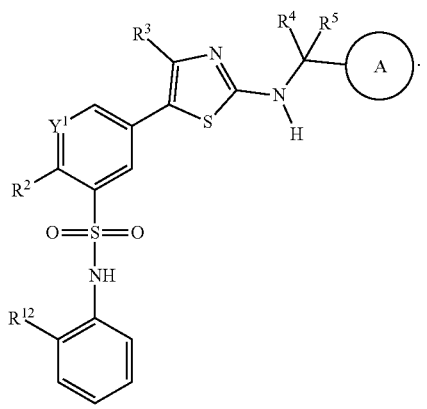
(IIA2j)
In certain embodiments, the formula (IIA) is of the formula (IIAa), (IIA1j) or (IIA2j):
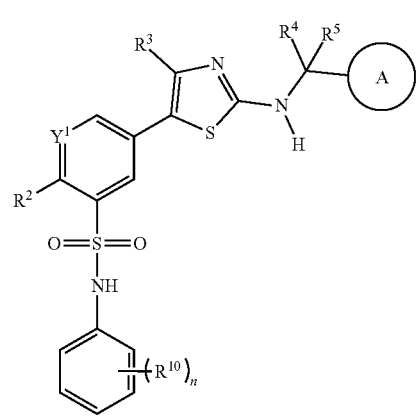
(IIAa)
In certain embodiments, the formula (IIA) is of the formula (IIAb), (IIA1k) or (IIA2k):
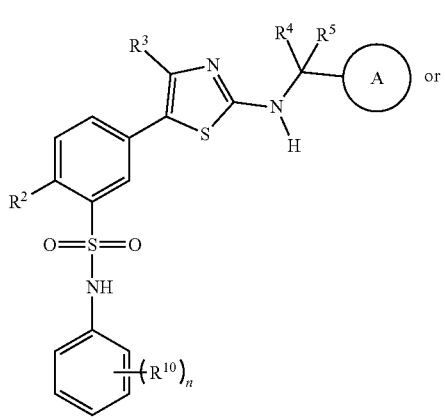
(IIAb)
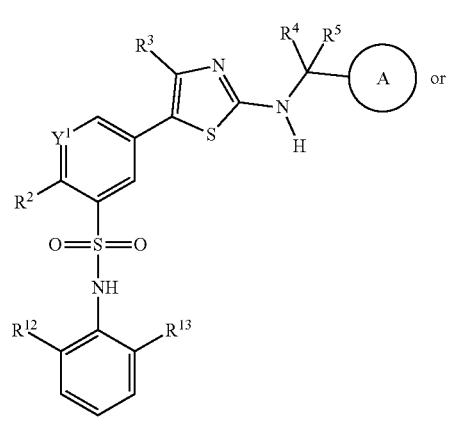
(IIA1j)
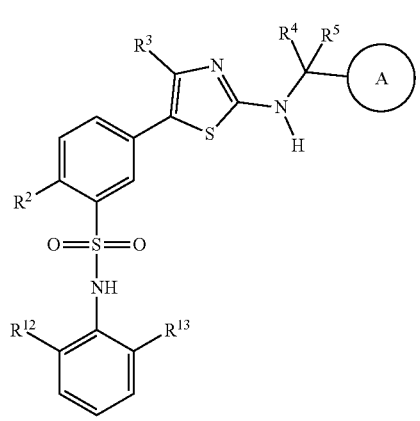
(IIA1k)

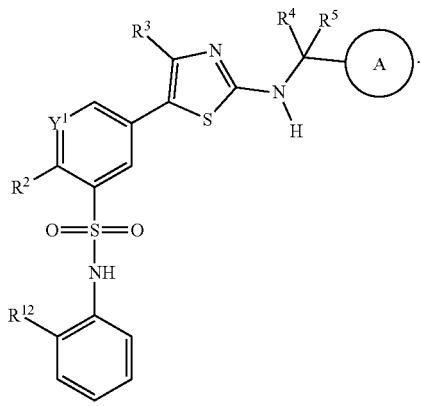

(IIA2k)

In some embodiments of formula (IIA) to (IIA2k), the A ring is selected from an aryl (e.g., a phenyl), optionally including one or more substituents. In some embodiments, the A ring is selected from a heteroaryl or a heterocycle (e.g., pyridyl, pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl) optionally including one or more substituents. In some embodiments, the A ring is selected from a cycloalkyl (e.g., a cyclohexane), optionally including one or more substituents. In some embodiments, the A ring is selected from phenyl, substituted phenyl, pyridyl, substituted pyridyl, 2-pyrimidinyl, substituted 2-pyrimidinyl, 3-pyrimidinyl, substituted 3-pyrimidinyl, 6-pyrimidinyl, substituted 6-pyrimidinyl, piperidine, substituted piperidine, piperazine, substituted piperazine, 2-oxopiperidine, 2-oxopiperazine, imidazole, substituted imidazole, thiazole, substituted thiazole, oxazole, substituted oxazole, tetrahydropyran, substituted tetrahydropyran, morpholine, substituted morpholine, cyclic sulfone, substituted cyclic sulfone, cycloalkyl and substituted cycloalkyl.

In other embodiments, the A ring is described by the formula (A1):

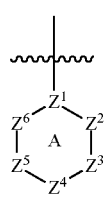

(A1)

where A1 is a 6-membered aryl, heteroaryl, heterocyclyl, or cycloalkyl, where $Z^1$-$Z^6$ are independently selected from N, O, $CR^{11}$, $NR^{11}$, $CR^{11}_2$, $SO_2$ and CO, provided that valency requirements are fulfilled, where $R^{11}$ are each independently selected from hydrogen, alkyl, substituted alkyl, hydroxy, alkoxy, substituted alkoxy, trifluoromethyl, halogen, acyl, substituted acyl, carboxy, carboxyamide, substituted carboxyamide, sulfonyl, substituted sulfonyl, sulfonamide and substituted sulfonamide. In certain cases, $Z^2$ and $Z^3$, or $Z^3$ and $Z^4$, or $Z^4$ and $Z^5$, or V and Z are $CR^{11}$, wherein each $R^{11}$ together with the carbons to which they are attached form a 5-membered or 6-membered cyclic group selected from aryl, substituted aryl, heteroaryl, substituted heteroaryl, heterocycle, substituted heterocycle, cycloalkyl and substituted cycloalkyl. In certain cases, A1 is an indole or a substituted indole. In some cases, A1 is a phenyl, or substituted phenyl. In some cases, A1 is a cycloalkyl, or a substituted cycloalkyl. In some cases, A1 is pyridyl or substituted pyridyl. In some cases, A1 is pyrimidinyl, such as 2-pyrimidinyl, substituted 2-pyrimidinyl, 3-pyrimidinyl, substituted 3-pyrimidinyl, 6-pyrimidinyl or substituted 6-pyrimidinyl. In some cases, A1 is a pyridazine, or a substituted pyridazine. In some cases, A1 is a triazine, or a substituted triazine. In some cases, A1 is piperidine or substituted piperidine. In some cases, A1 is piperazine or substituted piperazine. In some cases, A1 is 2-oxopiperidine or substituted 2-oxopiperidine. In some cases, A1 is 2-oxopiperazine or substituted 2-oxopiperazine. In some cases, A1 is tetrahydropyran or substituted tetrahydropyran. In some cases. A1 is a pyran or a substituted pyran. In some cases. A1 is morpholine or substituted morpholine. In some cases, A1 is a cyclic sulfone or a substituted cyclic sulfone.

In certain embodiments of the formula (IIA) to (IIA2k), the A ring is selected from any one of the formulae (B2) to (B8), e.g., as described herein. In certain embodiments of the formula (IIA) to (IIA2k) the A ring is selected from the following structures:

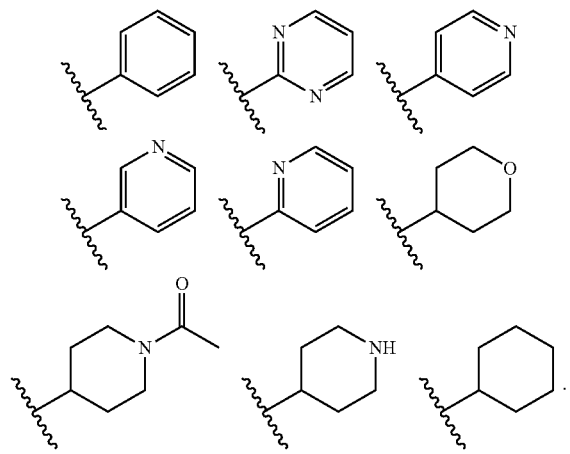

In some embodiments, the formula (IIA1) is of any one of the formulae (IIA1a) to (IIA1i):

(IIA1a)

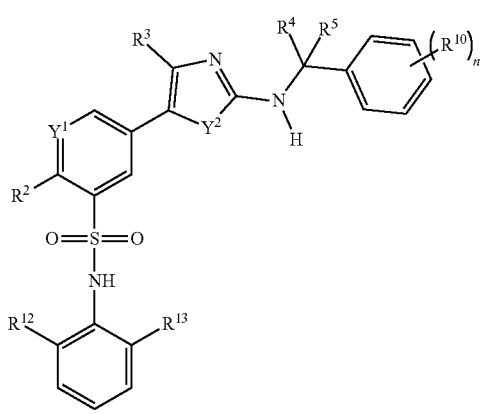

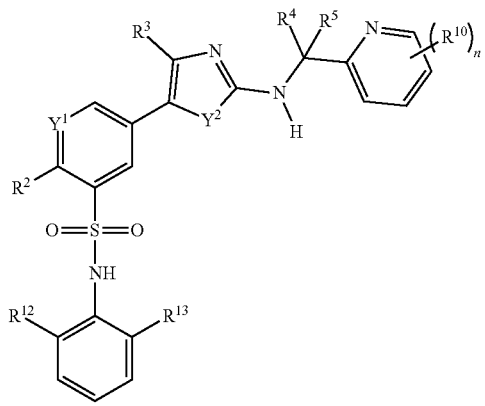
(IIA1b)
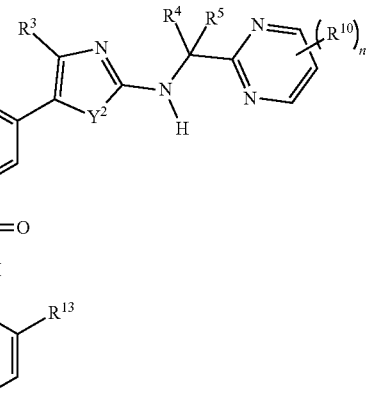
(IIA1e)
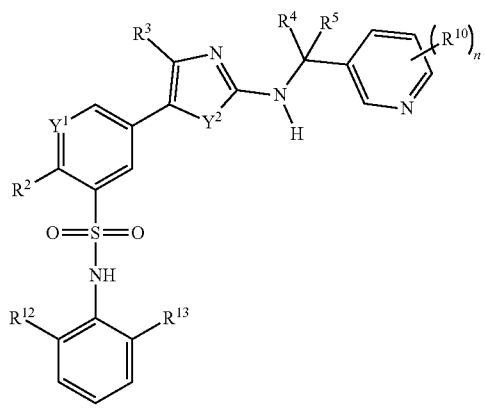
(IIA1c)
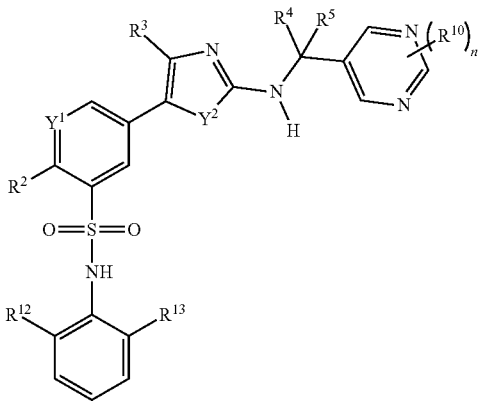
(IIA1f)
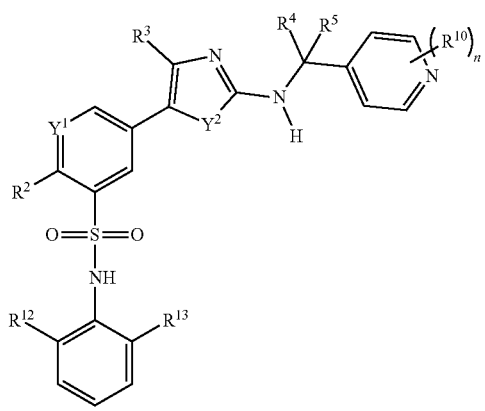
(IIA1d)
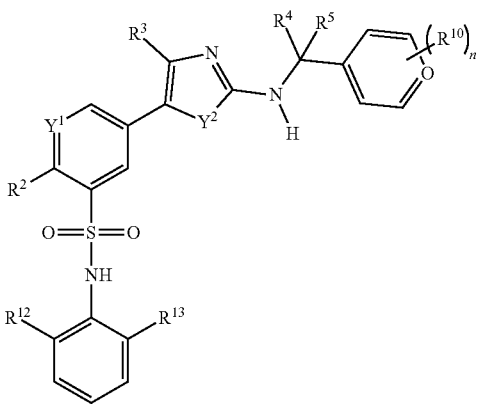
(IIA1g)

-continued

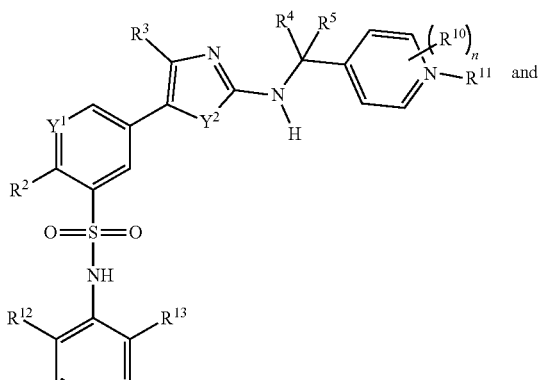

(IIA1h)

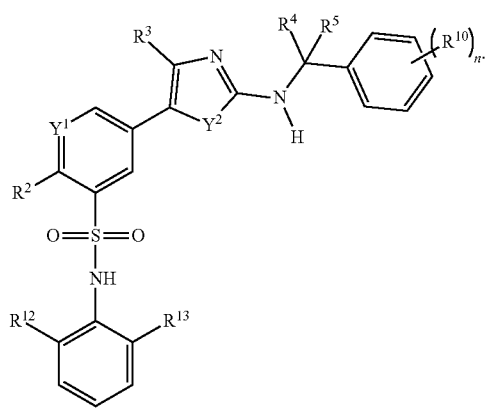

(IIA1i)

In some embodiments of any one of the formulae (IIA1a) to (IA1i), $Y^2$ is S. In some embodiments of any one of the formulae (IIA1a) to (IIA1i), $Y^1$ is CH. In some embodiments of any one of the formulae (IIA1a) to (IA1i), $Y^2$ is S and $Y^1$ is CH. In some embodiments of any one of the formulae (IIA1a) to (IIA1i), $Y^2$ is S and $Y^1$ is N. In some embodiments of any one of the formulae (IIA1a) to (IIA1i), $Y^2$ is O. In some embodiments of any one of the formulae (IIA1a) to (IIA1i), $Y^2$ is $NR^{19}$. In some embodiments of any one of the formulae (IIA1a) to (IA1i), $Y^2$ is NH. In some embodiments of any one of the formulae (IIA1a) to (IIA1i), $Y^2$ is O and $Y^1$ is CH. In some embodiments of any one of the formulae (IIA1a) to (IIA1i), $Y^2$ is $NR^{19}$ and $Y^1$ is CH. In some embodiments of any one of the formulae (IIA1a) to (IIA1i), $Y^2$ is NH and $Y^1$ is CH. In some embodiments of any one of the formulae (IIA1a) to (IIA1i), $Y^2$ is O and $Y^1$ is N. In some embodiments of any one of the formulae (IIA1a) to (IIA1i), $Y^2$ is $NR^{19}$ and $Y^1$ is N. In some embodiments of any one of the formulae (IIA1a) to (IIA1i), $Y^2$ is NH and $Y^1$ is N.

In certain embodiments of any one of (IIA1a) to (IIA1k), $R^{12}$ is selected from, alkyl, substituted alkyl, trifluoromethyl and halogen. In certain cases, $R^{12}$ is a lower alkyl group (e.g., methyl, ethyl, propyl, butyl, pentyl, hexyl). In certain cases, the lower alkyl group is methyl. In certain cases, $R^2$ is halogen. In certain cases, the halogen is chloride. In certain cases, the halogen is fluoride. In certain cases, $R^{12}$ is trifluoromethyl.

In certain embodiments of any one of formulae (IIA1a) to (IIA1k), $R^{13}$ is selected from, alkyl, substituted alkyl, trifluoromethyl and halogen. In certain cases, $R^{13}$ is a lower alkyl group (e.g., methyl, ethyl, propyl, butyl, pentyl, hexyl). In certain cases, the lower alkyl group is methyl. In certain cases, $R^3$ is halogen. In certain cases, the halogen is chloride. In certain cases, the halogen is fluoride.

In certain embodiments of any one of formulae (IA1a) to (IIA1k), $R^{12}$ is halogen and $R^{13}$ is lower alkyl. In some cases, $R^{12}$ is fluoride and $R^{13}$ is methyl.

In certain embodiments of any one of (IIA) to (IIA1k), $R^4$ and $R^5$ are each independently lower alkyl. In certain cases, both, $R^4$ and $R^5$ are methyl. In some cases of any one of formula (IIA) to (IIA1k), $R^4$ and $R^5$ together with the carbon to which they are attached form a cycloalkyl group.

In certain embodiments of any one of (IIA) to (IIA1k), $R^2$ is methoxy. In certain embodiments of any one of formulae (IIA) to (IIA1k), $R^3$ is methyl.

In certain embodiments of any one of (IIA) to (IIA1k), $R^2$, $R^3$, $R^4$, $R^5$ $R^{10}$ and $R^{14}$ are independently selected from corresponding groups as depicted in any of the structures of Table 1, 2 or 3.

In some embodiments, the compound is described by one of the following structures:

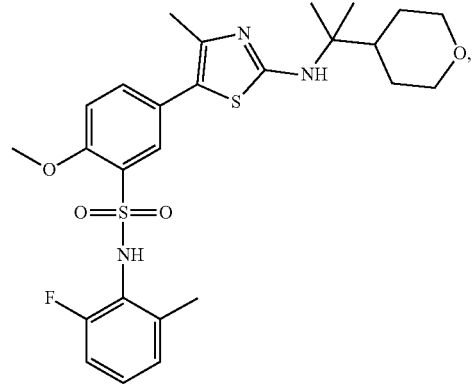 [SMILES: COc1ccc(-c2sc(NC(C)(C)C3CCCCC3)nc2C)cc1S(=O)(=O)Nc1c(C)cccc1F ; "."]

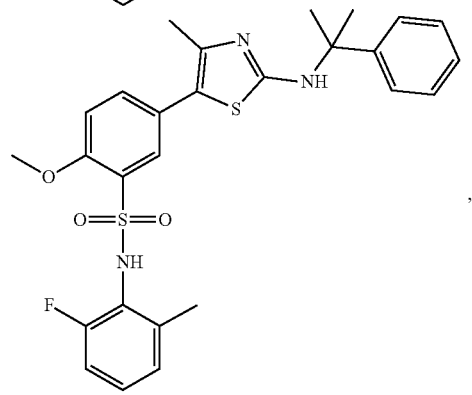

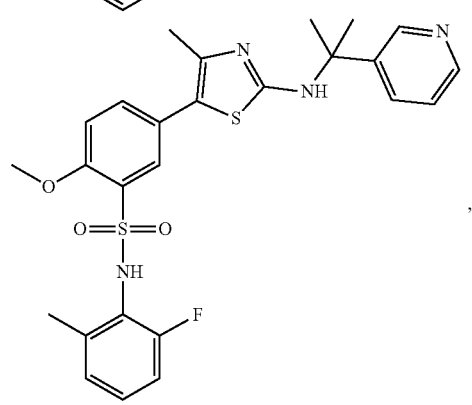

-continued
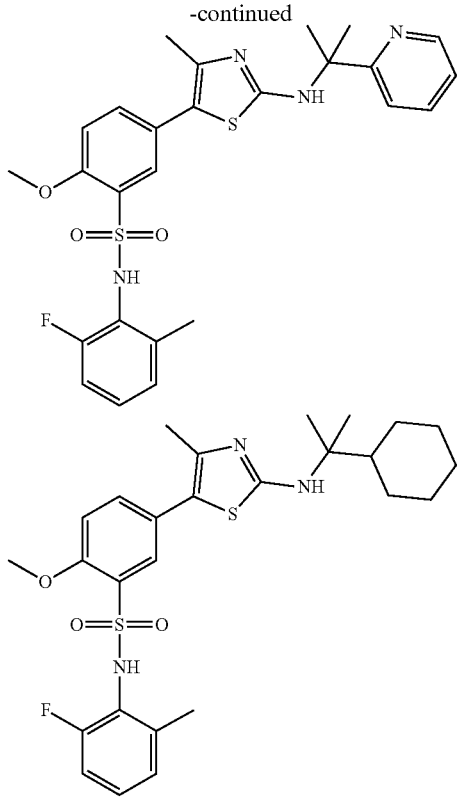
In some embodiments, the compound is described by one of the following structures:
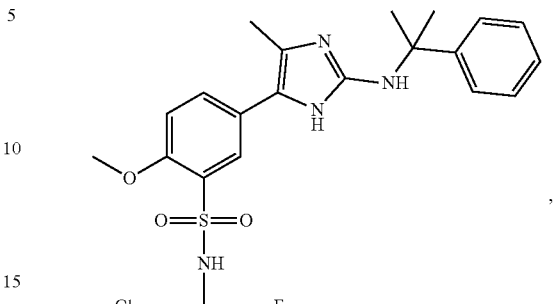
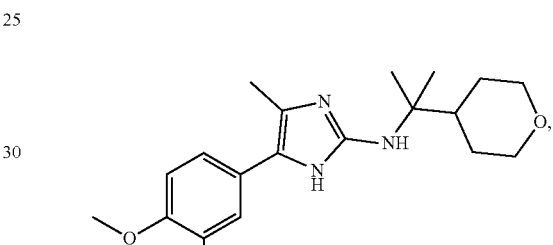
In some embodiments, the compound is described by one of the following structures:
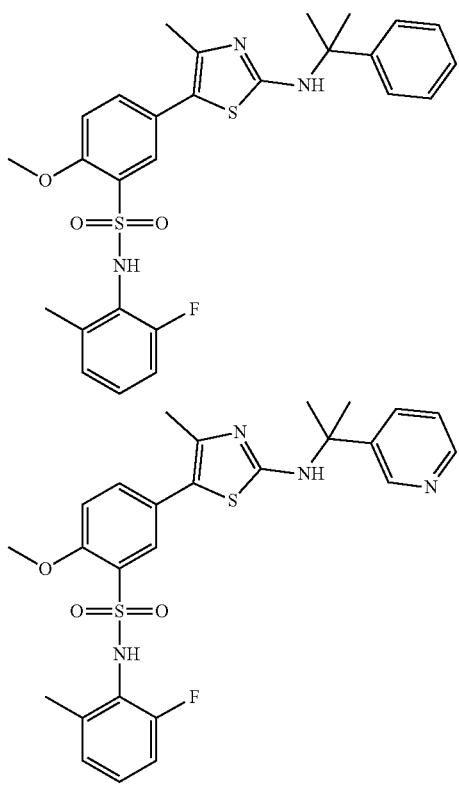
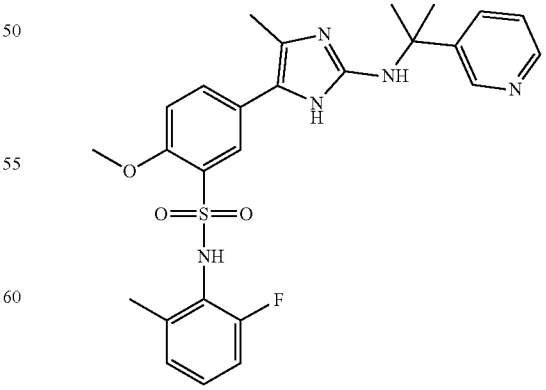
In some embodiments, the formula (IIA1) is of any one of the formulae (IA2a) to (IIA2i):

-continued
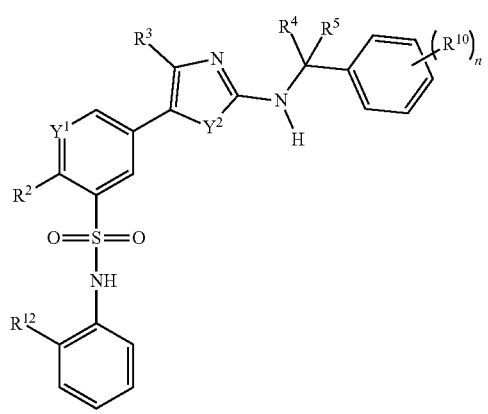
(IIA2a)
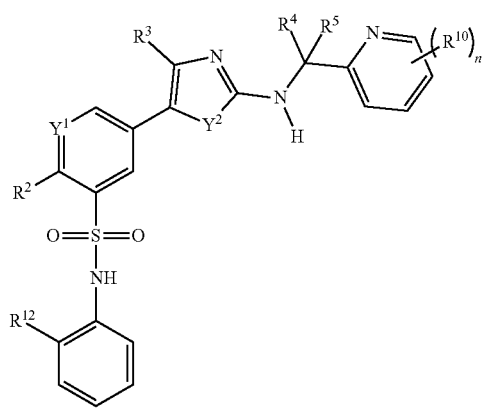
(IIA2b)
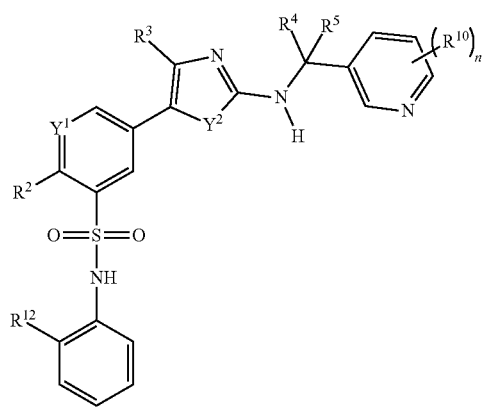
(IIA2c)
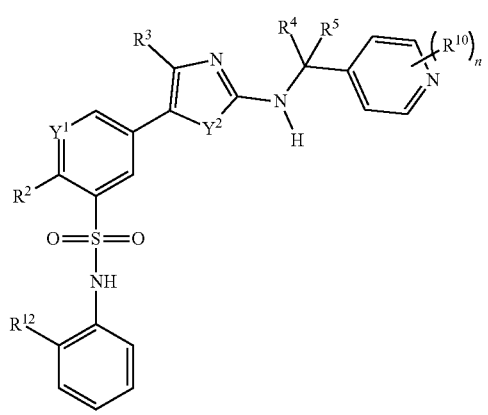
(IIA2d)
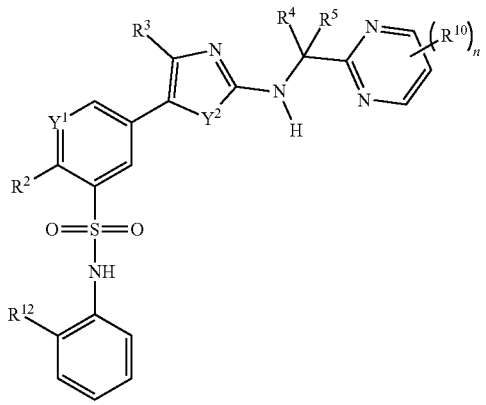
(IIA2e)
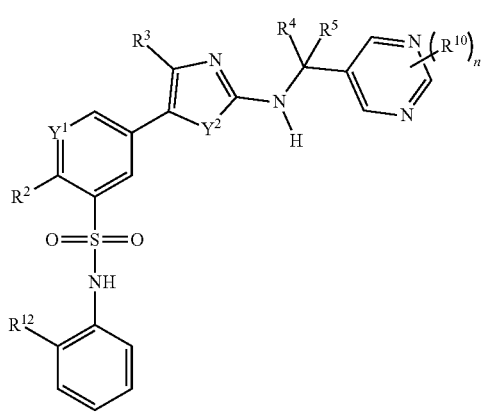
(IIA2f)
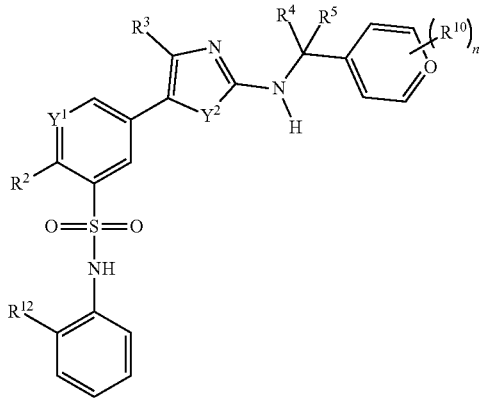
(IIA2g)
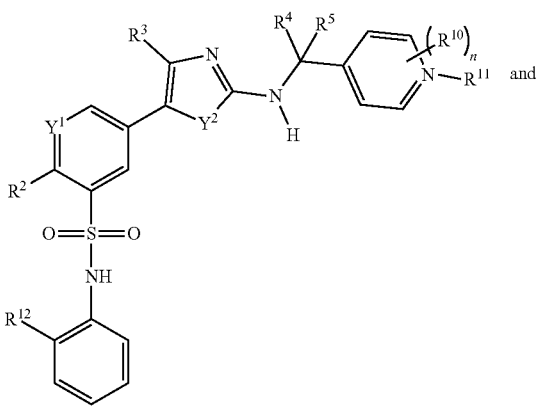
(IIA2h)
and

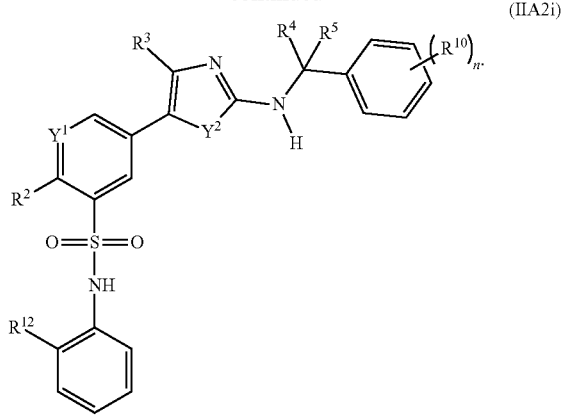

(IIA2i)

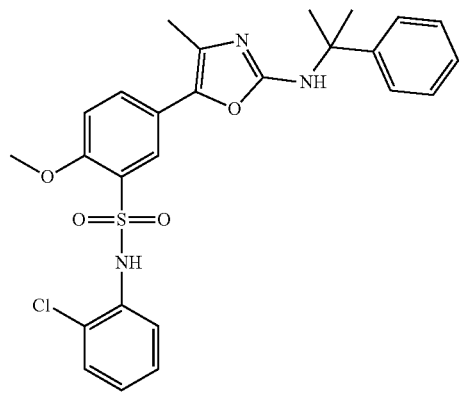

In some embodiments of any one of the formulae (IIA2a) to (IIA2i), $Y^2$ is S. In some embodiments of any one of the formulae (IIA2a) to (IIA2i), $Y^1$ is CH. In some embodiments of any one of the formulae (IIA2a) to (IIA2i), $Y^2$ is S and $Y^1$ is CH. In some embodiments of any one of the formulae (IIA2a) to (IIA2i), $Y^2$ is S and $Y^1$ is N. In some embodiments of any one of the formulae (IIA2a) to (IIA2i), $Y^2$ is O. In some embodiments of any one of the formulae (IIA2a) to (IIA2i), $Y^2$ is $NR^{19}$. In some embodiments of any one of the formulae (IIA2a) to (IIA2i), $Y^2$ is NH. In some embodiments of any one of the formulae (IIA2a) to (IIA2i), $Y^2$ is O and $Y^1$ is CH. In some embodiments of any one of the formulae (IIA2a) to (IIA2i), $Y^2$ is $NR^{19}$ and $Y^1$ is CH. In some embodiments of any one of the formulae (IIA2a) to (IIA2i), $Y^2$ is NH and $Y^1$ is CH. In some embodiments of any one of the formulae (IIA2a) to (IIA2i), $Y^2$ is O and $Y^1$ is N. In some embodiments of any one of the formulae (IIA2a) to (IIA2i), $Y^2$ is $NR^{19}$ and $Y^1$ is N. In some embodiments of any one of the formulae (IIA2a) to (IIA2i), $Y^2$ is NH and $Y^1$ is N.

In certain embodiments of any one of (IIA2) to (IIA2k), $R^{12}$ is selected from, alkyl, substituted alkyl, trifluoromethyl and halogen. In certain cases, $R^{12}$ is a lower alkyl group (e.g., methyl, ethyl, propyl, butyl, pentyl, hexyl). In certain cases, the lower alkyl group is methyl. In certain cases, $R^{11}$ is halogen. In certain cases, the halogen is chloride, provided that $Y^2$ is not S and the A ring is not an unsubstituted tetrahydropyran. In certain cases, $R^{12}$ is trifluoromethyl.

In certain embodiments of any one of (IA2) to (A2k), $R^4$ and $R^5$ are each independently lower alkyl. In certain cases, both, $R^4$ and $R^5$ are methyl. In some cases of any one of formula (IIA) to (IA2k), $R^4$ and $R^5$ together with the carbon to which they are attached form a cycloalkyl group.

In certain embodiments of any one of (IA2) to (IIA2k), $R^2$ is methoxy. In certain embodiments of any one of formulae (IIA2) to (IIA2k), $R^3$ is methyl.

In certain embodiments of any one of (IIA2) to (IIA2k), $R^2$, $R^3$, $R^4$, $R^5$ $R^{10}$ and $R^{14}$ are independently selected from corresponding groups as depicted in any of the structures of Table 1, 2 or 3.

In certain embodiments, the compound is described by one of the following structures:

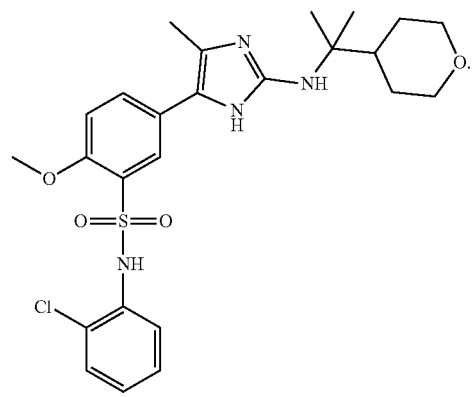

In certain embodiments, the compound of formula (IIA2) is not one of the following structures:

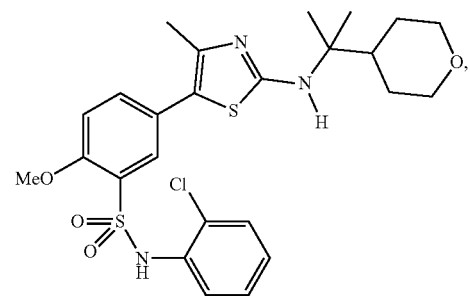

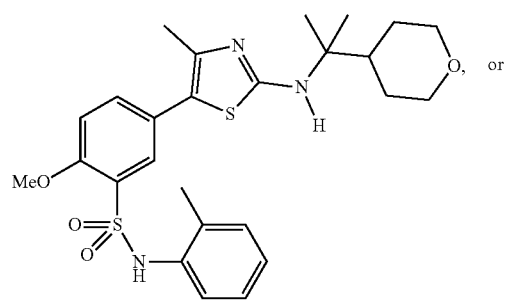

-continued
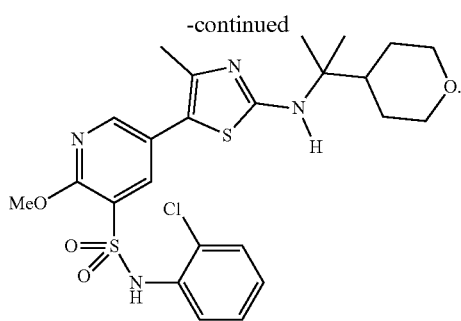
In certain embodiments of formula (II), the compound is described by the formula (IIB), (IIC) or (IID):
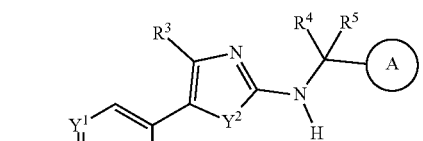
(IIB)
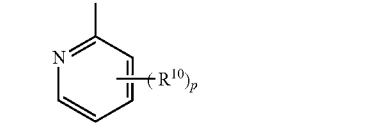
(IIC)
, or
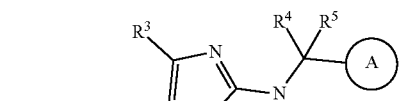
(IID)
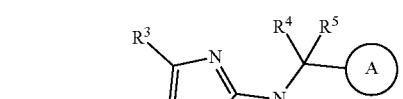
In certain embodiments, the compound is of the formula is (IIC1) or (IID1):
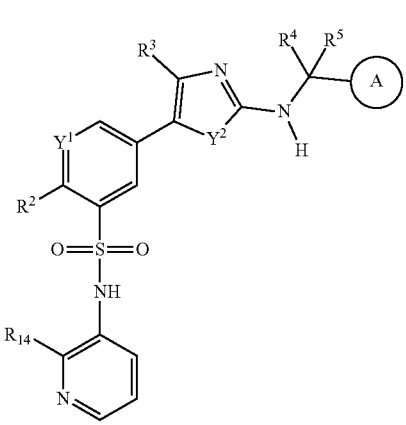
(IIC1)
or
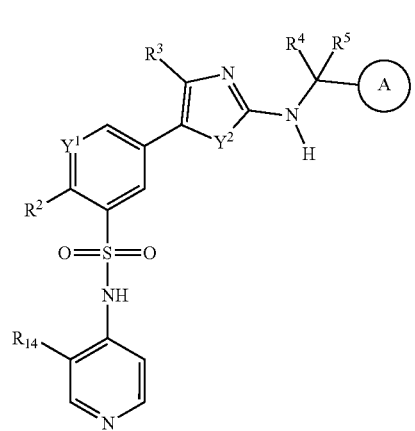
(IID1)
In certain embodiments, the compound is described by any one of the formulae (IIB1), (IIC2) or (IID2):
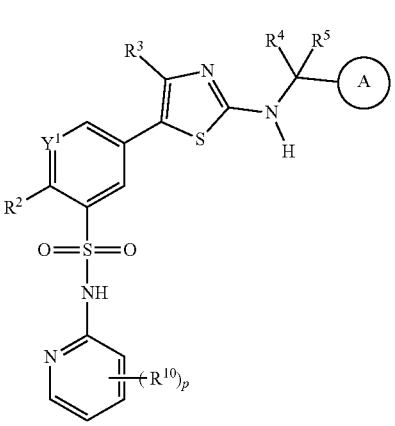
(IIB1)

(IIC2)
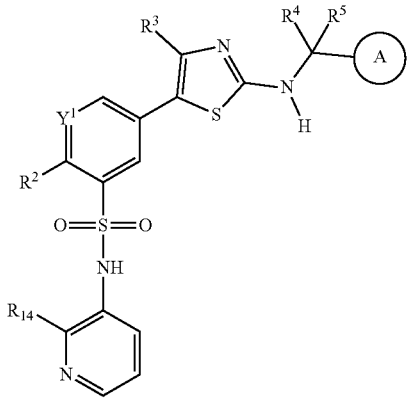

(IIC3)
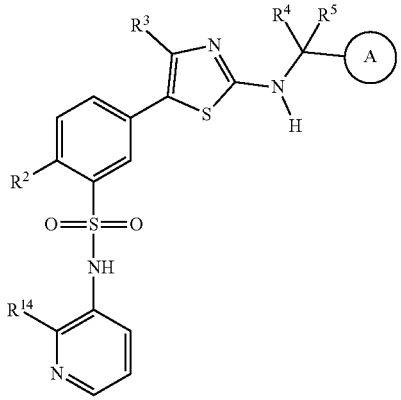

(IID2)
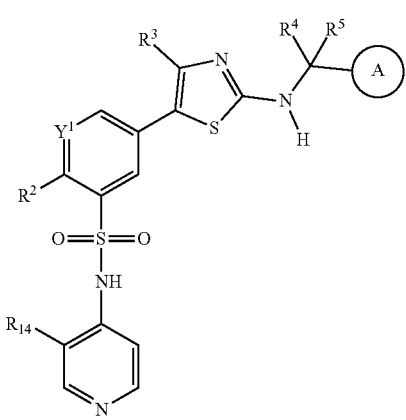

(IID3)
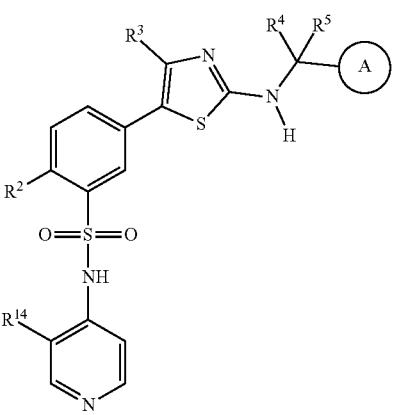

In certain embodiments, the compound is described by any one of the formulae (IIB2), (IIC3) or (IID3):

(IIB2)
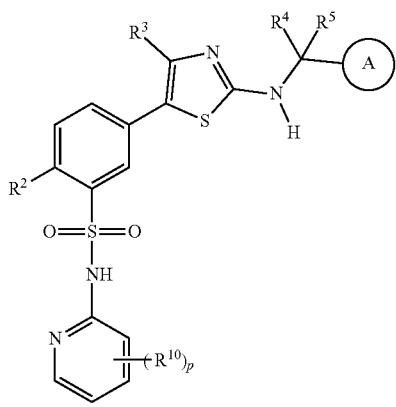

In some embodiments of any one of formulae (IB), (IIC) or (IID), the A ring is selected from an aryl (e.g., a phenyl), optionally including one or more substituents. In some embodiments, the A ring is selected from a heteroaryl or a heterocycle (e.g., pyridyl, pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl) optionally including one or more substituents. In some embodiments, the A ring is selected from a cycloalkyl (e.g., a cyclohexane), optionally including one or more substituents. In some embodiments, the A ring is selected from phenyl, substituted phenyl, pyridyl, substituted pyridyl, 2-pyrimidinyl, substituted 2-pyrimidinyl, 3-pyrimidinyl, substituted 3-pyrimidinyl, 6-pyrimidinyl, substituted 6-pyrimidinyl, piperidine, substituted piperidine, piperazine, substituted piperazine, 2-oxopiperidine, 2-oxopiperazine, imidazole, substituted imidazole, thiazole, substituted thiazole, oxazole, substituted oxazole, tetrahydropyran, substituted tetrahydropyran, morpholine, substituted morpholine, cyclic sulfone, substituted cyclic sulfone, cycloalkyl and substituted cycloalkyl.

In other embodiments, the A ring is described by the formula (A1):

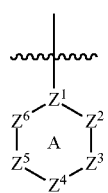
(A1)

where A1 is a 6-membered aryl, heteroaryl, heterocyclyl, or cycloalkyl, where $Z^1$-$Z^6$ are independently selected from N, O, $CR^{11}$, $NR^{11}$, $CR^{11}_2$, $SO_2$ and CO, provided that valency requirements are fulfilled, where $R^{11}$ are each independently selected from hydrogen, alkyl, substituted alkyl, hydroxy, alkoxy, substituted alkoxy, trifluoromethyl, halogen, acyl, substituted acyl, carboxy, carboxyamide, substituted carboxyamide, sulfonyl, substituted sulfonyl, sulfonamide and substituted sulfonamide. In certain cases, $Z^2$ and $Z^3$, or $Z^3$ and $Z^4$, or $Z^4$ and $Z^5$, or $Z^5$ and $Z^6$ are $CR^{11}$, wherein each $R^{11}$ together with the carbons to which they are attached form a 5-membered or 6-membered cyclic group selected from aryl, substituted aryl, heteroaryl, substituted heteroaryl, heterocycle, substituted heterocycle, cycloalkyl and substituted cycloalkyl. In certain cases, A1 is an indole or a substituted indole. In some cases, A1 is a phenyl, or substituted phenyl. In some cases, A1 is a cycloalkyl, or a substituted cycloalkyl. In some cases, A1 is pyridyl or substituted pyridyl. In some cases. A1 is pyrimidinyl, such as 2-pyrimidinyl, substituted 2-pyrimidinyl, 3-pyrimidinyl, substituted 3-pyrimidinyl, 6-pyrimidinyl or substituted 6-pyrimidinyl. In some cases, A1 is a pyridazine, or a substituted pyridazine. In some cases, A1 is a triazine, or a substituted triazine. In some cases. A1 is piperidine or substituted piperidine. In some cases, A1 is piperazine or substituted piperazine. In some cases, A1 is 2-oxopiperidine or substituted 2-oxopiperidine. In some cases, A1 is 2-oxopiperazine or substituted 2-oxopiperazine. In some cases. A1 is tetrahydropyran or substituted tetrahydropyran. In some cases, A1 is a pyran or a substituted pyran. In some cases, A1 is morpholine or substituted morpholine. In some cases, A1 is a cyclic sulfone or a substituted cyclic sulfone.

In some embodiments of any one of formulae (IIB), (IIC) or (IID), the A ring is selected from any of the formulae (B2) to (B8), e.g., as described herein. In certain embodiments of any one of formulae (IIB), (IIC) or (IID), the A ring is selected from the following structures:

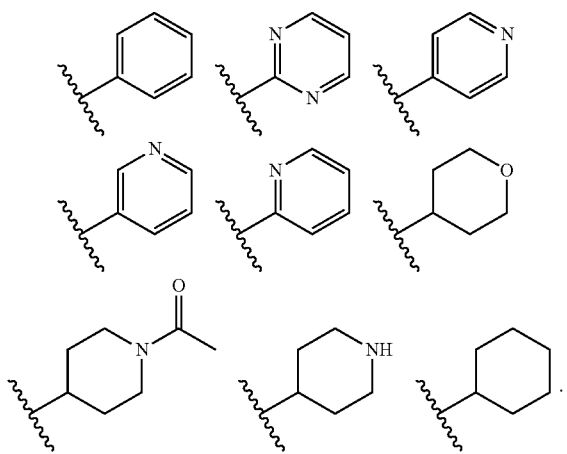

In some embodiments of formula (IIB), $Y^2$ is S. In some embodiments of formula (IIB), $Y^1$ is CH. In some embodiments of formula (IIB), $Y^2$ is S and $Y^1$ is CH. In some embodiments of formula (IIB), $Y^2$ is S and $Y^1$ is N. In some embodiments of formula (IIB), $Y^2$ is O. In some embodiments of formula (IIB), $Y^2$ is $NR^{19}$. In some embodiments of formula (IIB), $Y^2$ is NH. In some embodiments of formula (IIB), $Y^2$ is O and $Y^1$ is CH. In some embodiments of formula (IIB), $Y^2$ is $NR^{19}$ and $Y^1$ is CH. In some embodiments of formula (IIB), $Y^2$ is NH and $Y^1$ is CH. In some embodiments of formula (IIB), $Y^2$ is O and $Y^1$ is N. In some embodiments of formula (IIB), $Y^2$ is $NR^{19}$ and $Y^1$ is N. In some embodiments of formula (IIB), $Y^2$ is NH and $Y^1$ is N.

In certain embodiments of any one of (IIB) to (IIB2), $R^4$ and $R^5$ are each independently lower alkyl. In certain cases, both, $R^4$ and $R^5$ are methyl. In some cases of any one of formula (IIB) to (IIB2), $R^4$ and $R^5$ together with the carbon to which they are attached form a cycloalkyl group.

In certain embodiments of any one of (IIB) to (IIB2), $R^2$ is methoxy. In certain embodiments of any one of formulae (IIB) to (IIB2), $R^3$ is methyl.

In certain embodiments of any one of (IIB) to (IIB2), $R^2$, $R^3$, $R^4$, $R^5$ and $R^{10}$ are independently selected from corresponding groups as depicted in any of the structures of Table 1, 2 or 3.

In certain embodiments, the compound is described by the following structure:

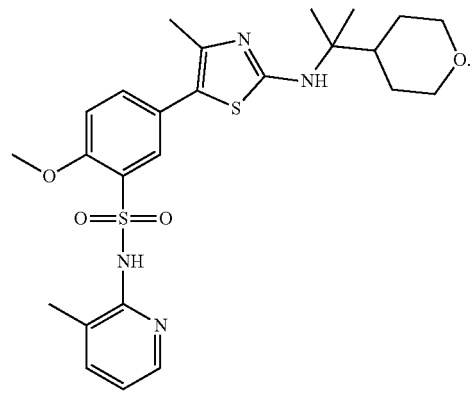 [SMILES: COc1ccc(-c2sc(NC(C)(C)C3CCOCC3)nc2C)cc1S(=O)(=O)Nc1ncccc1C]

In some embodiments, the formula (IIC1) is of any one of the formulae (IIC1a) to (IIC1i):

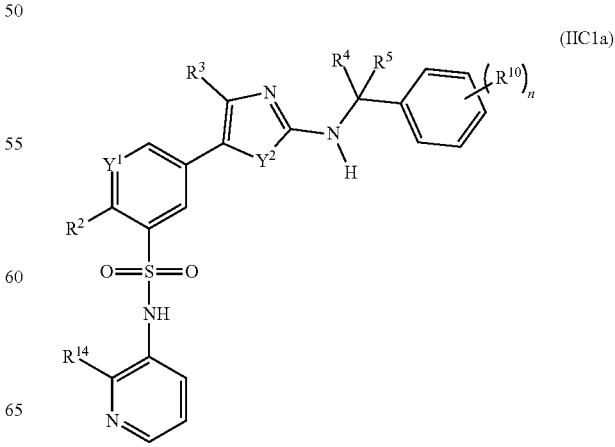
(IIC1a)

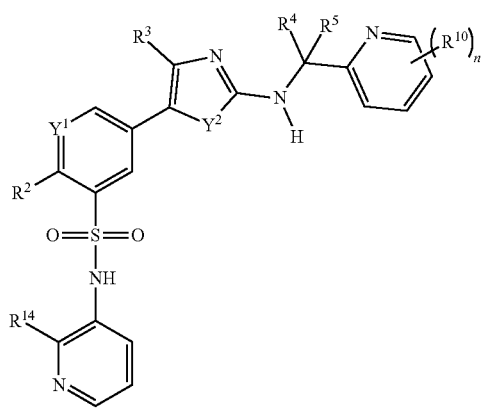
(IIC1b)
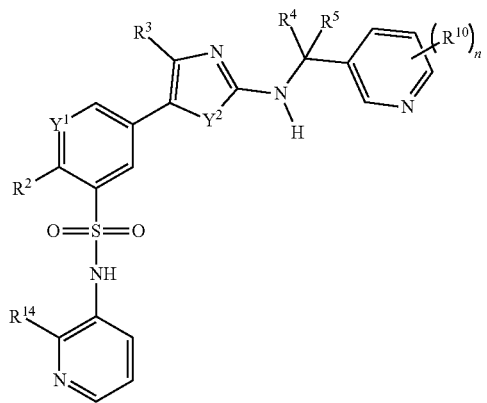
(IIC1c)
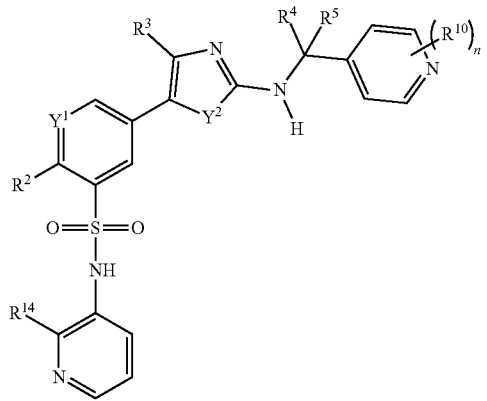
(IIC1d)
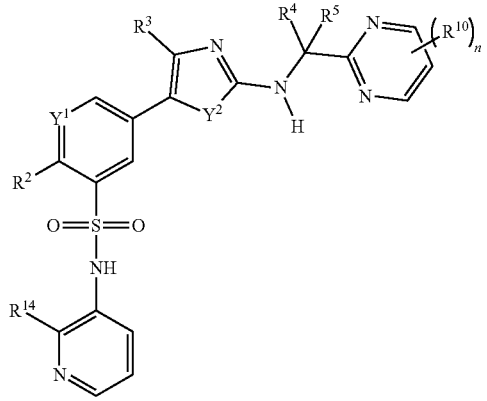
(IIC1e)
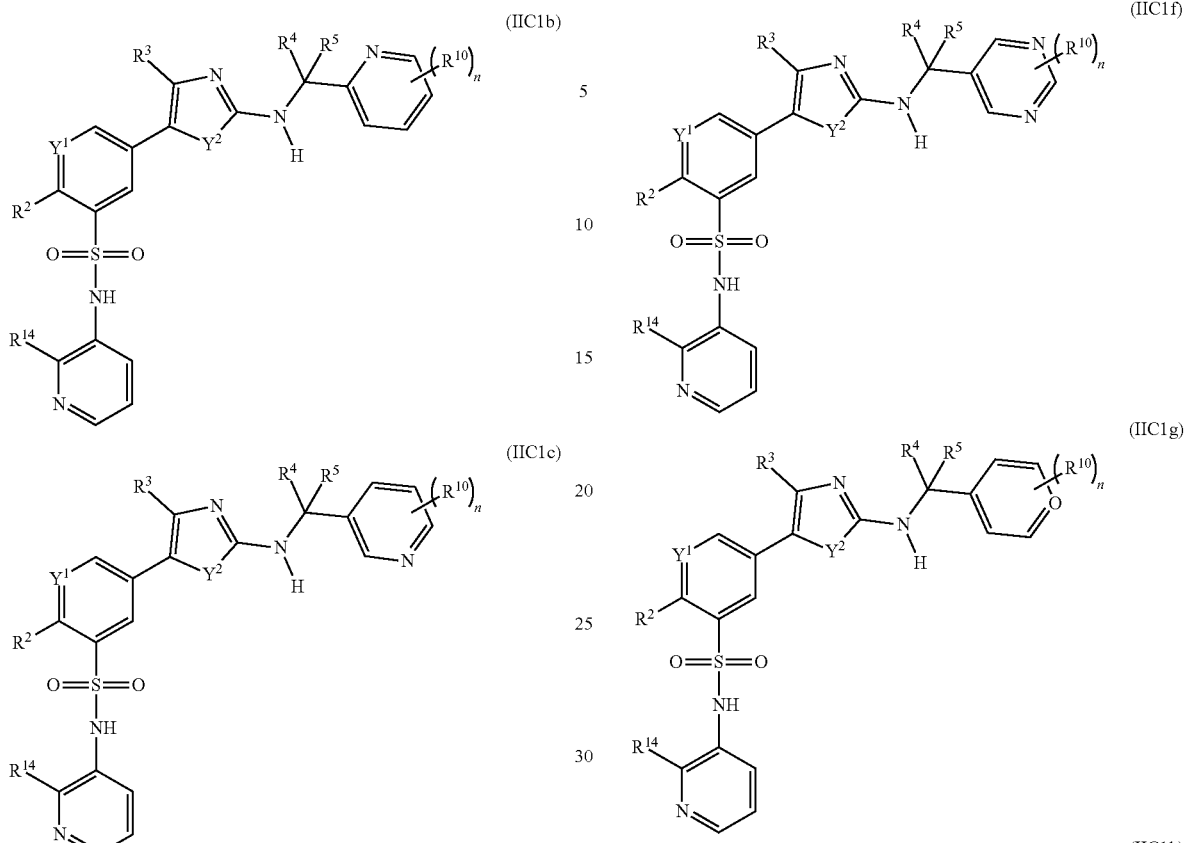
(IIC1f)
(IIC1g)
(IIC1h) and
(IIC1i)

In some embodiments of any one of the formulae (IIC1a) to (IIC1i), $Y^2$ is S. In some embodiments of any one of the formulae (IIC1a) to (IIC1i), $Y^1$ is CH. In some embodiments of any one of the formulae (IIC1a) to (IIC1i), $Y^2$ is S and $Y^1$ is CH. In some embodiments of any one of the formulae (IIC1a) to (IIC1i), $Y^2$ is S and $Y^1$ is N. In some embodiments of any one of the formulae (IIC1a) to (IIC1i), $Y^2$ is O. In some embodiments of any one of the formulae (IIC1a) to (IIC1i), $Y^2$ is $NR^{19}$. In some embodiments of any one of the formulae (IIC1a) to (IIC1i), $Y^2$ is NH. In some embodiments of anyone of the formulae (IIC1a) to (IIC1i), $Y^2$ is O and $Y^1$ is CH. In some embodiments of any one of the formulae (IIC1a) to (IIC1i), $Y^2$ is $NR^{19}$ and $Y^1$ is CH. In some embodiments of any one of the formulae (IIC1a) to (IIC1i), $Y^2$ is NH and $Y^1$ is CH. In some embodiments of any one of the formulae (IIC1a) to (IIC1i), $Y^2$ is O and $Y^1$ is N. In some embodiments of any one of the formulae (IIC1a) to (IIC1), $Y^2$ is $NR^{19}$ and $Y^1$ is N. In some embodiments of any one of the formulae (IIC1a) to (IIC1i), $Y^2$ is NH and $Y^1$ is N.

In certain embodiments of any one of (IIC1) to (IIC3), $R^{14}$ is selected from, alkyl, substituted alkyl, trifluoromethyl and halogen. In certain cases, $R^{14}$ is a lower alkyl group (e.g., methyl, ethyl, propyl, butyl, pentyl, hexyl). In certain cases, the lower alkyl group is methyl. In certain cases, $R^{14}$ is trifluoromethyl.

In certain embodiments of any one of (IIC) to (IIC3), $R^4$ and $R^5$ are each independently lower alkyl. In certain cases, both, $R^4$ and $R^5$ are methyl. In some cases of any one of formula (IC) to (IIC3), $R^4$ and $R^5$ together with the carbon to which they are attached form a cycloalkyl group.

In certain embodiments of any one of (IIC) to (IIC3), $R^2$ is methoxy. In certain embodiments of any one of formulae (IIC) to (IIC3), $R^3$ is methyl.

In certain embodiments of any one of (IIC) to (IIC3), $R^2$, $R^3$, $R^4$, $R^5$ $R^{10}$ and $R^{14}$ are independently selected from corresponding groups as depicted in any of the structures of Table 1, 2 or 3.

In certain embodiments, the compound is described by the following structure:

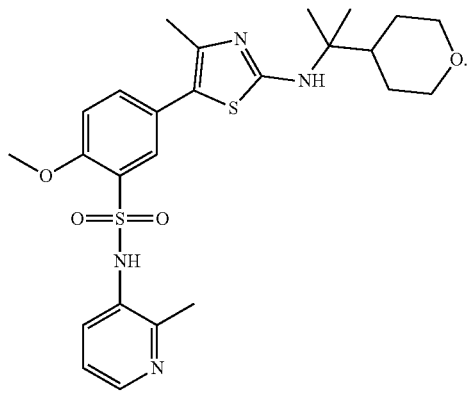 [SMILES: COc1ccc(-c2sc(NC(C)(C)C3CCOCC3)nc2C)cc1S(=O)(=O)Nc1cccnc1C]

In some embodiments, the formula (IID1) is of any one of the formulae (IID1a) to (IID1i):

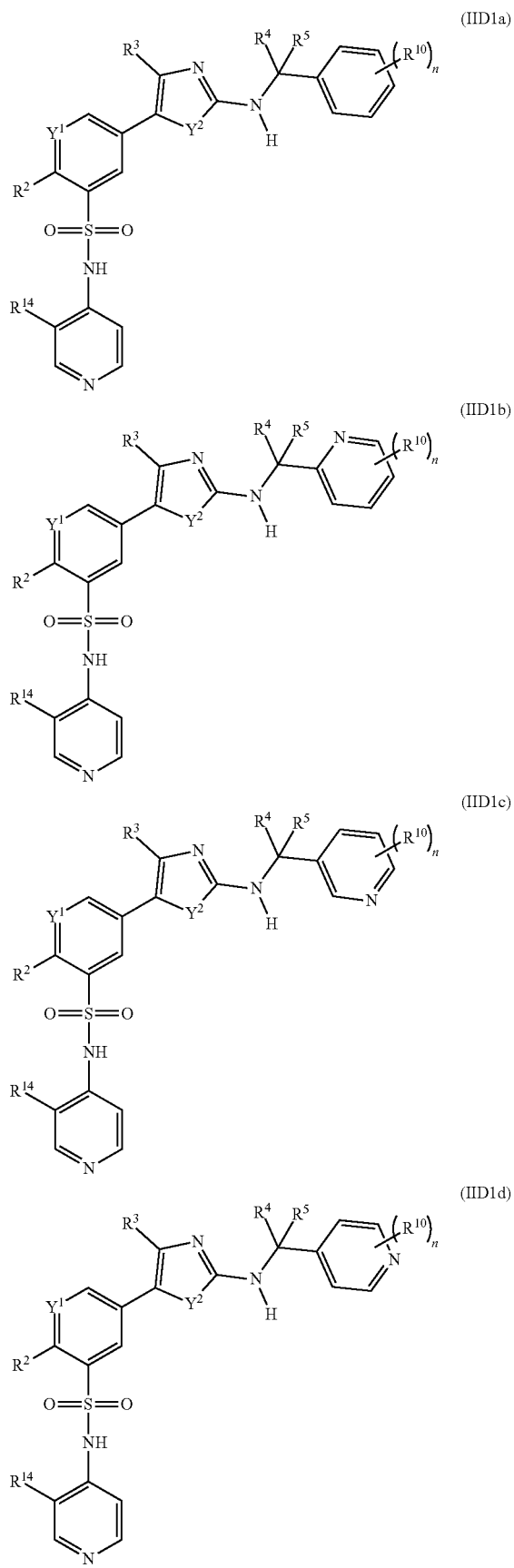

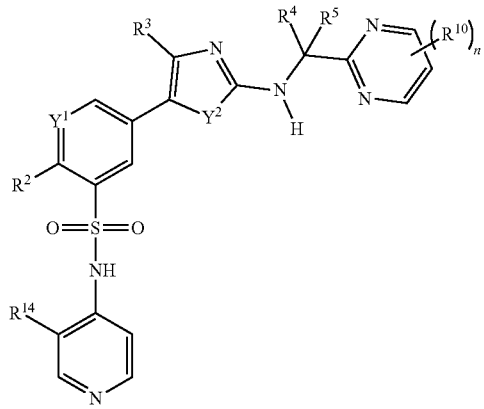

(IID1e)

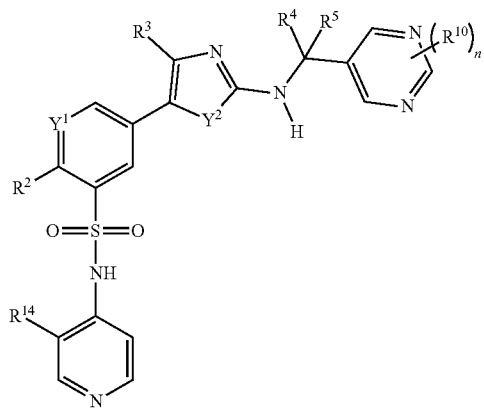

(IID1f)

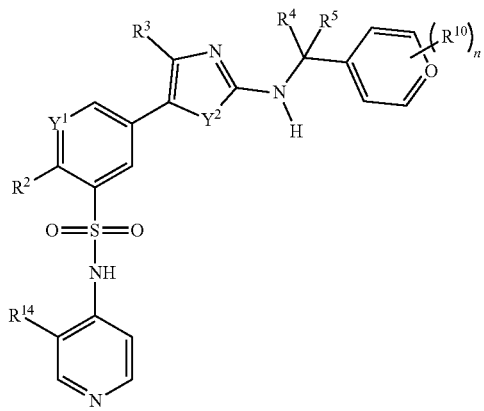

(IID1g)

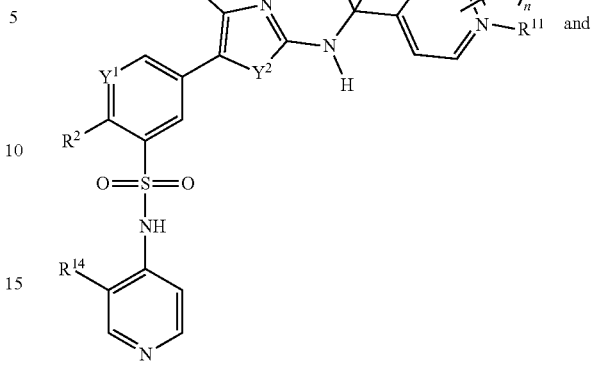

(IID1h) and (IID1i)

In some embodiments of any one of the formulae (IID1a) to (IID1i), $Y^2$ is S. In some embodiments of any one of the formulae (IID1a) to (IID1i), $Y^1$ is CH. In some embodiments of any one of the formulae (IID1a) to (IID1i), $Y^2$ is S and $Y^1$ is CH. In some embodiments of any one of the formulae (IID1a) to (IID1i), $Y^2$ is S and $Y^1$ is N. In some embodiments of any one of the formulae (IID1a) to (IID1i), $Y^2$ is O. In some embodiments of any one of the formulae (IID1a) to (IID1i), $Y^2$ is $NR^{19}$. In some embodiments of any one of the formulae (IID1a) to (IID1i), $Y^2$ is NH. In some embodiments of any one of the formulae (IID1a) to (IID1i), $Y^2$ is O and $Y^1$ is CH. In some embodiments of any one of the formulae (IID1a) to (IID1i), $Y^2$ is $NR^{19}$ and $Y^1$ is CH. In some embodiments of any one of the formulae (IID1a) to (IID1i), $Y^2$ is NH and $Y^1$ is CH. In some embodiments of any one of the formulae (IID1a) to (IID1i), $Y^2$ is O and $Y^1$ is N. In some embodiments of any one of the formulae (IID1a) to (IID1i), $Y^2$ is $NR^{19}$ and $Y^1$ is N. In some embodiments of any one of the formulae (IID1a) to (IID1i), $Y^2$ is NH and $Y^1$ is N.

In certain embodiments of any one of (IID1) to (IID3), $R^{14}$ is selected from, alkyl, substituted alkyl, trifluoromethyl and halogen. In certain cases, $R^{14}$ is a lower alkyl group (e.g., methyl, ethyl, propyl, butyl, pentyl, hexyl). In certain cases, the lower alkyl group is methyl. In certain cases, $R^{14}$ is trifluoromethyl.

In certain embodiments of any one of (IID) to (IID3), $R^4$ and $R^5$ are each independently lower alkyl. In certain cases, both, $R^4$ and $R^5$ are methyl. In some cases of any one of formula (IID) to (IID3), $R^4$ and $R^5$ together with the carbon to which they are attached form a cycloalkyl group.

In certain embodiments of any one of (ID) to (IID3), $R^2$ is methoxy. In certain embodiments of any one of formulae (IID) to (IID3), $R^3$ is methyl.

In certain embodiments of any one of (IID) to (IID3), $R^2$, $R^3$, $R^4$, $R^5$ $R^{10}$ and $R^{14}$ are independently selected from corresponding groups as depicted in any of the structures of Table 1, 2 or 3.

In certain embodiments, the compound is described by one of the following structures:

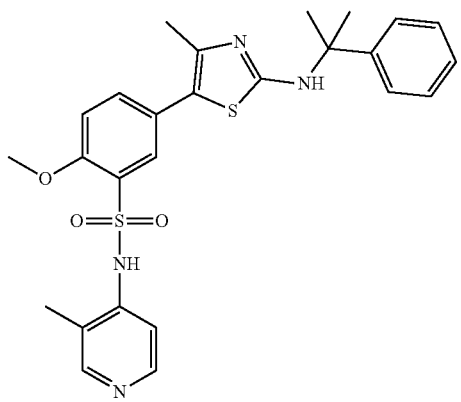
,

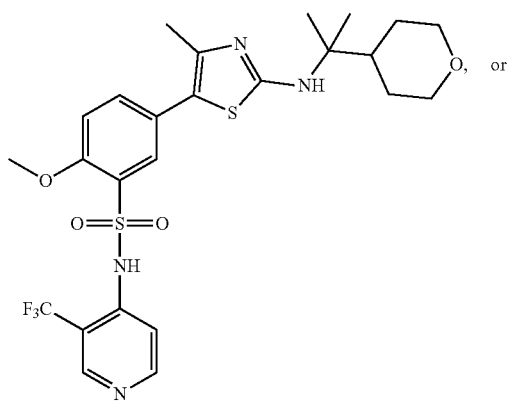
, or

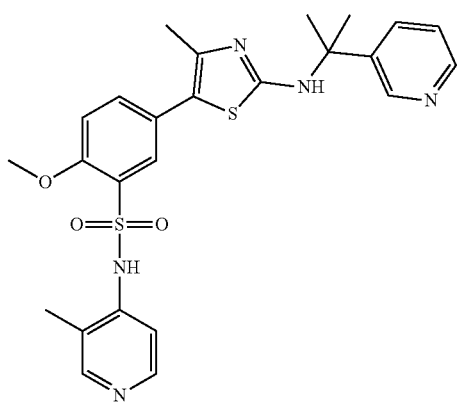

In certain embodiments, the compound is described by the following structure:

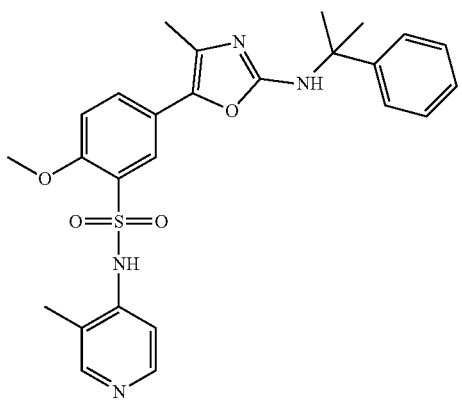 [SMILES: COc1ccc(-c2oc(NC(C)(C)c3ccccc3)nc2C)cc1S(=O)(=O)Nc1ccncc1C]
.

In certain embodiments of formula (II), the compound is described by the formula (IIE) or (IIF):

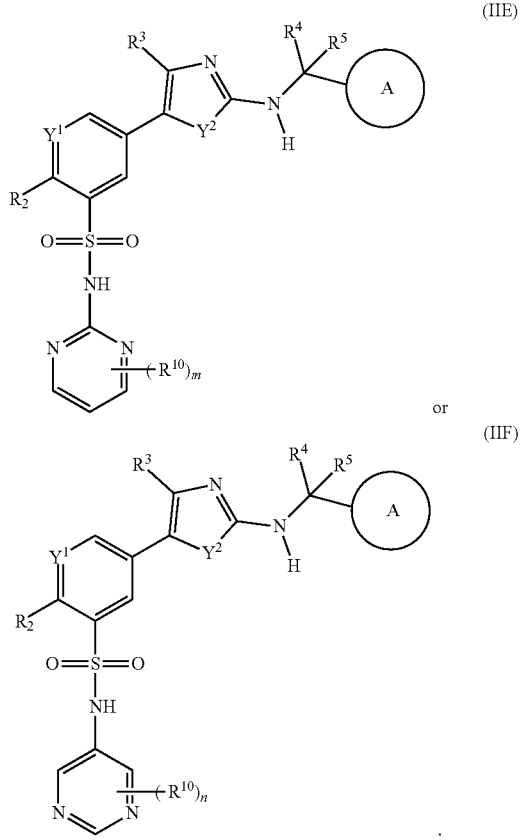

In some embodiments of formulae (IIE) or (IIF), $Y^2$ is S. In some embodiments of any one of the formulae (IIE) or (IIF), $Y^1$ is CH. In some embodiments of formulae (IIE) or (IIF), $Y^2$ is S and $Y^1$ is CH. In some embodiments formulae (IIE) or (IIF), $Y^2$ is S and $Y^1$ is N. In some embodiments of formulae (IIE) or (IIF), $Y^2$ is O. In some embodiments of (IIE) or (IIF), $Y^2$ is $NR^{19}$. In some embodiments of formulae (IIE) or (IIF). $Y^2$ is NH. In some embodiments of formulae (IIE) or (IIF). $Y^2$ is O and $Y^1$ is CH. In some embodiments of formulae (IIE) or (IIF), $Y^2$ is $NR^{19}$ and $Y^1$ is CH. In some embodiments of formulae (IIE) or (IIF), $Y^2$ is NH and $Y^1$ is CH. In some embodiments of formulae (IIE) or (II), $Y^2$ is O and Y¹ is N. In some embodiments of formulae (IIE) or (IIF), Y² is NR¹⁹ and Y¹ is N. In some embodiments of formulae (IIE) or (IIF), Y² is NH and Y¹ is N.

In certain embodiments of formula (II), the compound is described by the formulae (IIE1) or (IIF1):

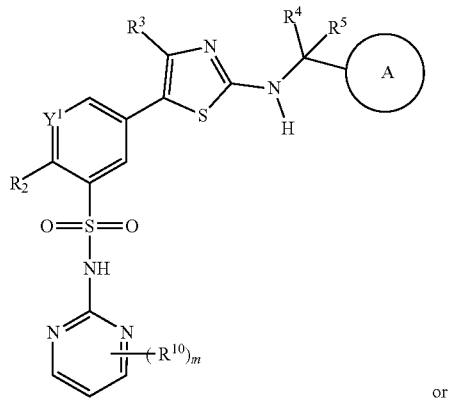

(IIE1)

or

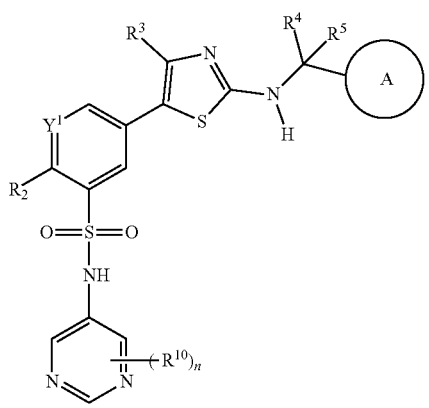

(IIF1)

In certain embodiments of formula (II), the compound is described by the formulae (IIE2) or (IIF2):

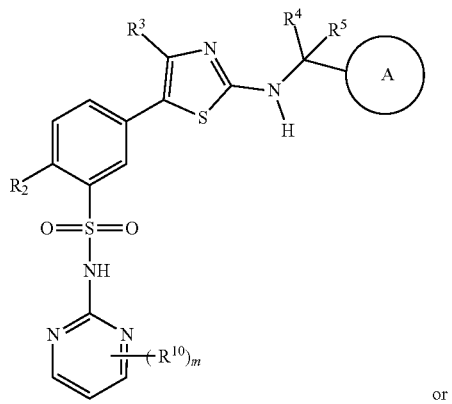

(IIE2)

or

-continued

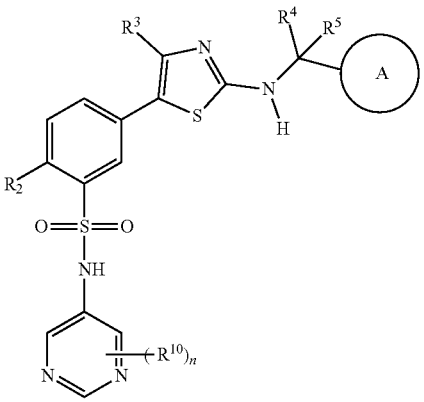

(IIF2)

In some embodiments of any one of formulae (IIE) to (IIE2) or (IIF) to (IIF2), the A ring is selected from an aryl (e.g., a phenyl), optionally including one or more substituents. In some embodiments, the A ring is selected from a heteroaryl or a heterocycle (e.g., pyridyl, pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl) optionally including one or more substituents. In some embodiments, the A ring is selected from a cycloalkyl (e.g., a cyclohexane), optionally including one or more substituents. In some embodiments, the A ring is selected from phenyl, substituted phenyl, pyridyl, substituted pyridyl, 2-pyrimidinyl, substituted 2-pyrimidinyl, 3-pyrimidinyl, substituted 3-pyrimidinyl, 6-pyrimidinyl, substituted 6-pyrimidinyl, piperidine, substituted piperidine, piperazine, substituted piperazine, 2-oxopiperidine, 2-oxopiperazine, imidazole, substituted imidazole, thiazole, substituted thiazole, oxazole, substituted oxazole, tetrahydropyran, substituted tetrahydropyran, morpholine, substituted morpholine, cyclic sulfone, substituted cyclic sulfone, cycloalkyl and substituted cycloalkyl.

In other embodiments, the A ring is described by the formula (A1):

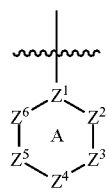

(A1)

where A1 is a 6-membered aryl, heteroaryl, heterocyclyl, or cycloalkyl, where $Z^1$-$Z^6$ are independently selected from N, O, $CR^{11}$, $NR^{11}$, $CR^{11}_2$, $SO_2$ and CO, provided that valency requirements are fulfilled, where $R^{11}$ are each independently selected from hydrogen, alkyl, substituted alkyl, hydroxy, alkoxy, substituted alkoxy, trifluoromethyl, halogen, acyl, substituted acyl, carboxy, carboxyamide, substituted carboxyamide, sulfonyl, substituted sulfonyl, sulfonamide and substituted sulfonamide. In certain cases, $Z^2$ and $Z^3$, or $Z^3$ and $Z^4$, or $Z^4$ and $Z^5$, or $Z^5$ and $Z^6$ are $CR^{11}$, wherein each $R^{11}$ together with the carbons to which they are attached form a 5-membered or 6-membered cyclic group selected from aryl, substituted aryl, heteroaryl, substituted heteroaryl, heterocycle, substituted heterocycle, cycloalkyl and substituted cycloalkyl. In certain cases, A1 is an indole or a substituted indole. In some cases, A1 is a phenyl, or substituted phenyl. In some cases, A1 is a cycloalkyl, or a substituted cycloalkyl. In some cases, A1 is pyridyl or substituted pyridyl. In some cases, A1 is pyrimidinyl, such as 2-pyrimidinyl, substituted 2-pyrimidinyl, 3-pyrimidinyl, substituted 3-pyrimidinyl, 6-pyrimidinyl or substituted 6-pyrimidinyl. In some cases, A1 is a pyridazine, or a substituted pyridazine. In some cases, A1 is a triazine, or a substituted triazine. In some cases. A1 is piperidine or substituted piperidine. In some cases, A1 is piperazine or substituted piperazine. In some cases, A1 is 2-oxopiperidine or substituted 2-oxopiperidine. In some cases, A1 is 2-oxopiperazine or substituted 2-oxopiperazine. In some cases. A1 is tetrahydropyran or substituted tetrahydropyran. In some cases, A1 is a pyran or a substituted pyran. In some cases, A1 is morpholine or substituted morpholine. In some cases, A1 is a cyclic sulfone or a substituted cyclic sulfone.

In certain embodiments of any one of formulae (IIE) to (IIE2) or (IIF) to (IIF2), the A ring is selected from any of the formulae (B2) to (B8), e.g., as described herein. In certain embodiments of any one of formulae (IIE) to (IIE2) or (IIF) to (IIF2), the A ring is selected from the following structures:

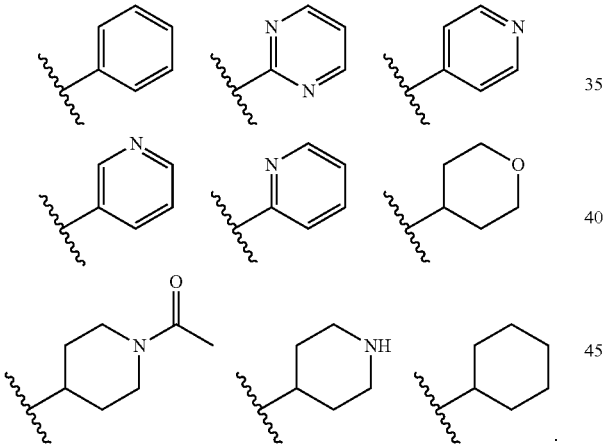

In certain embodiments of any one of (IIE) to (IIE2) or (IIF) to (IIF2). $R^4$ and $R^5$ are each independently lower alkyl. In certain cases, both, $R^4$ and $R^5$ are methyl. In some cases of any one of formula (IIE) to (IIE2) or (IIF) to (IIF2), $R^4$ and $R^5$ together with the carbon to which they are attached form a cycloalkyl group.

In certain embodiments of any one of (IIE) to (IIE2) or (IIF) to (IIF2), $R^2$ is methoxy. In certain embodiments of any one of formulae (IIE) to (IIE2) or (IIF) to (IIF2), $R^3$ is methyl.

In certain embodiments of any one of (IIE) to (IIE2) or (IIF) to (IIF2), $R^2$, $R^3$, $R^4$, $R^5$ and $R^{10}$ are independently selected from corresponding groups as depicted in any of the structures of Table 1, 2 or 3.

In certain embodiments, the compound is described by one of the following structures:

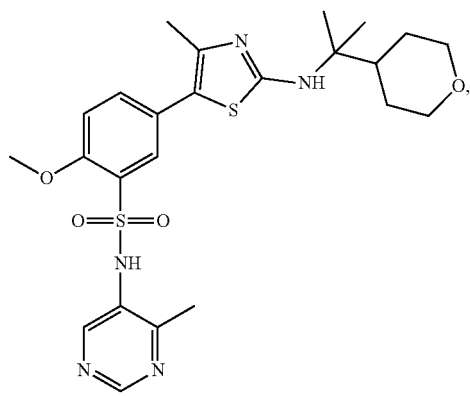

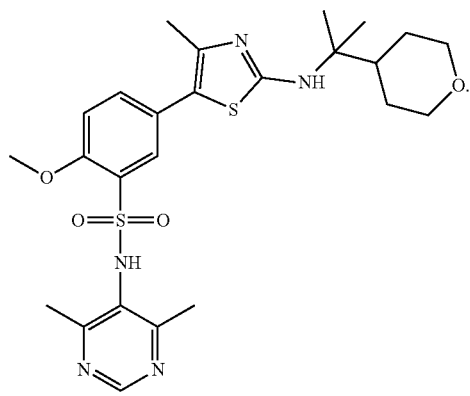

In certain embodiments of formula (II), the compound is described by formula (IIG):

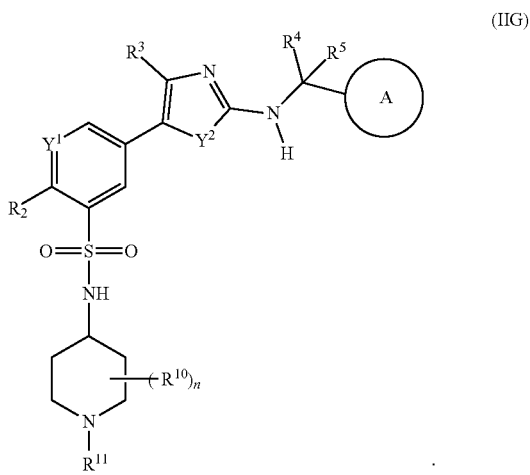

(IIG)

In certain embodiments of the formula (IIG), the compound is described by formula (IIG1):

(IIG1)

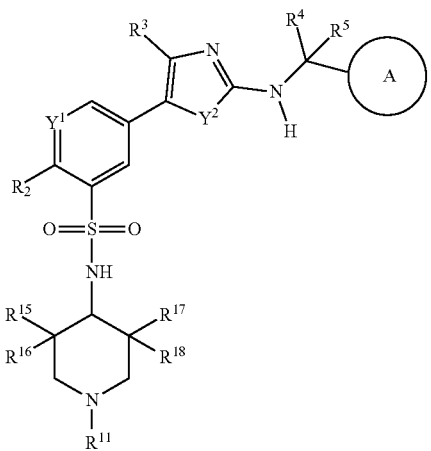

wherein:
$R^{11}$ is selected from $R^{10}$, acyl, substituted acyl, carboxy, carboxyamide, substituted carboxyamide, sulfonyl and substituted sulfonyl; and
$R^{15}$, $R^{16}$, $R^{17}$ and $R^{18}$ are each independently selected from, hydrogen, alkyl, substituted alkyl, hydroxy, alkoxy, substituted alkoxy, trifluoromethyl and halogen.

In certain embodiments of the formula (IIG), the compound is described by the formula (IIG2) or (IIG3):

(IIG2)

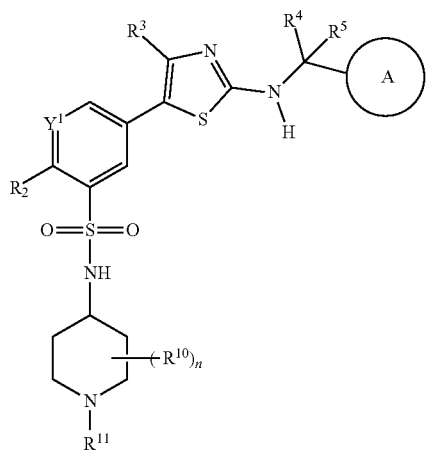

or (IIG3)

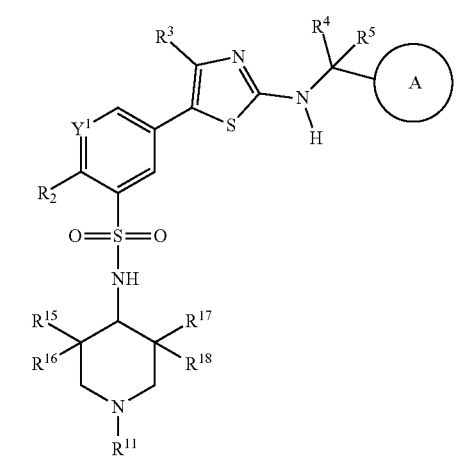

In certain embodiments of the formula (IIG), the compound is described by the formula (IIG2a) or (IIG3a):

(IIG2a)

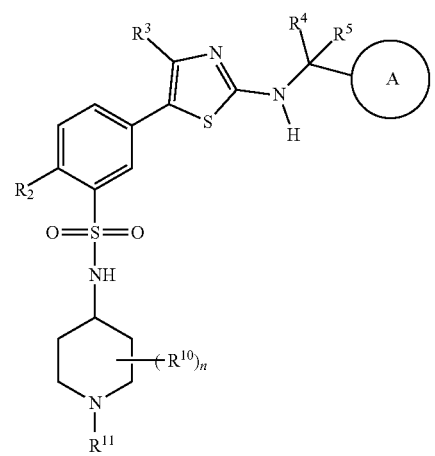

or (IIG3a)

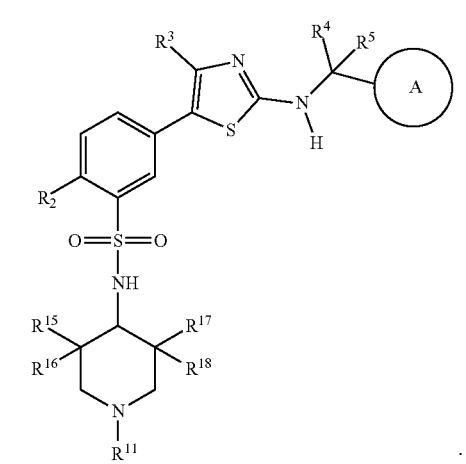

In certain embodiments, the formula (IIG1) has the relative configuration of formulae (IIG1ii) or (IIG1iii):

(IIG1ii)

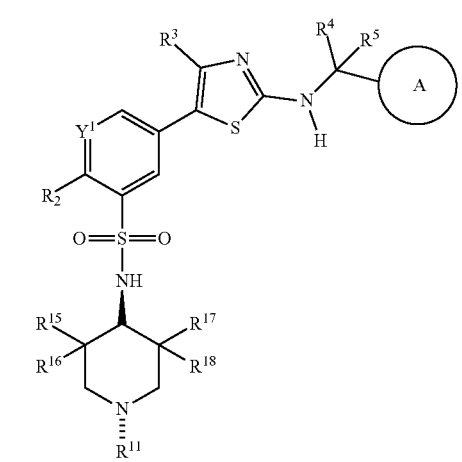

-continued (IIG1iii)

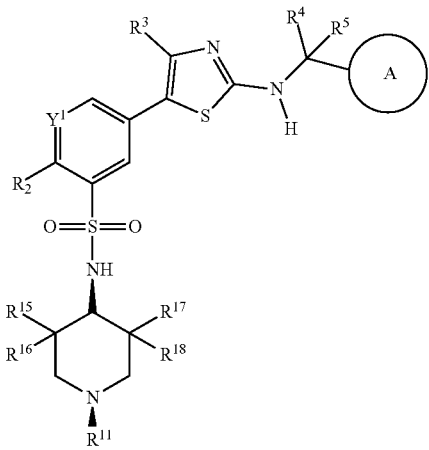

In some embodiments of any one of formulae (IIG) to (IIG3a), the A ring is selected from an aryl (e.g., a phenyl), optionally including one or more substituents. In some embodiments, the A ring is selected from a heteroaryl or a heterocycle (e.g., pyridyl, pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl) optionally including one or more substituents. In some embodiments, the A ring is selected from a cycloalkyl (e.g., a cyclohexane), optionally including one or more substituents. In some embodiments, the A ring is selected from phenyl, substituted phenyl, pyridyl, substituted pyridyl, 2-pyrimidinyl, substituted 2-pyrimidinyl, 3-pyrimidinyl, substituted 3-pyrimidinyl, 6-pyrimidinyl, substituted 6-pyrimidinyl, piperidine, substituted piperidine, piperazine, substituted piperazine, 2-oxopiperidine, 2-oxopiperazine, imidazole, substituted imidazole, thiazole, substituted thiazole, oxazole, substituted oxazole, tetrahydropyran, substituted tetrahydropyran, morpholine, substituted morpholine, cyclic sulfone, substituted cyclic sulfone, cycloalkyl and substituted cycloalkyl.

In other embodiments, the A ring is described by the formula (A1):

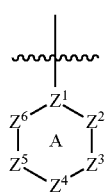

(A1)

where A1 is a 6-membered aryl, heteroaryl, heterocyclyl, or cycloalkyl, where $Z^1$-$Z^6$ are independently selected from N, O, $CR^{11}$, $NR^{11}$, $CR^{11}_2$, $SO_2$ and CO, provided that valency requirements are fulfilled, where $R^{11}$ are each independently selected from hydrogen, alkyl, substituted alkyl, hydroxy, alkoxy, substituted alkoxy, trifluoromethyl, halogen, acyl, substituted acyl, carboxy, carboxyamide, substituted carboxyamide, sulfonyl, substituted sulfonyl, sulfonamide and substituted sulfonamide. In certain cases, $Z^2$ and $Z^3$, or $Z^3$ and $Z^4$, or $Z^4$ and $Z^5$, or $Z^5$ and $Z^6$ are $CR^{11}$, wherein each $R^{11}$ together with the carbons to which they are attached form a 5-membered or 6-membered cyclic group selected from aryl, substituted aryl, heteroaryl, substituted heteroaryl, heterocycle, substituted heterocycle, cycloalkyl and substituted cycloalkyl. In certain cases, A1 is an indole or a substituted indole. In some cases, A1 is a phenyl, or substituted phenyl. In some cases, A1 is a cycloalkyl, or a substituted cycloalkyl. In some cases, A1 is pyridyl or substituted pyridyl. In some cases, A1 is pyrimidinyl, such as 2-pyrimidinyl, substituted 2-pyrimidinyl, 3-pyrimidinyl, substituted 3-pyrimidinyl, 6-pyrimidinyl or substituted 6-pyrimidinyl. In some cases, A1 is a pyridazine, or a substituted pyridazine. In some cases, A1 is a triazine, or a substituted triazine. In some cases, A1 is piperidine or substituted piperidine. In some cases, A1 is piperazine or substituted piperazine. In some cases, A1 is 2-oxopiperidine or substituted 2-oxopiperidine. In some cases, A1 is 2-oxopiperazine or substituted 2-oxopiperazine. In some cases, A1 is tetrahydropyran or substituted tetrahydropyran. In some cases, A1 is a pyran or a substituted pyran. In some cases, A1 is morpholine or substituted morpholine. In some cases, A1 is a cyclic sulfone or a substituted cyclic sulfone.

In some embodiments of any of the formulae (IIG) to (IIG3a), the A ring is selected from any of the formulae (B2) to (B8), e.g., as described herein. In certain embodiments of any one of formulae (IIG) to (IIG3a), the A ring is selected from the following structures:

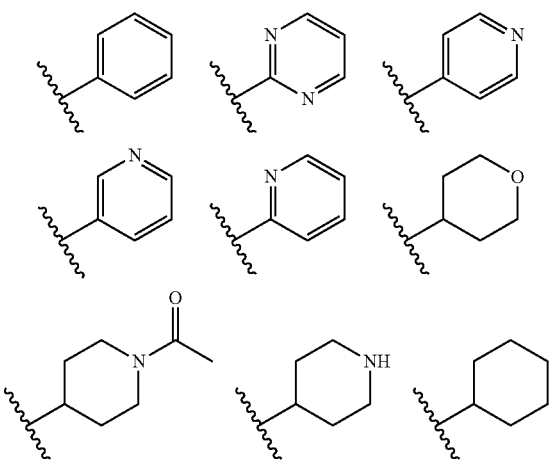

In certain embodiments of the formula (IIG1), the compound is described by any one of the formulae (IIG1a) to (IIG1i):

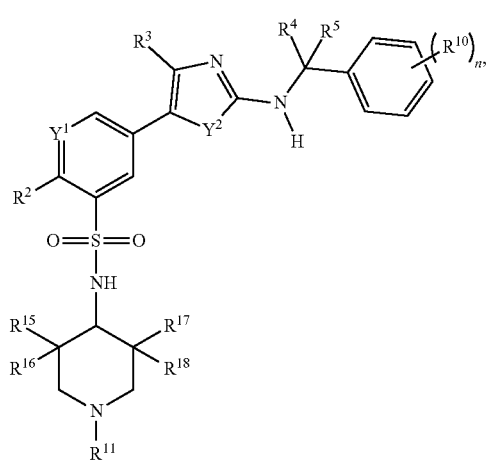
(IIG1a)
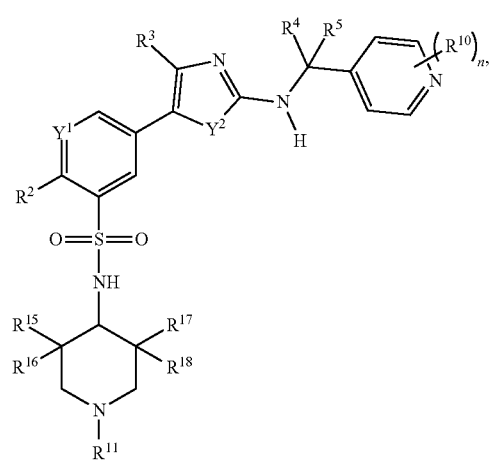
(IIG1d)
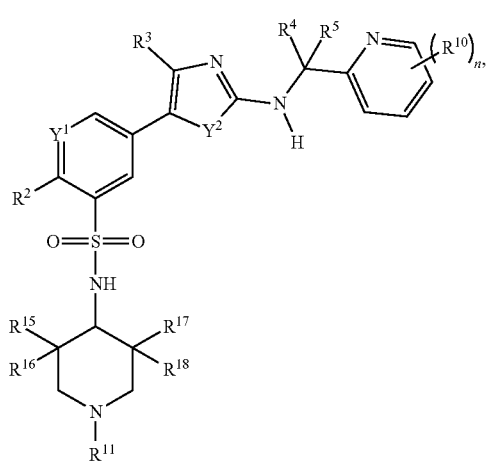
(IIG1b)
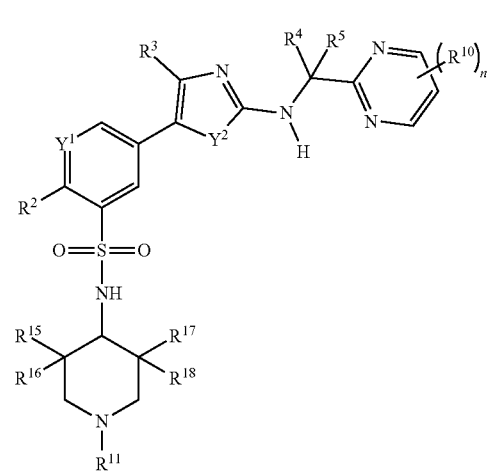
(IIG1e)
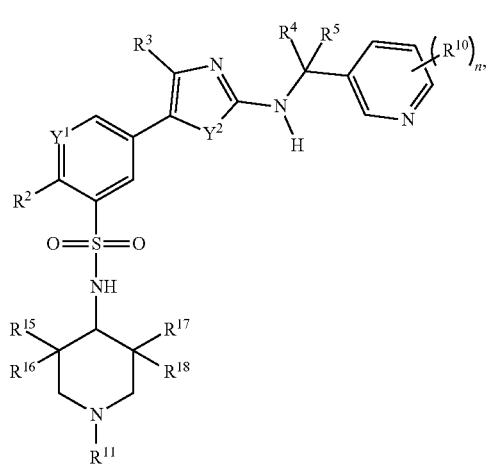
(IIG1c)
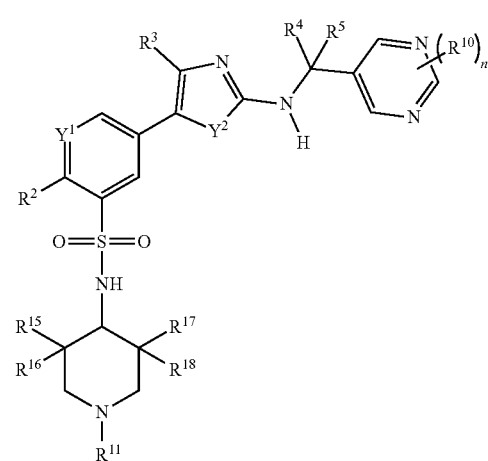
(IIG1f)

-continued

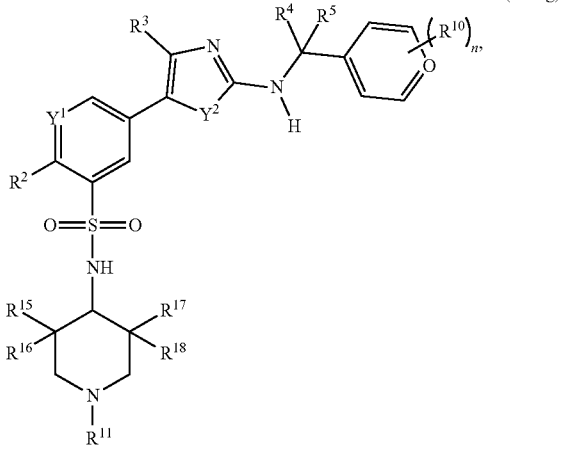
(IIG1g)

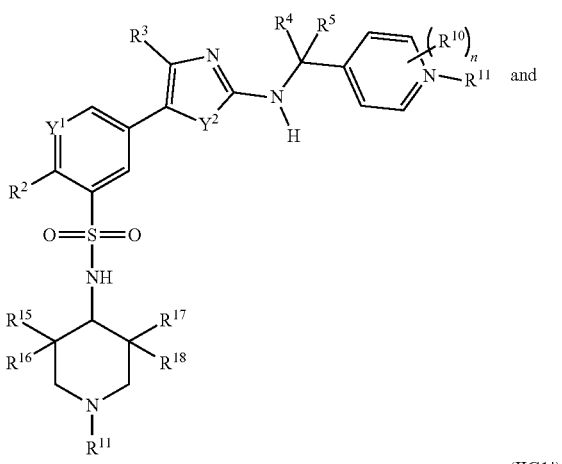
(IIG1h)

and

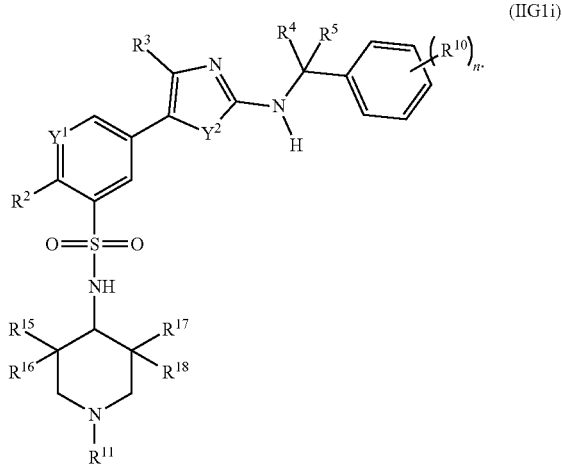
(IIG1i)

In certain embodiments, any one of formulae (IIG1a) to (IIG1i) has the relative configuration as described by formula (IIG1ii). In certain embodiments, any one of formulae (IIG1a) to (IIG1i) has the relative configuration as described by formula (IIG1iii).

In some embodiments of any one of the formulae (IIG1a) to (IIG1i), (IIG1ii) or (IIG1iii), $Y^2$ is S. In some embodiments of any one of the formulae (IIG1a) to (IIG1i), (IIG1ii) or (IIG1iii), $Y^1$ is CH. In some embodiments of any one of the formulae (IIG1a) to (IIG1i), (IIG1ii) or (IIG1iii), $Y^2$ is S and $Y^1$ is CH. In some embodiments of any one of the formulae (IIG1a) to (IIG1i), (IIG1ii) or (IIG1iii), $Y^2$ is S and $Y^1$ is N. In some embodiments of any one of the formulae (IIG1a) to (IIG1i), (IIG1ii) or (IIG1iii), $Y^2$ is O. In some embodiments of any one of the formulae (IIG1a) to (IIG1i), (IIG1ii) or (IIG1iii), $Y^2$ is $NR^{19}$. In some embodiments of any one of the formulae (IIG1a) to (IIG1i), (IIG1ii) or (IIG1iii), $Y^2$ is NH. In some embodiments of any one of the formulae (IIG1a) to (IIG1i), (IIG1ii) or (IIG1iii), $Y^2$ is O and $Y^1$ is CH. In some embodiments of any one of the formulae (IIG1a) to (IIG1i), (IIG1ii) or (IIG1iii), $Y^2$ is $NR^{19}$ and V is CH. In some embodiments of anyone of the formulae (IIG1a) to (IIG1i), (IIG1ii) or (IIG1iii), $Y^2$ is NH and $Y^1$ is CH. In some embodiments of any one of the formulae (IIG1a) to (IIG1i), (IIG1ii) or (IIG1iii), $Y^2$ is O and $Y^1$ is N. In some embodiments of any one of the formulae (IIG1a) to (IIG1i), (IIG1ii) or (IIG1iii), $Y^2$ is $NR^{19}$ and V is N. In some embodiments of any one of the formulae (IIG1a) to (IIG1i), (IIG1ii) or (IIG1iii), $Y^2$ is NH and $Y^1$ is N.

In certain embodiments of any one of (IIG) to (IIG3), $R^{11}$ is an acyl group. In certain cases, the acyl group is —C(O)CH$_3$. In certain cases, $R^{11}$ is hydrogen. In certain cases, $R^{11}$ is a sulfonyl group. In certain cases, the sulfonyl group is —SO$_2$CH$_3$.

In certain embodiments of any one of (IIG1), (IIG1a) to (IIG1i), (IIG1ii), (IIG1iii), (IIG3) or (IIG3a), $R^5$, $R^{16}$, $R^{17}$ and $R^{18}$ are each independently selected from, hydrogen, alkyl and substituted alkyl. In certain cases, $R^{15}$, $R^{16}$, $R^{17}$ and $R^{18}$ are each hydrogen. In certain cases, $R^{15}$ is lower alkyl (e.g., methyl, ethyl, propyl, butyl, pentyl or hexyl), and $R^{16}$, $R^{17}$ and $R^{18}$ are each hydrogen. In certain cases, $R^{15}$ and $R^{17}$ are each a lower alkyl, and $R^{16}$ and $R^{18}$ are each hydrogen. In some cases, $R^{15}$ and $R^{16}$ are hydrogen, and $R^{17}$ and $R^{18}$ are each lower alkyl.

In certain embodiments of any one of (IIG) to (IIG3). $R^4$ and $R^5$ are each independently lower alkyl. In certain cases, both, $R^4$ and $R^5$ are methyl. In some cases of any one of formula (IIG) to (IIG3), $R^4$ and $R^5$ together with the carbon to which they are attached form a cycloalkyl group.

In certain embodiments of any one of (IIG) to (IIG3), $R^2$ is methoxy. In certain embodiments of any one of formulae (IIG) to (IIG3), $R^3$ is methyl.

In certain embodiments of any one of (IIG) to (IIG3), $R^2$, $R^3$, $R^4$, $R^5$ $R^{10}$, $R^{11}$, $R^{15}$, $R^{16}$, $R^{17}$ and $R^{18}$ are independently selected from corresponding groups as depicted in any of the structures of Table 1, 2 or 3.

In certain embodiments, the compound is described by one of the following structures:

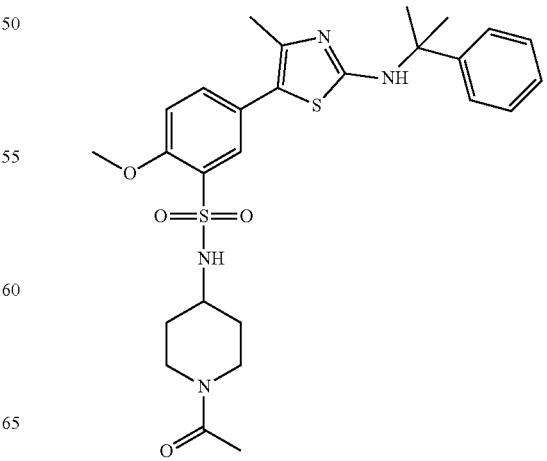

-continued

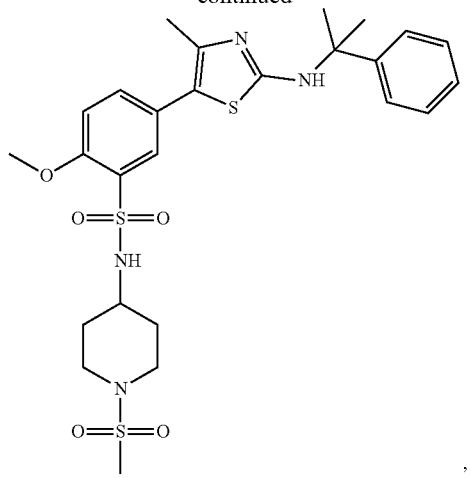

In certain embodiments, the compound is described by one of the following structures:

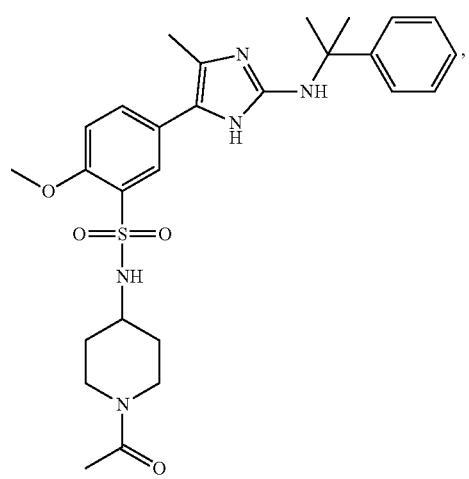

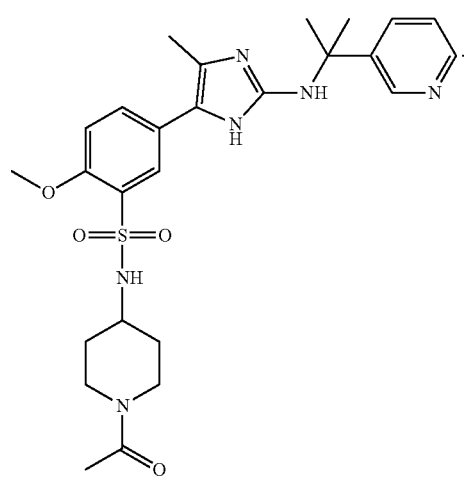

In certain embodiments of formula (II), the compound is described by formula (IIH):

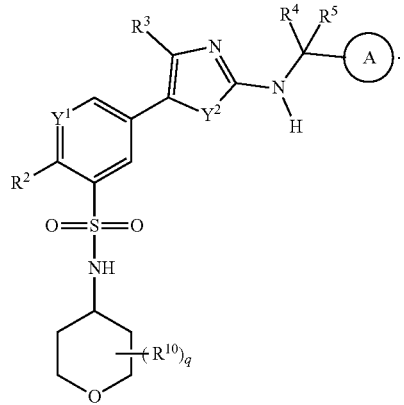

(IIH)

In certain embodiments of the formula (IIH), the compound is described by the formula (IIH1):

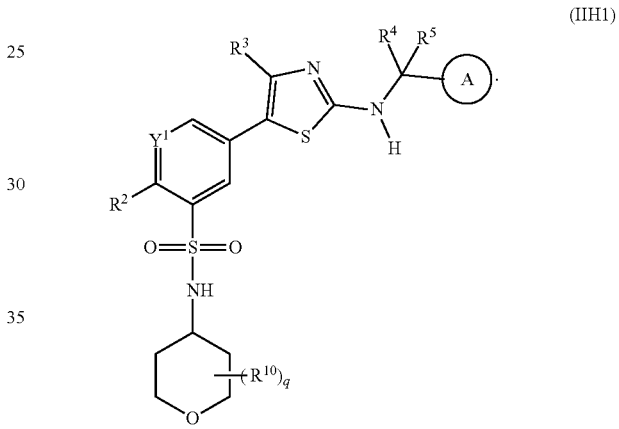

(IIH1)

In certain embodiments of the formula (IIH), the compound is described by the formula (IIH1a):

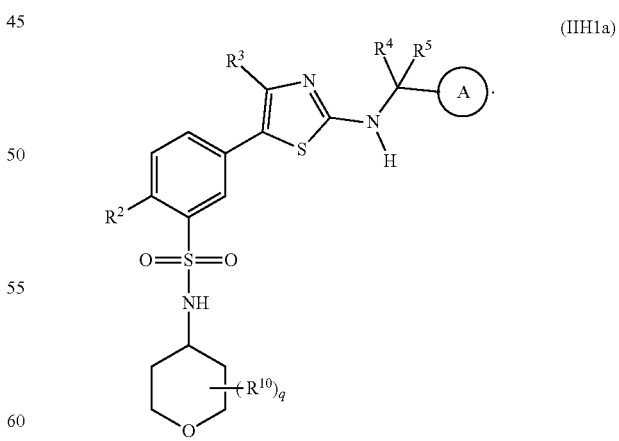

(IIH1a)

In some embodiments of any one of formulae (IIH) to (IIH1a), the A ring is selected from an aryl (e.g., a phenyl), optionally including one or more substituents. In some embodiments, the A ring is selected from a heteroaryl or a heterocycle (e.g., pyridyl, pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl) optionally including one or more substituents. In some embodiments, the A ring is selected from a cycloalkyl (e.g., a cyclohexane), optionally including one or more substituents. In some embodiments, the A ring is selected from phenyl, substituted phenyl, pyridyl, substituted pyridyl, 2-pyrimidinyl, substituted 2-pyrimidinyl, 3-pyrimidinyl, substituted 3-pyrimidinyl, 6-pyrimidinyl, substituted 6-pyrimidinyl, piperidine, substituted piperidine, piperazine, substituted piperazine, 2-oxopiperidine, 2-oxopiperazine, imidazole, substituted imidazole, thiazole, substituted thiazole, oxazole, substituted oxazole, tetrahydropyran, substituted tetrahydropyran, morpholine, substituted morpholine, cyclic sulfone, substituted cyclic sulfone, cycloalkyl and substituted cycloalkyl.

In other embodiments, the A ring is described by the formula (A1):

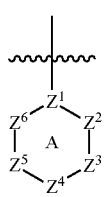

(A1)

where A1 is a 6-membered aryl, heteroaryl, heterocyclyl, or cycloalkyl, where $Z^1$-$Z^6$ are independently selected from N, O, $CR^{11}$, $NR^{11}$, $CR^{11}_2$, $SO_2$ and CO, provided that valency requirements are fulfilled, where $R^{11}$ are each independently selected from hydrogen, alkyl, substituted alkyl, hydroxy, alkoxy, substituted alkoxy, trifluoromethyl, halogen, acyl, substituted acyl, carboxy, carboxyamide, substituted carboxyamide, sulfonyl, substituted sulfonyl, sulfonamide and substituted sulfonamide. In certain cases, $Z^2$ and $Z^3$, or $Z^3$ and $Z^4$, or $Z^4$ and $Z^5$, or $Z^5$ and $Z^6$ are $CR^{11}$, wherein each $R^{11}$ together with the carbons to which they are attached form a 5-membered or 6-membered cyclic group selected from aryl, substituted aryl, heteroaryl, substituted heteroaryl, heterocycle, substituted heterocycle, cycloalkyl and substituted cycloalkyl. In certain cases, A1 is an indole or a substituted indole. In some cases, A1 is a phenyl, or substituted phenyl. In some cases, A1 is a cycloalkyl, or a substituted cycloalkyl. In some cases, A1 is pyridyl or substituted pyridyl. In some cases, A1 is pyrimidinyl, such as 2-pyrimidinyl, substituted 2-pyrimidinyl, 3-pyrimidinyl, substituted 3-pyrimidinyl, 6-pyrimidinyl or substituted 6-pyrimidinyl. In some cases, A1 is a pyridazine, or a substituted pyridazine. In some cases, A1 is a triazine, or a substituted triazine. In some cases, A1 is piperidine or substituted piperidine. In some cases, A1 is piperazine or substituted piperazine. In some cases, A1 is 2-oxopiperidine or substituted 2-oxopiperidine. In some cases, A1 is 2-oxopiperazine or substituted 2-oxopiperazine. In some cases, A1 is tetrahydropyran or substituted tetrahydropyran. In some cases, A1 is a pyran or a substituted pyran. In some cases, A1 is morpholine or substituted morpholine. In some cases, A1 is a cyclic sulfone or a substituted cyclic sulfone.

In some embodiments of any of the formulae (IIH) to (IIH1a), the A ring is selected from any of the formulae (B2) to (B8), e.g., as described herein. In certain embodiments of any one of formulae (IIH) to (IIH1a), the A ring is selected from the following groups:

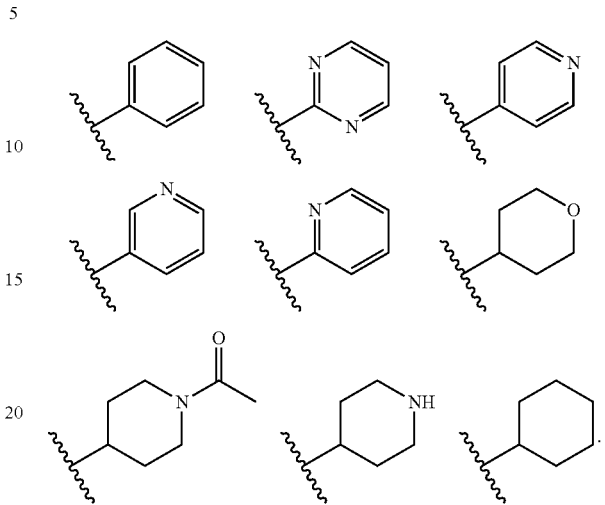

In certain embodiments, of any one of formulae (IIH), (IIH1) or (IIH1a), q is 0, such that there are no $R^{10}$ substituents.

In certain embodiments, of the formula (IIH), the compound is described by any of formulae (IIH1b) co (IIH1j):

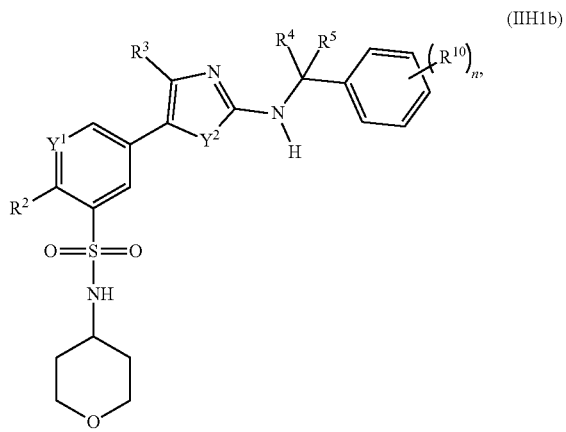

(IIH1b)

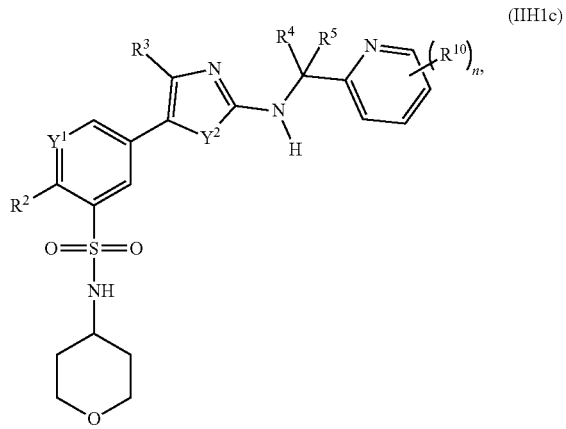

(IIH1c)

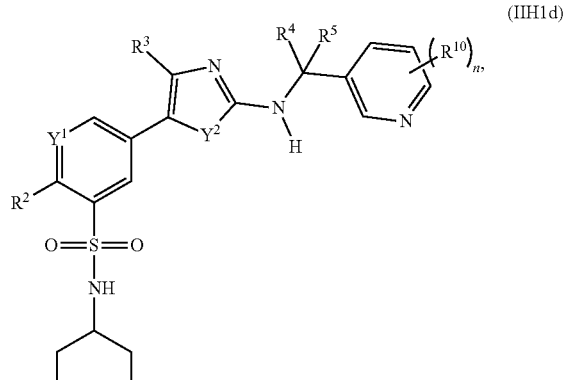
(IIH1d)

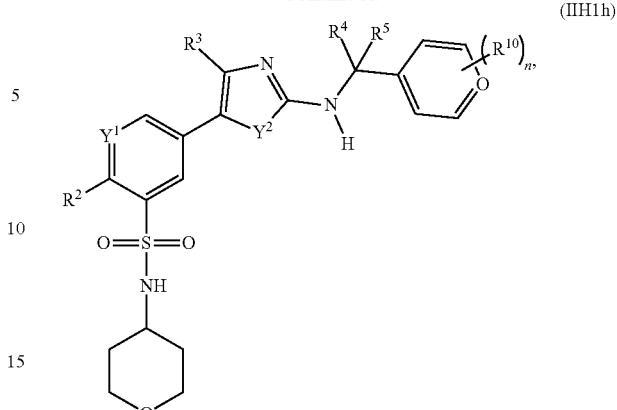
(IIH1h)

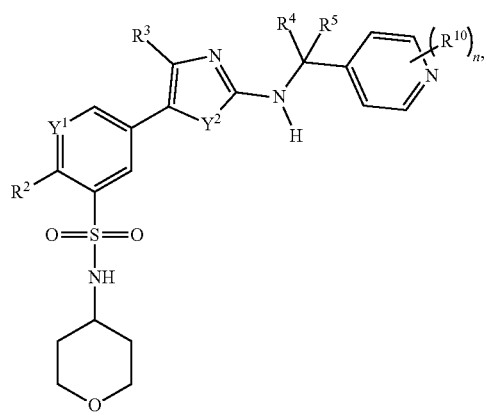
(IIH1e)

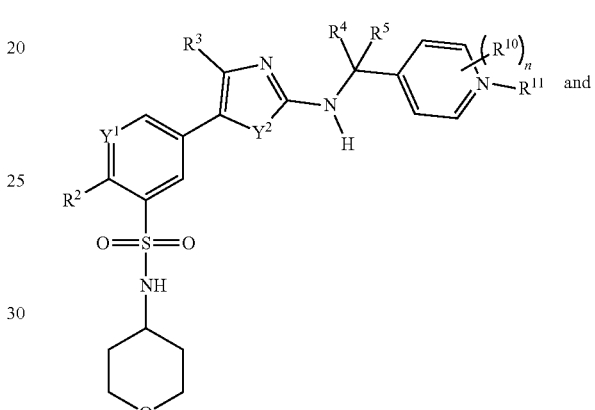
(IIH1i) and

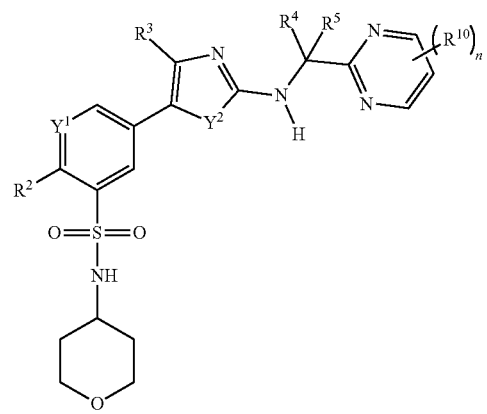
(IIH1f)

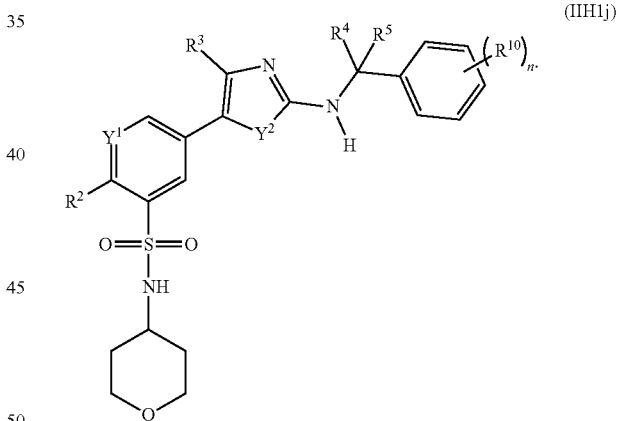
(IIH1j)

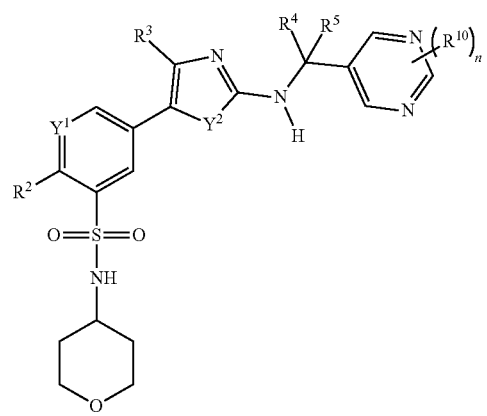
(IIH1g)

In some embodiments of any one of the formulae (IIH1b) to (IIH1j), $Y^2$ is S. In some embodiments of any one of the formulae (IIH1b) to (IIH1j), $Y^1$ is CH. In some embodiments of any one of the formulae (IIH1b) to (IIH1j), $Y^2$ is S and $Y^1$ is CH. In some embodiments of any one of the formulae (IIH1b) to (IIH1j), $Y^2$ is S and $Y^1$ is N. In some embodiments of any one of the formulae (IIH1b) to (IIH1j), $Y^2$ is O. In some embodiments of any one of the formulae (IIH1b) to (IIH1j), $Y^2$ is $NR^{19}$. In some embodiments of any one of the formulae (IIH1b) to (IIH1j), $Y^2$ is NH. In some embodiments of anyone of the formulae (IIH1b) to (IIH1j), $Y^2$ is C and $Y^1$ is CH. In some embodiments of any one of the formulae (IIH1b) to (IIH1j), $Y^2$ is $NR^{19}$ and $Y^1$ is CH. In some embodiments of any one of the formulae (IIH1b) to (IIH1j), $Y^2$ is NH and $Y^1$ is CH. In some embodiments of any one of the formulae (IIH1b) to (IIH1j), $Y^2$ is O and $Y^1$ is N. In some embodiments of any one of the formulae (IIH1b) to (IIH1j), $Y^2$ is $NR^{19}$ and $Y^1$ is N. In some embodiments of any one of the formulae (IIH1b) to (IIH1j), $Y^2$ is NH and $Y^1$ is N.

In certain embodiments of any one of (IIH) to (IIH1j), $R^4$ and $R^5$ are each independently lower alkyl. In certain cases, both, $R^4$ and $R^5$ are methyl. In some cases of any one of formula (IIH) to (IIH1j), $R^4$ and $R^5$ together with the carbon to which they are attached form a cycloalkyl group.

In certain embodiments of any one of (IIH) to (IIH1j), $R^2$ is methoxy. In certain embodiments of any one of formulae (IIH) to (IIH1j), $R^3$ is methyl.

In certain embodiments of any one of (IIH) to (IIH1j), $R^2$, $R^3$, $R^4$, $R^5$ and $R^{10}$ are independently selected from corresponding groups as depicted in any of the structures of Table 1, 2 or 3.

In certain embodiments of formula (II), the compound is described by formula (IIJ):

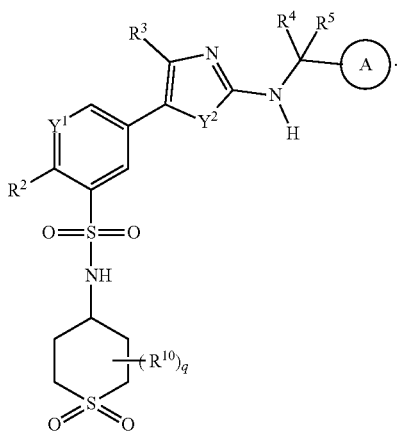

(IIJ)

In certain embodiments of the formula (IIJ), the compound is described by the formula (IIJ1a):

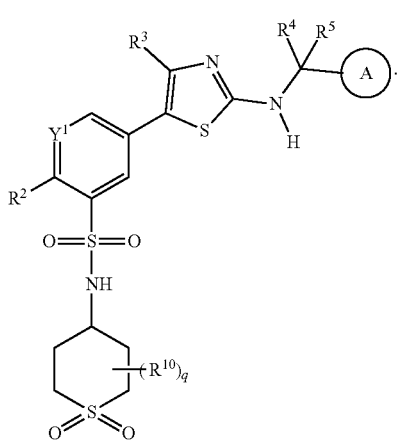

(IIJ1)

In certain embodiments of the formula (IIJ), the compound is described by the formula (IIJ1a):

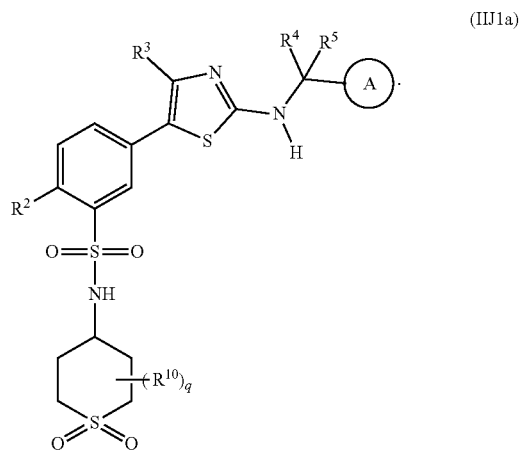

(IIJ1a)

In certain embodiments of any one of formulae (IIJ), (IIJ1) or (IIJ1a), q is 0, such that there are no $R^{10}$ substituents.

In some embodiments of any one of formulae (IIJ), (IIJ1) or (IIJ1a), the A ring is selected from an aryl (e.g., a phenyl), optionally including one or more substituents. In some embodiments, the A ring is selected from a heteroaryl or a heterocycle (e.g., pyridyl, pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl) optionally including one or more substituents. In some embodiments, the A ring is selected from a cycloalkyl (e.g., a cyclohexane), optionally including one or more substituents. In some embodiments, the A ring is selected from phenyl, substituted phenyl, pyridyl, substituted pyridyl, 2-pyrimidinyl, substituted 2-pyrimidinyl, 3-pyrimidinyl, substituted 3-pyrimidinyl, 6-pyrimidinyl, substituted 6-pyrimidinyl, piperidine, substituted piperidine, piperazine, substituted piperazine, 2-oxopiperidine, 2-oxopiperazine, imidazole, substituted imidazole, thiazole, substituted thiazole, oxazole, substituted oxazole, tetrahydropyran, substituted tetrahydropyran, morpholine, substituted morpholine, cyclic sulfone, substituted cyclic sulfone, cycloalkyl and substituted cycloalkyl.

In other embodiments, the A ring is described by the formula (A1):

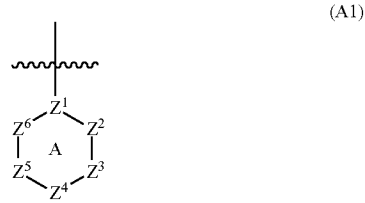

(A1)

where A1 is a 6-membered aryl, heteroaryl, heterocyclyl, or cycloalkyl, where $Z^1$-$Z^6$ are independently selected from N, O, $CR^{11}$, $NR^{11}$, $CR^{11}_2$, $SO_2$ and CO, provided that valency requirements are fulfilled, where $R^{11}$ are each independently selected from hydrogen, alkyl, substituted alkyl, hydroxy, alkoxy, substituted alkoxy, trifluoromethyl, halogen, acyl, substituted acyl, carboxy, carboxyamide, substituted carboxyamide, sulfonyl, substituted sulfonyl, sulfonamide and substituted sulfonamide. In certain cases, $Z^2$ and $Z^3$, or $Z^3$ and $Z^4$, or $Z^4$ and $Z^5$, or $Z^5$ and $Z^6$ are $CR^{11}$, wherein each $R^{11}$ together with the carbons to which they are attached form a 5-membered or 6-membered cyclic group selected from aryl, substituted aryl, heteroaryl, substituted heteroaryl, heterocycle, substituted heterocycle, cycloalkyl and substituted cycloalkyl. In certain cases, A1 is an indole or a substituted indole. In some cases, A1 is a phenyl, or substituted phenyl. In some cases, A1 is a cycloalkyl, or a substituted cycloalkyl. In some cases, A1 is pyridyl or substituted pyridyl. In some cases, A1 is pyrimidinyl, such as 2-pyrimidinyl, substituted 2-pyrimidinyl, 3-pyrimidinyl, substituted 3-pyrimidinyl, 6-pyrimidinyl or substituted 6-pyrimidinyl. In some cases, A1 is a pyridazine, or a substituted pyridazine. In some cases, A1 is a triazine, or a substituted triazine. In some cases, A1 is piperidine or substituted piperidine. In some cases, A1 is piperazine or substituted piperazine. In some cases, A1 is 2-oxopiperidine or substituted 2-oxopiperidine. In some cases, A1 is 2-oxopiperazine or substituted 2-oxopiperazine. In some cases, A1 is tetrahydropyran or substituted tetrahydropyran. In some cases, A1 is a pyran or a substituted pyran. In some cases, A1 is morpholine or substituted morpholine. In some cases. A1 is a cyclic sulfone or a substituted cyclic sulfone.

In some embodiments of any of formulae (IIJ), (IIJ1) or (IIJ1a), the A ring is selected from any of the formulae (B2) to (B8), e.g., as described herein. In certain embodiments of any one of formulae (IIJ), (IIJ1) or (IIJ1a), the A ring is selected from the following structures:

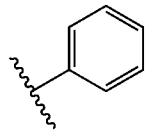 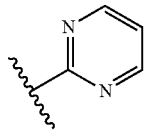 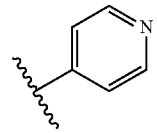

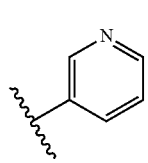 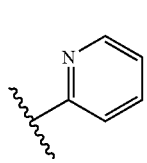 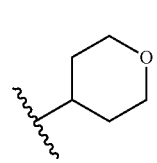

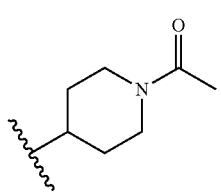 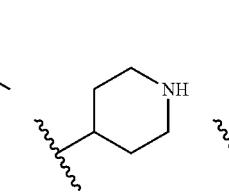 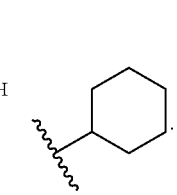

In certain embodiments, of the formula (IIJ), the compound is described by any of formulae (IIJ1b) to (IIJ1j):

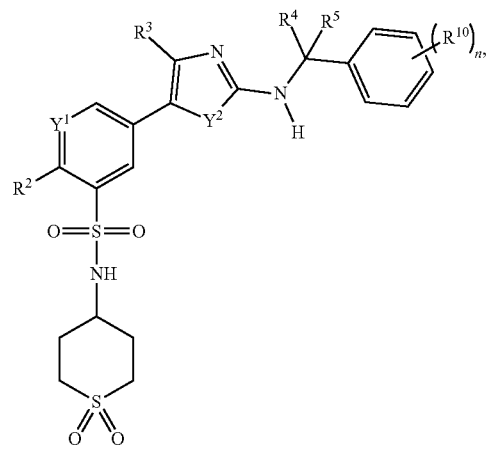

(IIJ1b)

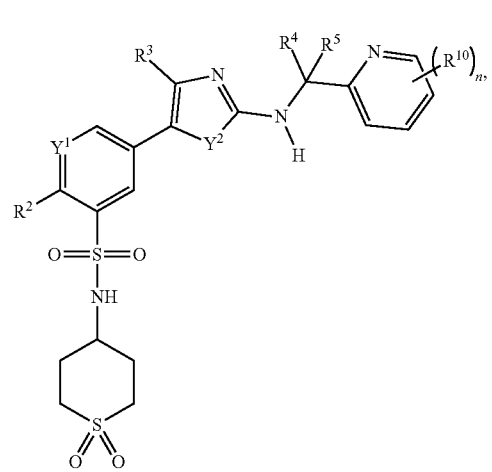

(IIJ1c)

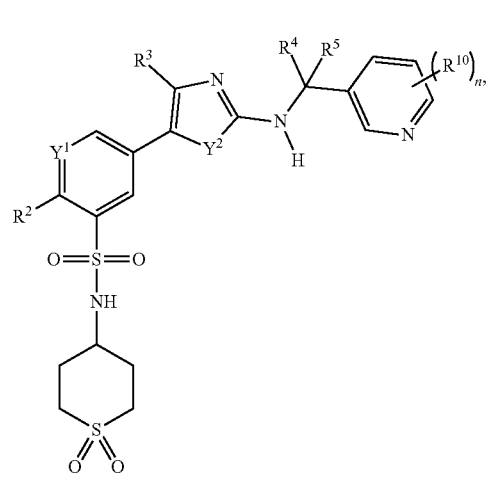

(IIJ1d)

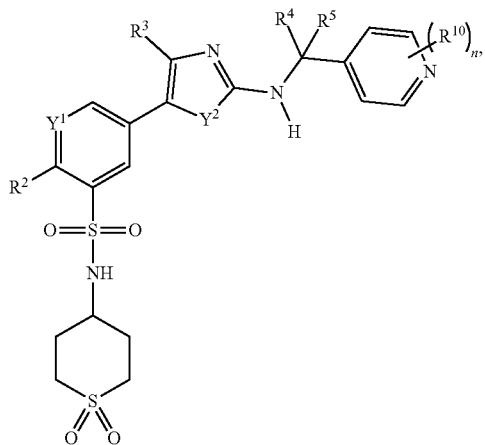
(IIJ1e)

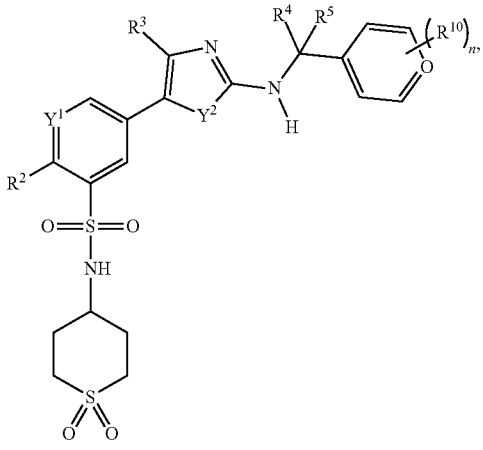
(IIJ1h)

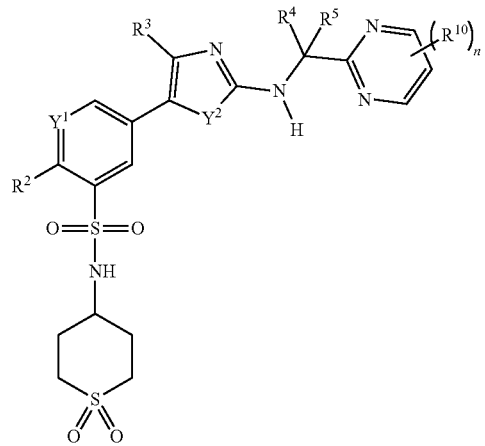
(IIJ1f)

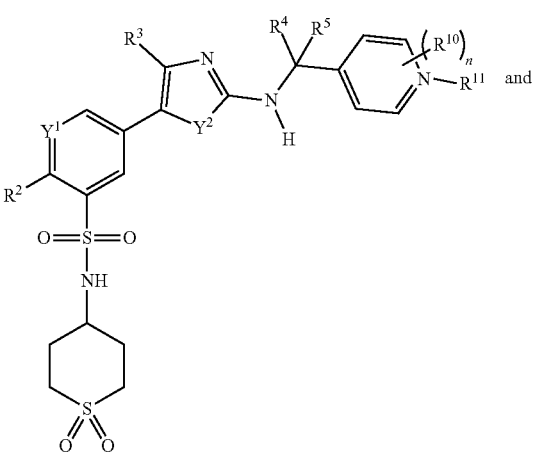
(IIJ1i)

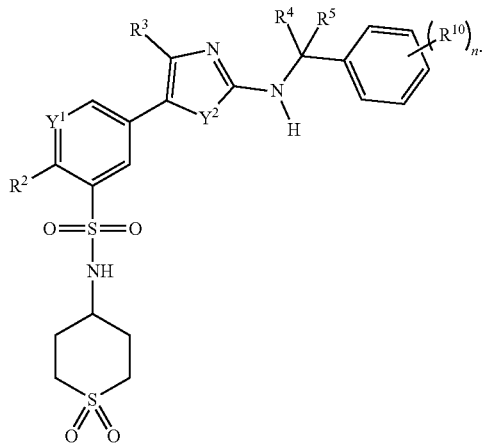
(IIJ1j)

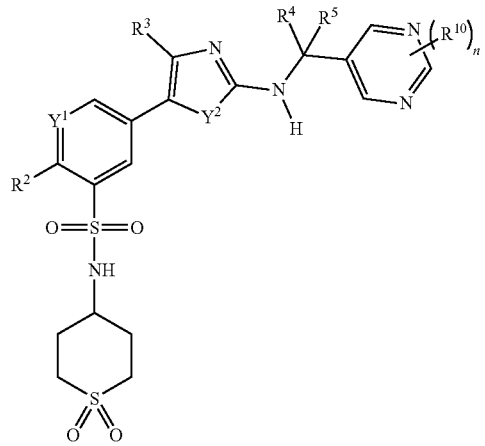
(IIJ1g)

In some embodiments of any one of the formulae (IIJ1b) to (IIJ1j), $Y^2$ is S. In some embodiments of any one of the formulae (IIJ1 b) to (IIJ1j), $Y^1$ is CH. In some embodiments of any one of the formulae (IIJ1b) to (IIJ1j), $Y^2$ is S and $Y^1$ is CH. In some embodiments of any one of the formulae (IIJ1b) to (IIJ1j), $Y^2$ is S and $Y^1$ is N. In some embodiments of any one of the formulae (IIJ1b) to (IIJ1j), $Y^2$ is O. In some embodiments of any one of the formulae (IIJ1b) to (IIJ1j), $Y^1$ is $NR^{19}$. In some embodiments of any one of the formulae (IIJ1b) to (IIJ1j), $Y^2$ is NH. In some embodiments of any one of the formulae (IIJ1b) to (IIJ1j), $Y^2$ is O and $Y^1$ is CH. In some embodiments of any one of the formulae (IIJ1b) to (IIJ1j), $Y^2$ is $NR^{19}$ and $Y^1$ is CH. In some embodiments of any one of the formulae (IIJ1b) to (IIJ1j), $Y^2$ is NH and $Y^1$ is CH. In some embodiments of any one of the formulae (IIJ1b) to (IIJ1j), $Y^2$ is O and $Y^1$ is N. In some embodiments of any one of the formulae (IIJ1b) to (IIJ1j), $Y^2$ is $NR^{19}$ and $Y^1$ is N. In some embodiments of any one of the formulae (IIJ1b) to (IIJ1j), $Y^2$ is NH and $Y^1$ is N.

In certain embodiments of any one of (IIJ) to (IIJ1j), $R^4$ and $R^5$ are each independently lower alkyl. In certain cases, both, $R^4$ and $R^5$ are methyl. In some cases of any one of formula (IIJ) to (IIJ1j), $R^4$ and $R^5$ together with the carbon to which they are attached form a cycloalkyl group.

In certain embodiments of any one of (IIJ) to (IIJ1j), $R^1$ is methoxy. In certain embodiments of any one of formulae (IIJ) to (IIJ1j), $R^3$ is methyl.

In certain embodiments of any one of (IIJ) to (IIJ1j), $R^2$, $R^3$, $R^4$, $R^5$ and $R^{10}$ are independently selected from corresponding groups as depicted in any of the structures of Table 1, 2 or 3.

In certain embodiments, the compound is described by the following structure:

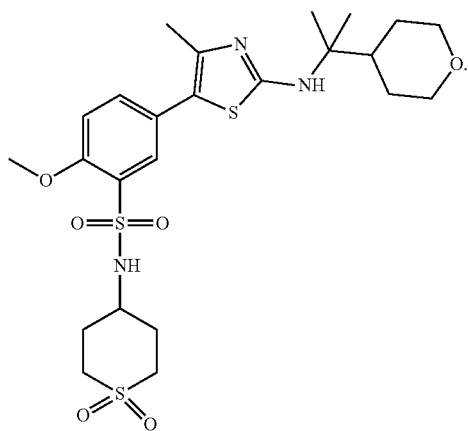 [SMILES: COc1ccc(-c2sc(NC(C)(C)C3CCOCC3)nc2C)cc1S(=O)(=O)NC1CCS(=O)(=O)CC1]

In certain embodiments of formula (II), the compound is described by formula (IIK):

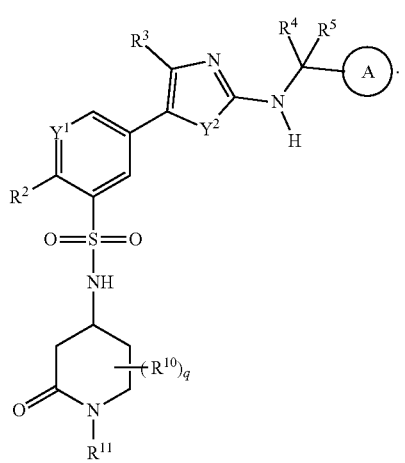

In certain embodiments of the formula (IIK), the compound is described by formula (IIK1):

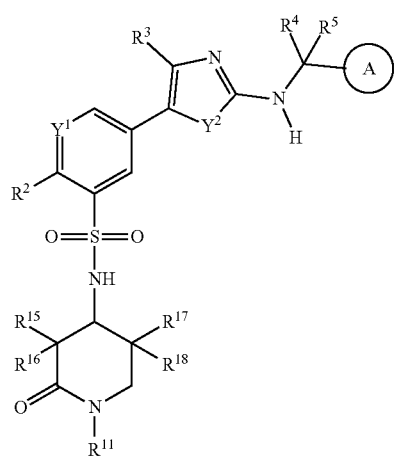

wherein:
$R^{11}$ is selected from $R^{10}$, acyl, substituted acyl, carboxy, carboxyamide, substituted carboxyamide, sulfonyl and substituted sulfonyl; and
$R^{15}$, $R^{16}$, $R^{17}$ and $R^{18}$ are each independently selected from, hydrogen, alkyl, substituted alkyl, hydroxy, alkoxy, substituted alkoxy, trifluoromethyl and halogen.

In certain embodiments of the formula (IIK), the compound is described by the formula (IIK2) or (IIK3):

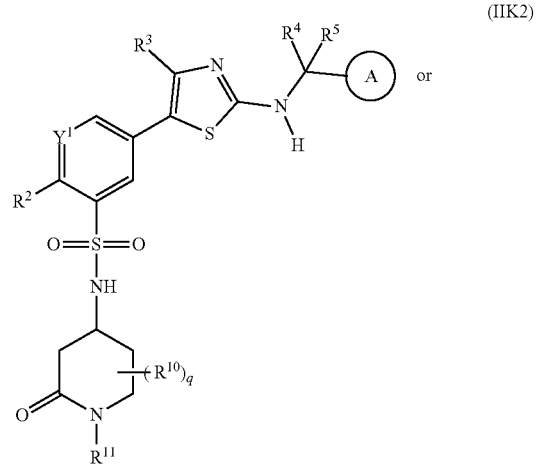

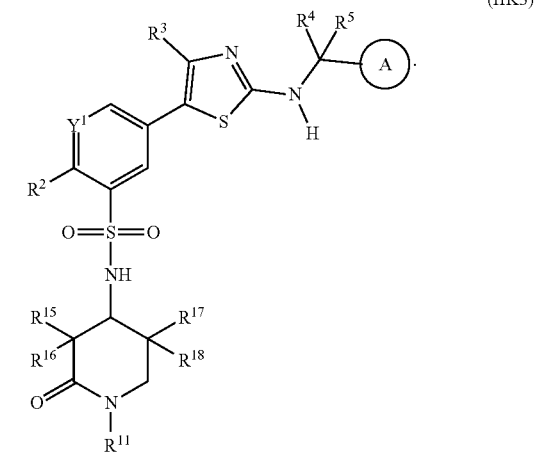

In certain embodiments of the formula (IIK), the compound is described by the formula (IIK2a) or (IIK3a):

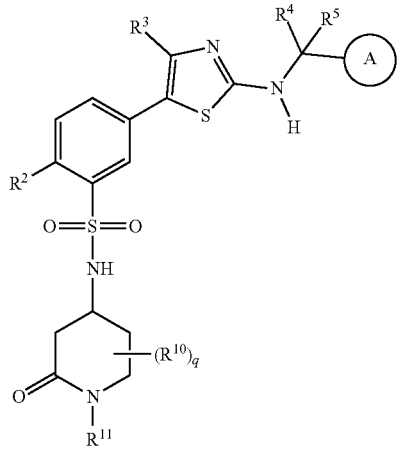

(IIK2a)

or

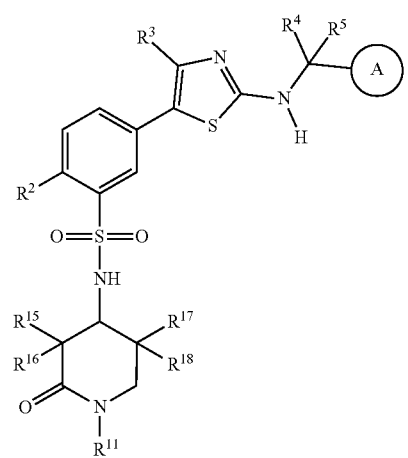

(IIK3a)

In certain embodiments, the formula (IIK1) has the relative configuration of formulae (IIK1ii) or (IIK1iii):

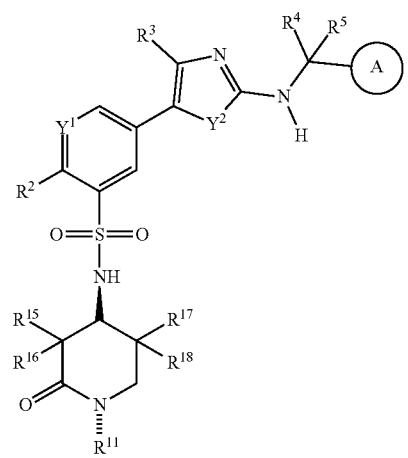

(IIK1ii)

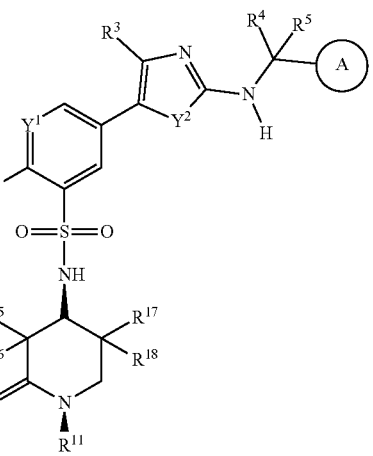

(IIK1iii)

In some embodiments of any one of formulae (IIK) to (IIK3), the A ring is selected from an aryl (e.g., a phenyl), optionally including one or more substituents. In some embodiments, the A ring is selected from a heteroaryl or a heterocycle (e.g., pyridyl, pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl) optionally including one or more substituents. In some embodiments, the A ring is selected from a cycloalkyl (e.g., a cyclohexane), optionally including one or more substituents. In some embodiments, the A ring is selected from phenyl, substituted phenyl, pyridyl, substituted pyridyl, 2-pyrimidinyl, substituted 2-pyrimidinyl, 3-pyrimidinyl, substituted 3-pyrimidinyl, 6-pyrimidinyl, substituted 6-pyrimidinyl, piperidine, substituted piperidine, piperazine, substituted piperazine, 2-oxopiperidine, 2-oxopiperazine, imidazole, substituted imidazole, thiazole, substituted thiazole, oxazole, substituted oxazole, tetrahydropyran, substituted tetrahydropyran, morpholine, substituted morpholine, cyclic sulfone, substituted cyclic sulfone, cycloalkyl and substituted cycloalkyl.

In other embodiments, the A ring is described by the formula (A1):

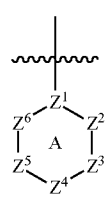

(A1)

where A1 is a 6-membered aryl, heteroaryl, heterocyclyl, or cycloalkyl, where $Z^1$-$Z^6$ are independently selected from N, O, $CR^{11}$, $NR^{11}$, $CR^{11}_2$, $SO_2$ and CO, provided that valency requirements are fulfilled, where $R^{11}$ are each independently selected from hydrogen, alkyl, substituted alkyl, hydroxy, alkoxy, substituted alkoxy, trifluoromethyl, halogen, acyl, substituted acyl, carboxy, carboxyamide, substituted carboxyamide, sulfonyl, substituted sulfonyl, sulfonamide and substituted sulfonamide. In certain cases, $Z^2$ and $Z^3$, or $Z^3$ and $Z^4$, or $Z^4$ and $Z^5$, or $Z^5$ and $Z^6$ are $CR^{11}$, wherein each $R^{11}$ together with the carbons to which they are attached form a 5-membered or 6-membered cyclic group selected from aryl, substituted aryl, heteroaryl, substituted heteroaryl, heterocycle, substituted heterocycle, cycloalkyl and substituted cycloalkyl. In certain cases, A1 is an indole or a substituted indole. In some cases, A1 is a phenyl, or substituted phenyl. In some cases, A1 is a cycloalkyl, or a substituted cycloalkyl. In some cases, A1 is pyridyl or substituted pyridyl. In some cases, A1 is pyrimidinyl, such as 2-pyrimidinyl, substituted 2-pyrimidinyl, 3-pyrimidinyl, substituted 3-pyrimidinyl, 6-pyrimidinyl or substituted 6-pyrimidinyl. In some cases, A1 is a pyridazine, or a substituted pyridazine. In some cases, A1 is a triazine, or a substituted triazine. In some cases, A1 is piperidine or substituted piperidine. In some cases, A1 is piperazine or substituted piperazine. In some cases, A1 is 2-oxopiperidine or substituted 2-oxopiperidine. In some cases, A1 is 2-oxopiperazine or substituted 2-oxopiperazine. In some cases, A1 is tetrahydropyran or substituted tetrahydropyran. In some cases, A1 is a pyran or a substituted pyran. In some cases, A1 is morpholine or substituted morpholine. In some cases. A1 is a cyclic sulfone or a substituted cyclic sulfone.

In some embodiments of any one of the formulae (IIK) to (IIK3), the A ring is selected from any of the formulae (B2) to (B8), e.g., as described herein. In certain embodiments of any one of formulae (IIK) to (IIK3), the A ring is selected from the following structures:

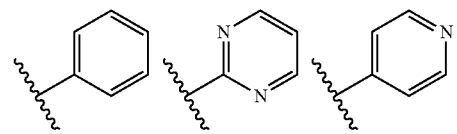

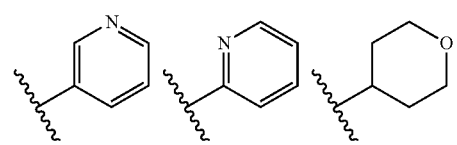

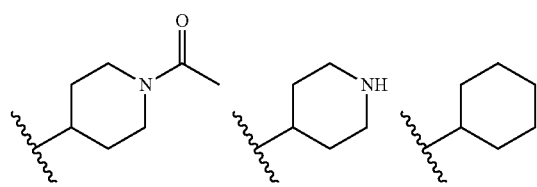

In certain embodiments of the formula (IIK1), the compound is described by any one of the formulae (IIK1a) to (IIK1i):

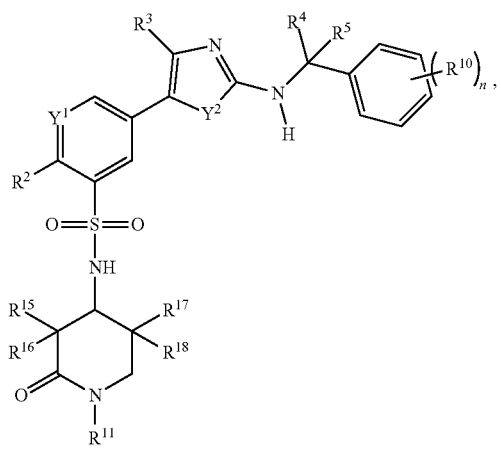
(IIK1a)

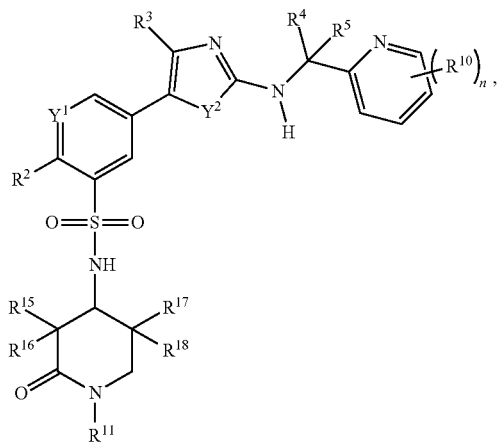
(IIK1b)

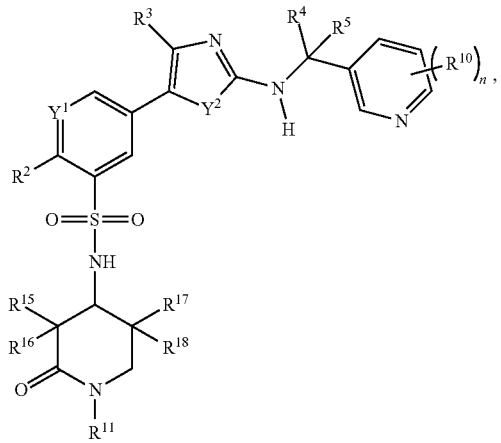
(IIK1c)

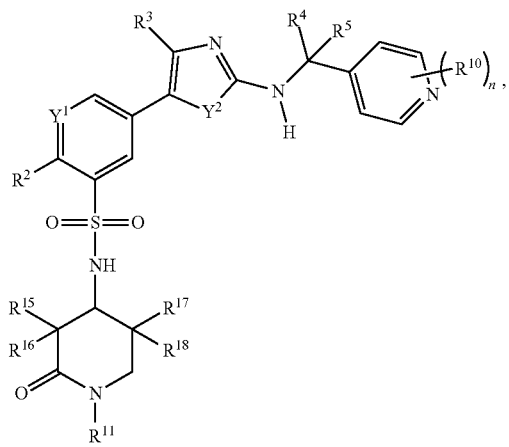

(IIK1d)

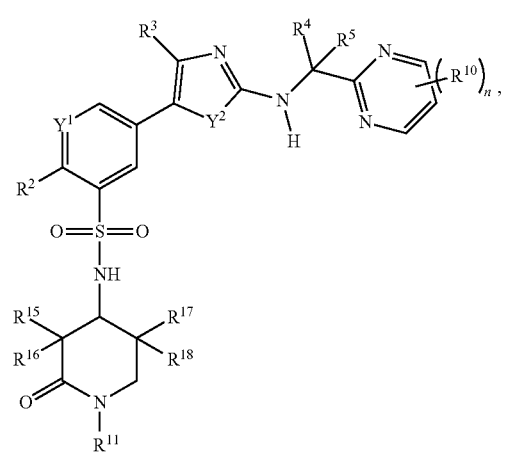

(IIK1e)

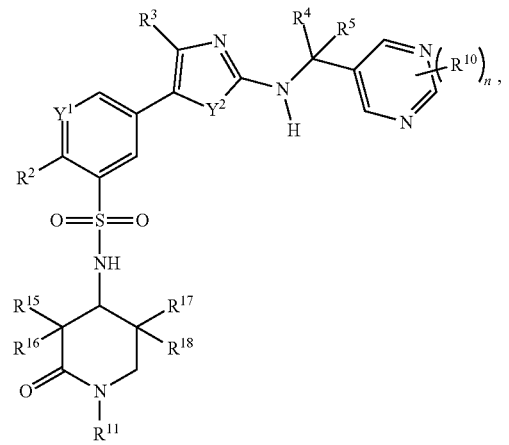

(IIK1f)

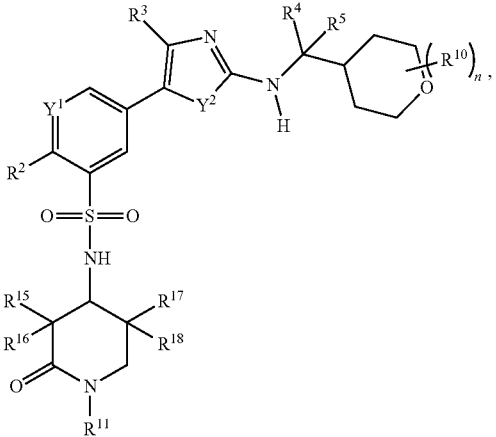

(IIK1g)

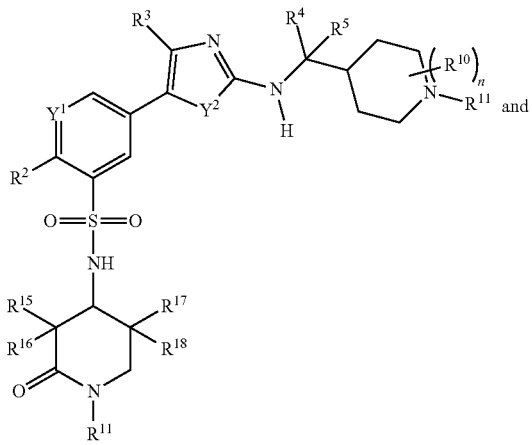

(IIK1h)

and

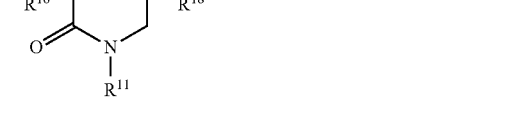

(IIK1i)

In certain embodiments, any one of formulae (IIK1a) to (IIK1i) has the relative configuration as described by formula (IIK1ii). In certain embodiments, any one of formulae (IIK1a) to (IIK1i) has the relative configuration as described by formula (UK liii).

In some embodiments of any one of the formulae (IIK1a) to (IIK1i), (IIK1ii) or (IIK1iii), $Y^2$ is S. In some embodiments of any one of the formulae (IIK1a) to (IIK1i), (IIK1ii) or (IIK1iii), $Y^1$ is CH.

In some embodiments of any one of the formulae (IIK1a) to (IIK1i), (IIK1ii) or (IIK1iii), Y² is S and Y¹ is CH. In some embodiments of any one of the formulae (IIK1a) to (IIK1i), (IIK1ii) or (IIK1iii), Y² is S and Y¹ is N. In some embodiments of any one of the formulae (IIK1a) to (IIK1i), (IIK1ii) or (IIK1iii), Y² is O. In some embodiments of any one of the formulae (IIK1a) to (IIG1i), (IIG1ii) or (IIG1iii), Y² is NR¹⁹. In some embodiments of any one of the formulae (IIG1a) to (IIG1i), (IIG1ii) or (IIG1iii), Y² is NH. In some embodiments of any one of the formulae (IIG1a) to (IIG1i), (IIG1ii) or (IIG1iii), Y² is O and Y¹ is CH. In some embodiments of any one of the formulae (IIG1a) to (IIG1i), (IIG1ii) or (IIG1 iii), Y² is NR and Y¹ is CH. In some embodiments of anyone of the formulae (IIG1a) to (IIG1i), (IIG1ii) or (IIG1iii), Y² is NH and Y¹ is CH. In some embodiments of any one of the formulae (IIG1a) to (IIG1i), (IIG1ii) or (IIG1iii). Y² is O and Y¹ is N. In some embodiment of any one of the formulae (IIG1a) to (IIG1i), (IIG1ii) or (IIG1iii), Y² is NR¹⁹ and Y¹ is N. In some embodiments of any one of the formulae (IIG1a) to (IIG1i), (IIG1ii) or (IIG1iii), Y² is NH and Y¹ is N.

In certain embodiments of any one of (IIK) to (IIK3a), R¹¹ is hydrogen. In certain embodiments of any one of (IIK1), (IIK1a) to (IIK1ii), (IIK1ii), (IIK1iii), (IIK3) or (IIK3a), R¹⁵, R¹⁶, R¹⁷ and R¹⁸ are each independently selected from, hydrogen, alkyl and substituted alkyl. In certain cases, R¹⁵, R¹⁶, R¹⁷ and R¹⁸ are each hydrogen. In certain cases, R¹⁵ is lower alkyl (e.g., methyl, ethyl, propyl, butyl, pentyl or hexyl), and R¹⁶, R¹⁷ and R¹⁸ are each hydrogen. In certain cases, R¹⁵ and R¹⁷ are each a lower alkyl, and R¹⁶ and R¹⁸ are each hydrogen. In some cases, R¹⁵ and R¹⁶ are hydrogen, and R¹⁷ and R¹⁸ are each lower alkyl.

In certain embodiments of any one of (IIK) to (IIK3a), R⁴ and R⁵ are each independently lower alkyl. In certain cases, both, R' and R' are methyl. In some cases of any one of formula (IIK) to (IIK3a), R⁴ and R⁵ together with the carbon to which they are attached form a cycloalkyl group.

In certain embodiments of any one of (IIK) to (IIK3a), R² is methoxy. In certain embodiments of any one of formulae (IIK) to (IIK3a), R³ is methyl.

In certain embodiments of any one of (IIK) to (IIK3a), R², R³, R⁴, R⁵ R¹⁰, R¹¹, R¹², R¹⁶, R¹⁷ and R¹⁸ are independently selected from corresponding groups as depicted in any of the structures of Table 1,2 or 3.

In certain embodiments, the compound is described by the following structure:

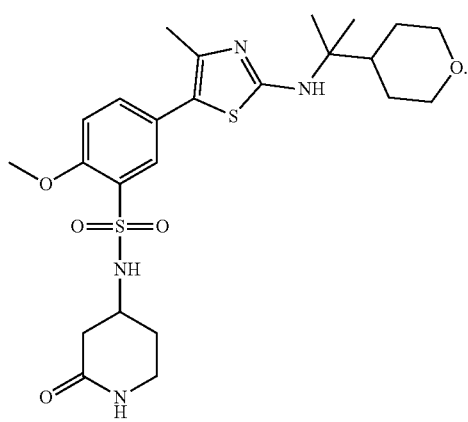 [SMILES: COc1ccc(-c2sc(NC(C)(C)C3CCOCC3)nc2C)cc1S(=O)(=O)NC1CCNC(=O)C1]

In certain embodiments, the compound is described by the structure of formula (III):

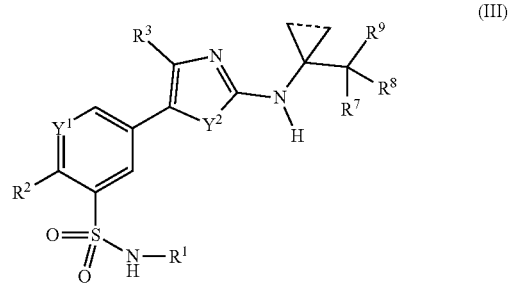

wherein:
--- is absent or a bond;
R⁷ and R⁸ are each independently selected from H, halogen, alkyl and substituted lower alkyl; and
R⁹ is a substituted alkyl cycloalkyl, substituted cycloalkyl, aryl, substituted aryl, heterocycle, substituted heterocycle, heteroaryl and substituted heteroaryl.

In certain embodiments, the compound of formula (III) is described by the formulae (IIA) or (IIB):

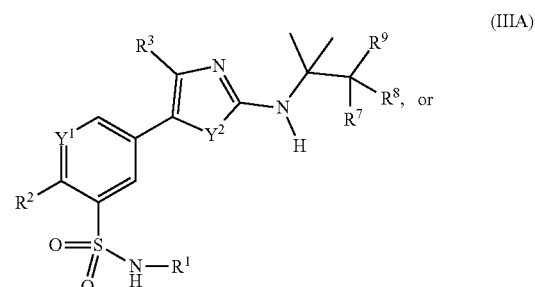

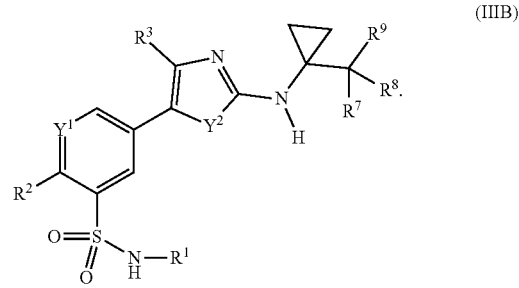

In some embodiments of any one of the formulae (III) to (IIIB), Y² is S. In some embodiments of any one of the formulae (III) to (IIIB), Y¹ is CH. In some embodiments of any one of the formulae (III) to (IIIB), Y² is S and Y¹ is CH. In some embodiments of any one of the formulae (III) to (IIIB), Y² is S and Y¹ is N. In some embodiments of any one of the formulae (III) to (IIIB), Y² is O. In some embodiments of any one of the formulae (III) to (IIIB), Y² is NR¹⁹. In some embodiments of any one of the formulae (III) to (IIIB), Y² is NH. In some embodiments of any one of the formulae (I) to (IIIB), Y² is O and Y¹ is CH. In some embodiments of any one of the formulae (III) to (IIIB), Y² is NR¹⁹ and Y¹ is CH. In some embodiments of any one of the formulae (III) to (IIIB), Y² is NH and Y¹ is CH. In some embodiments of any one of the formulae (III) to (IIIB), Y² is O and Y¹ is N. In some embodiments of any one of the formulae (III) to (IIIB), Y² is NR¹⁹ and Y¹ is N. In some embodiments of any one of the formulae (III) to (IIIB), Y² is NH and Y¹ is N.

In certain embodiments of any one of formulae (III) to (IIB), R⁷ and R⁸ are each hydrogen. In certain cases, R⁹ is trifluoromethyl. In some cases of any one of formulae (III) to (IIIB), R⁹ may be represented by the formula —(CH₂)ₙ—X¹, where n is 0, 1, 2 or 3; and X¹ hydroxyl, halogen, alkyl halide (e.g., CF₃), an aryl (e.g., a phenyl) or a heterocycle (e.g., pyridyl (e.g., 3-pyridyl), pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl). In some instances, X¹ is a cycloalkyl or a hetercycle (e.g., a 5- or 6-membered saturated N-containing heterocycle). In certain cases, X¹ is selected from a cyclohexyl, a cyclopentyl, a cyclopropyl, a pyrrolidinyl, a piperidinyl, a tetrahydrofuranyl, a phenyl and a pyridinyl. In certain cases, X¹ may be represented by ring A (e.g., as described herein).

In certain embodiments of any one of formulae (III) to (IIIB) R² is methoxy. In certain embodiments of any one of formulae (Ill) to (IB), R³ is methyl.

In some embodiments of any one of formula (III) to (IB), R¹ is described by the formula —(CH₂)ₙ—X¹, where n is 0, 1, 2 or 3; and X¹ is a lower alkyl (e.g., methyl), hydroxyl, halogen, alkyl halide, an aryl (e.g., a phenyl) or a heterocycle (e.g., pyridyl (e.g., 3-pyridyl), pyrimidinyl, pyrrolyl, pyrrolidinyl, quinolinyl, indolyl, furyl, imidazolyl, oxazolyl, thiazolyl, 1,2,4-triazolyl, tetrazolyl, pyrrolidino, morpholino, piperazino, piperidino, tetrahydrofuranyl). In some cases, R¹ or X¹ may be represented by ring B (e.g., as described herein).

In certain embodiments of any one of (III) to (IIIB), R¹, R², R³, R⁷ R⁸ and R⁹ are independently selected from corresponding groups as depicted in any of the structures of Table 1, 2 or 3.

In some embodiments, the subject compound is described by the structure of formula (VI):

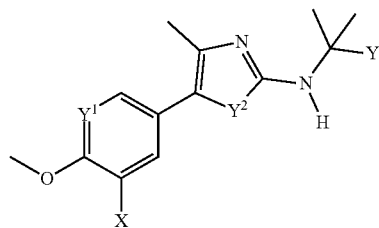

(VI)

where X and Y are independently selected from the substituents shown below:

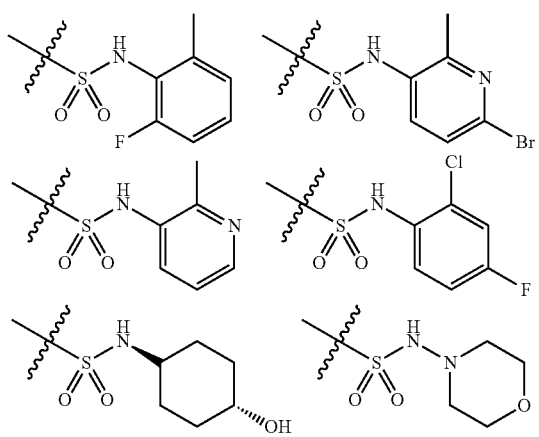

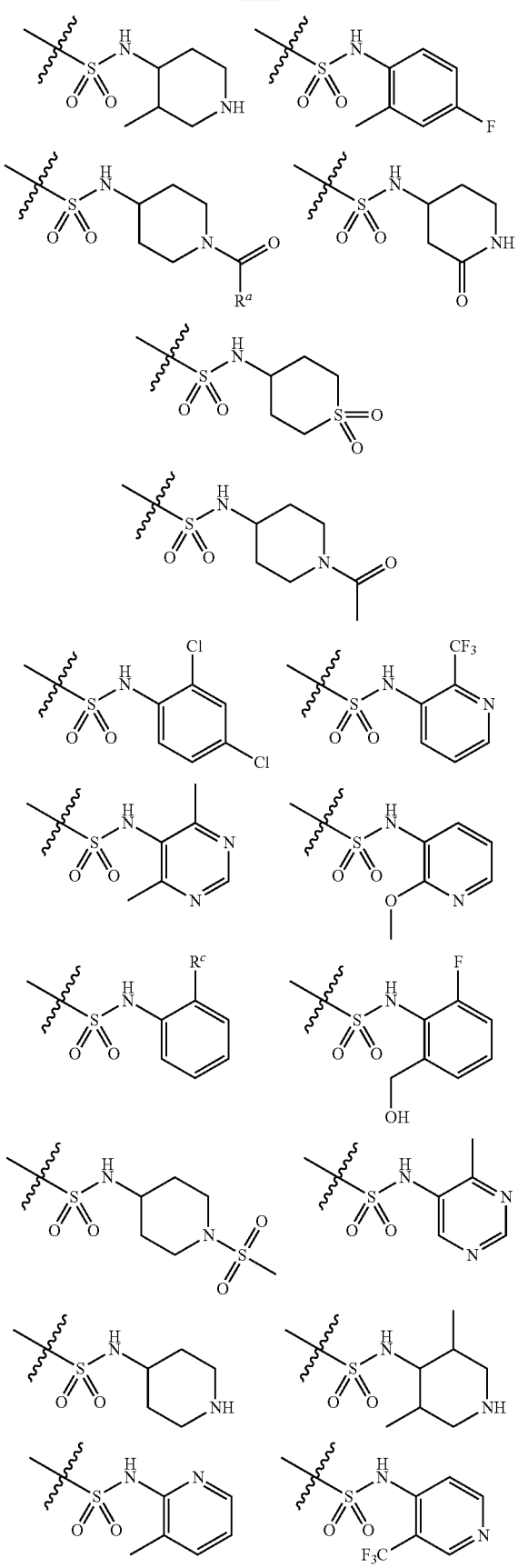

-continued

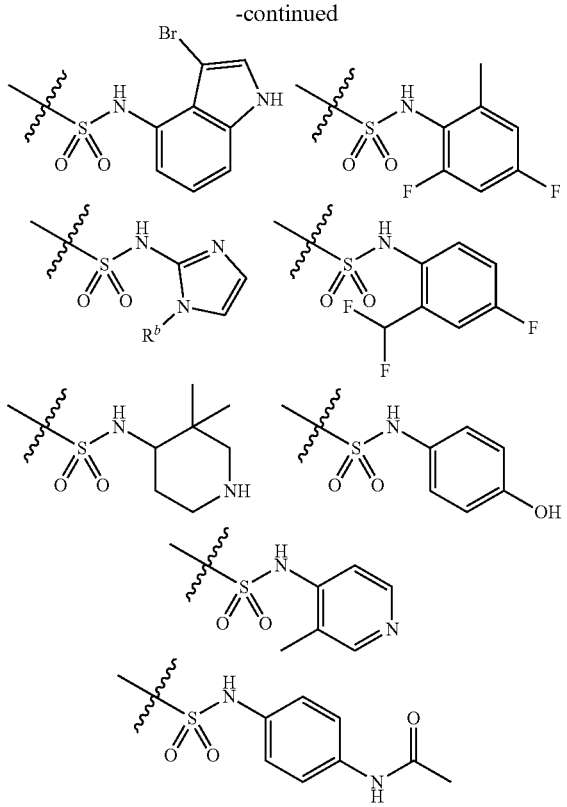

wherein:
R<sup>a</sup> is selected from hydrogen, methyl, OMe, OtBu, OCF$_3$;
R<sup>b</sup> is selected from methyl or hydrogen; and
R<sup>c</sup> is selected from a halogen or CF$_3$; and

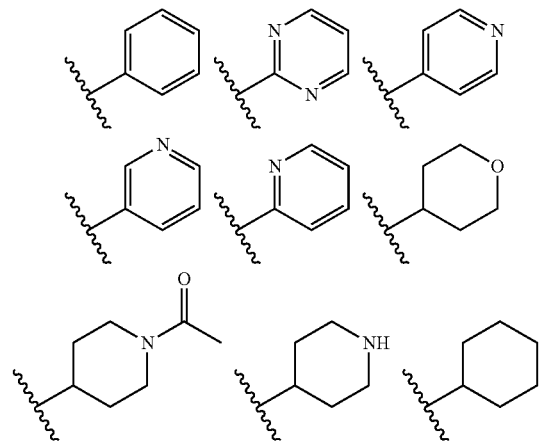

In some embodiments of formula (VI), $Y^2$ is S. In some embodiments of formula (VI). $Y^1$ is CH. In some embodiments of formula (VI), $Y^2$ is S and $Y^1$ is CH. In some embodiments of formula (VI), $Y^2$ is S and $Y^1$ is N. In some embodiments of formula (VI), $Y^2$ is O. In some embodiments of formula (VI), $Y^2$ is $NR^{19}$. In some embodiments of formula (VI), $Y^2$ is NH. In some embodiments of formula (VI), $Y^2$ is O and $Y^1$ is CH. In some embodiments of formula (VI), $Y^2$ is $NR^{19}$ and $Y^1$ is CH. In some embodiments of formula (VI). $Y^2$ is NH and $Y^1$ is CH. In some embodiments of formula (VI), $Y^2$ is O and $Y^1$ is N. In some embodiments of formula (VI), $Y^2$ is $NR^9$ and $Y^1$ is N. In some embodiments of formula (VI), $Y^2$ is NH and $Y^1$ is N.

In some embodiments of any one of the formulae (I) to (VI) (e.g., any of the formulae described herein), $R^2$ is methoxy. In some embodiments of any one of the formulae (I) to (VI), $R^3$ is methyl. In some embodiments of any of formulae (I) to (VI), $R^2$ is methoxy and $R^3$ is methyl. In some embodiments of any one of the formulae (I) to (VI), $R^2$ is a halogen (e.g., Cl or Br). In some embodiments of any one of the formulae (I) to (VI), $R^2$ is a substituted lower alkyl. In some embodiments of any one of the formulae (I) to (VI). $R^2$ is CF$_3$. In some embodiments of any one of the formulae (I) to (VI), $R^2$ is CHF$_2$. In some embodiments of any one of the formulae (I) to (VI), $R^2$ is CH$_2$F. In some embodiments of any one of the formulae (I) to (VI), $R^2$ is a lower alkyl. In some embodiments of any one of the formulae (I) to (VI), $R^2$ is methyl.

In certain embodiments, the compound is described by the structure of one of the compounds of Table 1, Table 2 or Table 3. It is understood that any of the compounds shown in Table 1, 2 or 3 may be present in a salt form, such as a trifluoroacetate salt (e.g., CF$_3$COOH salt). In some cases, the salt form of the compound is a pharmaceutically acceptable salt.

TABLE 1

Compounds

| Cmpd | Structure |
|---|---|
| S-1 | 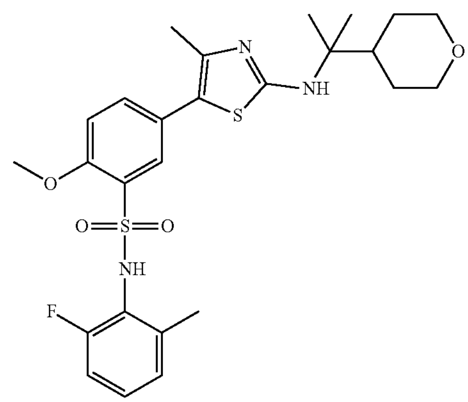 [SMILES: COc1ccc(-c2sc(NC(C)(C)C3CCOCC3)nc2C)cc1S(=O)(=O)Nc1c(C)cccc1F] |
| S-2 | 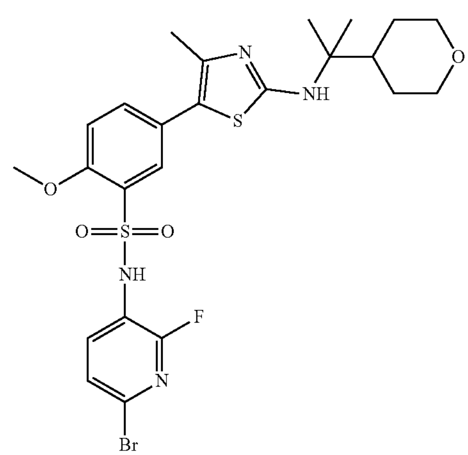 [SMILES: COc1ccc(-c2sc(NC(C)(C)C3CCOCC3)nc2C)cc1S(=O)(=O)Nc1ccc(Br)nc1F] |

TABLE 1-continued

| Cmpd | Structure |
|---|---|
| S-3 | 5-(4-methylthiazol-2-ylamino with tetrahydropyran); phenyl with OMe; sulfonamide N-H to 2-methylpyridin-3-yl |
| S-4 | same thiazole/phenyl core; sulfonamide N-H to 2-chloro-4-fluorophenyl |
| S-5 | same thiazole/phenyl core; sulfonamide N-H to trans-4-hydroxycyclohexyl |
| S-6 | same thiazole/phenyl core; sulfonyl-morpholine |
| S-7 | same thiazole/phenyl core; sulfonamide N-H to 2-hydroxyethyl |
| S-8 | same thiazole/phenyl core; sulfonamide N-H to 2-methyl-4-fluorophenyl |

TABLE 1-continued

Compounds

| Cmpd | Structure |
|---|---|
| S-9 | 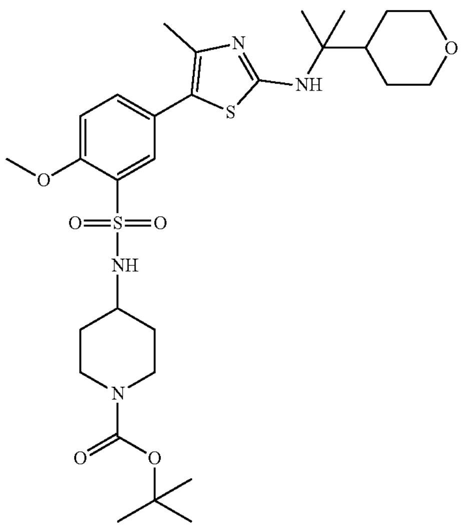 [SMILES: COc1ccc(-c2sc(NC(C)(C)C3CCOCC3)nc2C)cc1S(=O)(=O)NC1CCN(C(=O)OC(C)(C)C)CC1] |
| S-10 | 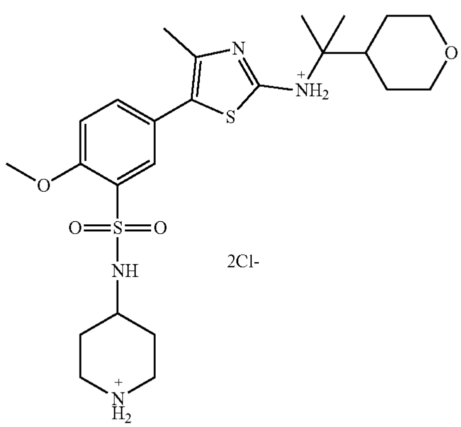 [SMILES: COc1ccc(-c2sc(NC(C)(C)C3CCOCC3)nc2C)cc1S(=O)(=O)NC1CCNCC1] |
| S-11 | 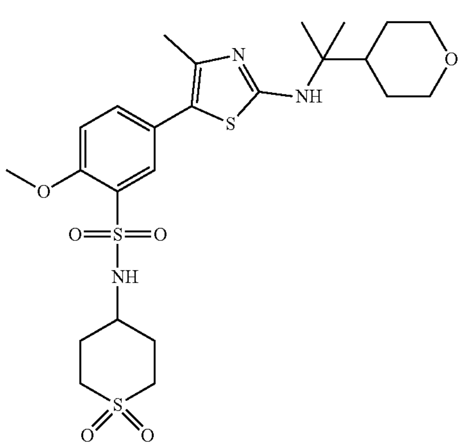 [SMILES: COc1ccc(-c2sc(NC(C)(C)C3CCOCC3)nc2C)cc1S(=O)(=O)NC1CCS(=O)(=O)CC1] |
| S-12 | |
| S-13 | |
| S-14 | |

TABLE 1-continued

Compounds

| Cmpd | Structure |
|---|---|
| S-15 | 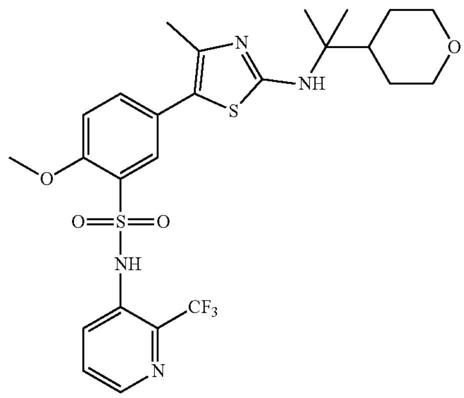 [SMILES: COc1ccc(-c2sc(NC(C)(C)C3CCOCC3)nc2C)cc1S(=O)(=O)Nc1cccnc1C(F)(F)F] |
| S-16 | 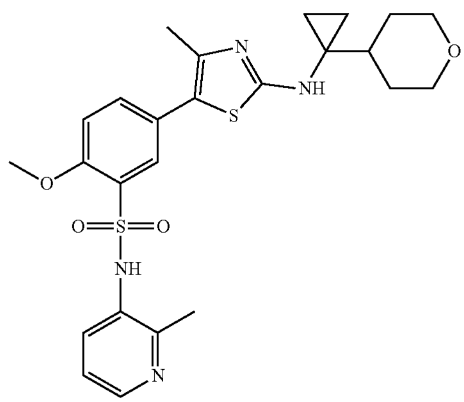 [SMILES: COc1ccc(-c2sc(NC3(C4CCOCC4)CC3)nc2C)cc1S(=O)(=O)Nc1cccnc1C] |
| S-17 | 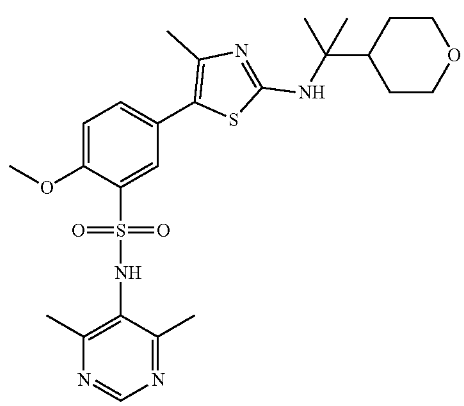 [SMILES: COc1ccc(-c2sc(NC(C)(C)C3CCOCC3)nc2C)cc1S(=O)(=O)Nc1c(C)ncnc1C] |
| S-18 | 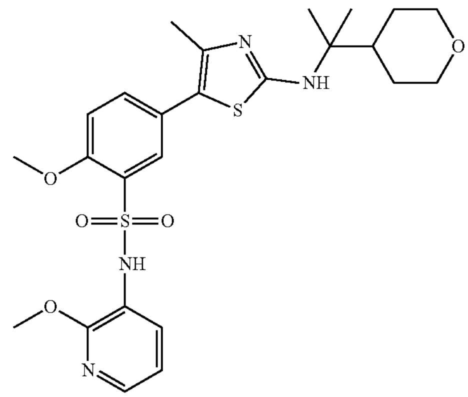 [SMILES: COc1ccc(-c2sc(NC(C)(C)C3CCOCC3)nc2C)cc1S(=O)(=O)Nc1cccnc1OC] |
| S-19 | 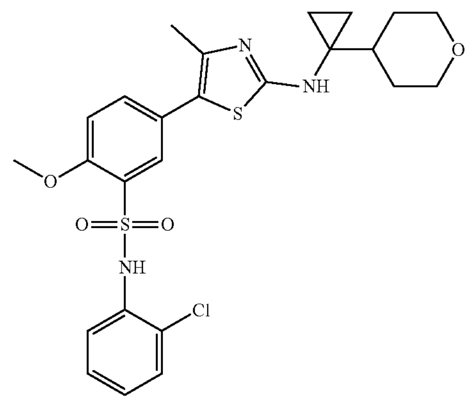 [SMILES: COc1ccc(-c2sc(NC3(C4CCOCC4)CC3)nc2C)cc1S(=O)(=O)Nc1ccccc1Cl] |
| S-20 | 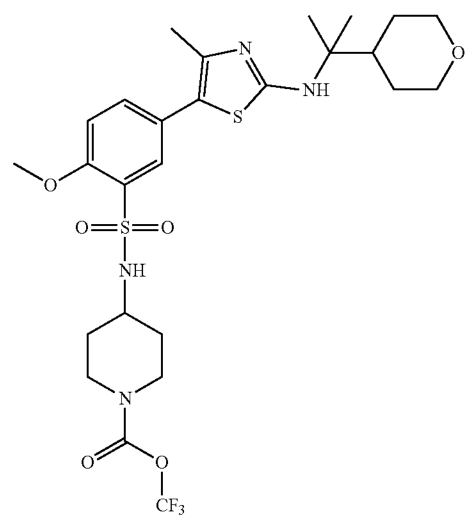 [SMILES: COc1ccc(-c2sc(NC(C)(C)C3CCOCC3)nc2C)cc1S(=O)(=O)NC1CCN(C(=O)OC(F)(F)F)CC1] |

TABLE 1-continued

| Cmpd | Structure |
|---|---|
| S-21 | 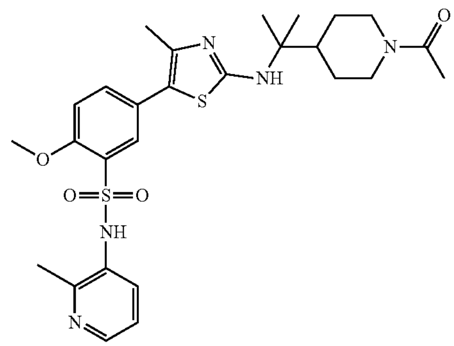 [SMILES: COc1ccc(-c2sc(NC(C)(C)C3CCN(C(C)=O)CC3)nc2C)cc1S(=O)(=O)Nc1cccnc1C] |
| S-22 | 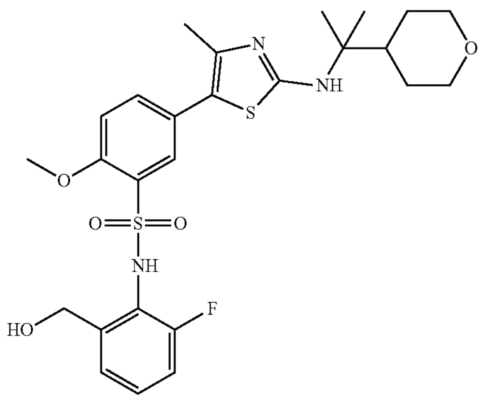 [SMILES: COc1ccc(-c2sc(NC(C)(C)C3CCOCC3)nc2C)cc1S(=O)(=O)Nc1c(F)cccc1CO] |
| S-23 | 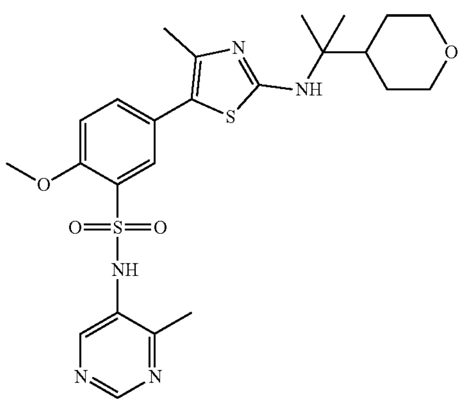 [SMILES: COc1ccc(-c2sc(NC(C)(C)C3CCOCC3)nc2C)cc1S(=O)(=O)Nc1cncnc1C] |
| S-24 | 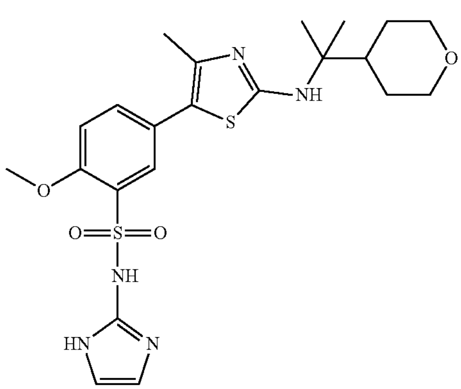 [SMILES: COc1ccc(-c2sc(NC(C)(C)C3CCOCC3)nc2C)cc1S(=O)(=O)Nc1ncc[nH]1] |
| S-25 | |
| S-26 | |
| S-27 | |

TABLE 1-continued

Compounds

| Cmpd | Structure |
|---|---|
| S-28 | 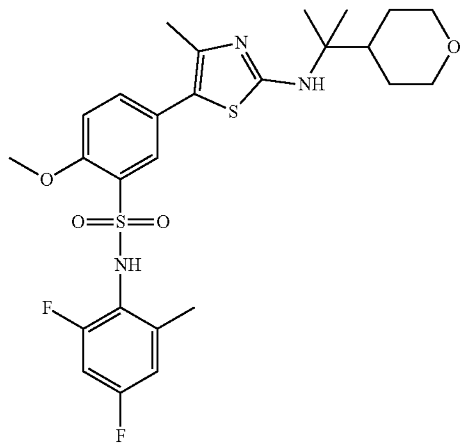 [SMILES: COc1ccc(-c2sc(NC(C)(C)C3CCOCC3)nc2C)cc1S(=O)(=O)Nc1c(C)cc(F)cc1F] |
| S-29 | 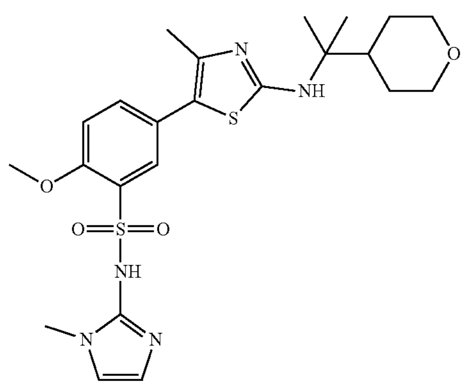 |
| S-30 | 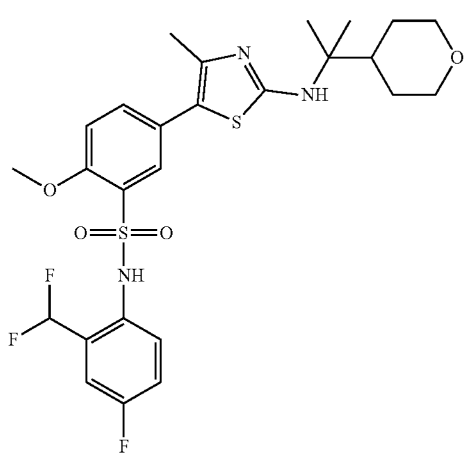 [SMILES: COc1ccc(-c2sc(NC(C)(C)C3CCOCC3)nc2C)cc1S(=O)(=O)Nc1ccc(F)cc1C(F)F] |
| S-31 | |
| S-32 | |
| S-33 | |

TABLE 1-continued

Compounds

| Cmpd | Structure |
|---|---|
| S-34 | 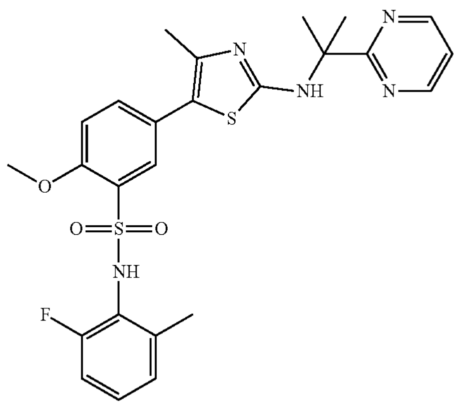 [SMILES: COc1ccc(-c2sc(NC(C)(C)c3ncccn3)nc2C)cc1S(=O)(=O)Nc1c(C)cccc1F] |
| S-35 | 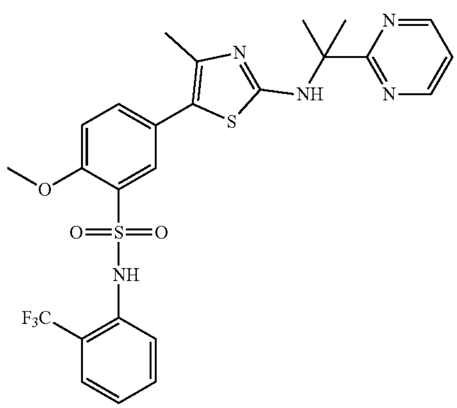 [SMILES: COc1ccc(-c2sc(NC(C)(C)c3ncccn3)nc2C)cc1S(=O)(=O)Nc1ccccc1C(F)(F)F] |
| S-36 | 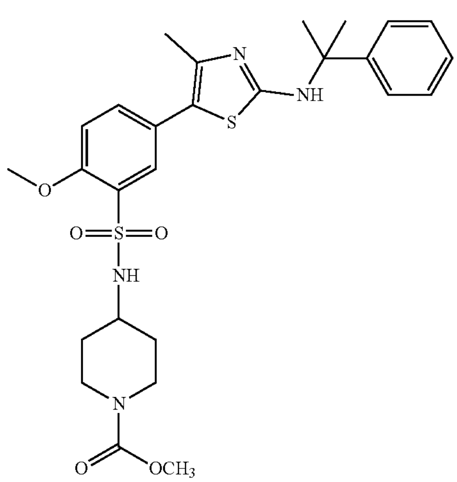 [SMILES: COC(=O)N1CCC(NS(=O)(=O)c2cc(-c3sc(NC(C)(C)c4ccccc4)nc3C)ccc2OC)CC1] |
| S-37 | |
| S-38 | |
| S-39 | |

TABLE 1-continued
Compounds
| Cmpd | Structure |
|---|---|
| S-40 | 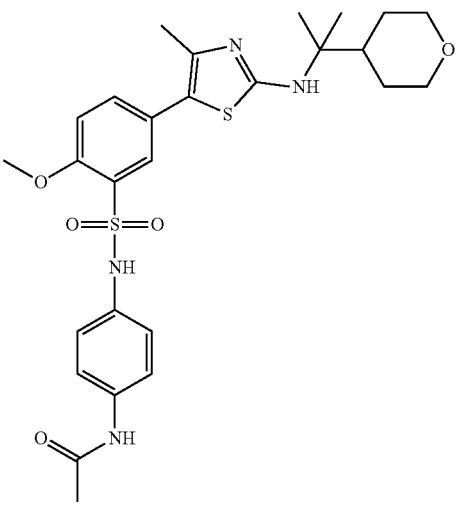 [SMILES: COc1ccc(-c2sc(NC(C)(C)C3CCOCC3)nc2C)cc1S(=O)(=O)Nc1ccc(NC(C)=O)cc1] |
| S-41 | 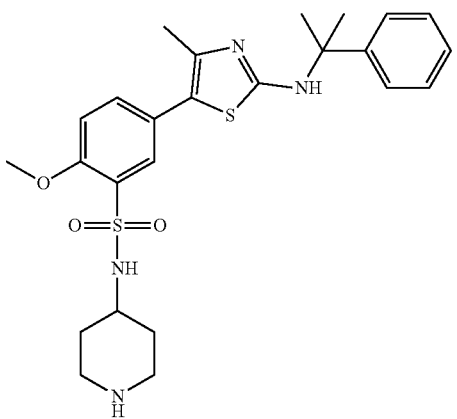 [SMILES: COc1ccc(-c2sc(NC(C)(C)c3ccccc3)nc2C)cc1S(=O)(=O)NC1CCNCC1] |
| S-42 | 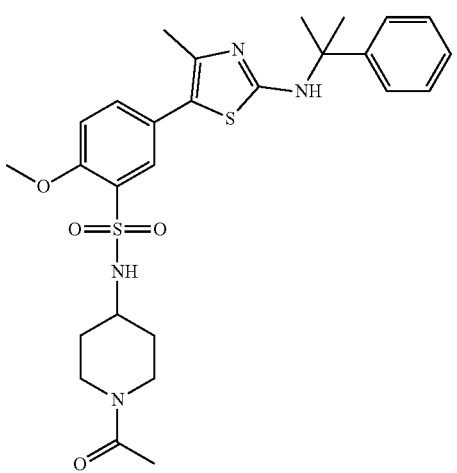 [SMILES: COc1ccc(-c2sc(NC(C)(C)c3ccccc3)nc2C)cc1S(=O)(=O)NC1CCN(C(C)=O)CC1] |
| S-43 | 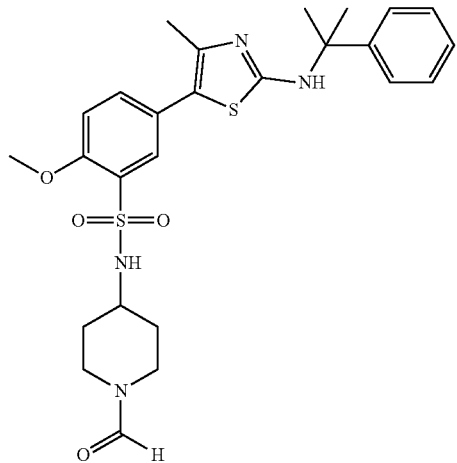 [SMILES: COc1ccc(-c2sc(NC(C)(C)c3ccccc3)nc2C)cc1S(=O)(=O)NC1CCN(C=O)CC1] |
| S-44 | 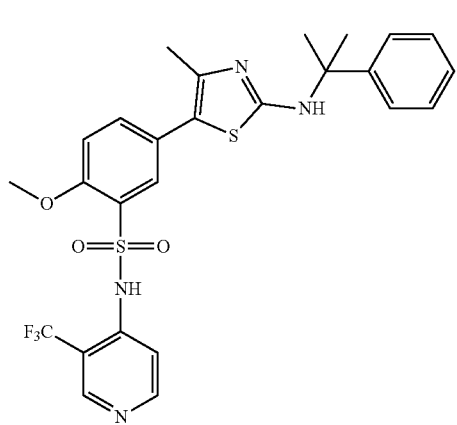 [SMILES: COc1ccc(-c2sc(NC(C)(C)c3ccccc3)nc2C)cc1S(=O)(=O)Nc1ccncc1C(F)(F)F] |
| S-45 | 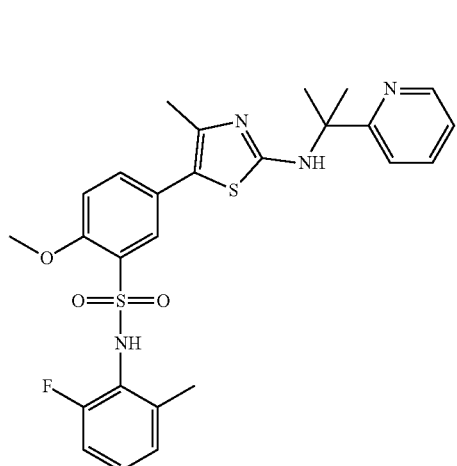 |

TABLE 1-continued
| Cmpd | Structure |
|---|---|
| S-46 | 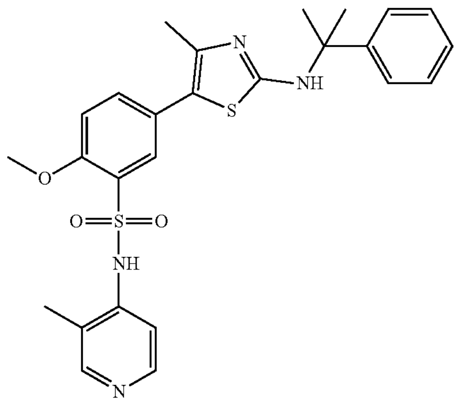 [SMILES: COc1ccc(-c2sc(NC(C)(C)c3ccccc3)nc2C)cc1S(=O)(=O)Nc1ccncc1C] |
| S-47 | 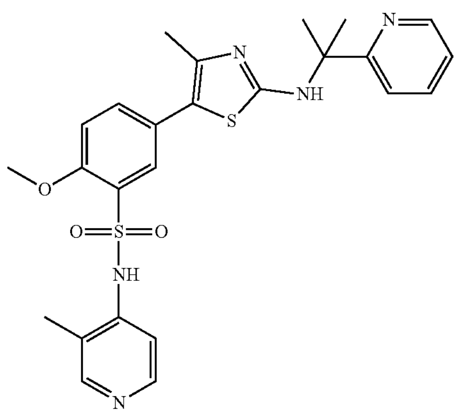 [SMILES: COc1ccc(-c2sc(NC(C)(C)c3ccccn3)nc2C)cc1S(=O)(=O)Nc1ccncc1C] |
| S-48 | 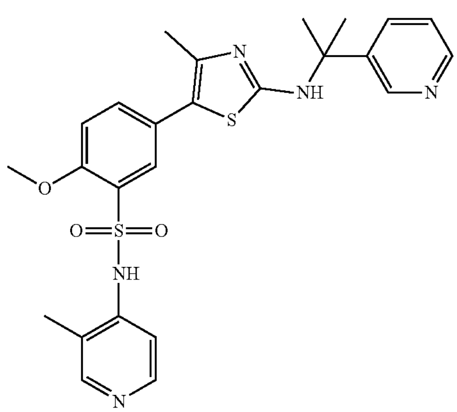 |
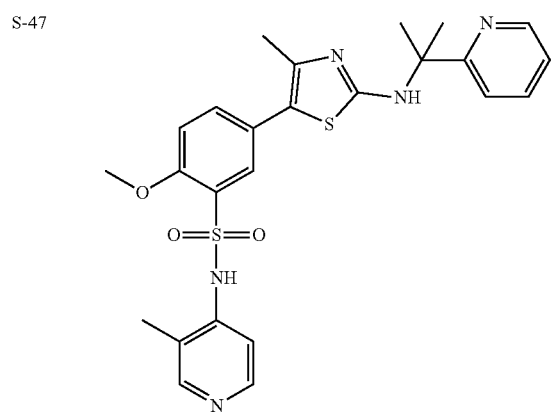
TABLE 1-continued
| Cmpd | Structure |
|---|---|
| S-49 | |
| S-50 | |
| S-51 | |
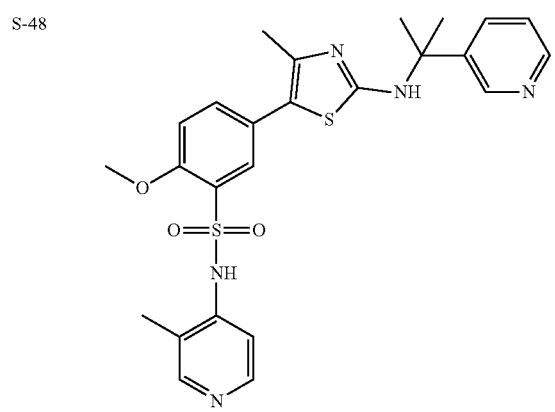

TABLE 1-continued

| Cmpd | Structure |
|---|---|
| S-52 | 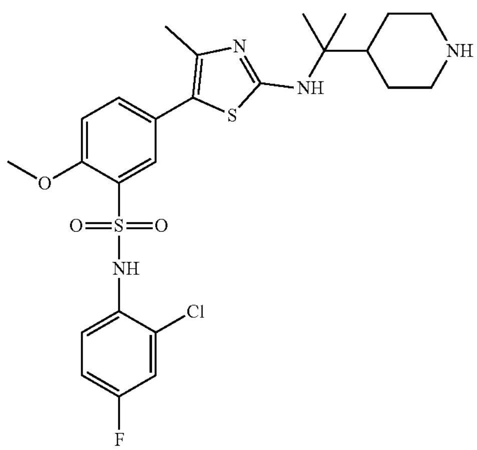 [SMILES: COc1ccc(-c2sc(NC(C)(C)C3CCNCC3)nc2C)cc1S(=O)(=O)Nc1ccc(F)cc1Cl] |
| S-53 | 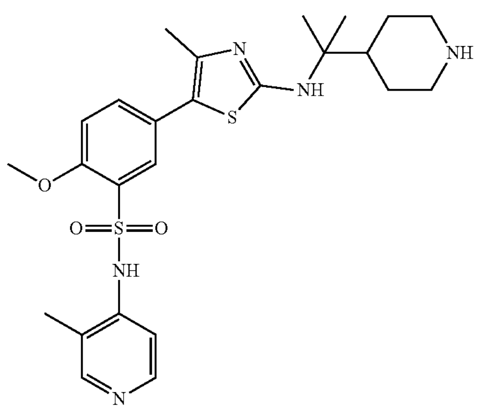 [SMILES: COc1ccc(-c2sc(NC(C)(C)C3CCNCC3)nc2C)cc1S(=O)(=O)Nc1ccncc1C] |
| S-54 | 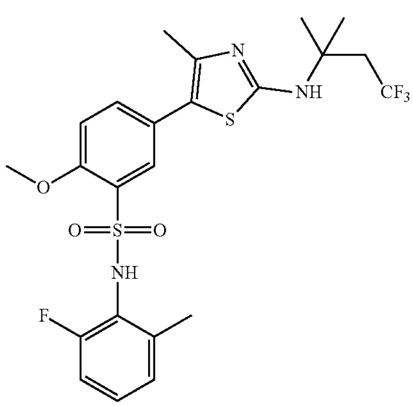 [SMILES: COc1ccc(-c2sc(NC(C)(C)CC(F)(F)F)nc2C)cc1S(=O)(=O)Nc1c(C)cccc1F] |
| S-55 | 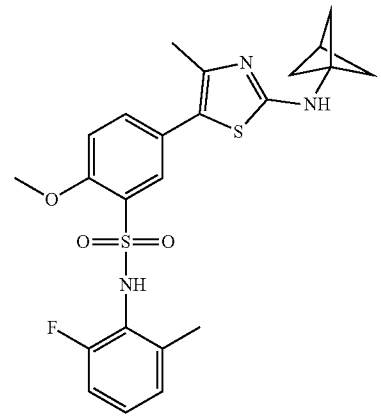 [SMILES: COc1ccc(-c2sc(NC34CC(C3)C4)nc2C)cc1S(=O)(=O)Nc1c(C)cccc1F] |
| S-56 | 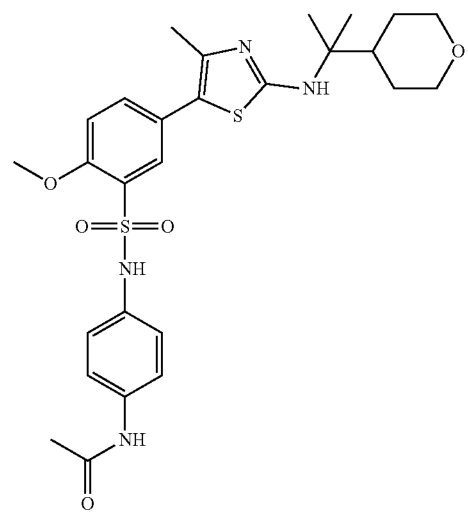 [SMILES: COc1ccc(-c2sc(NC(C)(C)C3CCOCC3)nc2C)cc1S(=O)(=O)Nc1ccc(NC(C)=O)cc1] |
| S-57 | 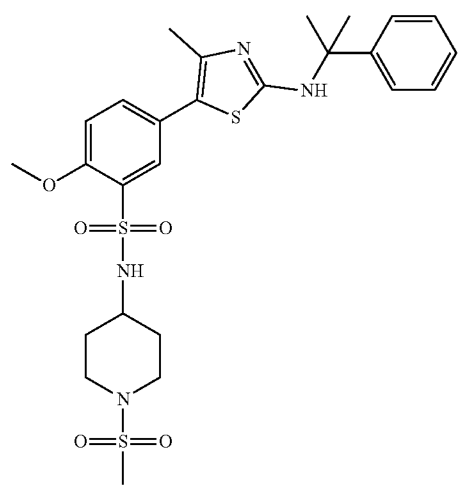 [SMILES: COc1ccc(-c2sc(NC(C)(C)c3ccccc3)nc2C)cc1S(=O)(=O)NC1CCN(S(C)(=O)=O)CC1] |

TABLE 1-continued
Compounds
| Cmpd | Structure |
|---|---|
| S-58 | 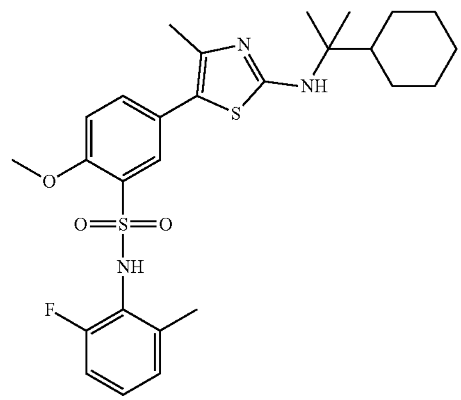 [SMILES: COc1ccc(-c2sc(NC(C)(C)C3CCCCC3)nc2C)cc1S(=O)(=O)Nc1c(C)cccc1F] |
| S-59 | 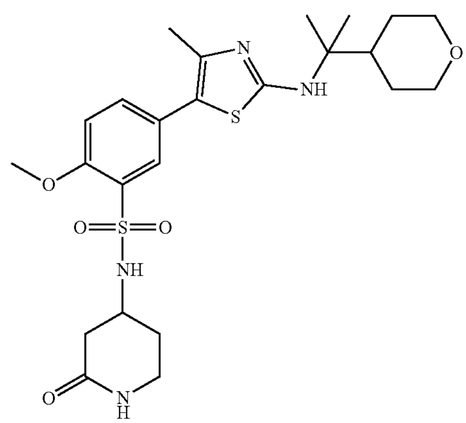 [SMILES: COc1ccc(-c2sc(NC(C)(C)C3CCOCC3)nc2C)cc1S(=O)(=O)NC1CCNC(=O)C1] |
| S-60 | 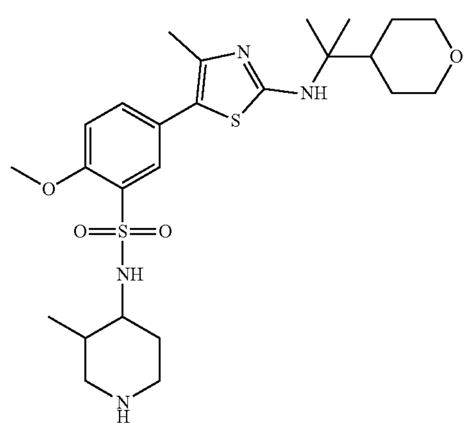 [SMILES: COc1ccc(-c2sc(NC(C)(C)C3CCOCC3)nc2C)cc1S(=O)(=O)NC1CCNCC1C] |
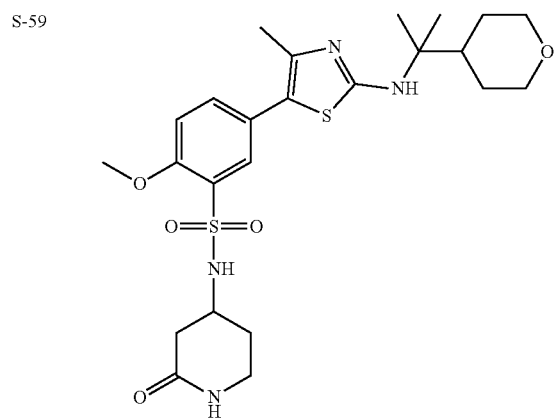
TABLE 1-continued
Compounds
| Cmpd | Structure |
|---|---|
| S-61 | 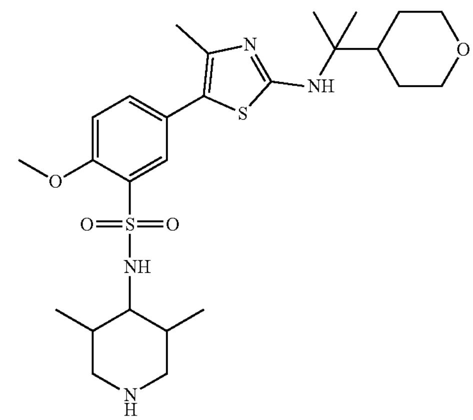 [SMILES: COc1ccc(-c2sc(NC(C)(C)C3CCOCC3)nc2C)cc1S(=O)(=O)NC1C(C)CNCC1C] |
| S-62 | 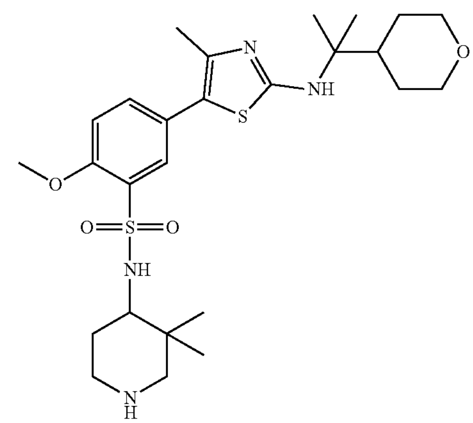 [SMILES: COc1ccc(-c2sc(NC(C)(C)C3CCOCC3)nc2C)cc1S(=O)(=O)NC1CCNCC1(C)C] |
| S-63 | 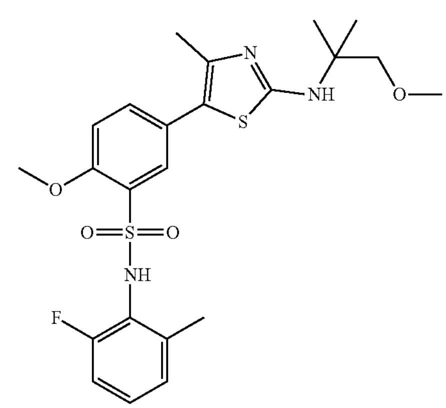 |
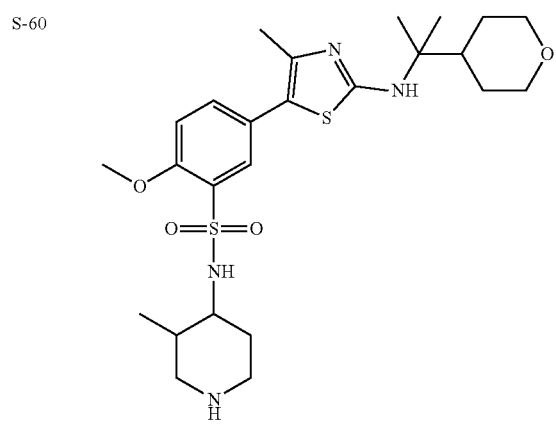

TABLE 2

| Cmpd | Structure |
|---|---|
| S-64 | (4-methyl-5-(4-methoxy-3-(N-(2-chlorophenyl)sulfamoyl)phenyl)thiazol-2-yl)-NH-C(CH₃)₂-phenyl |
| S-65 | (4-methyl-5-(4-methoxy-3-(N-(2-fluoro-6-methylphenyl)sulfamoyl)phenyl)thiazol-2-yl)-NH-C(CH₃)₂-phenyl |
| S-66 | (4-methyl-5-(4-methoxy-3-(N-(2-fluoro-6-methylphenyl)sulfamoyl)phenyl)thiazol-2-yl)-NH-C(CH₃)₂-(pyridin-3-yl) |

TABLE 2-continued

| Cmpd | Structure |
|---|---|
| S-67 | (4-methyl-5-(4-methoxy-3-(N-(3-methylpyridin-4-yl)sulfamoyl)phenyl)thiazol-2-yl)-NH-C(CH₃)₂-phenyl |

TABLE 3

| Cmpd | Structure |
|---|---|
| S-68 | (4-methyl-5-(4-methoxy-3-(N-(2-chlorophenyl)sulfamoyl)phenyl)thiazol-2-yl)-NH-C(CH₃)₂-(tetrahydropyran-4-yl) |
| S-69 | (4-methyl-5-(4-methoxy-3-(N-(2-chloro-6-fluorophenyl)sulfamoyl)phenyl)thiazol-2-yl)-NH-C(CH₃)₂-phenyl |

TABLE 3-continued

Compounds

| Cmpd | Structure |
|---|---|
| S-70 | 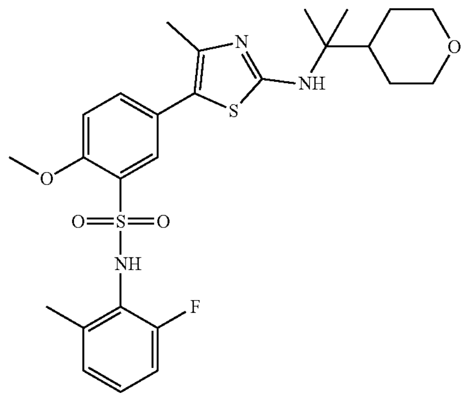 |
| S-71 | 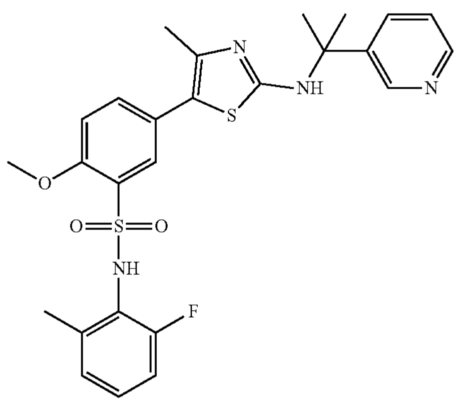 [SMILES: COc1ccc(-c2sc(NC(C)(C)c3cccnc3)nc2C)cc1S(=O)(=O)Nc1c(C)cccc1F] |
| S-72 | 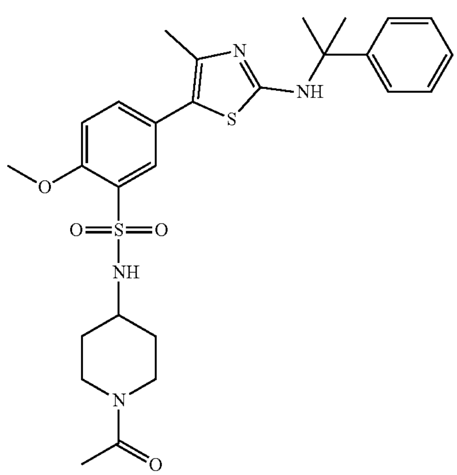 [SMILES: COc1ccc(-c2sc(NC(C)(C)c3ccccc3)nc2C)cc1S(=O)(=O)NC1CCN(C(C)=O)CC1] |
| S-73 | |

In certain embodiments, the compound is described by the structure of one of the compounds of Table 1. In certain embodiments, the compound is described by the structure of one of the compounds of Table 2. In certain embodiments, the compound is described by the structure of one of the compounds of Table 3. It is understood that any of the compounds shown in Table 1, 2 or 3 may be present in a salt form, such as a trifluoroacetate salt (e.g., CF₃COOH salt). In some cases, the salt form of the compound is a pharmaceutically acceptable salt.

Aspects of the present disclosure include PI-kinase inhibiting compounds, salts thereof (e.g., pharmaceutically acceptable salts), and/or solvate, hydrate and/or prodrug forms thereof. In addition, it is understood that, in any compound described herein having one or more chiral centers, if an absolute stereochemistry is not expressly indicated, then each center may independently be of R-configuration or S-configuration or a mixture thereof. It will be appreciated that all permutations of salts, solvates, hydrates, prodrugs and stereoisomers are meant to be encompassed by the present disclosure.

In some embodiments, the subject compounds, or a prodrug form thereof, are provided in the form of pharmaceutically acceptable salts. Compounds containing an amine or nitrogen containing heteroaryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)). In some cases, the promoiety is attached to a hydroxy or carboxylic acid group of the subject compounds. In certain cases, the promoiety is an acyl or substituted acyl group. In certain cases, the promoiety is an alkyl or substituted alkyl group, e.g., that forms an ester functional group when attached to a carboxylic acid group of the subject compounds.

In some embodiments, the subject compounds, prodrugs, stereoisomers or salts thereof are provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

In some embodiments, the subject compounds are provided by oral dosing and absorbed into the bloodstream. In some embodiments, the oral bioavailability of the subject compounds is 30% or more. Modifications may be made to the subject compounds or their formulations using any convenient methods to increase absorption across the gut lumen or their bioavailability.

In some embodiments, the subject compounds are metabolically stable (e.g., remain substantially intact in vivo during the half-life of the compound). In certain embodiments, the compounds have a half-life (e.g., an in vivo half-life) of 5 minutes or more, such as 10 minutes or more, 12 minutes or more, 15 minutes or more, 20 minutes or more, 30 minutes or more, 60 minutes or more, 2 hours or more, 6 hours or more, 12 hours or more, 24 hours or more, or even more.

Methods

As summarized above, aspects of the invention include PI4-kinase inhibiting compounds, and methods of inhibition using the same. The PI4-kinase inhibiting compounds are compounds that inhibit the activity of a PI4-kinase in a cell, upon contact with a cell or components thereof. In one embodiment, methods of treating a pathogen infection are provided. In one embodiment, methods or treating cancer are also provided.

PI4-Kinase Inhibition in Cells Infected with a Pathogen

In some instances, the types of cells in which the subject compounds exhibit activity are ones that have been infected with a pathogen, as described herein. By inhibiting a PI4-kinase it is meant that the activity of the enzyme is decreased by a factor of 2 or more, such as 3 or more, 5 or more, 10 or more, 100 or more, or 1000 or more, relative to its normal activity (e.g., relative to a positive control).

In some embodiments, the subject compounds are inhibitors of a PI3-kinase. In some embodiments, the subject compounds are inhibitors of a PI4-kinase, such as a PI4-III-kinase (e.g., PI4-IIIα or PI4-IIIβ). In some instances, the PI4-III-kinase is PI4-IIIα. In some instances, the PI4-III-kinase is PI4-IIIβ. In some embodiments, the subject compounds have a PI-kinase inhibition profile that reflects activity against two or more PI-kinases. In some embodiments, the subject compounds specifically inhibit both a type II PI3-kinase, such as PI3-kinase TIP, and a type III PI4-kinase, such as PI4K-IIIα and/or PI4K-IIIβ). In some embodiments, the subject compounds specifically inhibit a PI4-kinase without undesired inhibition of protein kinases. In some embodiments, the subject compounds specifically inhibit a PI4-kinase without undesired inhibition of PI3-kinase. In some embodiments, the subject compounds specifically inhibit a PI4-kinase and/or a specific PI3-kinase subclass without undesired inhibition of other PI3-kinase subclasses or protein kinases.

In some embodiments, the compounds of the disclosure interfere with the interaction of a BAAPP domain with PIP2 in a pathogen (e.g., HCV). For example, the subject compounds may act by decreasing the levels of PIP2 either directly or indirectly that bind specifically to the BAAPP domain of the pathogen. In general, pathogens that include a BAAPP domain are susceptible to inhibition by the subject compounds. Similarly, pathogens that depend of PI4-kinase activity are susceptible to inhibition by the subject compounds.

In some embodiments, the subject compounds inhibit a PI4-kinase, as determined by an inhibition assay, e.g., by an assay that determines the level of activity of the enzyme either in a cell-free system or in a cell after treatment with a subject compound, relative to a control, by measuring the $IC_{50}$ or $EC_{50}$ value, respectively. In certain embodiments, the subject compounds have an $IC_{50}$ value (or $EC_{50}$ value) of 10 µM or less, such as 3 µM or less, 1 µM or less, 500 nM or less, 300 nM or less, 200 nM or less, 100 nM or less, 50 nM or less, 30 nM or less, 10 nM or less, 5 nM or less, 3 nM or less, 1 nM or less, or even lower.

In some embodiments, the subject compounds inhibit a PI4-kinase, as determined by a kinase activity assay, e.g., by an assay that determines the level of incorporation of radiolabeled phosphate from $[\gamma\text{-}^{32}P]$-ATP into a substrate molecule after treatment with a subject compound, relative to a control, by measuring the beta-particle emission rate using a scintillation counter or phosphorimaging. In certain embodiments, the subject compounds have an $IC_{50}$ value for PI4K-IIIβ of less than about 1 µM, less than about 0.2 µM, less than about 0.1 µM, less than about 10 nM, less than about 1 nM, or even less, such as described in Tables 2-3. In certain embodiments, the subject compounds have an $IC_{50}$ value for PI4K-IIIα of less than about 50 µM, less than about 10 µM, less than about 1 µM, less than about 0.1 µM, less than about 10 nM, less than about 1 nM, or even less, such as described in Tables 2-3. In certain further embodiments, the subject compounds have an IC50 value for PI4K-IIIβ of 50 µM or less, [etc., etc.], 10 nM or less, 6 nM or less, or even less, such as described in Tables 2-3. In certain further embodiments, the subject compounds have an IC50 value for the PI3-kinase p110α-p85 complex of between about 8 and about 10 nM, between about 8 µM and about 10 µM, or even more. In certain further embodiments, the subject compounds have an IC50 value for the PI3-kinase p110γ-p85 complex of from about 2 to about 4 nM, of from about 4 µM to 5 µM, or even more, such as described herein. In certain further embodiments, the subject compounds have an IC50 value for the type II PI3-kinase beta of less than about 1 µM, less than about 150 nM, less than about 30 nM, or even less, such as described herein. In certain embodiments, the subject compounds have an IC50 value for type IT PI3-kinase alpha of less than 10 M. In certain further embodiments, more than one of the above criteria is independently satisfied by a particular compound.

In some embodiments, the potency of the PI4-kinase inhibiting compounds track with anti-infective (e.g., antiviral) activity. In some cases, the enzymatic and anti-infective activities of the subject compounds diverge. In some embodiments, the anti-infective activity of the subject compounds depends on a combination of inhibition of both PI4KIIIα and PI4KIIIβ, or a combination of inhibition of class III PI4-kinases and class II PI3-kinases (especially class II PI3-kinase beta). The subject compound may have increased specificity for one isoform of these PI-kinase family members.

In certain embodiments, the subject compounds have no significant effect on the viability of a mammalian cell, as determined by a cell cytotoxicity assay, e.g., as determined by administering a subject compound to a HeLa cell and determining the number of viable cells present. The subject compounds may exhibit a % cell viability, as compared to a control (e.g., a DMSO control), of 15% or more, such as 20% or more, 30% or more, 40% or more, 50% or more, 60% or more, 70% or more, 80% or more, 90% or more, 100% or more, 120% or more, or even higher. The subject compounds may exhibit a $CC_{50}$ value of 1 nM or higher, such as 100 nM or higher, 300 nM or higher, 1 M or higher, 3 µM or higher, 5 µM or higher, 10 µM or higher, 20 µM or higher, 30 µM or higher, 50 µM or higher, or even higher.

In certain embodiments, the compounds have a therapeutic index (e.g., the ratio of a compound's cytotoxicity (e.g., cell cytotoxicity, CC50) to bioactivity (e.g., antiviral activity, EC50)) that is 20 or more, such as 50 or more, 100 or more, 200 or more, 300 or more, 400 or more, 500 or more, or even more.

As summarized above, aspects of the disclosure include methods of inhibiting a PI-kinase (e.g., a PI3, a PI4-IIIα, or a PI4-IIIβ kinase). A subject compound (e.g., as described herein) may inhibit at least one activity of the PI-kinase in the range of 10% to 100%. e.g., by 10% or more, 20% or more, 30% or more, 40% or more, 50% or more, 60% or more, 70% or more, 80% or more, or 90% or more. In certain assays, a subject compound may inhibit its target with an $IC_{50}$ of $1\times10^{-6}$ M or less (e.g., $1\times10^{-6}$ M or less, $1\times10^{-7}$ M or less, $1\times10^{-8}$ M or less, $1\times10^{-9}$ M or less, $1\times10^{-10}$ M or less, or $1\times10^{-11}$ M or less).

The protocols that may be employed in determining PI-kinase activity are numerous, and include but are not limited to cell-free assays, e.g., binding assays; assays using purified enzymes, cellular assays in which PI4P levels are measured or a cellular phenotype is measured, e.g., gene expression assays; and in vivo assays that involve a particular animal (which, in certain embodiments may be an animal model for a condition related to the target pathogen).

In some embodiments, the subject method is an in vitro method that includes contacting a sample with a subject compound that specifically inhibits a target PI-kinase. In certain embodiments, the sample is suspected of containing the PI-kinase and the subject method further comprises evaluating whether the compound inhibits the PI-kinase. In certain embodiments, the PI-kinase is a PI4-kinase or a PI-3 kinase.

In certain embodiments, the subject compound is a modified compound that includes a label, e.g., a fluorescent label, and the subject method further includes detecting the label, if present, in the sample, e.g., using optical detection.

In certain embodiments, the compound is modified with a support or with affinity groups that bind to a support (e.g. biotin), such that any sample that does not bind to the compound may be removed (e.g., by washing). The specifically bound target PI-kinase, if present, may then be detected using any convenient means, such as, using the binding of a labeled target specific probe, or using a fluorescent protein reactive reagent.

In another embodiment of the subject method, the sample is known to contain the target PI-kinase.

Methods of Treating a Pathogen Infection

Contrary to the classic paradigm of anti-infective therapy, the present disclosure provides methods of treating pathogen infection by targeting a host function and/or molecule upon which the pathogen is dependent, thereby decreasing the ability of the pathogen to avoid the therapeutic agent by mutation. In addition, by utilizing such a target, the methods of the disclosure allow combination therapies in which multiple targets are addressed, thereby increasing the ability to eliminate the infectious agent. The methods also provide a broad platform for anti-infective therapies by targeting a host function. In addition, in cases where the pathogen encodes its own PI-kinase(s), the present disclosure provides methods of treating pathogen infection by targeting the pathogen PI-kinase.

Pathogens of interest include those described in Glenn et al., "PIP-2 Inhibition-Based Antiviral and Anti-Hyperlipidemic Therapies" WO2009/148541, the disclosure of which is herein incorporated by reference in its entirety. Pathogens of interest include, but are not limited to, pathogens of the viral families Picornaviridae, Flaviviridae, Retroviridae, Filoviridae, Togaviridae, Papovaviridae, Papillomaviridae, Polyomaviridae, Caliciviridae, Coronavirinae, Hepeviridae, Bunyaviridae, Poxviridae and Orthomyxoviridae. In some embodiments, the pathogen is selected from hepacivirus (e.g., HCV), norovirus, hepevirus (e.g., HEV), betacoronvirus (e.g., SARS virus, MERS virus, or SARS-CoV-2 virus), rhinovirus (e.g., B or C), *plasmodium* (e.g., *P. falciparum*), *toxoplasma*, Ebola virus, *Francisella tularensis*, hantavirus, vaccinia, smallpox, Japanese encephalitis virus, hepatitis A virus, influenza virus, Norovirus, PolioVirus, Enterovirus (e.g., A-D), EV71, EV68, human rhinovirus, human poliovirus, hepatovirus (e.g., HAV), West Nile Virus, and Dengue Virus (e.g., 1-4), coxsackie virus, BK virus, JC virus, human papiloma virus, HIV, rubella, cytomegalovirus and *P. aeruginosa*.

In some embodiments, where the pathogen is HCV, useful compounds include those having a high first-pass effect and consequent low systemic bioavailability, which are targeted to the liver, and which are typically discarded in early drug development. In other embodiments for the treatment of HCV, the compound, or formulation, is modified for liver-specific targeting.

Pathogens of interest also include pathogenic fungi. Fungal pathogens of interest that may be targeted using the subject compounds include, but are not limited to, *Candida, Aspergillus, Cryptococcus, Coccidiomycosis, Histoplasmosis*, etc. As such, fungal disease conditions in which the subject methods find use in treating include, but are not limited to, candidiasis, aspergillosis, coccidioidomycosis. *C. gattii* infection, histoplasmosis and the like.

In some cases, the method is a method of inhibiting a PI4-kinase in a sample. As such, aspects of the method include contacting a sample with a subject compound (e.g., as described above) under conditions by which the compound inhibits the PI4-kinase. Any convenient protocol for contacting the compound with the sample may be employed. The particular protocol that is employed may vary, e.g., depending on whether the sample is in vitro or in vivo. For in vitro protocols, contact of the sample with the compound may be achieved using any convenient protocol. In some instances, the sample includes cells that are maintained in a suitable culture medium, and the complex is introduced into the culture medium. For in vivo protocols, any convenient administration protocol may be employed. Depending upon the potency of the compound, the cells of interest, the manner of administration, the number of cells present, various protocols may be employed.

The term "sample" as used herein relates to a material or mixture of materials, typically, although not necessarily, in fluid form, containing one or more components of interest.

In some embodiments, the subject method is a method of treating a subject for an infective disease. In some embodiments, the subject method includes administering to the subject an effective amount of a subject compound (e.g., as described herein) or a pharmaceutically acceptable salt thereof.

The subject compound may be administered as part of a pharmaceutical composition (e.g., as described herein). In certain instances of the method, the compound that is administered is a compound of one of formulae (I)-(VI). In certain instances of the method, the compound that is administered is described by one of the compounds of Table 1, 2 or 3.

In some embodiments, an "effective amount" is an amount of a subject compound that, when administered to an individual in one or more doses, in monotherapy or in combination therapy, is effective to reduce viral load in the individual by at least about 20% (20% suppression), at least about 30% (30% suppression), at least about 40% (40% suppression), at least about 50% (50% suppression), at least about 60% (60% suppression), at least about 70% (70% suppression), at least about 80% (80% suppression), or at least about 90% (90% suppression), compared to the load in the individual in the absence of treatment with the compound, or alternatively, compared to the bacterial load in the individual before or after treatment with the compound.

In some embodiments, an "effective amount" of a compound is an amount that, when administered in one or more doses to an individual having a viral infection, is effective to achieve a 1.5-log, a 2-log, a 2.5-log, a 3-log, a 3.5-log, a 4-log, a 4.5-log, or a 5-log reduction in virus in the serum of the individual.

In some embodiments, an effective amount of a compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 sg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a compound is an amount that ranges from about 10 pg to about 100 mg. e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 pg, from about 1 µg to about 10 pg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg or about 3000 mg In some embodiments, a single dose of a compound is administered. In other embodiments, multiple doses are administered. Where multiple doses are administered over a period of time, the compound can be administered twice daily (qid), daily (qd), every other day (qod), every third day, three times per week (tiw), or twice per week (biw), or once pert week (qw) over a period of time. For example, a compound is administered qid, qd, qod, qw, tiw, or biw over a period of from one day to about 2 years or more. For example, a compound is administered at any of the aforementioned frequencies for one week, two weeks, one month, two months, six months, one year, or two years, or more, depending on various factors.

Administration of an effective amount of a subject compound to an individual in need thereof can result in one or more of: 1) a reduction in viral load; 2) a reduction in viral load in a target biological sample; 3) a reduction in the spread of a virus from one cell to another cell in an individual; 4) a reduction in viral entry into (e.g., reduction of internalization of a virus into) a cell; 5) a reduction in time to seroconversion; 6) an increase in the rate of sustained response to therapy; 7) a reduction of morbidity or mortality in clinical outcomes; 8) shortening the total length of treatment when combined with other anti-viral agents; and 9) an improvement in an indicator of disease response (e.g., a reduction in one or more symptoms of a viral infection, such as fever, etc.). Any of a variety of methods can be used to determine whether a treatment method is effective. For example, a biological sample obtained from an individual who has been treated with a subject method can be assayed.

In some embodiments of the methods of treatment, the infective disease condition results from infection with a positive-stranded RNA virus, negative stranded RNA virus, or a DNA virus. In some embodiments, the infective disease condition results from infection with a pathogen selected from the group of viral families consisting of Picomaviridae, Flaviviridae, Retroviridae, Filoviridae, Togaviridae, Papovaviridae, Papillomaviridae, Polyomaviridae, Caliciviridae, Coronavirinae, Hepeviridae, Bunyaviridae, Poxviridae and Orthomyxoviridae. In some embodiments, the infective disease condition results from infection with a pathogen selected from the phylum Apicomplexa or from the order Kinetoplastida. In some embodiments, the infective disease condition results from infection with a bacterium. In some embodiments, the infective disease condition results from infection with a fungus. In some embodiments, the infective disease condition results from infection with a pathogen selected from HCV, rhinovirus (e.g., A, B or C, as well as unclassified), plasmodium, P. falciparum, Ebola virus, Francisella tularensis, hantavirus, SARS virus, MERS virus, SARS-CoV-2 virus, vaccinia, smallpox, Japanese encephalitis virus, hepatitis A virus, and influenza virus, Norovirus, PolioVirus, Enterovirus (e.g., A-D), HEV, EV71, EV68, coxsackie virus, BK virus, JC virus, human papiloma virus, West Nile Virus, and Dengue Virus (e.g., 1-4). In some embodiments, the pathogen is HCV. In some embodiments, the pathogen is rhinovirus or P. falciparum. In some embodiments, the pathogen is hepatitis A virus. In certain embodiments of the method of treatment, the pathogen is a virus selected from EV71, EV68, human rhinoviruses, HAV, HCV, norovirus, coxsackie, BK, polio and ebola virus. In some embodiments, the pathogen is hepatitis A virus. In certain cases, the virus is EV71 or EV68. In certain cases, the virus is a human rhinovirus. In certain cases, the virus is HAV. In certain cases, the virus is a norovirus. In certain cases, the virus is coxsackie virus. In certain cases, the virus is BK virus. In certain cases, the virus is polio. In certain cases, the virus is ebola virus. Any of the compounds described herein can be utilized in the subject methods of treatment. In certain instances, the compound is of one of formulae I-VI. In certain cases, the compound is one of the compounds of Table 1, 2 or 3. In some cases, the compound that is utilized in the subject methods has broad spectrum activity against several of the pathogens (e.g., viruses) described herein. In certain instances, the compound has anti-viral activity against particular viruses, including one or more of the viruses described above. In certain instances, the compound has anti-fungal activity against a particular fungus.

In some embodiments, the pathogen is characterized by having a BAAPP domain that interacts with PIP-2, or a protein that binds PI(4,5)P$_2$ or PI(4)P. In some embodiments, the pathogen is characterized by having a protein that interacts with one or more PI-4 kinases or PI phosphatases. In some embodiments, the BAAPP domain is derived from NS5A or NS4B protein. In some embodiments, the infective disease condition is caused by infection of a pathogen susceptible to PI4-kinase inhibition. In some embodiments, the compound specifically inhibits the PT4-kinase. In some embodiments, the compound has broad spectrum activity against two or more pathogens. In some embodiments, the compound modulates the activity of PIP-2. In some embodiments, the compound interferes with the interaction of a BAAPP domain and PIP-2 of the pathogen. In some embodiments, the compound blocks pathogen replication.

In some embodiments, the subject method is a method of treating a subject for an elevated level of VLDL or LDL cholesterol. In some embodiments, the subject method includes administering to the subject an effective amount of a 2-aminophenylthiazole compound (e.g., as described above), alone or in combination with other drugs known to affect LDL or VLDL levels (e.g., 3-hydroxy-3-methylglutaryl-coenzyme A reductase inhibitors such as lovastatin, fluvastatin, atorvastatin, pravastatin, simvastatin, rosuvastatin, etc.; microsomal triglyceride transfer protein inhibitors such as lomitapide; inhibitors of intestinal cholesterol absorption such as ezetimibe; peroxisome proliferator-activated receptor type alpha activators such as fenofibrate).

In some embodiments, the subject is human. The subject may be in need of treatment for a viral infection, or may be at risk of a viral infection. In some instances, the subject methods include diagnosing a viral infection, including any one of the viruses described herein. In some embodiments, the compound is administered as a pharmaceutical preparation.

In some embodiments, the subject method is a method of inhibiting viral infection, the method including contacting virus-infected cells with an effective dose of a 2-aminophenylthiazole compound (e.g., as described above) to inhibit viral replication. In some embodiments, the method further includes contacting the cells with a second antiviral agent.

In some embodiments, the compound is formulated to be targeted to the liver.

In certain embodiments, the compound is a modified compound that includes a label, and the method further includes detecting the label in the subject. The selection of the label depends on the means of detection. Any convenient labeling and detection systems may be used in the subject methods, see e.g., Baker, "The whole picture," Nature, 463, 2010, p977-980. In certain embodiments, the compound includes a fluorescent label suitable for optical detection. In certain embodiments, the compound includes a radiolabel for detection using positron emission tomography (PET) or single photon emission computed tomography (SPECT). In some cases, the compound includes a paramagnetic label suitable for tomographic detection. The subject compound may be labeled, as described above, although in some methods, the compound is unlabeled and a secondary labeling agent is used for imaging.

PI-Kinase Inhibition in Cancer Cells

In some instances, the types of cells in which the compounds exhibit activity are cancer cells, as described herein. By inhibiting a PI4-kinase it is meant that the activity of the enzyme is decreased by a factor of 2 or more, such as 3 or more, 5 or more, 10 or more, 100 or more, or 1000 or more, relative to its normal activity (e.g., relative to a positive control).

The methods of the present disclosure can target cancer cells. The target cancer cells and their metastases can be considered "addicted" to increased PI4-kinase activity. The latter can result from amplification of chromosomal segments that harbor a PI4-kinase gene, such as PI4-III-kinase a or PI4-III-kinase $, or eukaryotic protein translation elongation factor 1 alpha 2 (eEF1A2). eEF1A2 is a translation factor that is involved in internal ribosome entry site (IRES) mediated translation. eEF1A2 also stimulates PI4-kinase activity and is overexpressed in many cancers. IRESs are often used by viruses as a means to ensure that viral translation is active when host translation is inhibited. IRES-mediated translation can contribute to the translation of certain cellular RNAs, particularly under abnormal cellular states. The target cancer cells can have the above chromosomal amplifications, or increased expression of eEF1A2 without chromosomal amplifications, any of which can lead to increased PI4 kinase activity. The inventors discovered that anti-viral PI4 kinase inhibitors that potently target IRES containing viruses were also effective in reducing proliferation of cancer cells and could find use in the treatment of cancer. In some embodiments, the cancer cells have normal levels of PI4-kinase activity, but are more sensitive to PI4-kinase activity than normal cells.

Cancer cells of interest which can be targeted according to the subject methods include a wide variety of cancer cells. In some instances, the cancer cell is selected from bladder, breast, colon, endometrial, cervix, testicle, liver, lung, non-small cell lung cancer (NSCLC), ovarian, prostate, pancreatic, brain, thyroid, stomach, kidney, melanoma and sarcoma cancer cells.

As such, aspects of this disclosure include assessing or measuring the level of expression of a PI4-kinase gene or a factor involved in IRES-mediated translation that stimulates PI4-kinase activity (e.g., eEF1A2 translation factor) in a target cell. In some cases, the assessing or measuring step includes determining whether the target cells have an elevated level of expression of a PI4-kinase gene or eEF1A2 translation factor. As used herein, the terms "elevated level of expression", "overexpression" and "overexpressed" are used interchangeably and refer to a level of expression in a target cell that is 20% or more than the native or basal level of expression in a control cell, such as 30% or more, 40% or more, 40% or more, 40% or more, 40% or more, 40% or more, 40% or more, 2-fold greater or more, 5-fold greater or more, 10-fold greater or more, 30-fold greater or more, 100-fold greater or more or 1000-fold greater or more, as compared to the native or basal level of expression in a control cell. In some cases, the control cell is one or more control cells from a plurality of subjects. In certain cases, the control cell is one or more control cells from a plurality of cells of the same type as the target cell from a plurality of subjects. In some cases, the control cells are normal cells.

The methods that may be employed in measuring or determining levels of expression in a cell are numerous and include but are not limited to cellular assays in which a cellular phenotype is measured, e.g., gene expression assays. The methods can be qualitative or quantitative. Expression levels can be determined directly or indirectly. In some cases, the gene copy number for the gene of interest in the target cells is measured. In certain cases, the gene copy number of PI4 is determined, e.g., PI4KIIIβ or PI4KIIIα. In certain cases, the gene copy number of eEF1A2 is determined. In some cases, the eEF1A2 transcription level is determined. In some cases, the target cancer cells have a greater than diploid copy number of the PI4KIIIβ gene.

Aspects of this disclosure include assessing or measuring the level of activity of a PI4-kinase in a target cell. In some cases, the assessing or measuring step includes determining whether the target cells have an elevated level of activity of a PI4-kinase. The term "elevated level of activity" refers to a level of activity in a target cell that is 20% or more than the native or basal level of activity in a control cell, such as 30% or more, 40% or more, 40% or more, 40% or more, 40% or more, 40% or more, 40% or more, 2-fold greater or more, 5-fold greater or more, 10-fold greater or more, 30-fold greater or more, 100-fold greater or more or 1000-fold greater or more, as compared to the native or basal level of activity in a control cell. In some cases, the control cell is one or more control cells from a plurality of subjects. In certain cases, the control cell is one or more control cells from a plurality of cells of the same type as the target cell from a plurality of subjects. In some cases, the control cells are normal cells.

The methods that may be employed in determining PI4-kinase activity are numerous, and include but are not limited to cell-free assays, e.g., binding assays; assays using purified enzymes, measurements of PI4-P levels, cellular assays in which a cellular phenotype is measured, e.g., gene expression assays; and in vivo assays that involve a particular animal (which, in certain embodiments may be an animal model for a condition dependent on PI-kinase activity). In some cases, the target cancer cells have an elevated level of PI4KIIIβ activity. In some embodiments of the subject methods, the target cancer cells are cells that are sensitive to PT4KIIIβ inhibition. In certain cases, these PI4KIIIβ inhibition-sensitive cells do not exhibit an elevated level of expression or activity of PI4KIIIβ. In some embodiments, the PI4-kinase inhibitors are inhibitors of a PI4-HI-kinase (e.g., PI4-Ha or PI4-IIIβ). In some embodiments, the PI4-kinase inhibitors have a PI-kinase inhibition profile that reflects activity against two or more PI-kinases. In some embodiments, the PI4-kinase inhibitors specifically inhibit both a type 11 PI3-kinase, such as PI3-kinase H, and a type III PI4-kinase, such as PI4K-IIIα and/or PI4KIIIβ). In some embodiments, the PI4-kinase inhibitors specifically inhibit a PI4-kinase without undesired inhibition of other protein kinases. In some embodiments, the PI4-kinase inhibitors specifically inhibit a PI4-kinase without undesired inhibition of PI3-kinase. In some embodiments, the PI4-kinase inhibitors specifically inhibit a PI4-kinase and/or a specific PI3-kinase subclass without undesired inhibition of other PI3-kinase subclasses or protein kinases.

In some embodiments, the PI4-kinase inhibitors interfere with the interaction of a basic amino acid PIP-2 pincer (BAAPP) domain with phosphatidylinositol-4,5-bisphosphate PIP2 in a cell. See e.g., Glenn et al. US2011/0262565 and U.S. Pat. No. 9,926,309. For example, the subject compounds may act by decreasing the levels of PIP2 either directly or indirectly that bind specifically to the BAAPP domain.

PI4-kinase inhibition can be as determined by an inhibition assay, e.g., by an assay that determines the level of activity of the enzyme either in a cell-free system or in a cell after treatment with a subject compound, relative to a control, by measuring the $IC_{50}$ or $EC_{50}$ value, respectively. In certain embodiments, the subject compounds have an $IC_{50}$ value (or $EC_{50}$ value) of 10 μM or less, such as 3 μM or less, 1 μM or less, 500 nM or less, 300 nM or less, 200 nM or less, 100 nM or less, 50 nM or less, 30 nM or less, 10 nM or less, 5 nM or less, 3 nM or less, 1 nM or less, or even lower.

PI4-kinase inhibition can be determined by a kinase activity assay, e.g., by an assay that determines the level of incorporation of radiolabeled phosphate from [γ-$^{12}$P]-ATP into a substrate molecule after treatment with a subject compound, relative to a control, by measuring the beta-particle emission rate using a scintillation counter or phosphorimaging. In certain embodiments, the inhibitors have an $IC_{50}$ value for PI4K-IIIβ of less than about 1 μM, less than about 0.2 μM, less than about 0.1 μM, less than about 10 nM, less than about 1 nM, or even less, such as described in Table 3. In certain embodiments, the inhibitors have an $IC_{50}$ value for PI4K-IIIα of less than about 50 μM, less than about 10 μM, less than about 1 μM, less than about 0.1 μM, less than about 10 nM, less than about 1 nM, or even less, such as described in Tables 2-3. In certain further embodiments, the inhibitors have an IC50 value for PI4K-IIIβ of 50 μM or less, such as 10 nM or less, 6 nM or less, or even less, such as described in Tables 2-3. In certain embodiments, the inhibitors have an IC50 value for type II PI3-kinase alpha of less than 10 μM. In certain embodiments, the inhibitors have an IC50 value for type II PI3-kinase alpha of 1 μM or more, such as 10 μM or more. In certain further embodiments, more than one of the above criteria is independently satisfied by a particular compound.

In some embodiments, the anti-cancer potency of the PI4-kinase inhibitors track with anti-infective (e.g., antiviral) activity. In some cases, the enzymatic and anti-cancer activities of the subject compounds diverge. In some embodiments, the anti-cancer activity of the subject compounds depends on a combination of inhibition of both PT4KIIIα and PT4KIIIβ, or a combination of inhibition of class III PI4-kinases and/or class II PI3-kinases (especially class II PI3-kinase beta). The subject compound may have increased specificity for one isoform of these PI-kinase family members.

In certain embodiments, the PI4-kinase inhibitors have no significant effect on the viability of a normal mammalian cell, as determined by a cell cytotoxicity assay, e.g., as determined by administering a compound to primary human liver cells and determining the number of viable cells present. The compound may exhibit a % cell viability, as compared to a control (e.g., a DMSO control), of 15% or more, such as 20% or more, 30% or more, 40% or more, 50% or more, 60% or more, 70% or more, 80% or more, 90% or more, 100% or more, 120% or more, or even higher. The subject compounds may exhibit a $CC_{50}$ value (the concentration at which 50% of the cells remain viable) of 1 nM or higher, such as 100 nM or higher, 300 nM or higher, 1 M or higher, 3 μM or higher, 5 μM or higher, 10 μM or higher, 20 μM or higher, 30 μM or higher, 50 μM or higher, or even higher.

In certain embodiments, the PI4-kinase inhibitors have a therapeutic index (e.g., the ratio of a compound's cytotoxicity (e.g., normal cell cytotoxicity, CC50) to bioactivity (e.g., anticancer activity, EC50—the concentration at which 50% of the cancer cells are inhibited)) that is 2 or more, such as 5 or more, such as 10 or more, such as 20 or more, 50 or more, 100 or more, 200 or more, 300 or more, 400 or more, 500 or more, or even more.

As summarized above, aspects of the disclosure include methods of inhibiting a PI4-kinase (e.g., a PI4-IIIα, and/or a PI4-IIIβ kinase) in a cell of interest. The compound (e.g., as described herein) may inhibit at least one activity of the PI4-kinase in the range of 10% to 100%, e.g., by 10% or more, 20% or more, 30% or more, 40% or more, 50% or more, 60% or more, 70% or more, 80% or more, or 90% or more. In certain assays, a PI4-kinase inhibitor may inhibit its target with an $IC_{50}$ (the concentration needed to inhibit 50% of the kinase activity) of $1\times10^{-6}$ M or less (e.g., $1\times10^{-6}$ M or less, $1\times10^{-7}$ M or less, $1\times10^{-8}$ M or less, $1\times10^{-9}$ M or less, $1\times10^{-10}$ M or less, or $1\times10^{-11}$ M or less).

The protocols that may be employed in determining PI-kinase activity are numerous, and include but are not limited to cell-free assays, e.g., binding assays; assays using purified enzymes, cellular assays in which PI4P levels are measured or a cellular phenotype is measured, e.g., gene expression assays; and in vivo assays that involve a particular animal (which, in certain embodiments may be an animal model for a condition dependent on PI-kinase activity).

In some embodiments, the subject method is an in vitro method that includes contacting a sample with a compound that specifically inhibits a target PI-kinase. In certain embodiments, the sample is suspected of containing the PT-kinase and the subject method further comprises evaluating whether the compound inhibits the PI-kinase, or a PI-kinase dependent function such as cancer cell growth. In certain embodiments, the PI-kinase is a PI4-kinase, e.g., a PI4-II kinase, such as a PT4-III kinase. In another embodiment of the subject method, the sample is known to contain the target PI-kinase.

Methods of Treating Cancer

In some embodiments, the subject method is an in vivo method that includes administering to a subject an effective amount of a compound that specifically inhibits a PI4-kinase. An "effective amount" is an amount of a compound that, when administered to an individual in one or more doses, in monotherapy or in combination therapy, is effective to inhibit a PT4-kinase by at least about 20% (20% inhibition), such as at least about 30% (30% inhibition), at least about 40% (40% inhibition), at least about 50% (50% inhibition), at least about 60% (60% inhibition), at least about 70% (70% inhibition), at least about 80% (80% inhibition), or at least about 90% (90% inhibition), compared to the PI4-kinase activity in the individual in the absence of treatment with the compound, or alternatively, compared to the PI4-kinase activity in the individual before or after treatment with the compound.

The subject may be one who has a cancer as described herein. Cancers of interest which can be treated according to the subject methods include, but are not limited to, bladder, breast, colon, endometrial, liver, cervical, testicular, lung, non-small cell lung cancer (NSCLC), ovarian, prostate, pancreatic, brain, melanoma, sarcoma, thyroid, stomach and kidney cancer. In some instances, the caner is lung cancer. In certain cases, the lung cancer is a lung adenocarcinoma. In some instances, the cancer is breast cancer. In certain cases, the breast cancer is a breast adenocarcinoma. In some instances, the cancer is a brain cancer. In some instances, the brain cancer is glioblastoma (GBM).

In some embodiments, a "therapeutically effective amount" is an amount of a compound that, when administered to an individual in one or more doses, in monotherapy or in combination therapy, is effective to decrease tumor burden in the subject by at least about 20%, such as at least about 30%, at least about 40%, at least about 50%, at least about 60%, at least about 70%, at least about 80%, or at least about 90%, compared to tumor burden in the individual in the absence of treatment with the compound, or alternatively, compared to the tumor burden in the subject before treatment with the compound. As used herein the term "tumor burden" refers to the total mass of tumor tissue carried by a subject with cancer.

In some embodiments, a "therapeutically effective amount" is an amount of a subject compound that, when administered to an individual in one or more doses, in monotherapy or in combination therapy, is effective to reduce the dose of radiotherapy required to observe tumor shrinkage in the subject by at least about 20%, at least about 30%, at least about 40%, at least about 50%, at least about 60%, at least about 70%, at least about 80%, or at least about 90%, compared to the dose of radiotherapy required to observe tumor shrinkage in the individual in the absence of treatment with the compound.

In some embodiments, a "therapeutically effective amount" is an amount of a compound that, when administered to an individual in one or more doses, in monotherapy or in combination therapy, is effective to decrease metastases burden in the subject by at least about 20%, such as at least about 30%, at least about 40%, at least about 50%, at least about 60%, at least about 70%, at least about 80%, or at least about 90%, compared to metastases burden in the individual in the absence of treatment with the compound, or alternatively, compared to the metastases burden in the subject before treatment with the compound. As used herein the term "metastases burden" refers to the total mass or number of metastases tissue carried by a subject with cancer.

In some embodiments, an effective amount of a compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a compound is an amount that ranges from about 10 µg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg or 3000 mg.

In some embodiments, a single dose of a compound is administered. In other embodiments, multiple doses are administered. Where multiple doses are administered over a period of time, the compound can be administered twice daily (bid), daily (qd), every other day (qod), every third day, once per week(qw), three times per week (tiw), or twice per week (biw) over a period of time. For example, a compound is administered bid, qd, qod, tiw, or biw over a period of from one day to about 2 years or more. For example, a compound is administered at any of the aforementioned frequencies for one week, two weeks, one month, two months, six months, one year, or two years, or more, depending on various factors. In some embodiments, the compound may be administered orally, intravenously, subcutaneously, intramuscularly, via inhalation, topically, or sublingually, among other routes of administration, including depot administration. In some embodiments, the compound is administered in combination with an inhibitor of its metabolism, such as an inhibitor of cytochrome P450 3A/4 (e.g. ritonavir or cobicistat). In some embodiments, the compound may be administered in courses wherein "drug holidays" are allowed that may last from 1-7 days.

Administration of a therapeutically effective amount of a subject compound to an individual with cancer can result in one or more of: 1) a reduction in tumor burden; 2) a reduction in the dose of radiotherapy required to effect tumor shrinkage; 3) a reduction in the spread of a cancer from one location to another in an individual; 4) a reduction of morbidity or mortality in clinical outcomes; 5) shortening the total length of treatment when combined with other anti-cancer agents; 6) a decrease in the size or number of metastases; and 7) an improvement in an indicator of disease response (e.g., a reduction in one or more symptoms of cancer). Any of a variety of methods can be used to determine whether a treatment method is effective. For example, a biological sample obtained from an individual who has been treated with a subject method can be assayed, or an imaging study may be performed.

Any of the PI4-kinase inhibitors described herein can be utilized in the subject methods of treatment. In certain instances, the PT4-kinase inhibitor is of any one of formulae (I) to (VI). In certain cases, the compound is one of the compounds of Table 1, 2 or 3.

In some embodiments, the compound specifically inhibits PI4-kinase. In some embodiments, the compound specifically inhibits PI4III-kinase. In some embodiments, the compound specifically inhibits PI4IIIβ-kinase. In some embodiments, the compound specifically inhibits PI4IIIα-kinase. In some embodiments, the compound modulates the activity of a cancer cell that includes an elevated expression of PT4-kinase or a factor involved in IRES-mediated translation that stimulates PI4-kinase activity (e.g. eEF1A2), or Golgi-mediated secretion. In some instances, the cancer cells include chromosome amplification of a PI4-kinase gene (such as PT4IIIβ or PI4IIIα), chromosome amplification of the eEF1A2 gene, or chromosome 1q amplification, i.e., a 1q-amplified cancer cell, which contains PI4IIIβ-kinase on the amplified segment. In some embodiments, the cancer cell has increased expression of eEF1A2 that is not a result of chromosome amplification of the eEF1A2 gene.

In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats. e.g., as in animal models of disease), as well as non-human primates (e.g., chimpanzees, and monkeys). The subject may be in need of treatment for cancer. In some instances, the subject methods include diagnosing cancer, including any one of the cancers described herein. In some embodiments, the compound is administered as a pharmaceutical preparation.

In certain embodiments, the PI4-kinase inhibitor is a modified compound that includes a label, and the method further includes detecting the label in the subject. The selection of the label depends on the means of detection. Any convenient labeling and detection systems may be used in the subject methods, see e.g., Baker, "The whole picture," Nature, 463, 2010, p977-980. In certain embodiments, the compound includes a fluorescent label suitable for optical detection. In certain embodiments, the compound includes a radiolabel for detection using positron emission tomography (PET) or single photon emission computed tomography (SPECT). In some cases, the compound includes a paramagnetic label suitable for tomographic detection. The subject compound may be labeled, as described above, although in some methods, the compound is unlabeled and a secondary labeling agent is used for imaging.

Co-Administration with a Metabolizing Enzyme Inhibitor

In some aspects of the subject methods, the subject PI4-kinase inhibitors can be administered to a subject in combination with an additional or second agent, such as an agent that extends the half-life, and/or increases the plasma concentration of the PI4-kinase inhibitor that is co-administered. The additional agent can be a compound that is capable of inhibiting in situ an enzyme that is responsible for metabolizing the PI4-kinase inhibitor from an active form to a less or inactive form or derivative of the compound. In some cases, the metabolizing enzyme is a cytochrome P-450. Any convenient cytochrome P-450s can be targeted for inhibition by use of the additional agent in the subject methods. In certain cases, the cytochrome P-450 is CYP3A4.

Metabolizing enzyme inhibitors of interest include, but are not limited to, clarithromycin, cobicistat, telithromycin, nefazodone, itraconazole, ketoconazole, atazanavir, darunavir, indinavir, lopinavir, nelfinavir, ritonavir, saquinavir and tipranavir. For example, ritonavir is a potent inhibitor of CYP3A4 that itself finds use as a therapeutic HIV protease inhibitor. In some cases, the metabolizing enzyme inhibitor is co-administered at a dose effective to inhibit the metabolizing enzyme action on the PI4-kinase inhibitor, but which is a subtherapeutic dose relative to its therapeutic application, e.g., in treating HIV.

The terms "co-administration" and "in combination with" include the administration of two or more agents either simultaneously, concurrently or sequentially within no specific time limits. In one embodiment, the agents are present in the cell or in the subject's body at the same time or exert their biological or therapeutic effect at the same time. In one embodiment, the agents are in the same composition or unit dosage form. In other embodiments, the agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second agent. Routes of administration of the two agents may vary, where representative routes of administration are described in greater detail below. A person of ordinary skill in the art would have no difficulty determining the appropriate timing, sequence and dosages of administration for a PI4-kinase inhibitor and the additional agent.

Combination Therapies

The PI4-kinase inhibitors disclosed herein can be administered to a subject alone or in combination with an additional, i.e., second, active agent. Combination therapeutic methods where the PI4-kinase inhibitors may be used in combination with a second active agent or an additional therapy, e.g., radiation therapy. The terms "agent," "compound," and "drug" are used interchangeably herein. For example, PI4-kinase inhibitors can be administered alone or in conjunction with one or more other drugs, such as drugs employed in the treatment of diseases of interest, including but not limited to, immunomodulatory diseases and conditions and cancer. In some embodiments, the subject method further includes coadministering concomitantly or in sequence a second agent, e.g., a small molecule, a chemotherapeutic, an antibody, an antibody fragment, an antibody-drug conjugate, an aptamer, a protein, or a checkpoint inhibitor. In some embodiments, the method further includes performing radiation therapy on the subject.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

"Concomitant administration" of a known therapeutic drug or additional therapy with a pharmaceutical composition of the present disclosure means administration of the compound and second agent or additional therapy at such time that both the known drug and the composition of the present invention will have a therapeutic effect. Such concomitant administration may involve concurrent (i.e. at the same time), prior, or subsequent administration of the drug with respect to the administration of a subject compound. Routes of administration of the two agents may vary, where representative routes of administration are described in greater detail below. A person of ordinary skill in the art would have no difficulty determining the appropriate timing, sequence and dosages of administration for particular drugs or therapies and compounds of the present disclosure.

In some embodiments, the compounds (e.g., a PI4-kinase inhibitor and the at least one additional compound or therapy) are administered to the subject within twenty-four hours of each other, such as within 12 hours of each other, within 6 hours of each other, within 3 hours of each other, or within 1 hour of each other. In certain embodiments, the compounds are administered within 1 hour of each other. In certain embodiments, the compounds are administered substantially simultaneously. By administered substantially simultaneously is meant that the compounds are administered to the subject within about 10 minutes or less of each other, such as 5 minutes or less, or 1 minute or less of each other.

Also provided are pharmaceutical preparations of the PI4-kinase inhibitor and the second active agent. In pharmaceutical dosage forms, the compounds may be administered in the form of their pharmaceutically acceptable salts, or they may also be used alone or in appropriate association, as well as in combination, with other pharmaceutically active compounds.

In conjunction with any of the subject methods, the PI4-kinase inhibitors (e.g., as described herein) (or pharmaceutical compositions comprising such compounds) can be administered in combination with another drug designed to reduce or prevent inflammation, treat or prevent chronic inflammation or fibrosis, or treat cancer. In each case, the PI4-kinase inhibitor can be administered prior to, at the same time as, or after the administration of the other drug. In certain cases, the cancer is selected from adrenal, liver, kidney, bladder, breast, colon, gastric, ovarian, cervical, uterine, esophageal, colorectal, prostate, pancreatic, lung (both small cell and non-small cell), thyroid, carcinomas, sarcomas, glioma, glioblastomas, melanoma and various head and neck tumors.

For the treatment of cancer, the PI4-kinase inhibitors can be administered in combination with a chemotherapeutic agent selected from the group consisting of alkylating agents, nitrosoureas, antimetabolites, antitumor antibiotics, plant (*vinca*) alkaloids, steroid hormones, taxanes, nucleoside analogs, steroids, anthracyclines, thyroid hormone replacement drugs, thymidylate-targeted drugs, Chimeric Antigen Receptor/T cell therapies, Chimeric Antigen Receptor/NK cell therapies, apoptosis regulator inhibitors (e.g., B cell CLL/lymphoma 2 (BCL-2) BCL-2-like 1 (BCL-XL) inhibitors), CARP-1/CCAR1 (Cell division cycle and apoptosis regulator 1) inhibitors, colony-stimulating factor-1 receptor (CSF1R) inhibitors, CD47 inhibitors, cancer vaccine (e.g., a Th17-inducing dendritic cell vaccine, or a genetically modified tyrosinase such as Oncept®) and other cell therapies.

Specific chemotherapeutic agents of interest include, but are not limited to, Gemcitabine, Docetaxel, Bleomycin, Erlotinib, Gefitinib, Lapatinib, Imatinib, Dasatinib, Nilotinib, Bosutinib, Crizotinib, Ceritinib, Trametinib, Bevacizumab, Sunitinib, Sorafenib, Trastuzumab, Ado-trastuzumab emtansine, Rituximab, Ipilimumab, Rapamycin, Temsirolimus, Everolimus, Methotrexate, Doxorubicin, Abraxane, Folfirinox, Cisplatin, Carboplatin, 5-fluorouracil, Teysumo, Paclitaxel, Prednisone, Levothyroxine, Pemetrexed, navitoclax, and ABT-199. Peptidic compounds can also be used. Cancer chemotherapeutic agents of interest include, but are not limited to, dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD).

In some embodiments, the PI4-kinase inhibitors can be administered in combination with a chemotherapeutic agent to treat cancer. In certain cases, the chemotherapeutic agent is Gemcitabine. In some cases, the chemotherapeutic agent is Docetaxel. In some cases, the chemotherapeutic agent is Abraxane.

For the treatment of cancer (e.g., solid tumor cancer), the PI4-kinase inhibitors can be administered in combination an immunotherapeutic agent. An immunotherapeutic agent is any convenient agent that finds use in the treatment of disease by inducing, enhancing, or suppressing an immune response. In some cases, the immunotherapeutic agent is an immune checkpoint inhibitor. Any convenient checkpoint inhibitors can be utilized, including but not limited to, cytotoxic T-lymphocyte-associated antigen 4 (CTLA-4) inhibitors, programmed death 1 (PD-1) inhibitors and PD-L1 inhibitors. In certain instances, the checkpoint inhibitor is selected from a cytotoxic T-lymphocyte-associated antigen 4 (CTLA-4) inhibitor, a programmed death 1 (PD-1) inhibitor and a PD-L1 inhibitor. Exemplary checkpoint inhibitors of interest include, but are not limited to, ipilimumab, pembrolizumab and nivolumab. In certain embodiments, for treatment of cancer and/or inflammatory disease, the immunomodulatory polypeptide(s) can be administered in combination with a colony-stimulating factor-1 receptor (CSF1R) inhibitor. CSF1R inhibitors of interest include, but are not limited to, emactuzumab.

Any convenient cancer vaccine therapies and agents can be used in combination with the PI4-kinase inhibitors, compositions and methods. For treatment of cancer, e.g., ovarian cancer, the PI4-kinase inhibitors can be administered in combination with a vaccination therapy, e.g., a dendritic cell (DC) vaccination agent that promotes Th1/Th17 immunity. Th17 cell infiltration correlates with markedly prolonged overall survival among ovarian cancer patients. In some cases, the ENPP1 inhibitor compound finds use as adjuvant treatment in combination with Th17-inducing vaccination.

Also of interest are agents that are CARP-1/CCAR1 (Cell division cycle and apoptosis regulator 1) inhibitors, including but not limited to those described by Rishi et al., Journal of Biomedical Nanotechnology, Volume 11, Number 9, September 2015, pp. 1608-1627(20), ENPP1 inhibitors, including but not limited to those described by Carozza et al, and CD47 inhibitors, including, but not limited to, anti-CD47 antibody agents such as Hu5F9-G4.

In certain instances, the combination provides an enhanced effect relative to either component alone; in some cases, the combination provides a supra-additive or synergistic effect relative to the combined or additive effects of the components. A variety of combinations of the subject compounds and the chemotherapeutic agent may be employed, used either sequentially or simultaneously. For multiple dosages, the two agents may directly alternate, or two or more doses of one agent may be alternated with a single dose of the other agent, for example. Simultaneous administration of both agents may also be alternated or otherwise interspersed with dosages of the individual agents. In some cases, the time between dosages may be for a period from about 1-6 hours, to about 6-12 hours, to about 12-24 hours, to about 1-2 days, to about 1-2 week or longer following the initiation of treatment.

Utility

The compounds and methods of the invention, e.g., as described herein, find use in a variety of applications. Applications of interest include, but are not limited to: research applications and therapeutic applications. Methods of the invention find use in a variety of different applications including any convenient application where inhibition of a PI4-kinase is desired.

The subject compounds and methods find use in a variety of research applications. The subject compounds and methods may be used in the optimization of the bioavailability and metabolic stability of compounds.

The subject compounds and methods find use in a variety of therapeutic applications. Therapeutic applications of interest include those applications in which pathogen infection is the cause or a compounding factor in disease progression. As such, the subject compounds find use in the treatment of a variety of different conditions in which the inhibition and/or treatment of viral infection in the host is desired. For example, the subject compounds and methods may find use in treating a pathogen caused infective disease (e.g., as described herein), such as HCV.

In some embodiments, the subject compound and methods find use in therapeutic applications in which an enterovirus infection is implicated. Enteroviruses (EVs) are among the most frequent infectious agents in humans worldwide and represent the leading cause of upper respiratory tract infections. EV infection with pulmonary exacerbations is implicated in cystic fibrosis (CF) patients. In certain instances, the subject methods and compounds (e.g., as described herein) find use in treating a cystic fibrosis (CF) patient, e.g., to reduce a symptom or condition associated with EV infection. In certain instances, the subject compounds and methods can be used to target the F508del-cystic fibrosis transmembrane conductance regulator (CFTR) folding defect.

In some embodiments, the subject compounds and methods find use in therapeutic applications in which a rhinovirus infection is implicated. Rhinoviruses are frequent infectious agents in humans worldwide and represent an important cause of asthma exacerbations. In certain instances, the subject methods and compounds (e.g., as described herein) find use in treating a patient with asthma, e.g., to reduce a symptom or condition associated with rhinovirus infection.

Therapeutic applications of interest also include those applications in cancer treatment. As such, the subject compounds find use in the treatment of a variety of different conditions in which the inhibition and/or treatment of cancer in the host is desired. For example, the subject compounds and methods may find use in treating a solid tumor cancer (e.g., as described herein).

Pharmaceutical Compositions

The herein-discussed compounds can be formulated using any convenient excipients, reagents and methods. Compositions are provided in formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the subject compound is formulated in an aqueous buffer. Suitable aqueous buffers include, but are not limited to, acetate, succinate, citrate, and phosphate buffers varying in strengths from 5 mM to 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures. In some embodiments, the subject compound is formulated for sustained release. In some embodiments, the subject compound is formulated for depot release.

Combination Pharmaceutical Compositions for Treating a Pathogen Infection

In some embodiments, the subject compound and an antiviral agent, e.g. interferon, ribavirin, Enfuvirtide; RFI-641 (4,4"-bis-{4,6-bis-[3-(bis-carbamoylmethyl-sulfamoyl)-phenylamino]-(1,3,5) triazin-2-ylamino}-biphenyl-2,2"-disulfonic acid); BMS-433771 (2H-Imidazo(4,5-c) pyridin-2-one, 1-cyclopropyl-1,3-dihydro-3-((1-(3-hydroxypropyl)-1H-benzimidazol-2-yl)methyl)); arildone; Pleconaril (3-(3,5-Dimethyl-4-(3-(3-methyl-5-isoxazolyl) propoxy)phenyl)-5-(trifluoromethyl)-1,2,4-oxadiazole); Amantadine (tricyclo[3.3.1.1.3,7]decane-1-amine hydrochloride); Rimantadine (alpha-methyltricyclo[3.3.1.1.3,7] decane-1-methanamine hydrochloride); Acyclovir (acycloguanosine); Valaciclovir; Penciclovir (9-(4-hydroxy-3-hydroxymethyl-but-1-yl)guanine); Famciclovir (diacetyl ester of 9-(4-hydroxy-3-hydroxymethyl-but-1-yl)-6-deoxyguanine); Gancyclovir (9-(1,3-dihydroxy-2-propoxymethyl)guanine); Ara-A (adenosine arabinoside); Zidovudine (3'-azido-2',3'-dideoxythymidine); Cidofovir (1-[(S)-3-hydroxy-2-(phosphonomethoxy)propyl]cytosine dihydrate); Dideoxyinosine (2',3'-dideoxyinosine); Zalcitabine (2',3'-dideoxycytidine); Stavudine (2',3'-didehydro-2',3'-dideoxythymidine); Lamivudine ((−)-β-L-3'-thia-2',3'-dideoxycytidine); Abacavir (1S,4R)-4-[2-amino-6-(cyclopropylamino)-9H-purin-9-yl]-2-cyclopentene-1-methanol succinate); Emtricitabine (−)-β-L-3'-thia-2',3'-dideoxy-5-fluorocytidine); Tenofovir disoproxil (Fumarate salt of bis(isopropoxycarbonyloxymethyl) ester of (R)-9-(2-phosphonylmethoxypropyl)adenine); Bromovinyl deoxyuridine (Brivudin); Iodo-deoxyuridine (Idoxuridine); Trifluorothymidine (Trifluridine); Nevirapine (11-cyclopropyl-5,11-dihydro-4-methyl-6H-dipyrido[3,2-b:2',3'-f][1,4]diazepin-6-one); Delavirdine (1-(5-methanesulfonamido-1H-indol-2-yl-carbonyl)-4-[3-(1-methylethyl-amino)pyridinyl) piperazine monomethane sulfonated); Efavirenz ((−)6-chloro-4-cyclopropylethynyl-4-trifluoromethyl-1,4-dihydro-2H-3,1-benzoxazin-2-one); Foscarnet (trisodium phosphonoformate); Ribavirin (1-β-D-ribofuranosyl-1H-1,2,4-triazole-3-carboxamide); Raltegravir (N-[(4-Fluorophenyl)methyl]-1,6-dihydro-5-hydroxy-1-methyl-2-[1-methyl-1-[[(5-methyl-1,3,4-oxadiazol-2-yl)carbonyl]amino]ethyl]-6-oxo-4-pyrimidinecarboxamide monopotassium salt); Neplanocin A; Fomivirsen; Saquinavir (SQ); Ritonavir ([5S-(5R,8R,10R,11R)]-10-hydroxy-2-methyl-5-(1-methylethyl)-1-[2-(methylethyl)-4-thiazolyl]-3,6-dioxo-8,I I-bis (phenylmethyl)-2,4,7,12-tetraazatridecan-13-oic acid 5-thiazolylmethyl ester); Indinavir ([(1S,2R,5(S)-2,3,5-trideoxy-N-(2,3-dihydro-2-hydroxy-1H-inden-1-yl)-5-[2-[[(1,1-dimethylethyl)amino]carbonyl]-4-pyridinylmethyl)-1-piperazinyl]-2-(phenylmethyl-erythro)pentonamide); Amprenavir; Nelfinavir; Lopinavir; Atazanavir; Bevirimat; Indinavir; Relenza; Zanamivir; Oseltamivir; Tarvacin; etc. are administered to individuals in a formulation (e.g., in the same or in separate formulations) with a pharmaceutically acceptable excipient(s).

In another aspect of the present invention, a pharmaceutical composition is provided, comprising, or consisting essentially of, a compound of the present invention, or a pharmaceutically acceptable salt, isomer, tautomer or prodrug thereof, and further comprising one or more additional anti-viral agents of interest. Any convenient anti-viral agents can be utilized in the subject methods in conjunction with the subject compounds. In some instances, the additional agent is an anti-HCV therapeutic agent selected from: an HCV NS3 protease inhibitor, an HCV NS5B RNA-dependent RNA polymerase inhibitor, a thiazolide, a sustained release thiazolide, a nucleoside analog, an interferon-alpha or lambda, a pegylated interferon, ribavirin, levovirin, viramidine, a TLR7 agonist, a TLR9 agonist, a cyclophilin inhibitor, an alpha-glucosidase inhibitor, an NS5A inhibitor, an NS3 helicase inhibitor, clemizole or clemizole analog (such as the benzimidizole and indazole analogs described in U.S. patent application Ser. No. 12/383,071 and 12/383,030), or other NS4B inhibitor including an NS4B amphipathic helix inhibitor. The subject compound and second antiviral agent, as well as additional therapeutic agents as described herein for combination therapies, can be administered orally, subcutaneously, intramuscularly, intranasally, parenterally, or other route. The subject compound and second antiviral agent may be administered by the same route of administration or by different routes of administration. The therapeutic agents can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into an affected organ. In certain cases, the therapeutic agents can be administered intranasally.

In some embodiments, the subject compound and an antimalarial agent, e.g., chloroquine, primaquine, mefloquine, doxycycline, atovaquone-proguanil, quinine, quinidine, artesunate, artemether, lumefantrine; etc. are administered to individuals in a formulation (e.g., in the same or in separate formulations) with a pharmaceutically acceptable excipient(s). The subject compound and second antimalarial agent, as well as additional therapeutic agents as described herein for combination therapies, can be administered orally, subcutaneously, intramuscularly, parenterally, or other route. The subject compound and second antimalarial agent may be administered by the same route of administration or by different routes of administration. The therapeutic agents can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into an affected organ.

The subject compounds may be administered in a unit dosage form and may be prepared by any methods well known in the art. Such methods include combining the subject compound with a pharmaceutically acceptable carrier or diluent which constitutes one or more accessory ingredients. A pharmaceutically acceptable carrier is selected on the basis of the chosen route of administration and standard pharmaceutical practice. Each carrier must be "pharmaceutically acceptable" in the sense of being compatible with the other ingredients of the formulation and not injurious to the subject. This carrier can be a solid or liquid and the type is generally chosen based on the type of administration being used.

Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Any drug delivery device or system that provides for the dosing regimen of the instant disclosure can be used. A wide variety of delivery devices and systems are known to those skilled in the art.

Although such may not be necessary, compounds and agents described herein can optionally be targeted to the liver, using any known targeting means. The compounds of the disclosure may be formulated with a wide variety of compounds that have been demonstrated to target compounds to hepatocytes. Such liver targeting compounds include, but are not limited to, asialoglycopeptides; basic polyamino acids conjugated with galactose or lactose residues; galactosylated albumin; asialoglycoprotein-poly-L-lysine) conjugates; lactosaminated albumin; lactosylated albumin-poly-L-lysine conjugates; galactosylated poly-L-lysine; galactose-PEG-poly-L-lysine conjugates; lactose-PEG-poly-L-lysine conjugates; asialofetuin; and lactosylated albumin.

The terms "targeting to the liver" and "hepatocyte targeted" refer to targeting of a compound to a hepatocyte, particularly a virally infected hepatocyte, such that at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, of the compound administered to the subject enters the liver via the hepatic portal and becomes associated with (e.g., is taken up by) a hepatocyte.

HCV infection is associated with liver fibrosis and in certain embodiments the inhibitors may be useful in treating liver fibrosis (particularly preventing, slowing of progression, etc.). The methods involve administering a compound of the disclosure as described above, in an amount effective to reduce viral load, thereby treating liver fibrosis in the subject. Treating liver fibrosis includes reducing the risk that liver fibrosis will occur; reducing a symptom associated with liver fibrosis; and increasing liver function.

Whether treatment with a compound as described herein is effective in reducing liver fibrosis is determined by any of a number of well-established techniques for measuring liver fibrosis and liver function. The benefit of anti-fibrotic therapy can be measured and assessed by using the Child-Pugh scoring system which comprises a multi-component point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

Treatment of liver fibrosis (e.g., reduction of liver fibrosis) can also be determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) *Hepatol.* 31:241-246; and METAVIR (1994) Hepatology 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features; I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) *Hepatol.* 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) *J. Hepatol.* 13:372.

The Ishak scoring system is described in Ishak (1995) *J. Hepatol.* 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

In some embodiments, a therapeutically effective amount of a compound of the disclosure is an amount of compound that effects a change of one unit or more in the fibrosis stage based on pre- and post-therapy measures of liver function (e.g., as determined by biopsies). In particular embodiments, a therapeutically effective amount of the subject compound reduces liver fibrosis by at least one unit in the Child-Pugh, METAVIR, the Knodell, the Scheuer, the Ludwig, or the Ishak scoring system.

Secondary, or indirect, indices of liver function can also be used to evaluate the efficacy of treatment. Morphometric computerized semi-automated assessment of the quantitative degree of liver fibrosis based upon specific staining of collagen and/or serum markers of liver fibrosis can also be measured as an indication of the efficacy of a subject treatment method. Secondary indices of liver function include, but are not limited to, serum transaminase levels, prothrombin time, bilirubin, platelet count, portal pressure, albumin level, and assessment of the Child-Pugh score. An effective amount of the subject compound is an amount that is effective to increase an index of liver function by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the index of liver function in an untreated individual, or to a placebo-treated individual. Those skilled in the art can readily measure such indices of liver function, using standard assay methods, many of which are commercially available, and are used routinely in clinical settings.

Serum markers of liver fibrosis can also be measured as an indication of the efficacy of a subject treatment method. Serum markers of liver fibrosis include, but are not limited to, hyaluronate, N-terminal procollagen III peptide, 7S domain of type IV collagen, C-terminal procollagen I peptide, and laminin. Additional biochemical markers of liver fibrosis include α-2-macroglobulin, haptoglobin, gamma globulin, apolipoprotein A, and gamma glutamyl transpeptidase.

In some cases, a therapeutically effective amount of the subject compound is an amount that is effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Those skilled in the art can readily measure such serum markers of liver fibrosis, using standard assay methods, many of which are commercially available, and are used routinely in clinical settings. Methods of measuring serum markers include immunological-based methods, e.g., enzyme-linked immunosorbent assays (ELISA), radioimmunoassays, and the like, using antibody specific for a given serum marker.

Qualitative or quantitative tests of functional liver reserve can also be used to assess the efficacy of treatment with an agent. These include: indocyanine green clearance (ICG), galactose elimination capacity (GEC), aminopyrine breath test (ABT), antipyrine clearance, monoethylglycine-xylidide (MEG-X) clearance, and caffeine clearance.

As used herein, a "complication associated with cirrhosis of the liver" refers to a disorder that is a sequelae of decompensated liver disease, i.e., or occurs subsequently to and as a result of development of liver fibrosis, and includes, but it not limited to, development of ascites, variceal bleeding, portal hypertension, jaundice, progressive liver insufficiency, encephalopathy, hepatocellular carcinoma, liver failure requiring liver transplantation, and liver-related mortality.

A therapeutically effective amount of a compound in this context can be regarded as an amount that is effective in reducing the incidence (e.g., the likelihood that an individual will develop) of a disorder associated with cirrhosis of the liver by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to an untreated individual, or to a placebo-treated individual.

Whether treatment with the subject compound is effective in reducing the incidence of a disorder associated with cirrhosis of the liver can readily be determined by those skilled in the art.

Reduction in HCV viral load, as well as reduction in liver fibrosis, can be associated with an increase in liver function. Thus, the disclosure provides methods for increasing liver function, generally involving administering a therapeutically effective amount of a compound of the disclosure. Liver functions include, but are not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyltranspeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

Whether a liver function is increased is readily ascertainable by those skilled in the art, using well-established tests of liver function. Thus, synthesis of markers of liver function such as albumin, alkaline phosphatase, alanine transaminase, aspartate transaminase, bilirubin, and the like, can be assessed by measuring the level of these markers in the serum, using standard immunological and enzymatic assays. Splanchnic circulation and portal hemodynamics can be measured by portal wedge pressure and/or resistance using standard methods. Metabolic functions can be measured by measuring the level of ammonia in the serum.

Whether serum proteins normally secreted by the liver are in the normal range can be determined by measuring the levels of such proteins, using standard immunological and enzymatic assays. Those skilled in the art know the normal ranges for such serum proteins. The following are non-limiting examples. The normal range of alanine transaminase is from about 7 to about 56 units per liter of serum. The normal range of aspartate transaminase is from about 5 to about 40 units per liter of serum. Bilirubin is measured using standard assays. Normal bilirubin levels are usually less than about 1.2 mg/dL. Serum albumin levels are measured using standard assays. Normal levels of serum albumin are in the range of from about 35 to about 55 g/L. Prolongation of prothrombin time is measured using standard assays. Normal prothrombin time is less than about 4 seconds longer than control.

A therapeutically effective amount of a compound in this context is one that is effective to increase liver function by at least about 10%, at least about 20%, at least about 30%, at least about 40%, at least about 50%, at least about 60%, at least about 70%, at least about 80%, or more. For example, a therapeutically effective amount of a compound is an amount effective to reduce an elevated level of a serum marker of liver function by at least about 10%, at least about 20%, at least about 30%, at least about 40%, at least about 50%, at least about 60%, at least about 70%, at least about 80%, or more, or to reduce the level of the serum marker of liver function to within a normal range. A therapeutically effective amount of a compound is also an amount effective to increase a reduced level of a serum marker of liver function by at least about 10%, at least about 20%, at least about 30%, at least about 40%, at least about 50%, at least about 60%, at least about 70%, at least about 80%, or more, or to increase the level of the serum marker of liver function to within a normal range.

HCV infection is associated with hepatic cancer and in certain embodiments the present disclosure provides compositions and methods of reducing the risk that an individual will develop hepatic cancer. The methods involve administering the subject compound, as described above, wherein viral load is reduced in the individual, and wherein the risk that the individual will develop hepatic cancer is reduced. An effective amount of a compound is one that reduces the risk of hepatic cancer by at least about 10%, at least about 20%, at least about 25%, at least about 30%, at least about 35%, at least about 40%, at least about 45%, at least about 50%, at least about 55%, at least about 60%, at least about 65%, at least about 70%, or more. Whether the risk of hepatic cancer is reduced can be determined in, e.g., study groups, where individuals treated according to the subject methods have reduced incidence of hepatic cancer.

Combination Pharmaceutical Compositions for Treating Cancer

In some embodiments, the PI4-kinase inhibitor and a second active agent (e.g., as described herein), e.g. a small molecule, a chemotherapeutic, an antibody, an antibody fragment, an antibody-drug conjugate, an aptamer, or a protein, etc. are administered to individuals in a formulation (e.g., in the same or in separate formulations) with a pharmaceutically acceptable excipient(s). In some embodiments, the second active agent is a checkpoint inhibitor, e.g., a cytotoxic T-lymphocyte-associated antigen 4 (CTLA-4) inhibitor, a programmed death 1 (PD-1) inhibitor, or a PD-L1 inhibitor.

In another aspect, a pharmaceutical composition is provided, comprising, or consisting essentially of, a PI4-kinase inhibitor, or a pharmaceutically acceptable salt, isomer, tautomer or prodrug thereof, and further comprising one or more additional anti-cancer agents of interest. Any convenient anti-cancer agents can be utilized in the subject methods in conjunction with the subject compounds. The subject compounds may be administered in a unit dosage form and may be prepared by any methods well known in the art. Such methods include combining the subject compound with a pharmaceutically acceptable carrier or diluent which constitutes one or more accessory ingredients. A pharmaceutically acceptable carrier is selected on the basis of the chosen route of administration and standard pharmaceutical practice. Each carrier must be "pharmaceutically acceptable" in the sense of being compatible with the other ingredients of the formulation and not injurious to the subject. This carrier can be a solid or liquid and the type is generally chosen based on the type of administration being used.

Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Any drug delivery device or system that provides for the dosing regimen of the instant disclosure can be used. A wide variety of delivery devices and systems are known to those skilled in the art.

Although such may not be necessary, compounds and agents described herein can optionally be targeted to the site of cancer, using any known targeting means. The compounds of the disclosure may be formulated with a wide variety of compounds that have been demonstrated to target compounds to the site of cancer. The terms "targeting to the site of cancer" and "cancer targeted" refer to targeting of a compound to a site of cancer, such that at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, of the compound administered to the subject enters the site of cancer.

Subjects Amenable to Treatment Using the Compounds of the Disclosure

Individuals who have been clinically diagnosed as infected with a pathogen of interest are suitable for treatment with the methods of the present disclosure. In particular embodiments of interest, individuals of interest for treatment according to the disclosure have detectable pathogen titer indicating active replication, for example an HCV titer of at least about $10^4$, at least about $10^5$, at least about $5 \times 10^5$, or at least about $10^6$, or greater than 2 million genome copies of HCV per milliliter of serum. Similar methods may be used to determine whether subjects infected with another pathogen are suitable for treatment using the subject methods.

The effectiveness of the anti-infective treatment may be determined using any convenient method. For example, whether a subject method is effective in treating a virus infection can be determined by measuring viral load, or by measuring a parameter associated with infection.

Viral load can be measured by measuring the titer or level of virus in serum. These methods include, but are not limited to, a quantitative polymerase chain reaction (PCR) and a branched DNA (bDNA) test. Many such assays are available commercially, including a quantitative reverse transcription PCR (RT-PCR) (Amplicor HCV Monitor™, Roche Molecular Systems, New Jersey); and a branched DNA (deoxyribonucleic acid) signal amplification assay (Quantiplex™ HCV RNA Assay (bDNA), Chiron Corp., Emeryville, California). See, e.g., Gretch et al. (1995) *Ann. Intern. Med.* 123:321-329.

Individuals who have been clinically diagnosed as having cancer are also suitable for treatment with the methods of the present disclosure. In particular embodiments of interest, individuals of interest for treatment according to the disclosure have detectable cancer. Any convenient methods may be used to determine whether subjects who have cancer are suitable for treatment using the subject methods. The effectiveness of the anti-cancer treatment may be determined using any convenient method. For example, whether a subject method is effective in treating cancer can be determined by measuring amelioration of one or more symptoms, decrease in tumor or metastasis size on imaging, or by measuring cancer cells in a biological sample of the subject being treated.

Definitions

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112. In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as." or "including" are meant to introduce examples that further clarify more general subject matter. These examples are provided only as an aid for understanding the disclosure and are not meant to be limiting in any fashion.

The Basic Amino Acid PIP2 Pincer (BAAPP) domain, as described by Glenn et al., "PIP-2 Inhibition-Based Antiviral and Anti-Hyperlipidemic Therapies" WO2009/1148541, and which is herein incorporated by reference in its entirety, provides a mechanism by which a protein or peptide recognizes (including but not limited to binding, as well as activation or suppression of activity) PIP2 (phosphatidylinositol 4,5-bisphosphate [PtdIns(4,5)P2], PI(4,5)P2). Alterations or variations of the BAAPP domain may result in recognition of other phosphatidylinositol variants.

Phosphoinositides, such as phosphatidylinositol (PI)-4-phosphate (PI(4)P) and PI-4,5-bisphosphate (PI(4,5)P$_2$, or "PIP2"), are enriched in various specific plasma membrane and intracellular locations. The steady state location and abundance of specific PT isoform pools within the cell is regulated by a family of PI-kinases and phosphatases. There are least 4 human PI4-kinases, with family members PI4KIIIα and PT4KIIIβ being primarily localized to ER and Golgi-derived membranes where they contribute to the PT(4)P and PI(4,5)P$_2$ pools associated with these membranes, and with family members PI4KIIα and PI4KIIβ contributing primarily to other pools.

The BAAPP domain mediates specific interaction with PIP2, resulting in a conformational change in the BAAPP domain that affects a key pathogen regulator. In HCV, replication complexes are established at intracellular PIP2-enriched sites, and point mutations in the BAAPP domain abrogate PIP2 binding and HCV RNA replication. Such critical dependence on PIP2 is widespread among pathogens. Targeting specific intracellular PIP2 pools by siRNA-mediated knockdown of enzymes responsible for PIP2 production—such as PT4KIIIα and PT4KIIIβ—abrogates HCV replication, yet is well tolerated by the host cell.

Molecules that inhibit the enzymatic pathways responsible for production of PIP-2 are of interest for use in the methods of the disclosure. Such inhibitors include, without limitation, inhibitors of phosphatidylinositol 4-kinase III alpha (see, for example Berger et al. (2009) PNAS 106: 7577-7582, herein specifically incorporated by reference) and inhibitors of phosphatidylinositol 4-kinase III beta.

BAAPP domains have been identified in multiple organisms, including but not limited to pathogens such as viruses, bacteria, fungi and parasites, as well as hosts, such as the human. BAAPP domain peptides, molecules that mimic the BAAPP domain, enzymes involved in PIP-2 metabolism, and molecules that inhibit or activate the BAAPP domain act in treating infectious diseases as well as affecting host physiology or pathophysiology.

Examples of proteins having a BAAPP domain include, without limitation, the 2C protein of Picornaviridae, Rhinovirus 14, Rhinovirus B, Rhinovirus C, PolioVirus, Enterovirus A, Enterovirus B, Enterovirus C, Enterovirus D, Enterovirus 71, and Coxsackie A virus 18. The core protein of Japanese Encephalitis Virus, West Nile Virus, Dengue Virus 1, Dengue Virus 2, Dengue Virus 3, and Dengue Virus 4 have BAAPP domains, as does the *P. falciparum* PfNDH2 protein. In the Flaviviridae, the NS4B AH 1 of HCV; the NS5A protein of HCV which has a BAAPP domain that comprises the conserved lysine residues at residue 20 and 26 of the processed protein, for example a peptide with the amino acid sequence SGSWLRDVWDWTCTVLT-DFKTWLQSKLL (SEQ ID NO:1) that includes the lysine residues K20 and K26. Other BAAPP-domain harboring pathogens include HAV, Vaccinia, *Ebola* virus, *F. tularensis*, influenza virus polymerase protein. Variola major (smallpox), Sin Nombre virus (hantavirus), *Pseudomonas aeruginosa*, CMV.

NS5 encoding viruses include without limitation flaviviruses, pestiviruses and hepatitis C viruses, e.g. yellow fever virus (YFV); Dengue virus, including Dengue types 1-4; Japanese Encephalitis virus; Murray Valley Encephalitis virus; St. Louis Encephalitis virus; West Nile virus; tick-borne encephalitis virus; Hepatitis C virus; Kunjin virus; Central European encephalitis virus; Russian spring-summer encephalitis virus; Powassan virus; Kyasanur Forest disease virus; and Omsk hemorrhagic fever virus.

By "Flaviviridae virus" is meant any virus of the Flaviviridae family, including those viruses that infect humans and non-human animals. The polynucleotide and polypeptide sequences encoding these viruses are well known in the art, and may be found at NCBI's GenBank database, e.g., as Genbank Accession numbers NC_004102, AB031663, D11355, D11168, AJ238800, NC_001809, NC_001437, NC_004355 NC_004119, NC_003996, NC_003690, NC_003687, NC_003675, NC_003676, NC_003218, NC_001563, NC_000943, NC_003679, NC_003678, NC_003677, NC_002657, NC_002032, and NC_001461, the contents of which database entries are incorporated by references herein in their entirety.

By "Piconaviridae virus" is meant any virus of the Picornaviridae family, including those viruses that infect humans and non-human animals, including, but not limited to, enteroviruses. The polynucleotide and polypeptide sequences encoding these viruses are well known in the art, and may be found at NCBI's GenBank database.

By "Caliciviridae virus" is meant any virus of the Caliciviridae family, including those viruses that infect humans and non-human animals, such as norovirus. The polynucleotide and polypeptide sequences encoding these viruses are well known in the art, and may be found at NCBI's GenBank database.

By "Filoviridae virus" is meant any virus of the Filoviridae family, including those viruses that infect humans and non-human animals, such as ebolavirus. The polynucleotide and polypeptide sequences encoding these viruses are well known in the art, and may be found at NCBI's GenBank database.

By "Hepeviridae virus" is meant any virus of the Hepeviridae family, including those viruses that infect humans and non-human animals, such as hepevirus (e.g., HEV). The polynucleotide and polypeptide sequences encoding these viruses are well known in the art, and may be found at NCBI's GenBank database.

By "Polyomaviridae virus" is meant any virus of the Polyomaviridae family, including those viruses that infect humans and non-human animals, such as BK virus and JC virus. The polynucleotide and polypeptide sequences encoding these viruses are well known in the art, and may be found at NCBI's GenBank database.

By "Papillomaviridae virus" is meant any virus of the Papillomnaviridae family, including those viruses that infect humans and non-human animals, such as human papilloma virus (e.g. HPV). The polynucleotide and polypeptide sequences encoding these viruses are well known in the art, and may be found at NCBI's GenBank database.

By "Coronavirinae virus" is meant any virus of the Coronavirinae family, including those viruses that infect humans and non-human animals, such as betacoronovirus (e.g., SARS, MERS, and SARS-CoV-2). The polynucleotide and polypeptide sequences encoding these viruses are well known in the art, and may be found at NCBI's GenBank database. In some embodiments, the Coronavirinae virus is selected from human coronavirus 229E (HCoV-229E), human coronavirus OC43 (HCoV-OC43), SARS-CoV (the causative agent of severe acute respiratory syndrome (SARS)), human coronavirus NL63 (HCoV-NL63, New Haven coronavirus), human coronavirus HKU1, MERS-CoV ("Middle East Respiratory Syndrome Coronavirus" or MERS), and severe acute respiratory syndrome coronavirus 2 (SARS-CoV-2) or COVID-19 (the coronavirus disease 2019). In some cases, the Coronavirinae virus is SARS-CoV-2.

The terms "active agent," "antagonist", "inhibitor", "drug" and "pharmacologically active agent" are used interchangeably herein to refer to a chemical material or compound which, when administered to an organism (human or animal) induces a desired pharmacologic and/or physiologic effect by local and/or systemic action.

As used herein, the terms "treatment," "treating," and the like, refer to obtaining a desired pharmacologic and/or physiologic effect, such as reduction of viral titer. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease (as in liver fibrosis that can result in the context of chronic HCV infection); (b) inhibiting the disease, i.e., arresting its development; and (c) relieving the disease, i.e., causing regression of the disease (e.g., reduction in viral titers).

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The terms "individual," "host," "subject," and "patient" are used interchangeably herein, and refer to an animal, including, but not limited to, human and non-human primates, including simians and humans; rodents, including rats and mice; bovines; equines; ovines; felines; canines; and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms "determining," "measuring," "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, s-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound (e.g., an aminopyrimidine compound, as described herein) calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general, a "pharmaceutical composition" is sterile, and preferably free of contaminants that are capable of eliciting an undesirable response within the subject (e.g., the compound(s) in the pharmaceutical composition is pharmaceutical grade).

Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$.

The term "alkyl" as used herein refers to a branched or unbranched saturated hydrocarbon group (i.e., a monoradical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" is meant to include an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "C1-C6 alkoxy" or "lower alkoxy" herein may, for example, may contain 1 to 3 carbon atoms, and as a further example, such substituents may contain 1 or 2 carbon atoms (i.e., methoxy and ethoxy).

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated $C_3$-$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$-$C_8$ alkoxy, $C_1$-$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" as used herein refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing. "Lower alkylene" refers to alkylene linkages containing from 1 to 6 carbon atoms. Examples include, methylene (—$CH_2$—), ethylene (—$CH_2CH_2$—), propylene (—$CH_2CH_2CH_2$—), 2-methylpropylene (—$CH_2$—$CH(CH_3)$—$CH_2$—), hexylene (—$(CH_2)_6$—) and the like.

Similarly, the terms "alkenylene," "alkynylene," "arylene," "aralkylene," and "alkarylene" as used herein refer to di-radical alkenyl, alkynyl, aryl, aralkyl, and alkaryl groups, respectively.

The term "amino" is used herein to refer to the group —NRR' wherein R and R' are independently hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

"Carboxyl," "carboxy" or "carboxylate" refers to —$CO_2H$ or salts thereof.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO— heteroaryl, —$SO_2$-alkyl, —$SO_2$-substituted alkyl, —$SO_2$-aryl and —$SO_2$-heteroaryl.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl, and trihalomethyl.

As used herein, the terms "Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. A hydrocarbyl may be substituted with one or more substituent groups. The term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties C1-C24 alkyl (including C1-C18 alkyl, further including C1-C12 alkyl, and further including C1-C6 alkyl), C2-C24 alkenyl (including C2-C18 alkenyl, further including C2-C12 alkenyl, and further including C2-C6 alkenyl), C2-C24 alkynyl (including C2-C18 alkynyl, further including C2-C12 alkynyl, and further including C2-C6 alkynyl), C5-C30 aryl (including C5-C20 aryl, and further including C5-C12 aryl), and C6-C30 aralkyl (including C6-C20 aralkyl, and further including C6-C12 aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

By the term "functional groups" is meant chemical groups such as halo, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—NH2), mono-substituted C1-C24 alkylcarbamoyl (—(CO)—NH(C1-C24 alkyl)), di-substituted alkylcarbamoyl (—(CO)—N(C1-C24 alkyl)2), mono-substituted arylcarbamoyl (—(CO)—NH-aryl), thiocarbamoyl (—(CS)—NH2), carbamido (—NH—(CO)—NH2), cyano (—C≡N), isocyano (—N+≡C—), cyanato (—O—C≡N), isocyanato (—O—N+=C—), isothiocyanato (—S—C≡N), azido (—N=N+=N—), formyl (—(CO)—H), thioformyl (—(CS)—H), amino (—NH2), mono- and di-(C1-C24 alkyl)-substituted amino, mono- and di-(C5-C20 aryl)-substituted amino, C2-C24 alkylamido (—NH—(CO)-alkyl), C5-C20 arylamido (—NH—(CO)-aryl), imino (—CR=NH where R=hydrogen, C1-C24 alkyl, C5-C20 aryl, C6-C20 alkaryl, C6-C20 aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO$_2$-alkyl), C5-C20 arylsulfonyl (—SO$_2$-aryl), phosphono (—P(O)(OH)$_2$), phosphonato (—P(O)(O—)$_2$), phosphinato (—P(O)(O—)), phospho (—PO$_2$), and phosphino (—PH$_2$), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

By "linking" or "linker" as in "linking group," "linker moiety," etc., is meant a bivalent radical moiety that connects two groups via covalent bonds. Examples of such linking groups include alkylene, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), carbonyldioxy (—O—CO—O—), alkyldioxy (—O—(CH2)n-O—), epoxyimino (—O—NH—), epimino (—NH—), carbonyl (—CO—), etc. Any convenient orientation and/or connections of the linkers to the linked groups may be used.

When the term "substituted" appears prior to a list of possible substituted groups, it is intended that the term apply to every member of that group. For example, the phrase "substituted alkyl and aryl" is to be interpreted as "substituted alkyl and substituted aryl."

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$C$^-$M$^+$, —OSO$_2$OR$^{70}$, —P(O)(O$^-$)(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{10}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^7$ is independently hydrogen or R$^{60}$; each R$^{80}$ is independently R$^{70}$ or alternatively, two R$^{80}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$ (M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S) R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR)NR$^{80}$R$^{80}$, where R$^{60}$, R$^{70}$. R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

Definitions of other terms and concepts appear throughout the detailed description.

Notwithstanding the appended claims, the disclosure set forth herein is also described by the following clauses:

Clause 1. A compound of formula (I):

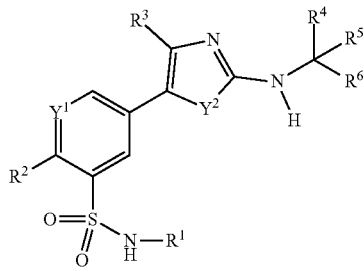

(I)

wherein: $Y^1$ is selected from CH or N; $Y^2$ is selected from S, O or $NR^{19}$, wherein $R^{19}$ is selected from hydrogen, alkyl, and substituted alkyl; $R^1$ is selected from aryl, substituted aryl, heteroaryl, substituted heteroaryl, alkyl, substituted alkyl, cycloalkyl, substituted cycloalkyl, heterocycle and substituted heterocycle; $R^2$ is selected from alkoxy and substituted alkoxy; $R^3$ is selected from hydrogen, lower alkyl and substituted lower alkyl; $R^4$ and $R^5$ are each independently selected from lower alkyl and substituted lower alkyl; or $R^4$ and $R^5$ together with the carbon to which they are attached provide a cyclic group selected from cycloalkyl, substituted cycloalkyl, heterocycle, substituted heterocycle, aryl, substituted aryl, heteroaryl and substituted heteroaryl; and $R^6$ is selected from substituted alkyl, cycloalkyl, substituted cycloalkyl, aryl, substituted aryl, heterocycle, substituted heterocycle, heteroaryl and substituted heteroaryl; or $R^4$, $R^5$ and $R^6$ together with the carbon to which they are attached provide a bridged cyclic group selected from bridged cycloalkyl, substituted bridged cycloalkyl, bridged heterocycle and substituted bridged heterocycle; or a prodrug thereof, or a pharmaceutically acceptable salt thereof, provided that the compound of formula (I) is not

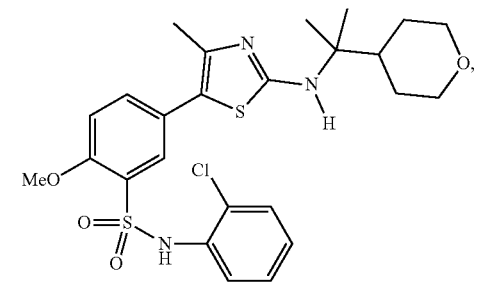

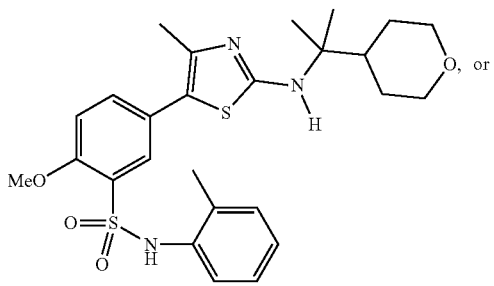, or

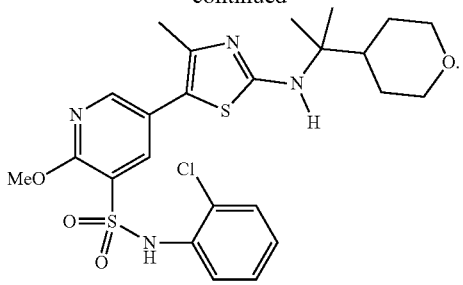

Clause 2. The compound of clause 1, wherein the compound is of formula (II):

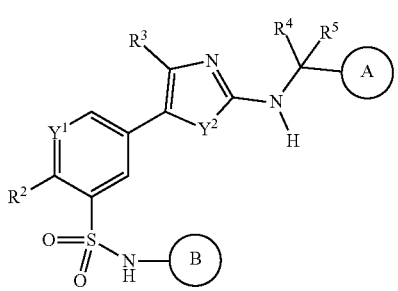

(II)

wherein: A is a ring system selected from aryl, substituted aryl, heteroaryl, substituted heteroaryl, cycloalkyl, substituted cycloalkyl, heterocycle and substituted heterocycle; and B is a ring system selected from aryl, substituted aryl, heteroaryl, substituted heteroaryl, cycloalkyl, substituted cycloalkyl, heterocycle and substituted heterocycle.

Clause 3. The compound of clause 2, wherein the B ring system is selected from phenyl, substituted phenyl, pyridyl, substituted pyridyl, 2-pyrimidinyl, substituted 2-pyrimidinyl, 3-pyrimidinyl, substituted 3-pyrimidinyl, 4-pyrimidinyl, substituted 4-pyrimidinyl, 6-pyrimidinyl, substituted 6-pyrimidinyl, piperidine, substituted piperidine, piperazine, substituted piperazine, 2-oxopiperidine, 2-oxopiperazine, imidazole, substituted imidazole, thiazole, substituted thiazole, oxazole, substituted oxazole, tetrahydropyran, substituted tetrahydropyran, morpholine, substituted morpholine, cyclic sulfone and substituted cyclic sulfone.

Clause 4. The compound of clause 2 or 3, wherein the B ring system is selected from B2-B9:

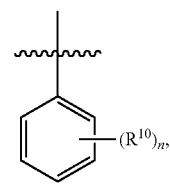

(B2)

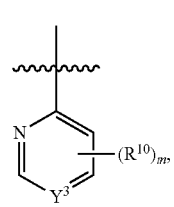

(B3)

-continued

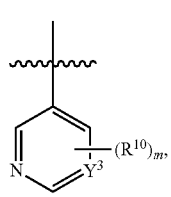
(B4)

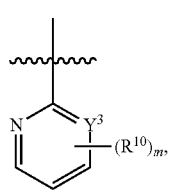
(B5)

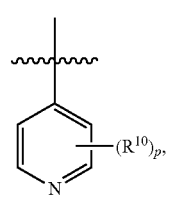
(B6)

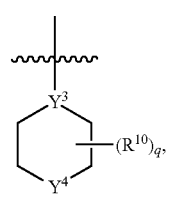
(B7)

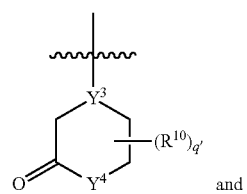
(B8)

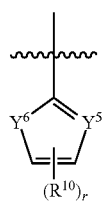
(B9)

wherein: $Y^3$ and $Y^5$ are each independently selected from N and $CR^{11}$, wherein $R^{11}$ is selected from hydrogen, $R^{10}$, acyl, substituted acyl, carboxy, carboxyamide, substituted carboxyamide, sulfonyl, substituted sulfonyl, sulfonamide and substituted sulfonamide; $Y^4$ is selected from $CR^{11}_2$, $NR^{11}$, $SO_2$ and O; $Y^6$ is selected from $CR^{11}_2$ and $NR^{11}$; each $R^{10}$ is selected from, alkyl, substituted alkyl, hydroxy, alkoxy, substituted alkoxy, trifluoromethyl and halogen; n is an integer from 0 to 5; m is an integer from 0 to 3; p is an integer from 0 to 4; q is an integer from 0 to 8 q' is an integer from 0 to 6; and r is an integer from 0 to 2.

Clause 5. The compound of any one of clauses 2-4, wherein the A ring system is selected from phenyl, substituted phenyl, pyridyl, substituted pyridyl, 2-pyrimidinyl, substituted 2-pyrimidinyl, 3-pyrimidinyl, substituted 3-pyrimidinyl, 4-pyrimidinyl, substituted 4-pyrimidinyl, 6-pyrimidinyl, substituted 6-pyrimidinyl, piperidine, substituted piperidinc, piperazine, substituted piperazinc, tetrahydropyran, substituted tetrahydropyran, morpholine and substituted morpholine.

Clause 6. The compound of any one of clauses 2-5, wherein the A ring is selected from:

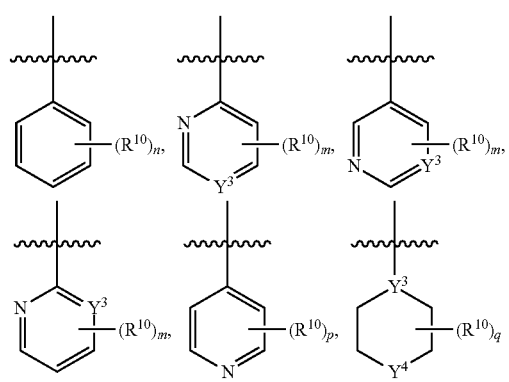

wherein: $Y^3$ is selected from N and $CR^{11}$, wherein $R^{11}$ is selected from hydrogen. $R^{10}$, acyl, substituted acyl, carboxy, carboxyamide, substituted carboxyamide, sulfonyl, substituted sulfonyl, sulfonamide and substituted sulfonamide; $Y^4$ is selected from $CR^{11}_2$, $NR^{11}SO_2$ and O; $R^{10}$ is one or more optional substituents independently selected from, alkyl, substituted alkyl, hydroxy, alkoxy, substituted alkoxy, trifluoromethyl and halogen; n is an integer from 0 to 5; m is an integer from 0 to 3; p is an integer form 0 to 4; and q is an integer from 0 to 8.

Clause 7. The compound of any one of clauses 2-6, wherein the compound is of one of formulae (IIIA)-(IIF):

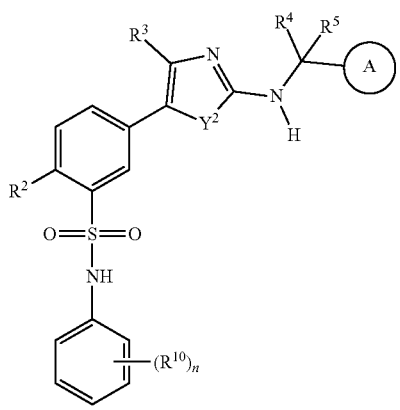
(IIA)

-continued

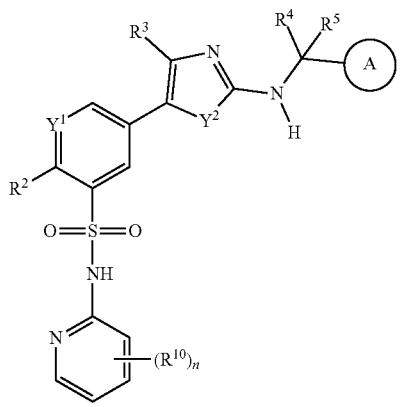
(IIB)

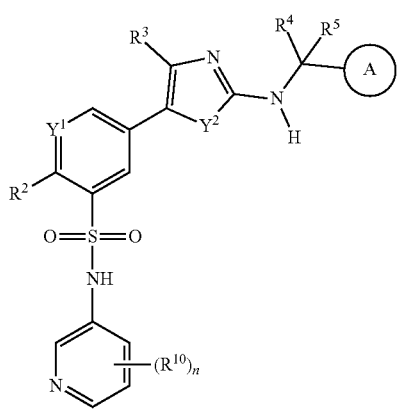
(IIC)

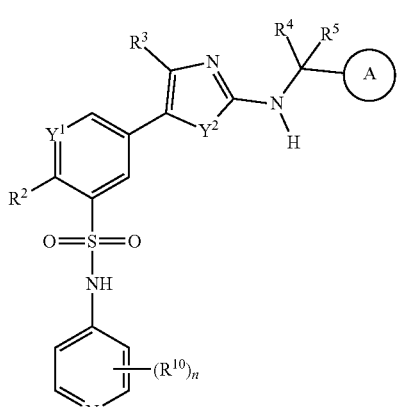
(IID)

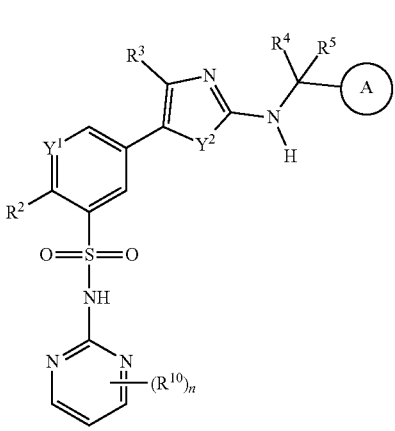
(IIE)

, and

-continued

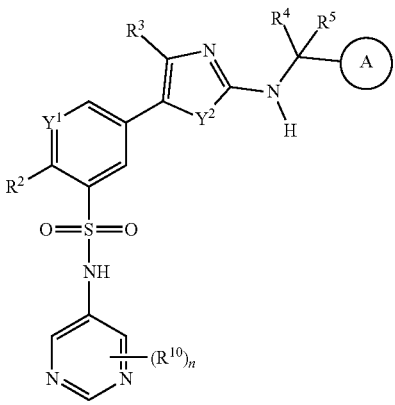
(IIF)

wherein: the A ring system is selected from aryl, substituted aryl, heteroaryl, substituted heteroaryl, cycloalkyl, substituted cycloalkyl, heterocycle and substituted heterocycle; each $R^{10}$ is independently selected from, alkyl, substituted alkyl, hydroxy, alkoxy, substituted alkoxy, trifluoromethyl and halogen; n is an integer from 0 to 5; m is an integer from 0 to 3; and p is an integer from 0 to 4.

Clause 8. The compound of clause 7, wherein the compound is of formula (IIA1), (IIA2), (IIC1) or (IID1):

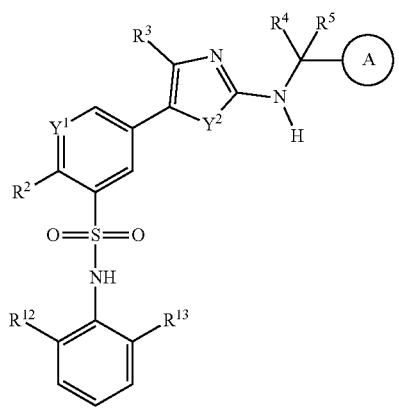
(IIA1)

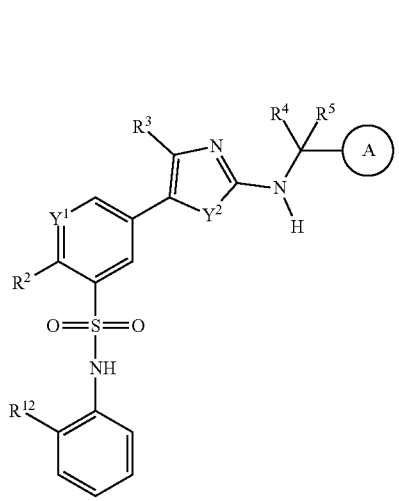
(IIA2)

167
-continued

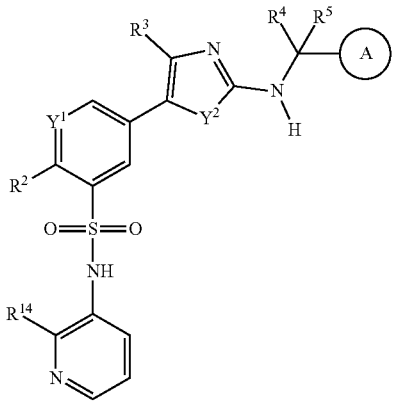

(IIC1)

(IID1)

wherein: $R^{12}$, $R^{13}$ and $R^{14}$ are each independently selected from, alkyl, substituted alkyl, hydroxy, alkoxy, substituted alkoxy, trifluoromethyl and halogen.

Clause 9. The compound of any one of clauses 2-6, wherein the compound is of formula (IIG), (IIH), (IIJ) or (IIK):

(IIG)

168
-continued

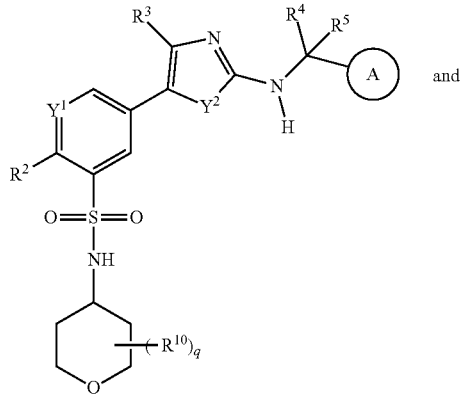

(IIH) and (IIJ)

(IIK)

wherein: the A ring system is selected from aryl, substituted aryl, heteroaryl, substituted heteroaryl, cycloalkyl, substituted cycloalkyl, heterocycle and substituted heterocycle; each R*° is independently selected from, alkyl, substituted alkyl, hydroxy, alkoxy, substituted alkoxy, trifluoromethyl and halogen; $R^{11}$ is selected from hydrogen, $R^{10}$, acyl, substituted acyl, carboxy, carboxyamide, substituted carboxyamide, sulfonyl and substituted sulfonyl; and q is an integer from 0 to 8.

Clause 10. The compound of clause 9, wherein the compound is of formula (IIG1) or (IIK1):

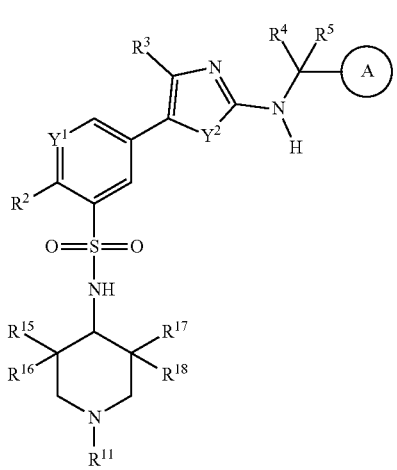
(IIG1)

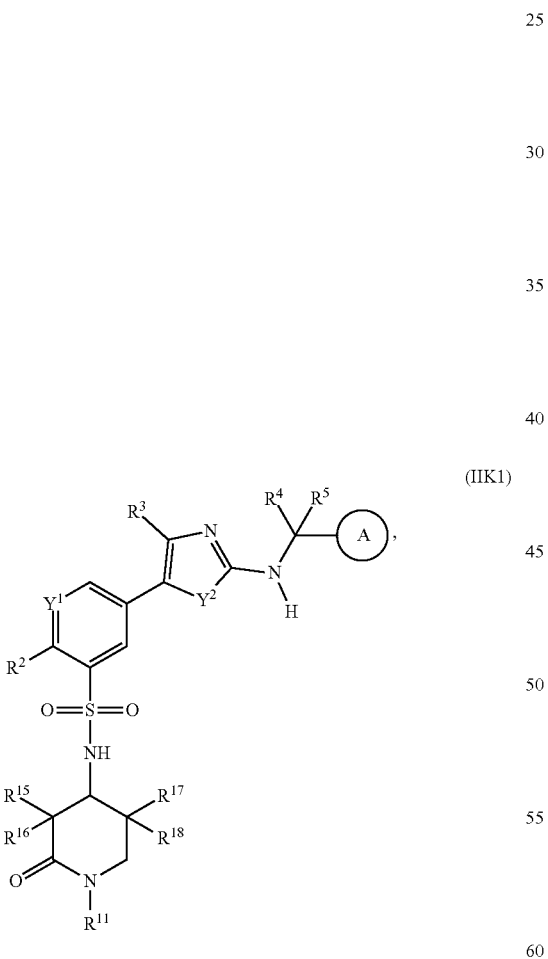
(IIK1)

wherein: $R^{11}$ is selected from $R^{10}$, acyl, substituted acyl, carboxy, carboxyamide, substituted carboxyamide, sulfonyl and substituted sulfonyl; and $R^{15}$, $R^{16}$, $R^{17}$ and $R^{18}$ are each independently selected from, hydrogen, alkyl, substituted alkyl, hydroxy, alkoxy, substituted alkoxy, trifluoromethyl and halogen.

Clause 11. The compound of clause 10, wherein the compounds is of formula (IIG1ii), (IIG1iii), (IIK1ii) or (IIK1iii):

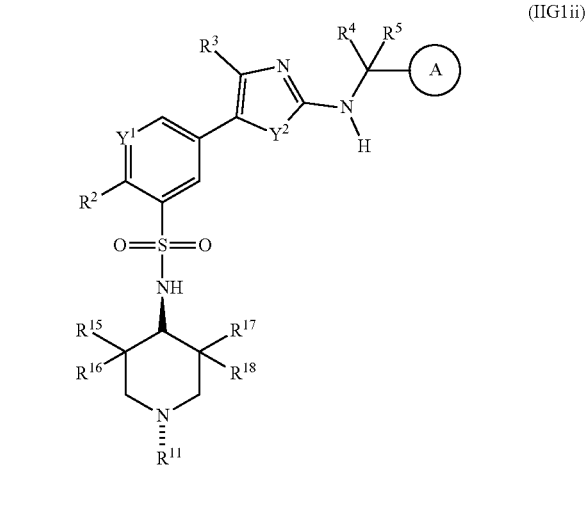
(IIG1ii)

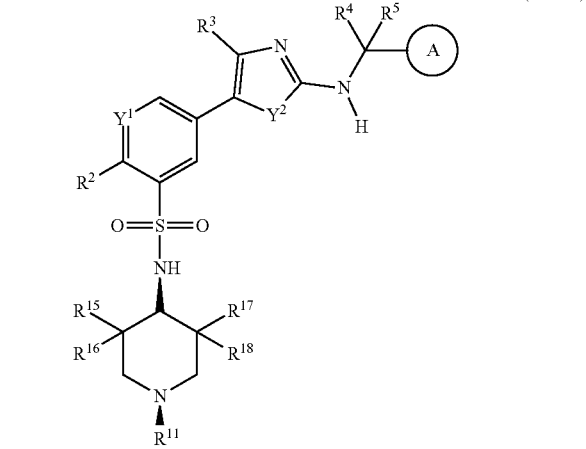
(IIG1iii)

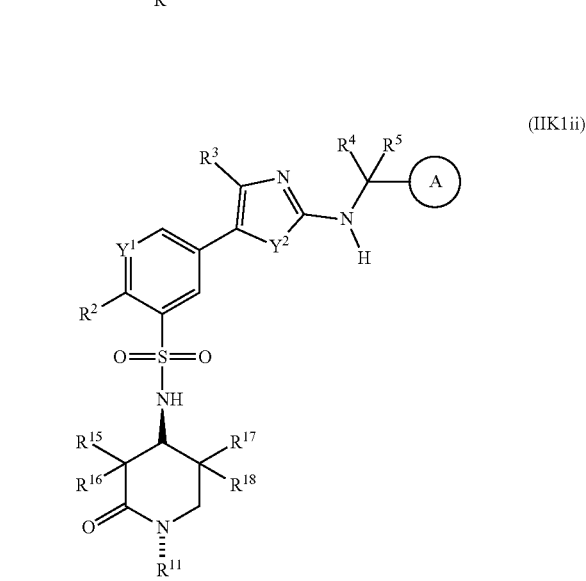
(IIK1ii)

-continued
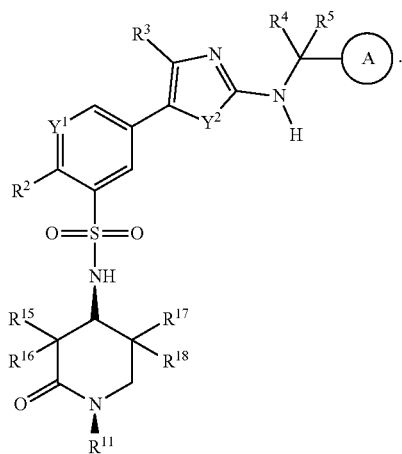
(IIK1iii)
Clause 12. The compound of clause 8, wherein the compound is of one of the following formulae:
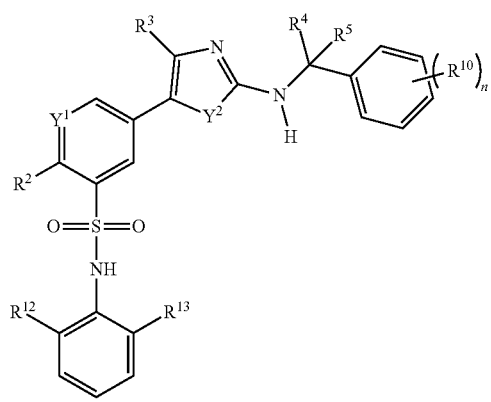
(IIA1a)
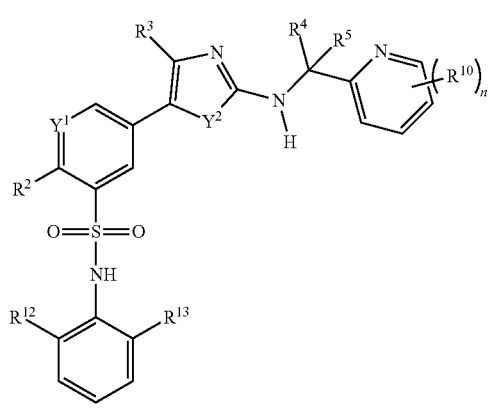
(IIA1b)
-continued
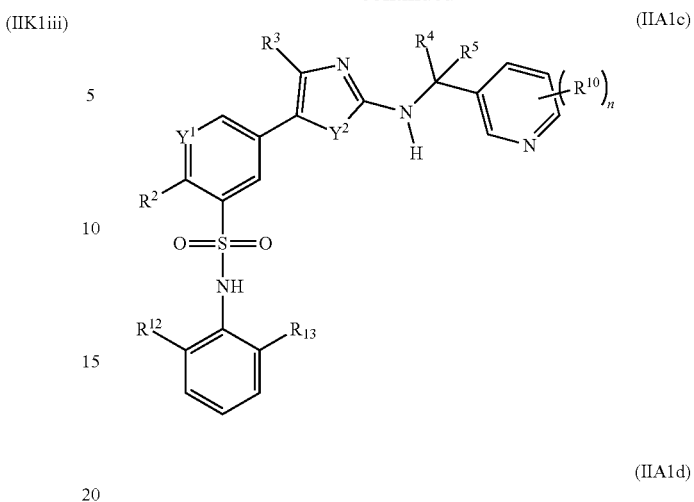
(IIA1c)
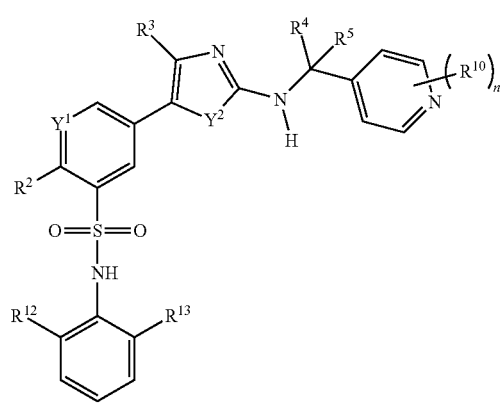
(IIA1d)
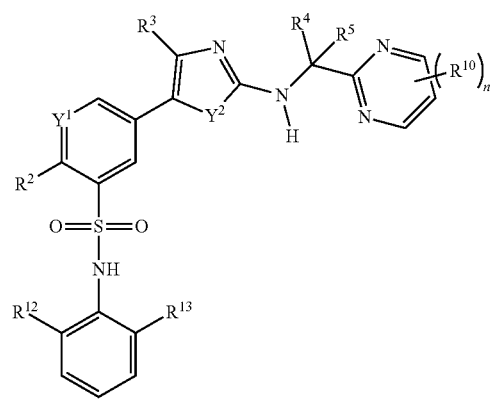
(IIA1e)
(IIA1f)

(IIA1g)
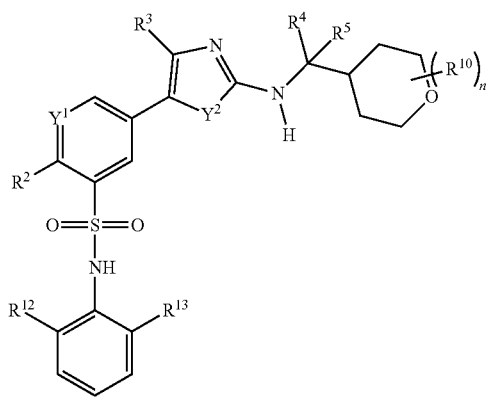
(IIA2a)
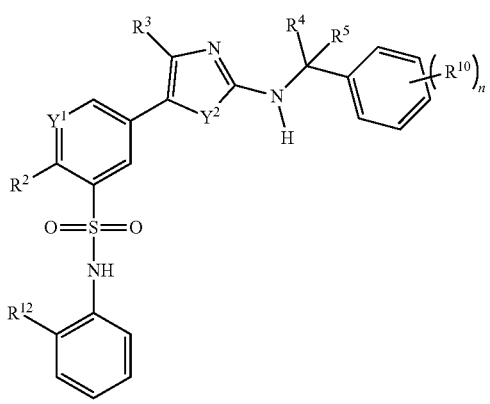
(IIA1h)
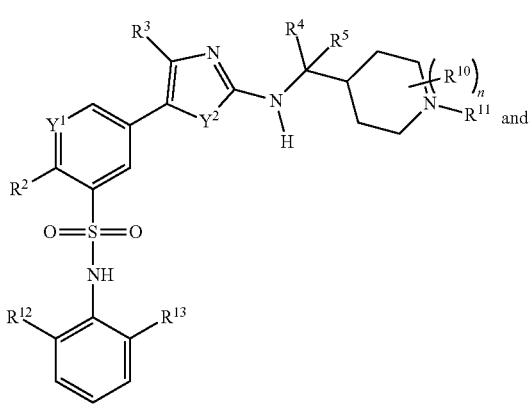
and
(IIA2b)
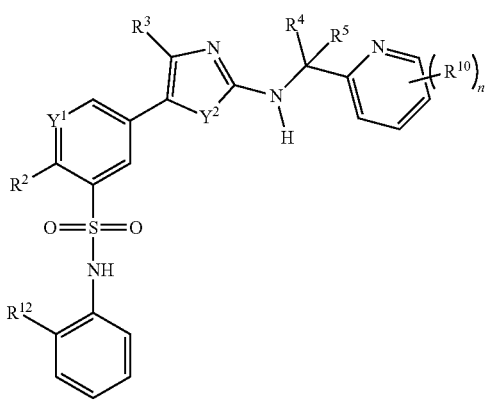
(IIA2c)
(IIA1i)
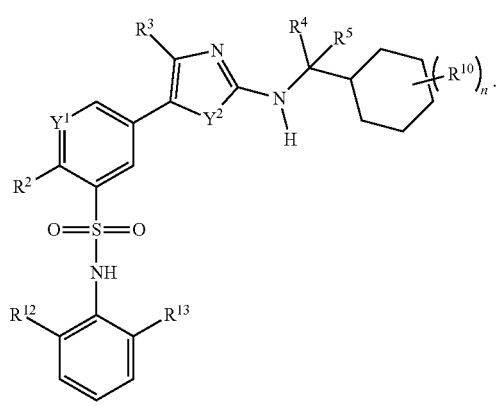
(IIA2d)
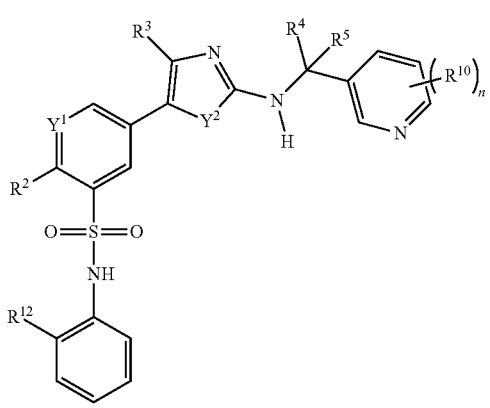
Clause 13. The compound of clause 8, selected from the following formulae:

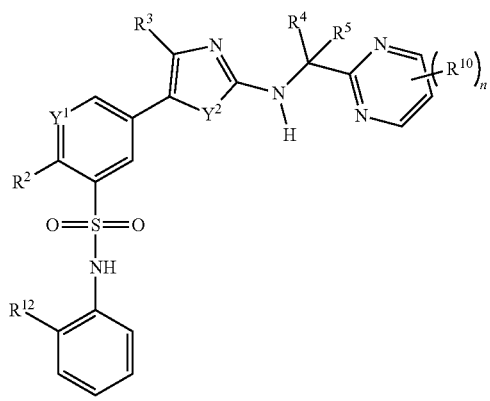
(IIA2e)
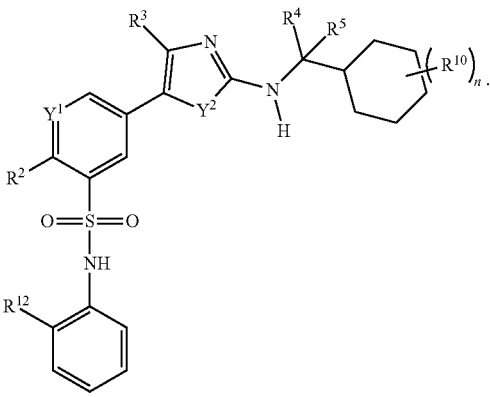
(IIA2i)
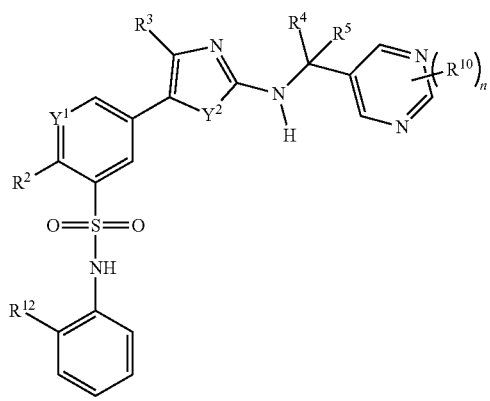
(IIA2f)
Clause 14. The compound of clause 8, wherein the compound is of one of the following formulae:
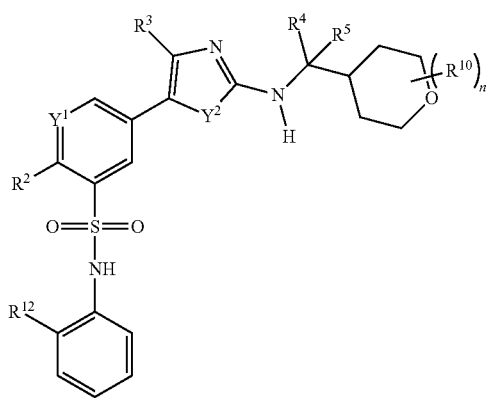
(IIA2g)
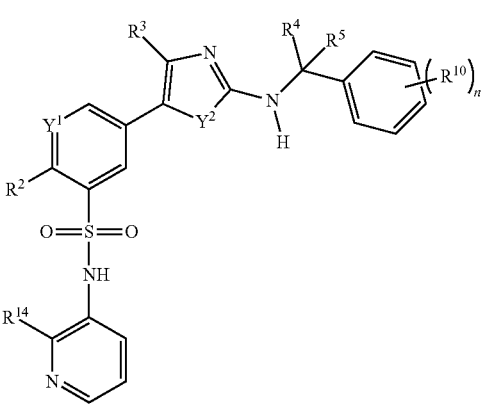
(IIC1a)
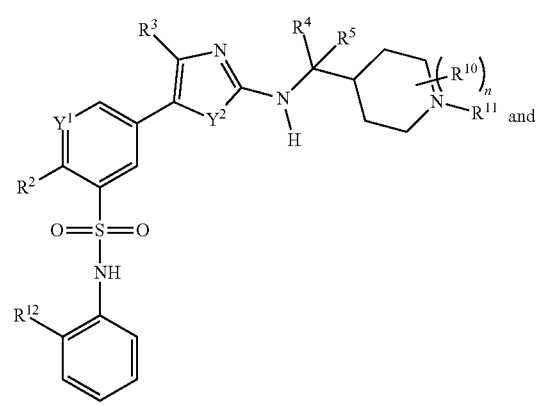
(IIA2h)
and
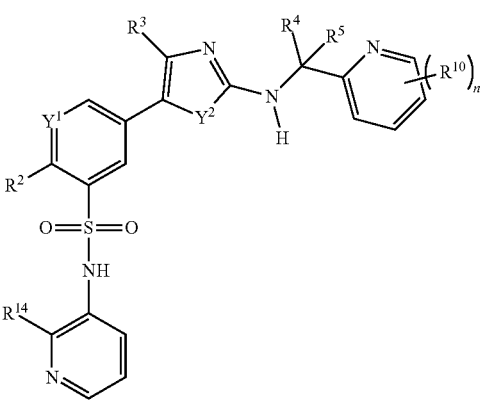
(IIC1b)

-continued
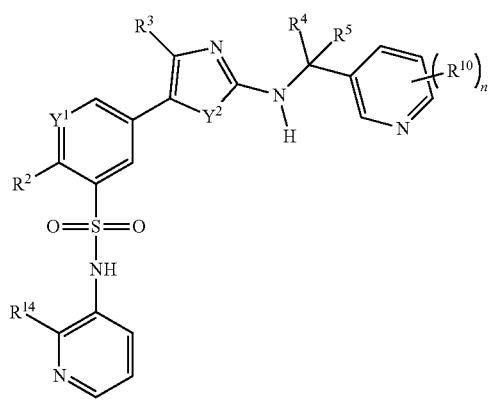
(IIC1c)
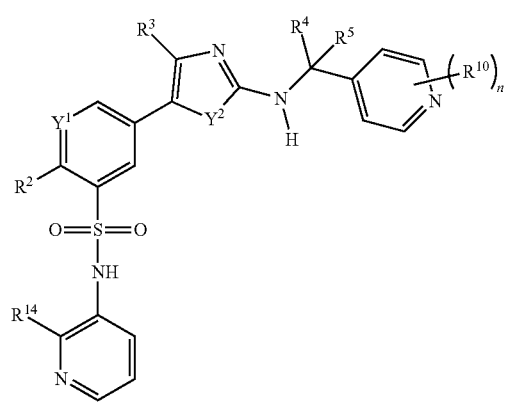
(IIC1d)
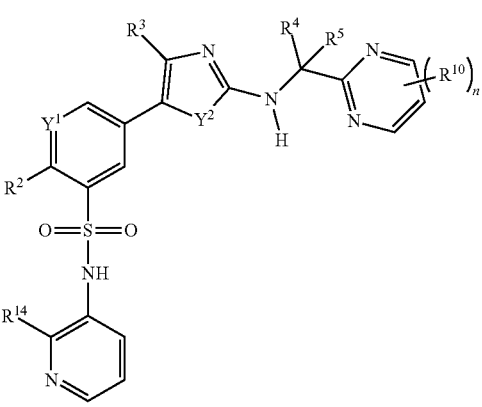
(IIC1e)
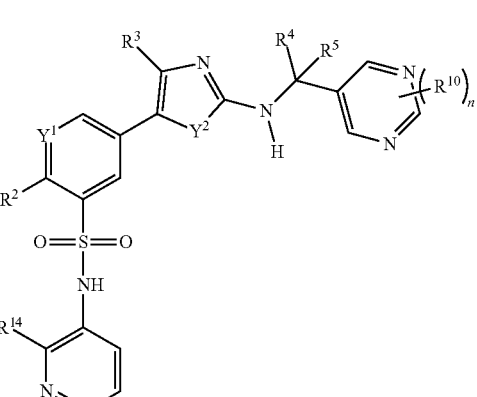
(IIC1f)
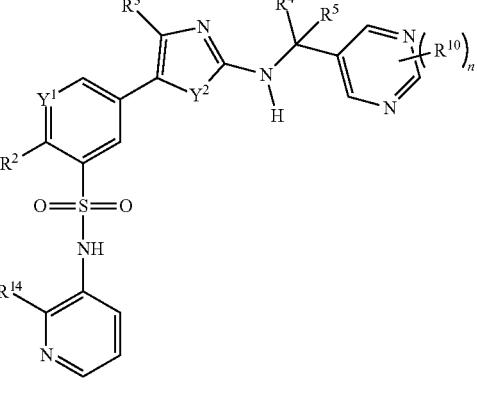
(IIC1g)
(IIC1h)
and
(IIC1i)
Clause 15. The compound of clause 8, wherein the compound is of one of the following formulae:

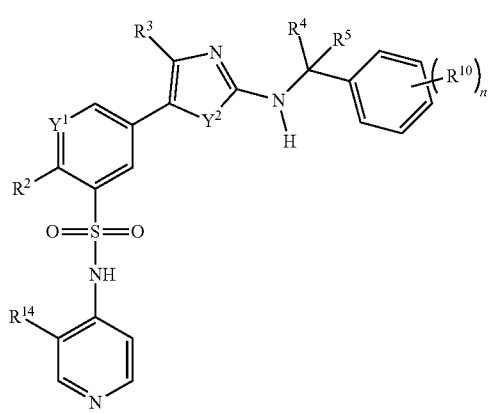
(IID1a)
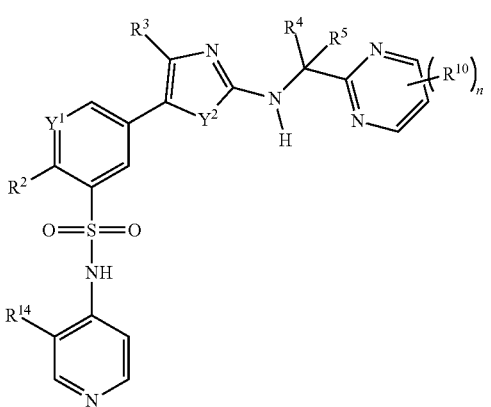
(IID1e)
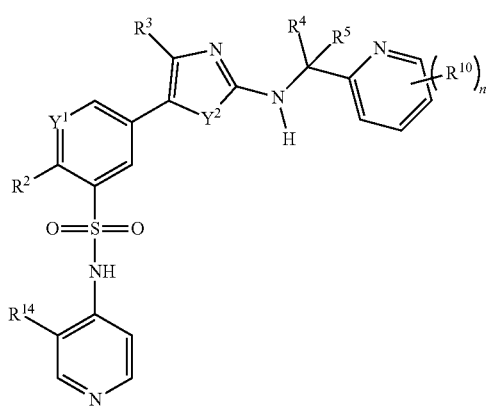
(IID1b)
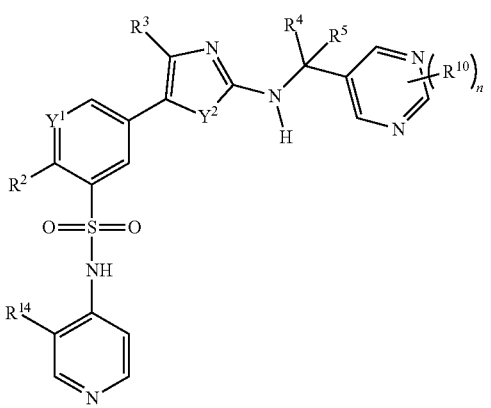
(IID1f)
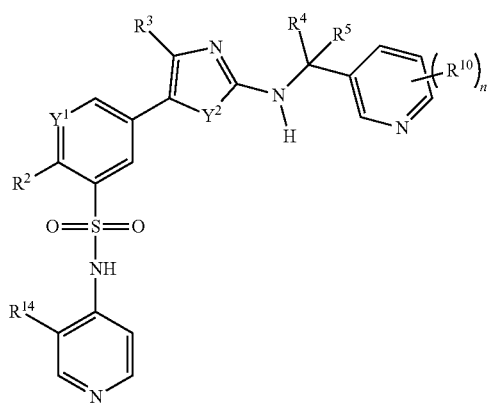
(IID1c)
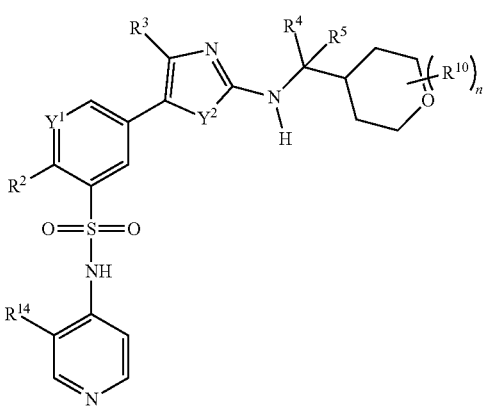
(IID1g)
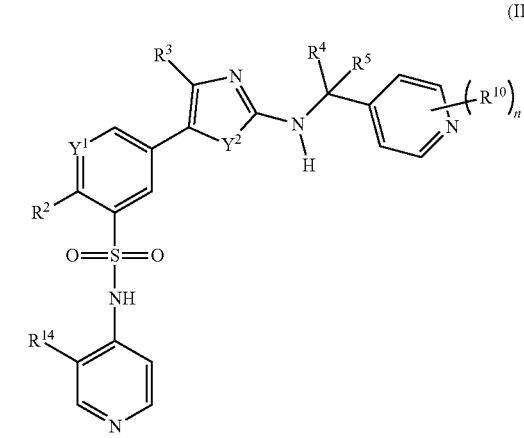
(IID1d)
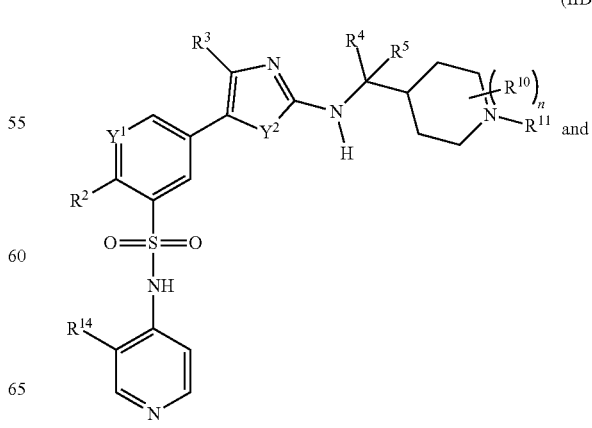
(IID1h)
and -continued (IID1i)

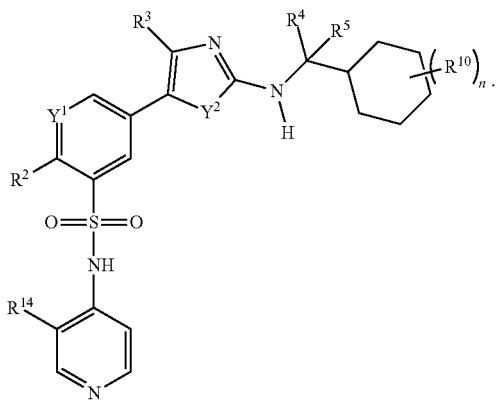

Clause 16. The compound of any one of clauses 12 to 15, wherein $R^{12}$, $R^{13}$ and $R^{14}$ are each independently selected from, alkyl, substituted alkyl, trifluoromethyl and halogen.

Clause 17. The compound of clause 12 or 13, wherein: $R^{11}$ is a halogen; and $R^{13}$ is a lower alkyl.

Clause 18. The compound of clause 14 or 15, wherein: $R^{14}$ is a lower alkyl group or trifluoromethyl.

Clause 19. The compound of clause 10 or 11, wherein the compound is of one of the following formulae:

(IIG1a)

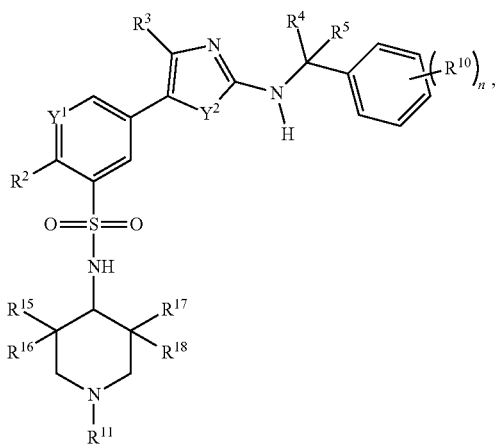

(IIG1b)

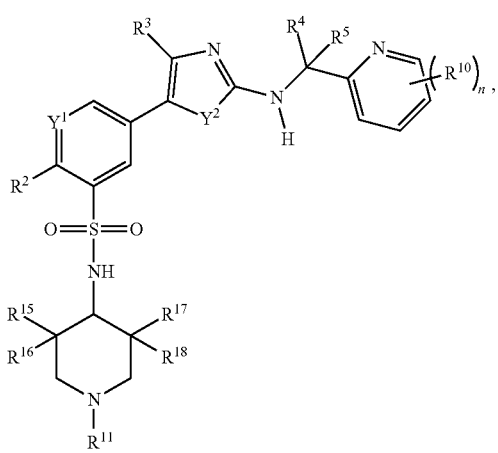

-continued (IIG1c)

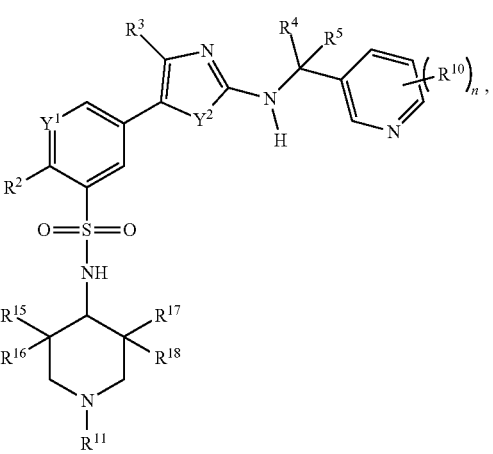

(IIG1d)

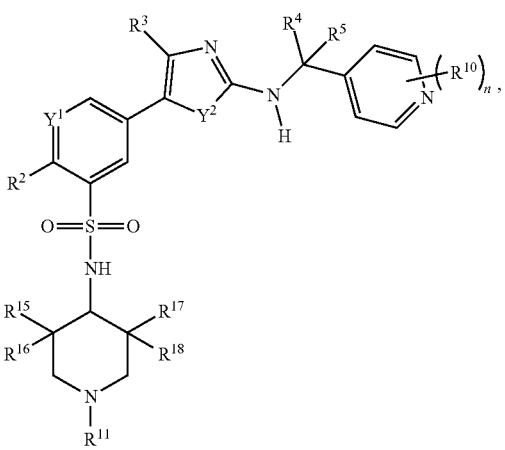

(IIG1e)

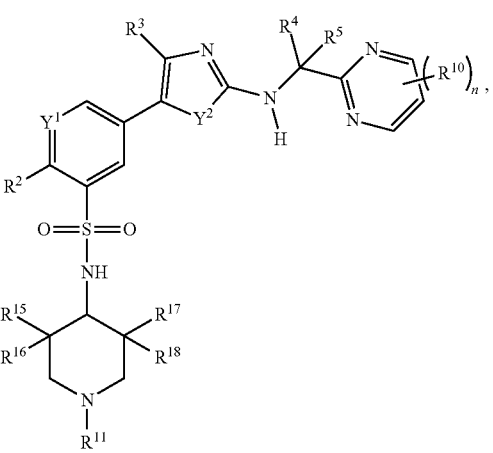

-continued
(IIG1f)
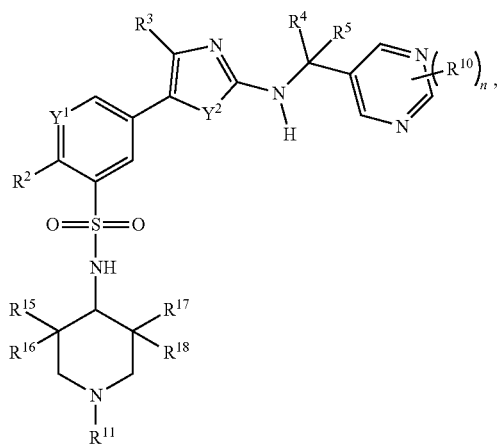
(IIG1g)
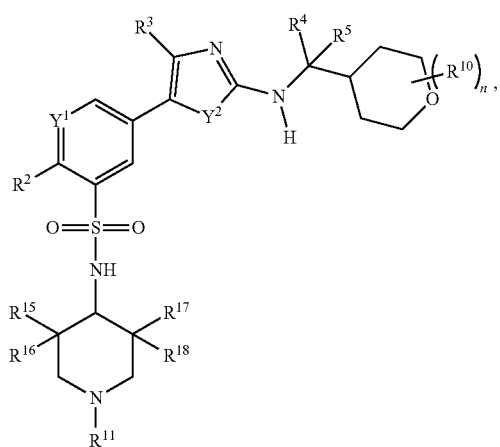
(IIG1h)
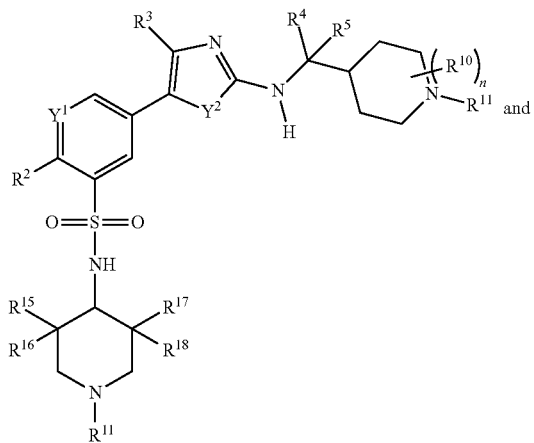
-continued
(IIG1i)
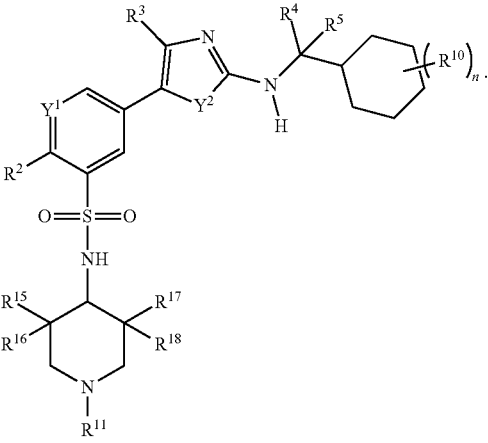
Clause 20. The compound of clause 10 or 11, wherein the compound is of one of the following formulae:
(IIK1a)
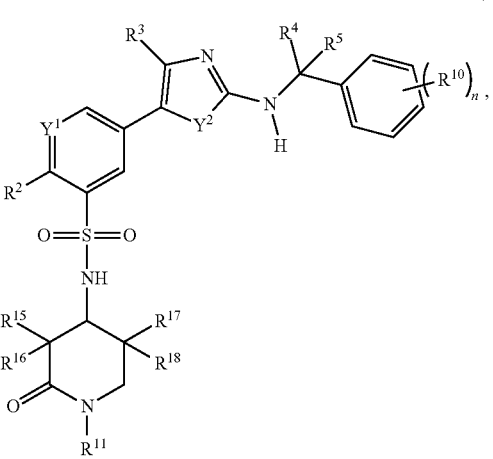
(IIK1b)
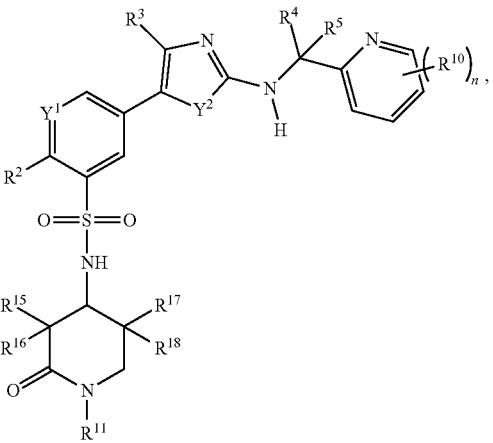

(IIK1c)
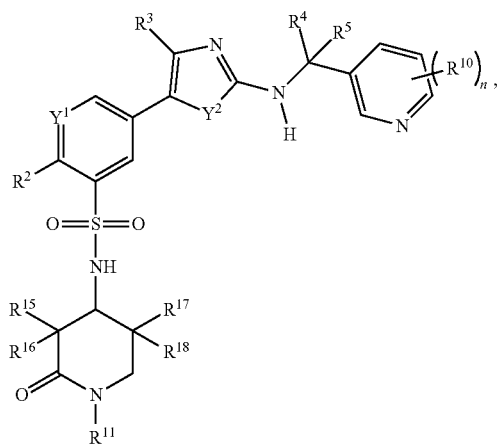
(IIK1f)
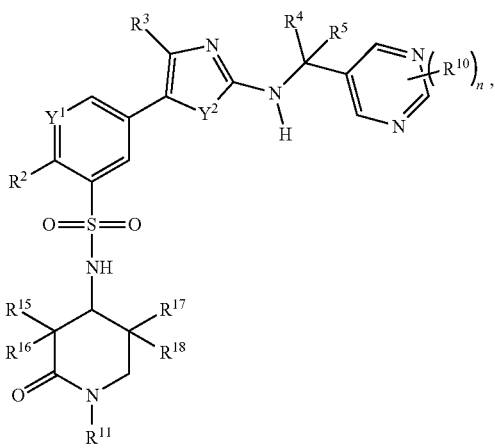
(IIK1d)
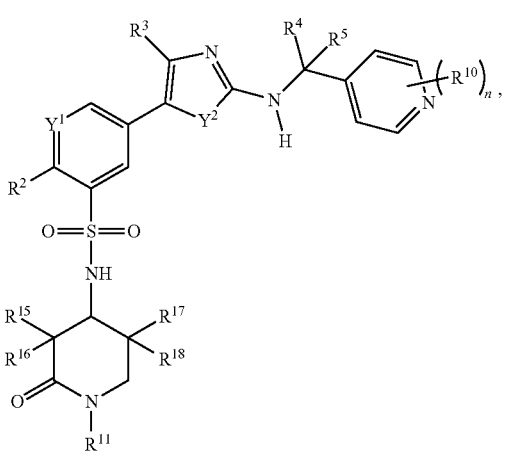
(IIK1g)
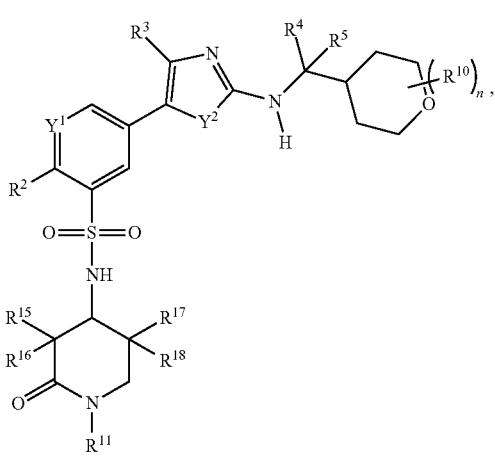
(IIK1e)
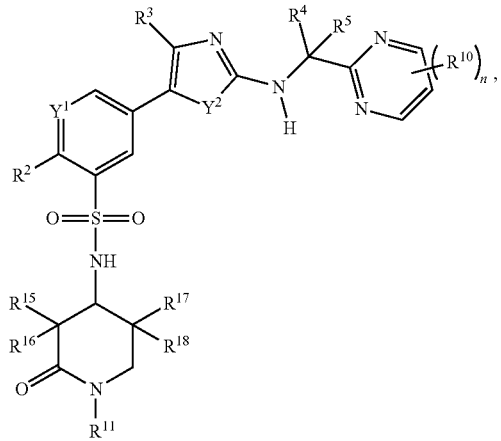
(IIK1h)
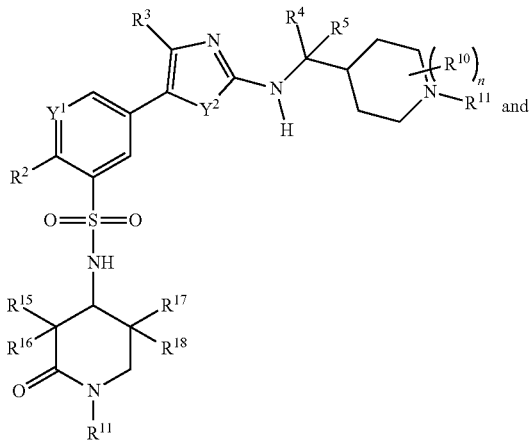
and

187

-continued

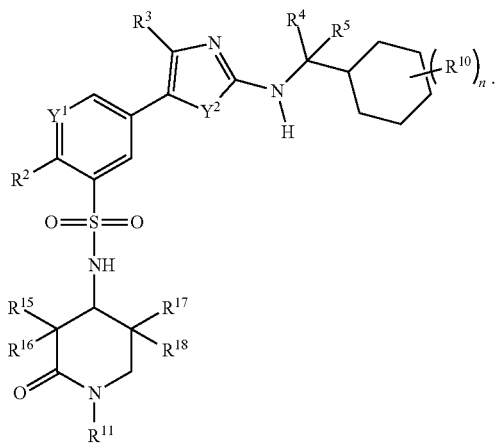
(IIK1i)

Clause 21. The compound of clause 19 or 20, wherein $R^{11}$ is an acyl group.

Clause 22. The compound of any one of clauses 19-21, wherein $R^{15}$, $R^{16}$, $R^{17}$ and $R^{18}$ are each independently selected from, hydrogen, alkyl and substituted alkyl.

Clause 23. The compound of clause 22, wherein each of $R^{15}$, $R^{16}$, $R^{17}$ and $R^{18}$ are hydrogen.

Clause 24. The compound of clause 22, wherein: $R^{15}$ is a lower alkyl; and each of $R^{16}$, $R^{17}$ and $R^{18}$ are hydrogen.

Clause 25. The compound of clause 22, wherein: $R^{15}$ and $R^{16}$ are each lower alkyl; and $R^{16}$ and $R^{18}$ are each hydrogen.

Clause 26. The compound of clause 22, wherein: $R^{15}$ and $R^{16}$ are each hydrogen; and $R^{17}$ and $R^{18}$ are each a lower alkyl.

Clause 27. The compound of any one of clauses 1 to 26, wherein $R^4$ and $R^5$ are each independently lower alkyl; or $R^4$ and $R^5$ together with the carbon to which they are attached provide a cycloalkyl or substituted cycloalkyl cyclic group Clause 28. The compound of clause 27, wherein $R^4$ and $R^5$ together with the carbon to which they are attached from a cyclopropyl.

Clause 29. The compound of any one of clauses 1 to 26, wherein $R^4$ and $R^5$ are both methyl.

Clause 30. The compound of any one of clauses 1 to 29, wherein $Y^2$ is S.

Clause 31. The compound of any one of clauses 1 to 29, wherein $Y^2$ is O.

Clause 32. The compound of any one of clauses 1 to 29, wherein $Y^2$ is $NR^{19}$.

Clause 33. The compound of clause 32, wherein $R^{19}$ is hydrogen.

188

Clause 34. The compound of clause 1 or 2, wherein the compound is of one of the following structures:

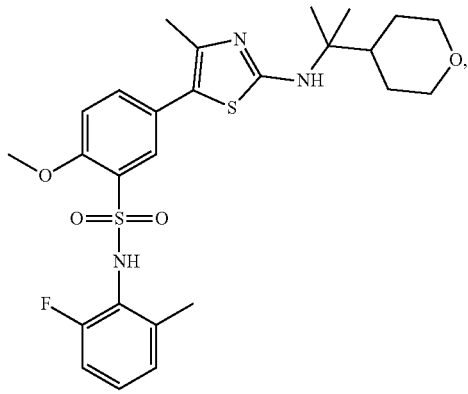

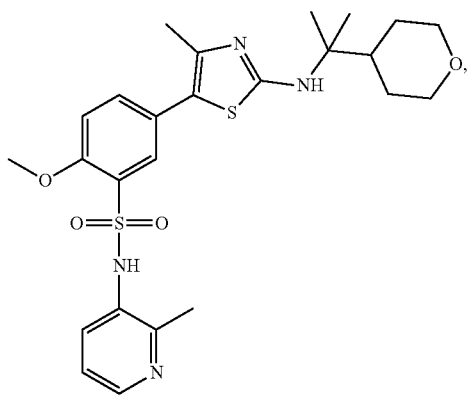

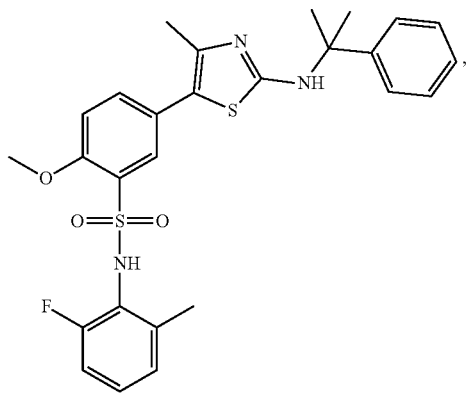

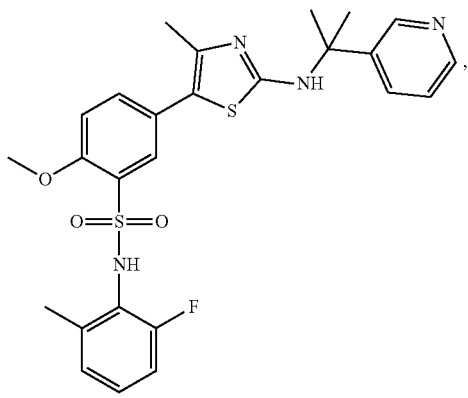

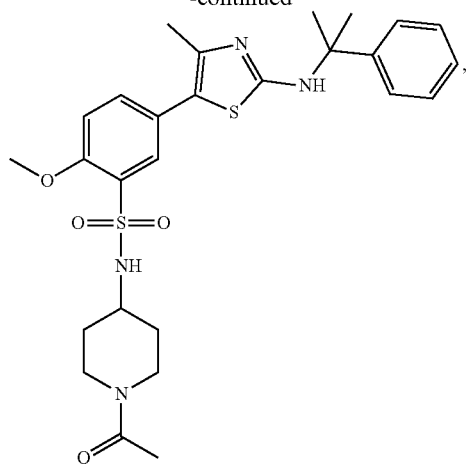
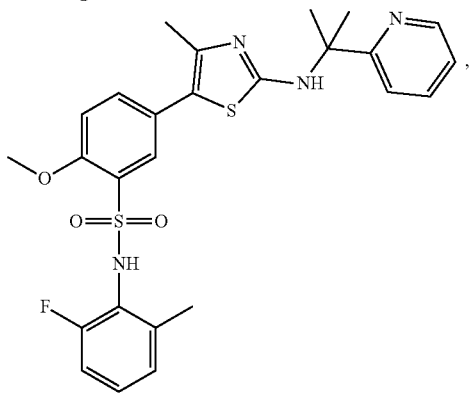
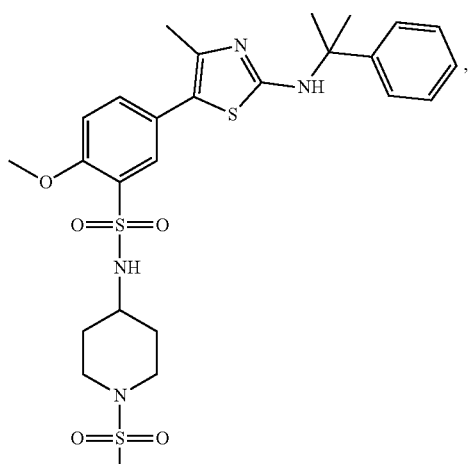
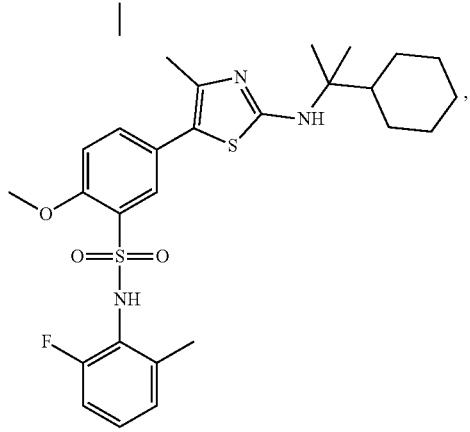
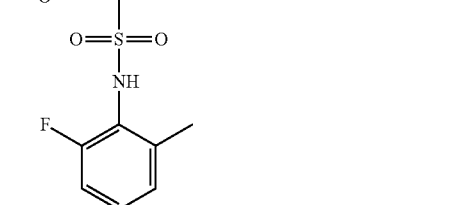
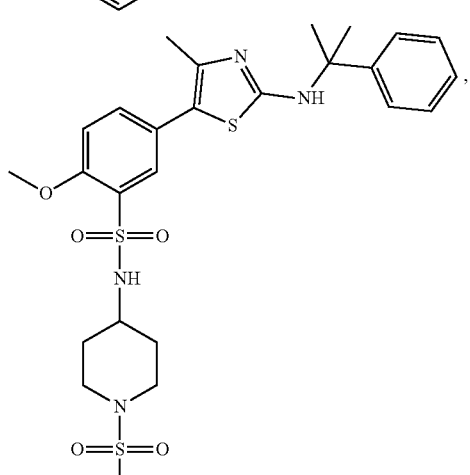
or a pharmaceutically acceptable salt thereof.

Clause 35. The compound of clause 1 or 2, wherein the compound is of one of the following structures:
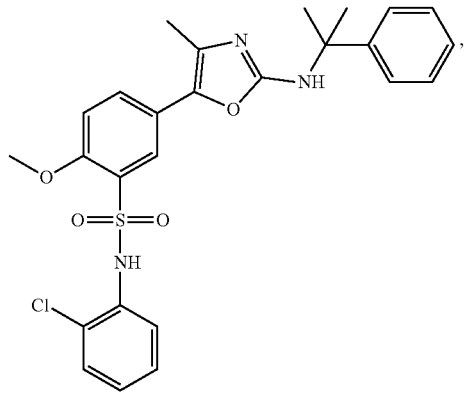
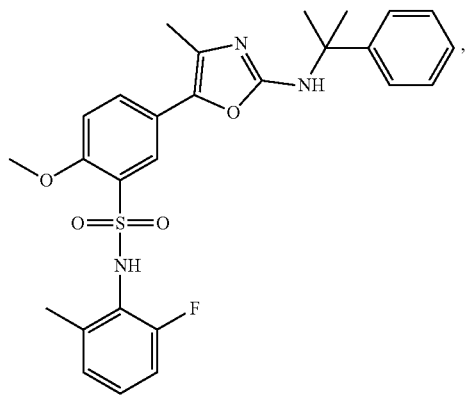
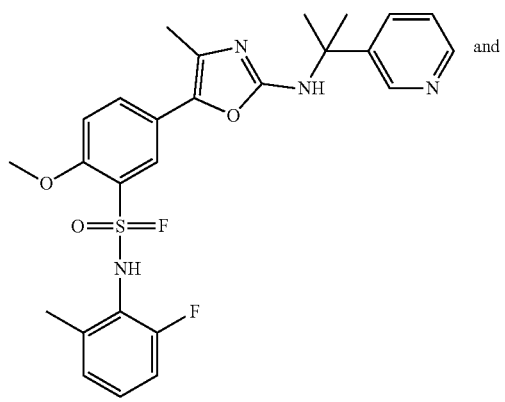 and
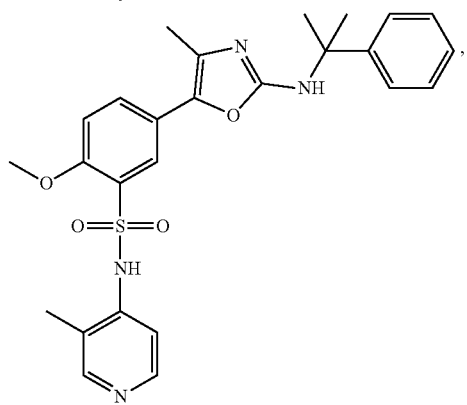
or a pharmaceutically acceptable salt thereof.
Clause 36. The compound of clause 1 or 2, wherein the compound is of one of the following structures:
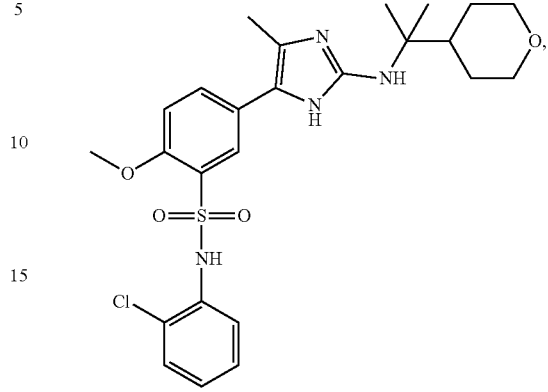
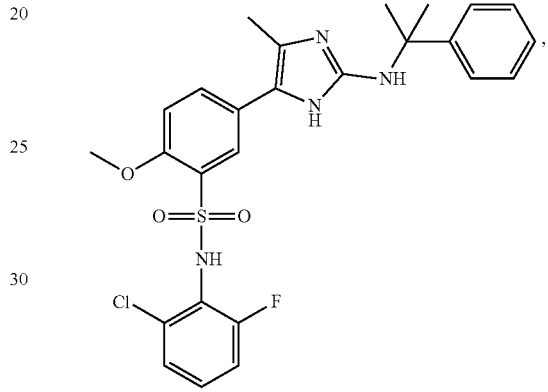
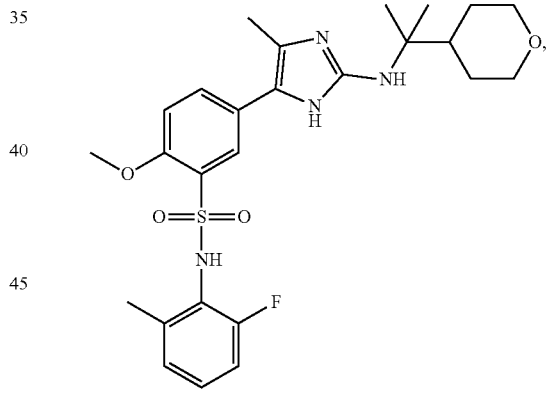
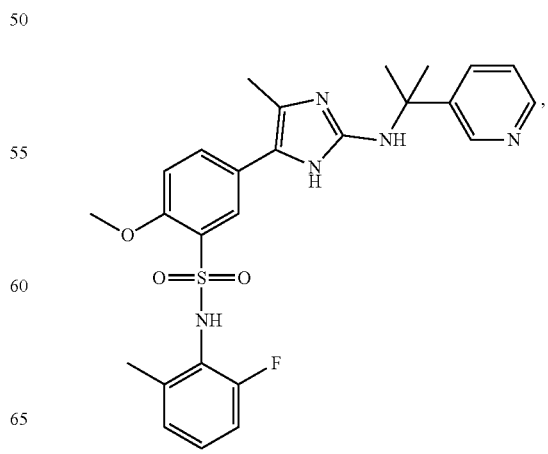

-continued

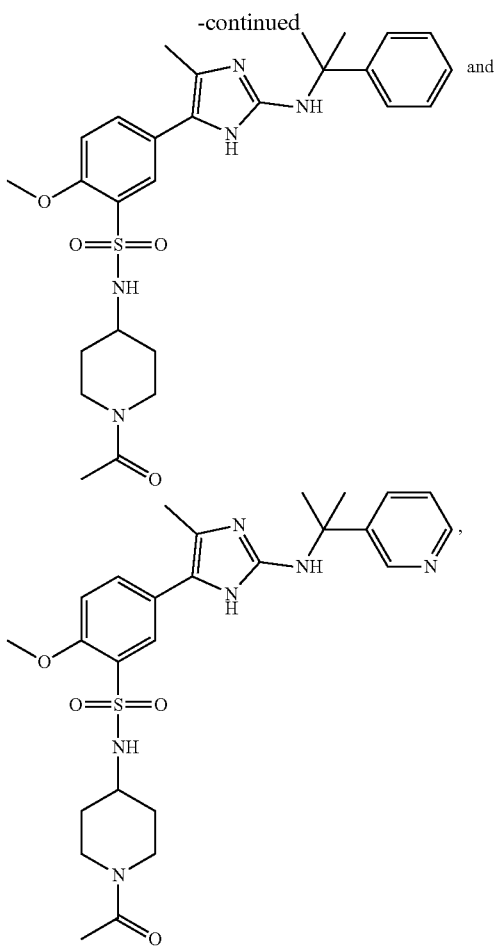

and

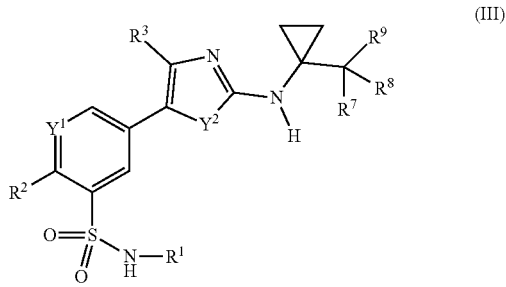

or a pharmaceutically acceptable salt thereof.

Clause 37. The compound of clause 1, wherein the compound is of formula (III):

$$\text{(III)}$$

wherein: --- is absent or a covalent bond; $R^7$ and $R^8$ are each independently selected from hydrogen, halogen, alkyl and substituted alkyl; and $R^9$ is selected from substituted alkyl, cycloalkyl, substituted cycloalkyl, aryl, substituted aryl, heterocycle, substituted heterocycle, heteroaryl and substituted heteroaryl.

Clause 38. The compound of clause 1, wherein $R^1$ is selected from aryl, di-substituted aryl, tri-substituted aryl, tetra-substituted aryl, penta-substituted aryl, heteroaryl, substituted heteroaryl, alkyl, substituted alkyl, cycloalkyl, substituted cycloalkyl, heterocycle and substituted heterocycle.

Clause 39. The compound of clause 1, wherein the compound is selected from any one of the compounds of Table 1, Table 2 or Table 3, or a prodrug thereof, or a pharmaceutically acceptable salt thereof.

Clause 40. The compound of any one of clauses 1-38, wherein $Y^1$ is CH.

Clause 41. The compound of any one of clauses 1-38, wherein $Y^1$ is N.

Clause 42. The compound of any one of clauses 1-38, wherein $Y^2$ is S.

Clause 43. The compound of any one of clauses 1-38, wherein $Y^2$ is O.

Clause 44. The compound of any one of clauses 1-38, wherein $Y^2$ is $NR^{19}$.

Clause 45. The compound of any one of clauses 1-38, wherein $Y^2$ is NH.

Clause 46. A pharmaceutical composition comprising: a compound of any one of clauses 1 to 45; and a pharmaceutically acceptable excipient.

Clause 47. A method of inhibiting a PI4-kinase, the method comprising contacting a sample comprising the PI4-kinase with a compound of any one of clauses 1 to 45.

Clause 48. The method of clause 47, wherein the PI4-kinase is a PI4-III kinase.

Clause 49. The method of clause 47, wherein the PI4-III kinase is a PI4KIIIβ-kinase.

Clause 50. The method of clause 47, wherein the PI4-III kinase is a PI4KIIIα-kinase.

Clause 51. A method of treating a subject for an infective disease condition, the method comprising administering to the subject a pharmaceutical composition comprising an effective amount of a compound of any one of clauses 1 to 45, or a pharmaceutically acceptable salt thereof, wherein the infective disease condition is caused by infection of a pathogen susceptible to PI4-kinase inhibition.

Clause 52. The method of clause 51, wherein the infective disease condition results from infection with a virus selected from the Retroviridae, Picornaviridae, Flaviviridae, Caliciviridae, Filoviridae, Hepeviridae, Togaviridae, Polyomaviridae, Papillomaviridae, Papovaviridae and Coronavirinae families.

Clause 53. The method of clause 51, wherein the infective disease condition results from infection with a pathogen selected from HCV, rhinovirus, plasmodium (e.g., P. falciparum), toxoplasma, ebola virus, Francisella tularensis, hantavirus, SARS virus, MERS virus, SARS-CoV-2 virus, vaccinia, smallpox, Japanese encephalitis virus, hepatitis A virus, influenza virus, Norovirus, PolioVirus, Enterovirus, HEV, EV71, EV68, coxsackie virus, BK virus, JC virus, human papiloma virus (HPV), HIV, rubella, West Nile Virus, cytomegalovirus, P. aeruginosa, and Dengue Virus.

Clause 54. The method of clause 53, wherein the pathogen is selected from EV71, EV68, human rhinoviruses, hepatitis A virus, HCV, norovirus, coxsackie virus, BK virus, JC virus, HPV, poliovirus and ebola virus.

Clause 55. The method of clause 54, wherein the compound is selected from the compounds of Tables 1, 2 and 3.

Clause 56. The method of clause 51, wherein the compound has activity against two or more pathogens.

Clause 57. A method of treating cancer, the method comprising: administering to a subject with cancer a therapeutically effective amount of a compound of any one of clauses 1 to 45.

Clause 58. The method of clause 57, wherein the cancer is a carcinoma.

Clause 59. The method of clauses 57 or 58, wherein the cancer is a solid tumor cancer.

Clause 60. The method of clause 59, wherein the compound inhibits metastasis of the solid tumor.

Clause 61. The method of any one of clauses 57-60, wherein the cancer arises from bladder (e.g., urothelium), breast, colon, endometrial, cervical, testicular, liver, lung (e.g. non-small cell lung cancer (NSCLC)), ovarian, prostate, pancreatic, brain, melanoma, sarcoma, thyroid, stomach and kidney.
Clause 62. The method of clause 61, wherein the cancer is lung cancer.
Clause 63. The method of clause 62, wherein the cancer is a lung adenocarcinoma.
Clause 64. The method of clause 61, wherein the cancer is breast cancer.
Clause 65. The method of clause 61, wherein the cancer is brain cancer.
Clause 66. The method of clause 61, wherein the cancer is glioblastoma (GBM).
Clause 67. The method of any one of clauses 57 to 66, wherein cancer cells of the subject comprise an elevated level of PI4K expression (e.g., relative to a basal level in one or more normal or control cells).
Clause 68. The method of clause 67, wherein the PI4K expression is PI4KIII expression.
Clause 69. The method of clause 68, wherein the PI4KIII expression is PI4KIIIβ expression.
Clause 70. The method of any one of clauses 57 to 69, wherein cancer cells of the subject comprise an elevated expression level of a factor involved in IRES-mediated translation that stimulates PI4-kinase activity (e.g. eEF1A2).
Clause 71. The method of any one of clauses 57 to 70, wherein cancer cells of the subject comprise an elevated level of PI4KIII activity.
Clause 72. The method of clause 71, wherein cancer cells of the subject comprise an elevated level of PI4KIIIβ activity.
Clause 73. The method of any one of clauses 57 to 72, wherein cancer cells of the subject are sensitive to PT4KIIIβ inhibition.
Clause 74. The method of any one of clauses 57 to 73, further comprising: measuring the expression level or activity level of PI4KIIIβ in cancer cells of a biological sample obtained from the subject; and determining whether the expression level or activity level of PI4KIIIβ in the cancer cells is elevated relative to one or more control cells.
Clause 75. The method of any one of clauses 57 to 74, wherein the cancer cells of the subject have a greater than diploid copy number of the PI4K gene.
Clause 76. The method of clause 75, wherein the PIK gene is the PI4KIII gene.
Clause 77. The method of clause 76, wherein the PIKII gene is the PI4KIIIβ gene.
Clause 78. The method of any one of clauses 57 to 74, wherein the compound is selective for PI4-kinase over PT3-kinase.
Clause 79. The method of any one of clauses 57 to 78, wherein compound is a PI4KIIIβ inhibitor.
Clause 80. The method of any one of clauses 57 to 78, wherein the compound is a PT4KIIIα inhibitor.
Clause 81. The method of any one of clauses 57 to 80, further comprising co-administering an effective amount of an additional agent to the subject.
Clause 82. The method of clause 81, wherein the additional agent is a chemotherapeutic agent or an immunotherapeutic agent.
Clause 83. The method of clause 81, wherein the additional agent is an inhibitor of a compound-metabolizing enzyme.
Clause 84. The method of clause 83, wherein the metabolizing enzyme is a cytochrome P-450 (e.g., CYP3A4).
Clause 85. The method of clause 81 or 83, wherein the additional agent is selected from clarithromycin, cobicistat, telithromycin, nefazodone, itraconazole, ketoconazole, atazanavir, darunavir, indinavir, lopinavir, nelfinavir, ritonavir, saquinavir and tipranavir (e.g., ritonavir or cobicistat).
Clause 86. A method of inhibiting proliferation of a cancer cell, the method comprising: contacting a cancer cell with an effective amount of a compound of any one of clauses 1 to 45.
Clause 87. The method of clause 86, wherein the cancer cell is selected from bladder (e.g., urothelial), breast, colon, endometrial, cervical, testicular, liver, lung, non-small cell lung cancer (NSCLC), ovarian, prostate, pancreatic, brain, melanoma, sarcoma, thyroid, stomach and kidney cancer cells.
Clause 88. The method of clause 86 or 87, wherein cancer cell expresses PI4K at elevated levels (e.g., relative to a basal level in one or more normal or control cells).
Clause 89. The method of clause 88, wherein the PI4K expression is PI4KIIIβ expression.
Clause 90. The method of clause 89, wherein the PI4KIII expression is PI4KIIIβ expression.
Clause 91. The method of clause 86 or 87, wherein the cancer cell comprises an elevated expression level of a factor involved in IRES-mediated translation that stimulates PI4-kinase activity (e.g. eEF1A2).
Clause 92. The method of any one of clauses 86 to 91, wherein the cancer cell comprises an elevated level of PI4KIIIβ activity.
Clause 93. The method of any one of clauses 86 to 92, wherein the cancer cell is sensitive to PI4KIIIβ inhibition.
Clause 94. An anti-cancer kit, comprising: an effective dose of a compound of any one of clauses 1 to 45; an effective dose of an additional anticancer agent; and instructions for use in treating cancer.

EXAMPLES

The following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths. John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present disclosure. All such modifications are intended to be within the scope of the claims appended hereto.

Example 1: Synthesis

Compounds may be prepared using any convenient method. For example, by similar methods to those described by Shokat et al. "A pharmacological map of the PI3-K family defines a role for p110alpha in insulin signaling." Cell. 20016; 125(4):733-47. Starting materials are obtained from Aldrich or Alfa Aesar. Reactions are monitored by LC/MS and reaction products characterized by LC/MS and 1H NMR. Intermediates and final products are purified by silica gel chromatography or by reverse phase HPLC.

Exemplary synthetic scheme 1, which can be adapted for the synthesis of subject compounds-, is shown below:

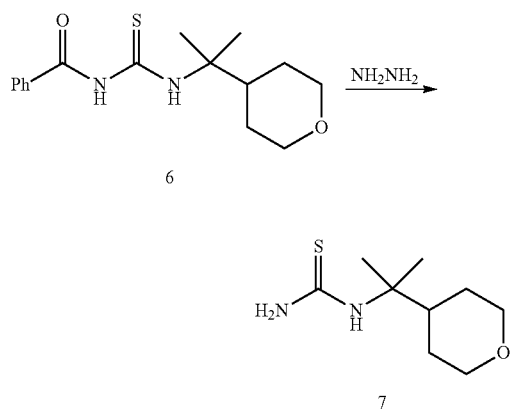

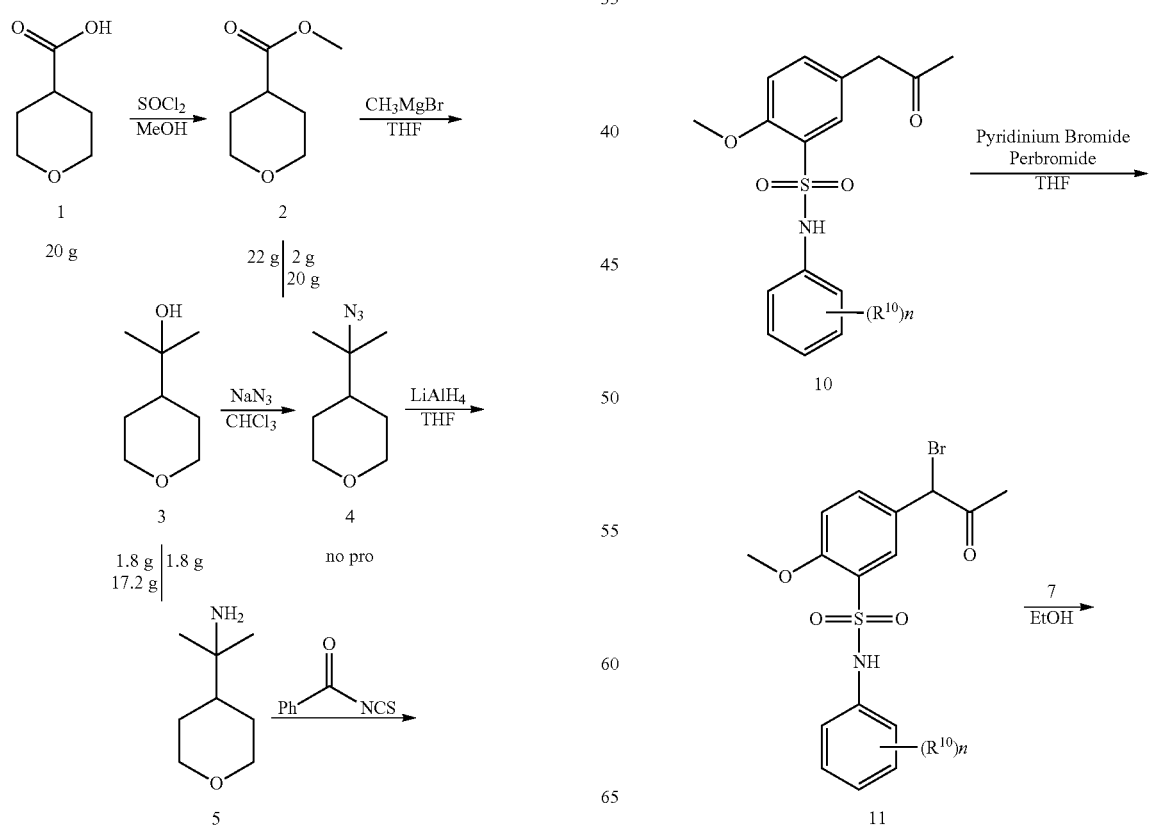

-continued

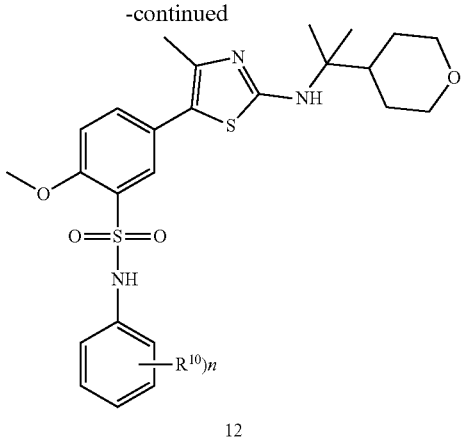

12

Example 2: Assays

PI-kinase assay: Compounds are tested in C.1.1. PI kinase assays as described by Shokat et al., "A membrane capture assay for lipid kinase activity." Nat. Protoc. 2007; 2(10): 2459-66.

Anti-HCV assay: Anti-HCV assays are performed as described by Cho et al. "Identification of a class of HCV inhibitors directed against the nonstructural protein NS4B." Sci. Transl. Med. 2011; 2(15):15ra6.

Broad-spectrum anti-infective assays: Compounds are tested for activity against selected agents harboring proteins with BAAPP domains, or other PI-4 or PIP2 binding motifs, (i.e. Vaccinia virus, Japanese encephalitis virus, hepatitis A virus, and influenza virus) in clinical studies. Activity against multiple NIAID Category A, B, and C pathogens is assayed.

Vaccinia virus assay: Standard plaque assays are performed on CV-1 cells, using methods described by Glenn et al., "Amphipathic helix-dependent localization of NS5A mediates hepatitis C virus RNA replication." J. Virol. 2003; 77(10):6055-61, in the presence of vehicle or vehicle plus various concentrations of compound.

HAV assay: Huh7 cells harboring HAV replicons encoding a blasticidin resistance gene (Yang et al., "Disruption of innate immunity due to mitochondrial targeting of a picornaviral protease precursor." Proc Natl Acad Sci USA 2007; 104(17):7253-8) is grown in media containing blasticidin, with or without various concentrations of compound. Anti-HAV activity is assessed by both cell plating efficiency and HAV RNA levels using quantitative RT-PCR assays. A luciferase-linked HAV replicon for transient replication assays is used to evaluate the effects of HAV BAAPP domain mutants.

JEV assay: JEV assays are performed using both infectious virus in cell culture, as well as in an in vivo animal model, using similar methods to those described by Shah et al. "Molecular characterization of attenuated Japanese encephalitis live vaccine strain ML-17." Vaccine. 2006; 24(4):402-11.

Influenza virus assay: Influenza virus assays are performed using infectious virus in cell culture, using similar methods to those described by Hossain et al. "Establishment and characterization of a Madin-Darby canine kidney reporter cell line for influenza A virus assays." J. Clin. Microbiol. 48(7):2515-23.

*Plasmodium falciparum* assay: *Plasmodium falciparum* assays are performed using an erythrocyte-fed culture of *P. falciparum* ring forms, using similar methods to those described by Deu et al. "Functional Studies of *Plasmodium falciparum* Dipeptidyl Aminopeptidase I Using Small Molecule Inhibitors and Active Site Probes." Chemistry & Biology 17, 808-819.

Rhinovirus assay: Rhinovirus assays are performed by determining to what extent the compound protects HeLa S3 cells from the cytopathic effect of an inoculum of human rhinovirus 14, using similar methods to those described by Buckwold et al., "Synergistic In Vitro Interactions between Alpha Interferon and Ribavirin against Bovine Viral Diarrhea Virus and Yellow Fever Virus as Surrogate Models of Hepatitis C Virus Replication," Antimicrobial Agents and Chemotherapy 47(7), 2293-2298.

HAV assay: HAV assays are performed by co-culturing Huh7-derived cells harboring the blasticidin-selectable HAV replicon (HAV-Bla, described by Yang et al, "Disruption of innate immunity due to mitochondrial targeting of a picornaviral protease precursor", PNAS 104(17), 7253-7258) for over two weeks in DMEM with 10% FBS, 1% Pen-Strep, 1% L-Glutamine, 1% nonessential amino acids, and 4 μg/mL blasticidin, with various concentrations of compound or vehicle control in 6-well plates at a density of 1000 HAV-Bla cells per well and 1/72 confluent plate worth of Huh7 feeder cells per well. At the end of this culture, large colonies in each well are counted and an effective concentration at which plating efficiency is decreased by 50% (EC50) is calculated.

For all of the assays described above, EC50, EC90, and CC50 values are determined, and experiments are performed starting drug treatments at various times post initiation of infection to help localize the most sensitive aspects of each pathogen's life cycle to PI4-kinase inhibition.

Resistance assays: The capacity for emergence of resistance and its nature is determined using any convenient methods, for example methods that involve sequencing of any resistant isolates that are able to be propagated. Co-treatments with other drugs are also performed. Experiments are conducted under BL2+ conditions where appropriate.

Humanized mouse model: The performance characteristics of the compounds are assessed by dosing the compounds in a mouse model with a humanized liver to determine their in vivo pharmacokinetic (PK) and pharmacodynamic properties. This model consists of immunodeficient NOG mice (NOD/shi SCID Il2rg -/-) harboring a Herpes virus-derived thymidine kinase (TK) transgene under the control of an albumin promoter (Hasegawa et al., "The reconstituted 'humanized liver' in TK-NOG mice is mature and functional." Biochem Biophys Res Commun. 2011; 405(3):405-10). A brief exposure to ganciclovir targets destruction of the endogenous mouse liver, which is followed by the transplantation of human liver cells. High level engraftment of human hepatocytes can be achieved and efficient HCV infection established. A quantitative analysis of in vivo PK parameters and efficacy of the compounds and metabolites in the plasma of the humanized mice is performed.

PK and PD: Cohorts of humanized TK-NOG mice (e.g. 5 mice per treatment group) are gavaged with one dose of compound. Doses are chosen so as to maintain a concentration above the respective EC50s. Serial aliquots of plasma are obtained at baseline, 15 minutes, 30 minutes, 1 hr and 2 hr post dosing. Similarly treated groups of mice are sacrificed to analyze levels of the drugs and key metabolites in the liver. Concentrations of compounds and their metabolites are measured. PK parameters, such as Cmax, T1/2, AUC, and oral clearance are determined. Based on these parameters, cohorts of humanized TK-NOG mice (5 mice per treatment group) infected with HCV inoculums consisting of the infectious 2a clone (25) or de-identified patient-derived sera are gavaged (Glenn et al., "In vivo antiviral efficacy of prenylation inhibitors against hepatitis delta virus (HDV)." Journal of Clinical Investigation. 2003; 112(3): 407-14) for multiple doses and serial serum aliquots are obtained and antiviral efficacy determined by measuring HCV titers by quantitative real-time PCR. Individually-treated mice can also serve as their own control wherein the HCV titers before, during, and after treatment can be used to assess antiviral efficacy wherein an antiviral effect in indicated by a drop in titer during the treatment phase compared to the pretreatment phase, with (in the case where the virus has not been completely eliminated during the treatment period) or without (in the case where the virus has been completely eliminated during the treatment period) an increase in titer following cessation of treatment.

Assessment of drug resistance: (In vitro) Huh7 cells harboring a bicistronic genotype 1b subgenomic replicon, wherein the first cistron encodes the neomycinphosphotransferase gene (which confers resistance to G418) and the second cistron encodes the HCV non-structural proteins required for RNA genome replication, are grown in media containing G418 plus increasing concentrations of compounds to select for drug resistant colonies. This, along with extraction of the replicons harbored in the resistant cells, sequencing to identify candidate resistance mutations, and cloning of these mutations back into a wild-type replicon to confirm they are truly causative of the resistance, is performed using convenient methods. (In vivo) Inoculums consist of the infectious 2a clone and de-identified patient-derived sera. Once establishment of infection has been confirmed, humanized mice are treated by oral gavage with a resistance-promoting regimen of compounds involving progressive dose escalation from a low dose (0.1 mg/kg/day), with drug holidays. Serum samples for analysis are taken at time 0, and serially thereafter on a weekly basis. The focus is first on any samples that display a rebound in titer of greater than 1 log after a previous nadir. Standard DNA sequencing of individual clones isolated from RT-PCR cloning is performed. Ultradeep pyrosequencing is reserved to determine earliest evidence of any observed resistance. As a control, similar experiments with an HCV NS3 protease inhibitor (e.g. Boceprevir) are performed.

General methods of materials: In the assays described here, p110α-p85 complex and p110γ were acquired from Millipore. Assays were performed with La-phosphatidylinositol (Avanti) as described in Knight et al. Nat Protoc. 2007; 2 (10):2459-66. Inhibitor series were prepared 10% DMSO as 5× stocks for the assay. Assays of HsVps34 were performed as described in Knight et al, except that the final assay buffer composition used was changed to 20 mM HEPES 7.5, 100 mM NaCl, 3 mM MgCl, 1 mg/mL PI and 44 nM hvps34 was used in the assay. For inhibitors with an apparent IC50 less than or equal to 22 nM, values were reassayed using 4.4 nM hvps34 with 3 mM $MnCl_2$. COS-7 cells were cultured in 10 cm dishes and transfected at 70% confluence with 10 µg of plasmid DNA (IIA-tagged bovine PI4KIIIβ, HA-tagged human PI4KIIIα) using Lipofectamine 2000 and 5 ml Opti-MEM following the manufacturer's instructions. After 5 hours the transfection medium was replaced with 10 ml complete DMEM. 36 hrs post transfection, cells were washed once with 5 ml PBS (pH 7.4) and lysed in 1 ml of lysis buffer (1) on ice. Lysates were collected by scraping and after 15 min they were centrifuged at 13,000 rpm for 10 min. To the lysates was added 200 µl of protein G Sepharose 4 fast flow beads that were pre-washed with PBS and lysis buffer and 2 µg of anti-HA antibody. The tubes were then incubated overnight at 4 degrees C. in a tube rotator. The Sepharose beads in the lysate were washed twice with 150 mM NaCl in RIPA buffer, twice with RIPA buffer and once with kinase buffer (50 mM Tris/HCl, pH 7.5, 20 mM MgCl2, 1 mM EGTA, 1 mM PtdIns, 0.4% Triton X-100, 0.5 mg/mL BSA) and finally the beads were resuspended in 200 µL kinase buffer. Kinase reactions were run in a mixture of 45 µL of PI buffer (1 mM PI in kinase buffer), 10 µL of immunoprecipitated beads, 2 µL of inhibitors (dissolved and diluted in DMSO) or DMSO and 5 µL of [$\gamma$-$^{32}$P]-ATP (1 mM and 2 µCi/tube). The immunoprecipitates in PI buffer were pre-incubated with the drugs for 20 min prior the initiation of kinase reaction by adding ATP and the reactions were carried out for 30 min in 15 ml polyproplyene tubes. Reactions were terminated by addition of 3 ml of $CHCl_3$:$CH_3OH$:HCl (200:100:0.75) followed by 0.6 ml of 0.6N HCl to induce phase separation. The mixtures were vortexed, centrifuged at 2000 rpm for 2 min and the upper phase was discarded. To the lower phase was added 1.5 ml of $CHCl_3$:$CH_3OH$:0.6N HC (3:48:47) and the mixture vortexed and centrifuged at 2000 rpm for 2 min. The lower phase was then transferred to counting vials and evaporated. Samples were counted in a scintillation beta counter after adding 5 ml of Instafluor (Perkin-Elmer).

Example 3: PI Kinase Inhibition

Selected compounds of Tables 1-3 were prepared and tested for inhibition activity in a variety of kinase assays.

TABLE 4

Comparison of PI4K and PI3K Kinase activity of select compounds
A = <100 nM; B = 100 nM-1 uM; C = 1-10 uM; D = >10 uM

| Compound | PI4KIIIalpha | PI4KIIIbeta |
| --- | --- | --- |
| Compound A | A | A |
| Compound B | D | A |
| Compound C | D | A |
| S-32 | D | A |
| S-42 | D | A |
| S-45 | D | A |

Example 4: Anti-viral Activity

Tables 5-8 show the results of testing selected compounds for anti-viral ($EC_{50}$) activity in various assays, such as a HCV genotype 2a in Huh7.5 cells by luciferase reporter assay, for cell toxicity ($CC_{50}$) and metabolic halflife (t1/2), according to the methods described herein.

TABLE 5

Comparison of antiviral activity of select PI4K inhibitors.

| Compound | HCV EC$_{50}$ (uM) | HRV CC$_{50}$ (uM) | EV71 EC$_{50}$ (uM) | EV71 CC$_{50}$ (uM) | EV68 EC$_{50}$ (uM) | EV68 CC$_{50}$ (uM) |
|---|---|---|---|---|---|---|
| S-1 | 0.005 | 14.981 | 0.0002 | 100 | 0.0024 | 18.228 |
| S-2 | 0.0023 | 33.408 | 0.0008 | 66.575 | | |
| S-3 | 0.0005 | 70.536 | 0.0005 | 86.583 | 0.0013 | 47.47 |
| S-4 | 0.0013 | 17.305 | 0.0058 | 36.485 | | |
| S-5 | 0.0017 | 57.003 | 0.0008 | 47.193 | | |
| S-8 | 0.0008 | 8.467 | 0.0003 | 91.87 | | |
| S-9 | 0.005 | 100 | 0.0048 | 69.31 | 0.029 | 100 |
| S-11 | 0.0571 | 40.685 | 0.0072 | 25.955 | 3.8325 | 43.3 |
| S-51 | 0.0015 | 52.655 | 0.0013 | 62.09 | 0.0115 | 37.035 |
| S-52 | 75.029 | 2.3202 | 75.017 | 3.0665 | 100 | 2.2272 |
| S-12 | 0.0175 | 65.875 | 0.0041 | 53.83 | 0.1063 | 66.225 |
| S-13 | 0.0081 | 101.5 | 0.0013 | 99.4 | 0.0391 | 102.1 |
| S-14 | 0.0144 | 36.363 | 0.0104 | 37.227 | 33.348 | 39.391 |
| S-15 | 0.082 | 100 | 0.0653 | 100 | 0.3352 | 63.68 |
| S-16 | 0.6828 | 38.26 | 0.5681 | 21.24 | 2.0997 | 39.183 |
| S-17 | 0.0107 | 100 | 0.0037 | 99.86 | 0.0255 | 100 |
| S-18 | 0.0119 | 62.125 | 0.0044 | 43.24 | 0.014 | 79.975 |
| S-19 | 0.0315 | 37.7 | 0.0158 | 18.291 | 22.077 | 39.375 |
| S-20 | 0.0257 | 49.377 | 0.0036 | 18.86 | 0.0507 | 51.633 |
| S-53 | 12.4 | 100 | 3.5555 | 47.94 | 12.29 | 100 |
| S-21 | 0.0024 | 87.599 | 0.0031 | 91.342 | 0.0107 | 94.837 |
| S-22 | 0.0027 | 15.51 | 0.0008 | 16.525 | 0.0048 | 19.29 |
| S-23 | 0.138 | 100 | 0.049 | 100 | 0.7964 | 66.065 |
| S-24 | 0.0037 | 9.6205 | 0.0046 | 73.05 | 0.0111 | 13.36 |
| S-25 | 0.0206 | 24.825 | 0.0141 | 90.68 | 0.0931 | 23.99 |
| S-26 | 0.0181 | 38.739 | 0.0023 | 88.717 | 1.409 | 39.131 |
| S-27 | 0.0023 | 1.4065 | 0.0036 | 6.234 | 0.0059 | 1.757 |
| S-28 | 0.0049 | 87.41 | 0.0042 | 100 | 0.0091 | 77.62 |
| S-29 | 0.0057 | 98.69 | 0.0098 | 100 | 0.0391 | 101.85 |
| S-30 | 0.0112 | 3.7865 | 0.0022 | 20.155 | 0.0592 | 6.451 |
| S-63 | 0.0015 | 27.68 | 0.0084 | 83.765 | 0.0034 | 40.585 |
| S-65 | 0.0018 | 46.304 | 0.0027 | 31.286 | 0.0024 | 1.6975 |
| S-31 | 0.0005 | 52.33 | 0.0002 | 70.627 | 0.0008 | 61.755 |
| S-32 | 0.0002 | 100 | 0.0001 | 100 | 0.0006 | 100 |
| S-33 | 0.0001 | 30.508 | 0.0001 | 71.268 | 0.0007 | 5.229 |
| S-34 | 0.001 | 19.45 | 0.0018 | 100 | 0.0068 | 22.125 |
| S-35 | 0.0002 | 100 | 0.0001 | 100 | 0.0006 | 100 |
| S-36 | 0.0001 | 30.508 | 0.0001 | 71.268 | 0.0007 | 5.229 |
| S-55 | 0.001 | 19.45 | 0.0018 | 100 | 0.0068 | 22.125 |
| S-37 | 0.0001 | 4.393 | 0.0001 | 21.75 | 0.0005 | 3.884 |
| S-38 | 0.0006 | 2.123 | 0.0014 | 0.8278 | 0.0029 | 1.8987 |
| S-39 | 0.0002 | 47.688 | 0.0002 | 99.023 | 0.0008 | 19.87 |
| S-40 | 0.0002 | 40.8 | 0.000075055 | 78.055 | 0.0012 | 42.705 |
| S-41 | 0.0099 | 1.9035 | 0.0009 | 0.7761 | 0.0585 | 2.0905 |
| S-42 | 0.0007 | 100 | 0.0003 | 102.88 | 0.0019 | 100 |
| S-43 | 0.0021 | 100.5 | 0.0003 | 17.495 | 0.0051 | 100 |
| S-44 | 0.0306 | 32.1 | 0.0035 | 18.207 | 1.9875 | 33.53 |
| S-45 | 0.0004 | 66.219 | 0.0003 | 87.326 | 0.002 | 73.174 |
| S-46 | 0.0009 | 52.443 | 0.0004 | 24.5 | 0.0026 | 44.545 |
| S-47 | 0.0096 | 49.49 | 0.0012 | 21.095 | 0.0276 | 49.065 |
| S-48 | 0.0745 | 100 | 0.0045 | 100 | 0.2174 | 100 |
| S-49 | 0.01 | 66.305 | 0.001 | 29.485 | 0.0507 | 71.4 |
| S-50 | 0.0076 | 46.6 | 0.0012 | 38.105 | 0.0128 | 37.595 |
| S-57 | 0.0009 | 95.165 | 0.0009 | 96.08 | 0.001 | 100 |
| S-58 | 0.0225 | 100 | 0.0068 | 100 | 0.0135 | 100 |

Compounds of interest were tested in a variety of cell-based assays for antiviral activity. Compounds of interest were tested in a variety of pharmarokinetic assays including microsomal stability assays in vitro against human liver microsomes (HLM) and mouse liver microsomes (MLM), and Caco-2 permeability assay to give apparent permeability coefficients (Papp).

TABLE 6

Antiviral activity and in vitro microsomal stability and permeability properties of PI4K inhibitors.

| Compound | S-1 | S-3 | S-32 | S-39 | S-42 | S-45 |
|---|---|---|---|---|---|---|
| HRV EC$_{50}$ | 0.5 nM | 0.5 nM | 65 pM | 0.2 nM | 0.9 nM | 0.5 nM |
| HRV CC$_{50}$ | 15 uM | 70 uM | 100 uM | 47 uM | 100 uM | 52 uM |
| EV71 EC$_{50}$ | 0.2 nM | 0.5 nM | 57 pM | 0.2 nM | 0.3 nM | 0.3 nM |
| EV71 CC$_{50}$ | 100 uM | 86 uM | 100 uM | 99 uM | 100 uM | 77 uM |

TABLE 6-continued

Antiviral activity and in vitro microsomal stability and permeability properties of PI4K inhibitors.

| Compound | S-1 | S-3 | S-32 | S-39 | S-42 | S-45 |
|---|---|---|---|---|---|---|
| EV68 $EC_{50}$ | 2.4 nM | 1 nM | 0.3 nM | 0.8 nM | 1.6 nM | 2.9 nM |
| EV68 $CC_{50}$ | 18.2 uM | 47 uM | 100 uM | 19 uM | 100 uM | 38 uM |
| HLM/MLM (t ½ min) | 6/8 | 58/58 | 17/22 | 83/67 | 10/14 | 14/10 |
| HLM/MLM (t ½ min) + Ritonavir | 68/50 | 159/159 | 159/133 | 159/83 | 159/82 | 159/67 |
| Caco2 Papp × 1e−6 cm/s | 4.0 | 7.42 | 0.04 | 7.6 | 14 | n/a |

TABLE 7

Antiviral activity of PI4K inhibitors.

| Compound | S-57 | S-58 | S-4 | S-14 | S-38 |
|---|---|---|---|---|---|
| HRV $EC_{50}$ | 0.9 nM | 022 nM | 1.3 nM | 14 nM | 0.2 nM |
| HRV $CC_{50}$ | 95 uM | 100 uM | 17 uM | 36 uM | 100 nM |
| EV71 $EC_{50}$ | 0.9 nM | 6 nM | 5.8 uM | 10 nM | 0.1 nM |
| EV71 $CC_{50}$ | 95 uM | 100 uM | 36 uM | 37uM | 100 uM |
| EV68 $EC_{50}$ | 1 nM | 13 nM | | 33 uM | 0.6 nM |
| EV68 $CC_{50}$ | 100 uM | 100 uM | | 39 uM | 100 uM |

TABLE 8

Antiviral activity of PI4K inhibitors.

| Compound | | Compound B | Compound C | S-76 | S-45 | S-42 | PC1 | PC2 |
|---|---|---|---|---|---|---|---|---|
| BK virus | $EC_{50}$ | 0.019 | 0.07 | <0.0006 | | | 0.31 | |
| (Polyomaviridae) | $CC_{50}$ | >100 | >100 | 27 | | | >100 | |
| JC virus | $EC_{50}$ | | | | 4.7 | 8.1 | 29.5 | |
| (Polyomaviridae) | $CC_{50}$ | | | | >150 | >150 | >150 | |
| Human HPV | $EC_{50}$ | 2.1 | | | 5.3 | | | 2.8 |
| (Papillomaviridae) | $CC_{50}$ | 131 | | | 77 | | | >150 |

PC1 is positive control agent 1, cidofovir, PC2 is positive control agent 2, 9-[2-(phosphono-methoxy)ethyl]guanine. Compounds exhibiting more potent activity than control were considered highly active.

Example 5: Anti-Viral Activity of Exemplary Compounds

It was observed that selected compounds which incorporate a gem dimethyl group (e.g., such as compound S-32) showed a potency and selectivity that is superior relative to that of a mono methyl equivalent compound (e.g., such as the enantiomers S-74 and S-75). This is illustrated in Table 9 below:

TABLE 9

Comparison of gen-dimethyl benzyl and mono-methyl benzyl compounds.

| Compound | S-74 | S-75 | S-32 |
|---|---|---|---|
| HRV $EC_{50}$ | 0.9 nM | 022 nM | 1.3 nM |
| HRV $CC_{50}$ | 95 uM | 100 uM | 17 uM |
| EV71 $EC_{50}$ | 0.9 nM | 6 nM | 5.8 u M |
| EV71 $CC_{50}$ | 95 uM | 100 uM | 36 uM |
| EV68 $EC_{50}$ | 1 nM | 13 nM | |
| EV68 $CC_{50}$ | 100 uM | 100 uM | |

The compounds S-74, 5-75 and S-32 have the following structures:

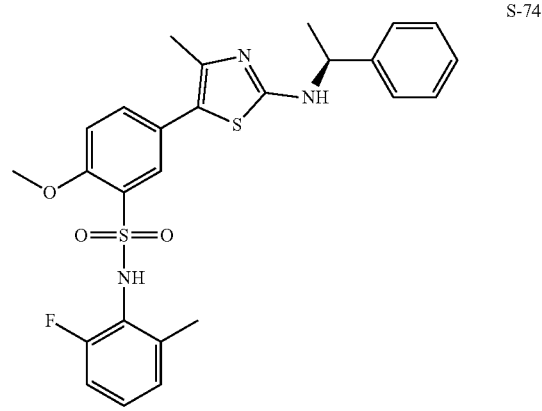

S-74

-continued

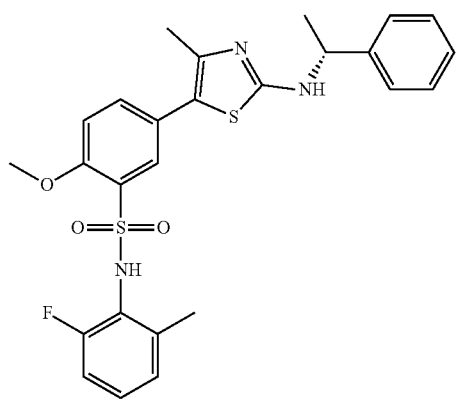
S-75

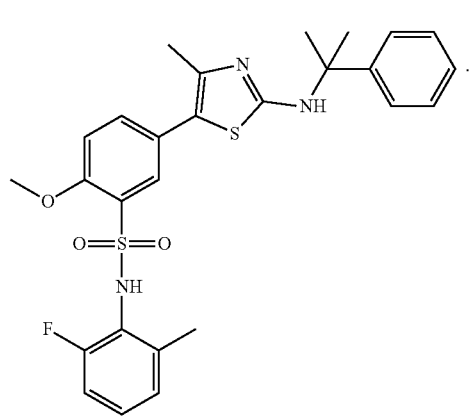
S-32

In another example, gem-dimethyl compound S-1 was found to have improved potency and selectivity relative to the monomethyl compound S-76. These results are shown below in Table 10.

TABLE 10

Comparison of gen-dimethyl pyran and mono-methyl pyran compounds.

| Compound | S-76 | S-1 |
|---|---|---|
| HRV EC$_{50}$ | 1.9 nM | 0.5 nM |
| HRV CC$_{50}$ | 9.3 uM | 14 uM |
| EV71 EC$_{50}$ | 1.8 nM | 0.2 nM |
| EV71 CC$_{50}$ | 36 uM | 100 uM |
| EV68 EC$_{50}$ | 5 nM | 2 nM |
| EV68 CC$_{50}$ | 9.4 uM | 18 uM |

The compounds S-76 and S-1 have the following structures:

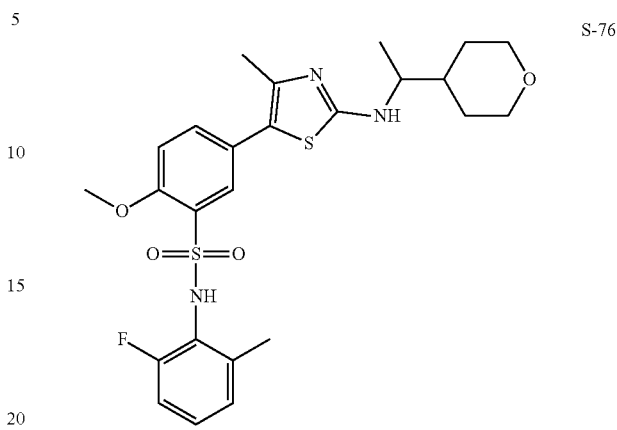

Exemplary gem-dimethyl compounds were also observed to have improved potency and selectivity relative to unsubstituted methylpyran derivatives. For example, compound S-4 exhibited superior potency and selectivity relative to compound S-77. These results are shown in Table 11.

TABLE 11

Comparison of gen-dimethyl pyran and unsubstituted methyl pyran compounds.

| Compound | S-77 | S-4 |
|---|---|---|
| HRV EC$_{50}$ | 826 nM | 1.3 nM |
| HRV CC$_{50}$ | 66 uM | 17 uM |

The compounds S-77 and S-4 have the following structures:

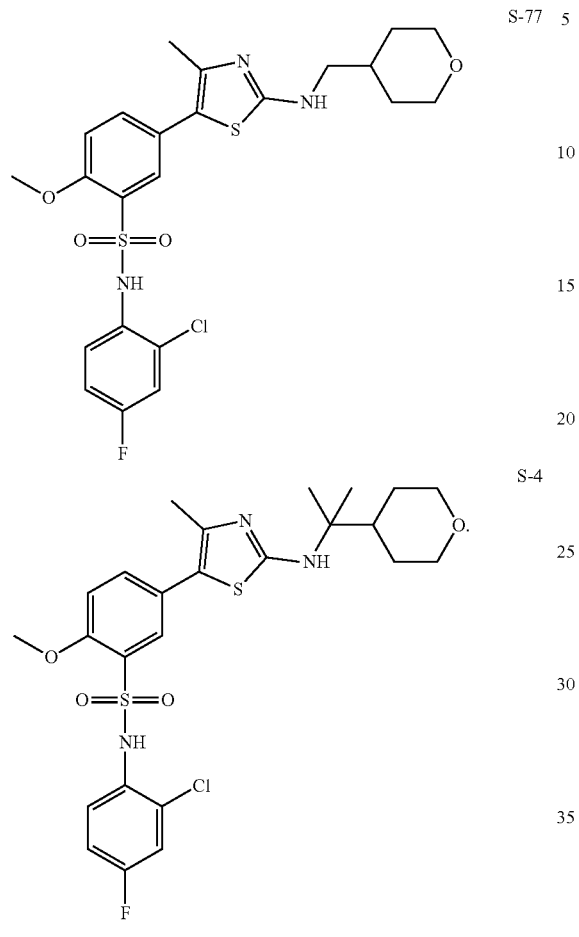

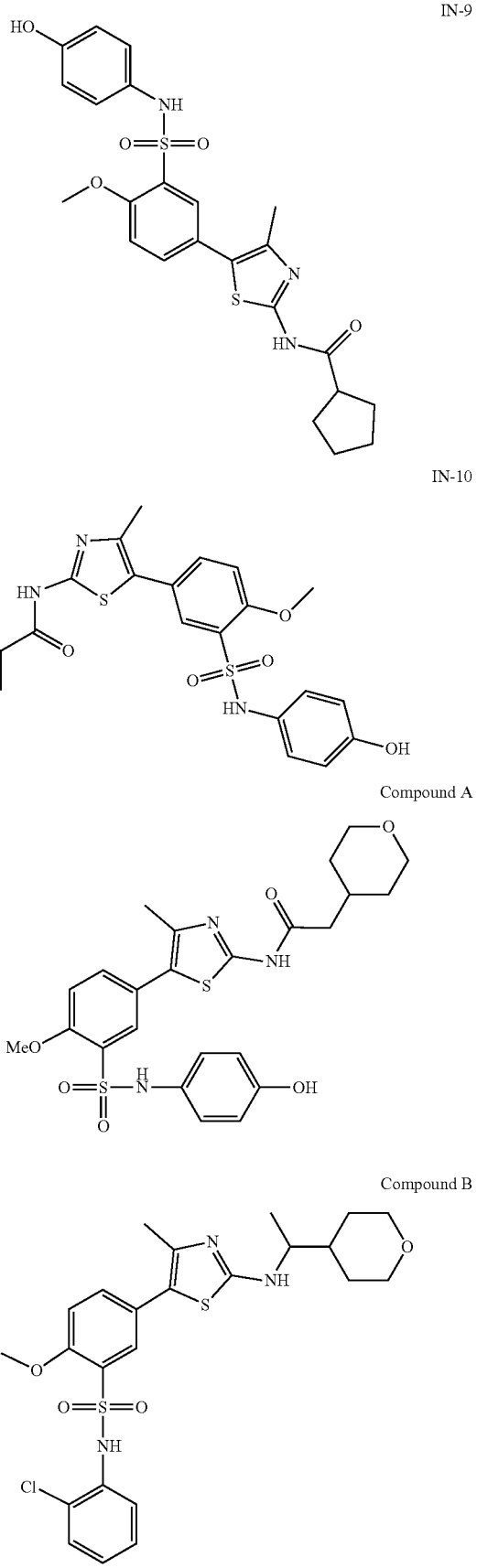

Example 6: EV-71 Antiviral Activity in Mice

Figure 4:
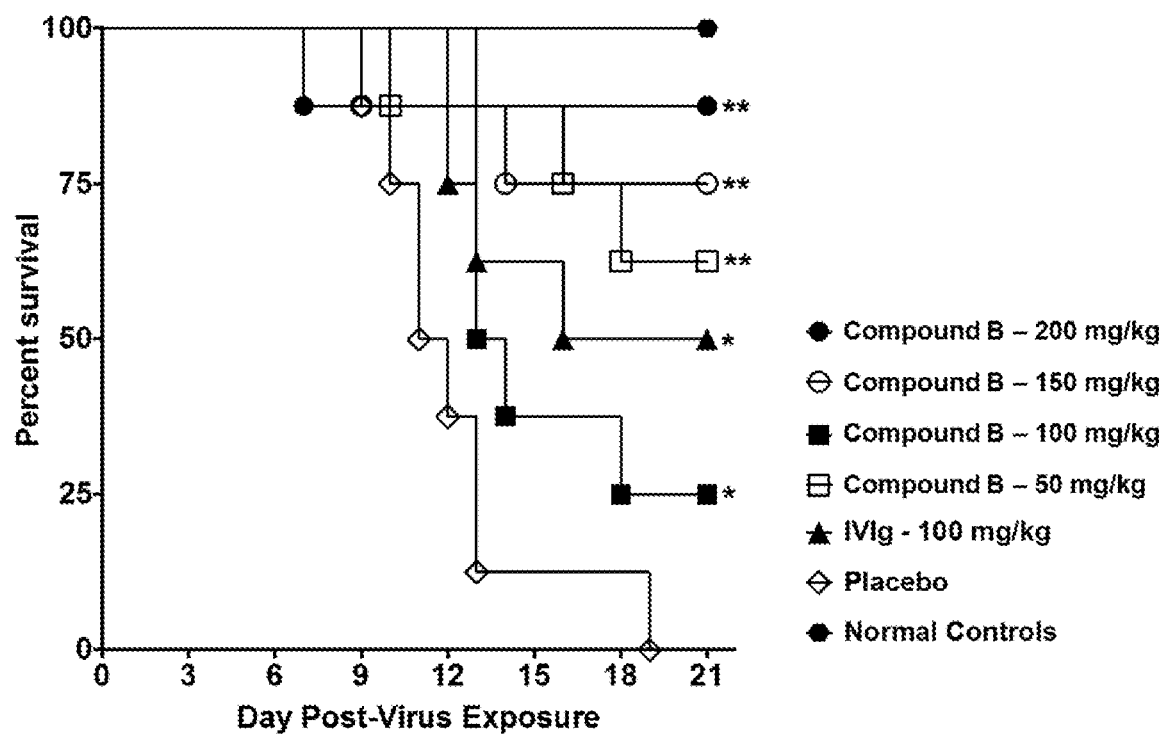
FIG. 4 illustrates the survival of four-week-old AG129 mice challenged with EV-71 virus and treated with exemplary Compound B. Groups of eight AG129 mice were challenged with EV-71 at $10^{6.5}$ $CCID_{50}$/mouse via the i.p. route. Mice were treated b.i.d. for five days per os with doses of Compound B as shown, starting four hours post-infection. Placebo-treated mice received a vehicle control on the same schedule. Mice treated with IVIg, as a positive control, received a single administration of 100 mg/kg via the i.p. route four hours post-infection. A dose response was observed in survival following treatment with Compound B. Kaplan-Meier survival curves were generated and compared by the Log-rank (Mantel-Cox) test followed by pairwise comparison using the Gehan-Breslow-Wilcoxon test in Prism 7.0c (GraphPad Software Inc., La Jolla, CA). (*$P<0.05$, **$P<0.01$).

FIG. 4 illustrates the survival of four-week-old AG129 mice challenged with EV-71 virus and treated with exemplary Compound B. Groups of eight AG129 mice were challenged with EV-71 at $10^{6.5}$ $CCID_{50}$/mouse via the i.p. route. Mice were treated b.i.d. for five days per os with doses of Compound B as shown, starting four hours post-infection. Placebo-treated mice received a vehicle control on the same schedule. Mice treated with IVIg, as a positive control, received a single administration of 10 mg/kg via the i.p. route four hours post-infection. A dose response was observed in survival following treatment with Compound B. Kaplan-Meier survival curves were generated and compared by the Log-rank (Mantel-Cox) test followed by pairwise comparison using the Gehan-Breslow-Wilcoxon test in Prism 7.0c (GraphPad Software Inc., La Jolla, CA). (*$P<0.05$, **$P<0.01$).

Example 7: Anti-Cancer Activity of Exemplary Compounds

Exemplary 5-aryl-thiazole PI4KIIIβ inhibitor compounds including IN-9, IN-10 and compounds A, B and C were obtained and tested for anti-cancer activity as described below. PI4KIIIβ inhibitors IN-9 and IN-10 are described by Rutaganira et al. (J Med Chem. 2016 Mar. 10; 59(5):1830-9) and are commercially available.

-continued

Compound C

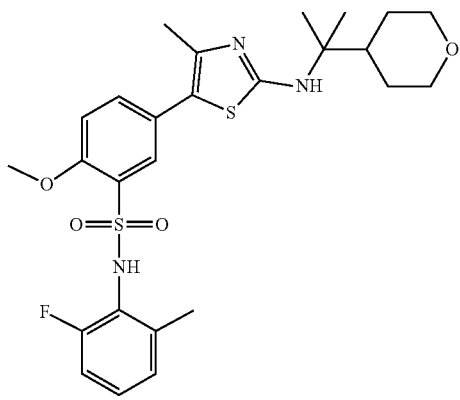

PI4KIIIbeta-IN-9 is a PI4KIIIβ inhibitor with an IC50 of 7 nM. PI4KIIIbeta-IN-9 also inhibits PI3Kδ and PI3Kγ with IC50s of 152 nM and 1046 nM, respectively. PI4KIIIbeta-IN-10 is a PI4KIIIβ inhibitor with very minor off-target inhibition of PI4KIIIβ related lipid kinases. PI4KIIIbeta-IN-10 shows weak inhibition of PI3KC2γ (IC50~1 μM), PI3Kα (~10 μM), and PI4KIIIα (~3 μM), and <20% inhibition at concentrations up to 20 μM for PI4K2α, PI4K2β, and PI3Kβ.

General Methods

Mice received standard care and were euthanized according to the standards set forth by the Institutional Animal Care and Use Committee. To generate orthotopic lung tumors using human lung adenocarcinoma cell lines, nu/nu mice (n=10 mice per cohort) were subjected to intrathoracic injection with $10^6$ human tumor cells, necropsied after a week or more of treatment, and primary tumor size and the number of metastases on the contralateral lung surface measured.

To treat mice bearing human orthotopic lung tumors with the PI4KIIIβ inhibitor compound B, nu/nu mice were injected with $10^6$ human lung adenocarcinoma cells by the intra-thoracic approach and treatment initiated with compound B (20 or 40 mg/kg each plus 20 mg/kg ritonavir) or vehicle (5% DMSO, 20% HPBCD, 2% Poly 80 and 10% PEG300) one week after tumor cell injection. Drugs were administered subcutaneously twice daily for three weeks. On the last day of treatment, mice were subjected to micro-computed tomography to measure primary tumor size. The following day, mice were necropsied to measure primary tumor size, count metastases to the contralateral lung, and obtain lung tissues for analysis.

To treat mice bearing human orthotopic lung tumors with the PI4KIIIβ inhibitor compound A, nu/nu mice were injected with $10^6$ human lung adenocarcinoma cells by the intra-thoracic approach and treatment initiated with compound A (100 mg/kg) or vehicle (5% DMSO, 20% HPBCD, 2% Poly 80 and 10% PEG300) one week after tumor cell injection. Drugs were administered intraperitoneally twice daily for 8 days. On the last day of treatment, mice were subjected to micro-computed tomography to measure primary tumor size. The following day, mice were necropsied to measure primary tumor size, count metastases to the contralateral lung, and obtain lung tissues.

To treat mice bearing human breast tumor xenografts with the PI4KIIIβ inhibitor compound A, nu/nu mice were injected with MDA-MB-468 human breast adenocarcinoma cells under the mammary fat pad. Following establishment of the human breast tumor xenografts, treatment was initiated with compound A (100 mg/kg) or vehicle (5% DMSO, 20% HPBCD, 2% Poly 80 and 10% PEG300). Drugs were administered intraperitoneally twice daily for 5 days. Mice were necropsied to measure primary tumor size.

Human lung cancer cells (A549, H1299, H460, H23, H2122, and H3122) were cultured in RPMI 1640 containing 10% FBS. Cells were maintained at 37° C. in an incubator with a humidified atmosphere containing 5% $CO_2$.

Results: Anti-cancer activity of PI4K antagonists

Small-molecule PI4K antagonists have been used as anti-viral agents against single stranded RNA viruses that require PI4KIIIβ for replication (Rutaganira, F. U., et al. Design and Structural Characterization of Potent and Selective Inhibitors of Phosphatidylinositol 4 Kinase IIIbeta. J. Med. Chem. 59, 1830-1839, 2016). Applicants understood that PI4K inhibitors could find use in anti-cancer applications.

To assess the anti-cancer activity of exemplary PT4K antagonists, a panel of lung cancer cell lines annotated for the presence or absence of PI4K amplifications were treated with PI4K inhibitors (IN-9, IN-10, or compound B) that have greater than 1000-fold selectivity against PI4KIIIβ over class I and class III PI3K family members. PI4K inhibitor treatment decreased PI4P levels in a dose-dependent fashion and reduced cell proliferation in monolayer culture, migration and invasion in Boyden chambers, and colony formation in soft agar and on plastic. IC50 values were even lower with the presence of PI4K amplifications.

PI4K inhibition leads to decreased PI-4P dependent processes including PI-4P mediated membrane association and intracellular trafficking. Moreover, PI4K antagonists demonstrated robust anti-tumor activity in nu/nu mice bearing H2122 human orthotopic lung tumors (FIGS. 1F-1G and FIGS. 2B-2C)

Figure 1B:
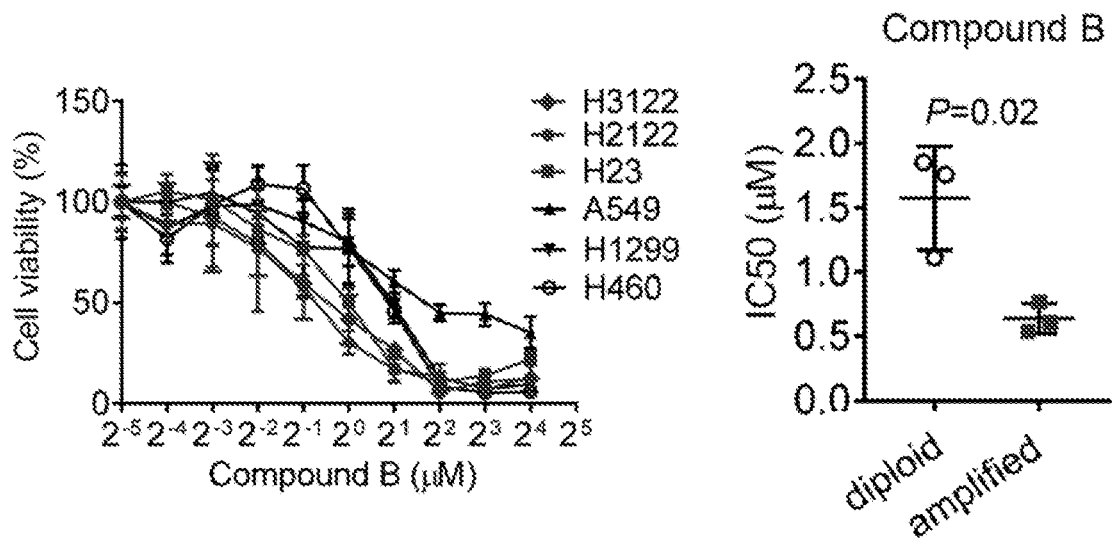
FIG. 1B Left panel: Relative densities of PI4KIIIβ-amplified (red) and -diploid (black) human lung adenocarcinoma cell lines by WST-1 assays after 5 days of compound B treatment. Results expressed relative to the lowest dose, which was set at 100%. Right panel: Half maximal inhibitory (IC50) concentrations of compound B determined from left panel data.
Figure 1C:
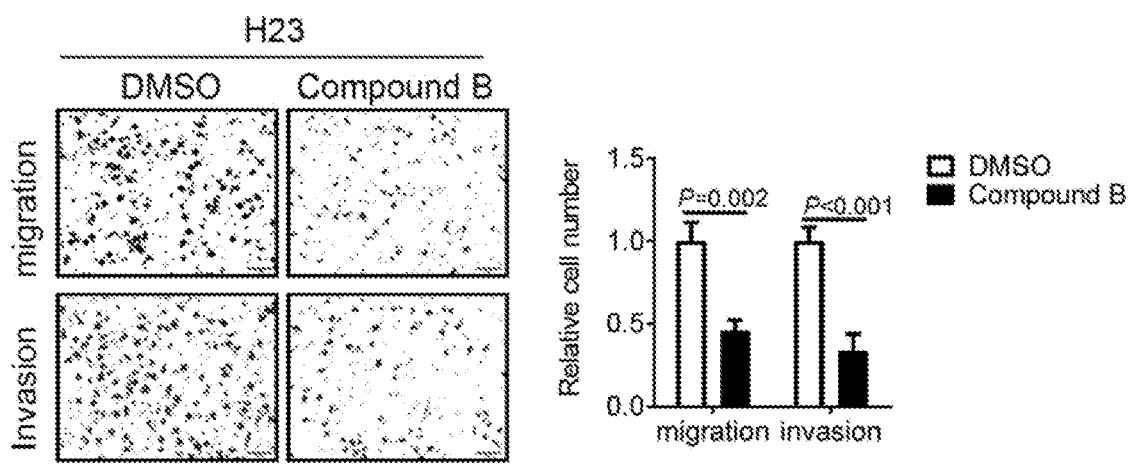
FIG. 1C. Migrated and invaded H23 human lung cancer cells in Transwell chambers were photographed (images) and counted (bar graphs) after treatment with compound B. Results expressed relative to DMSO-treated cells, which were set at 1.0.
Figure 1D:
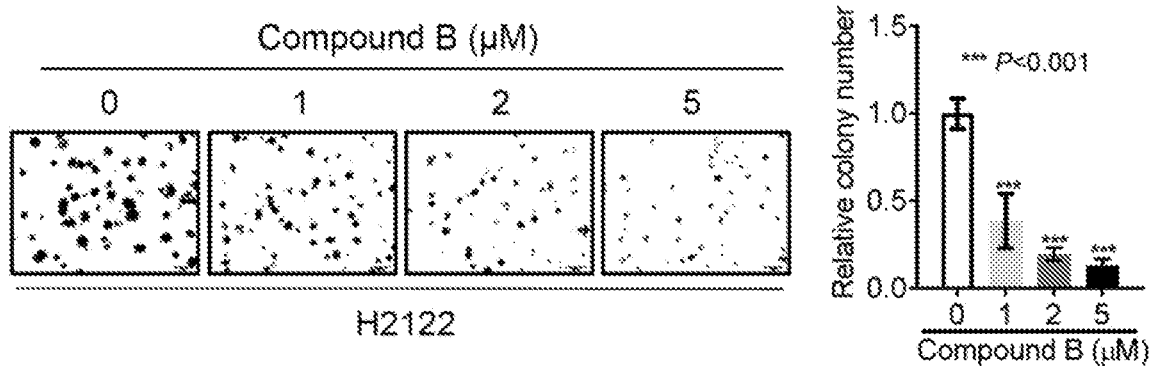
FIG. 1D-1E. Colonies formed by H2122 human lung cancer cells in soft agarose (FIG. 1D) and on plastic (FIG. 1E) were photographed (images) and counted (bar graphs) after 7 days of treatment with the indicated doses of compound B or vehicle DMSO (0 μM). Results expressed relative to DMSO control, which were set at 1.0.
Figure 1E:
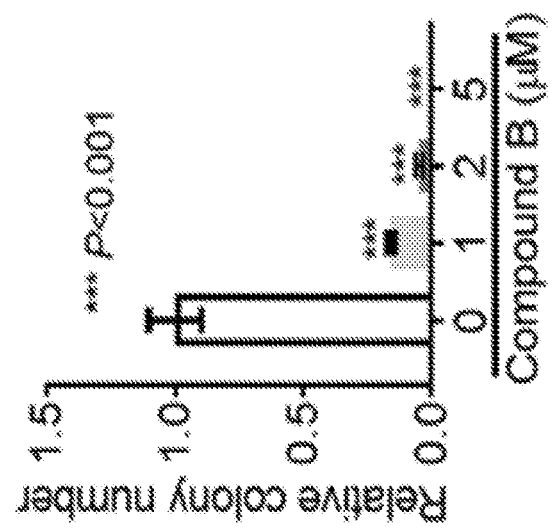
Figure 1E:
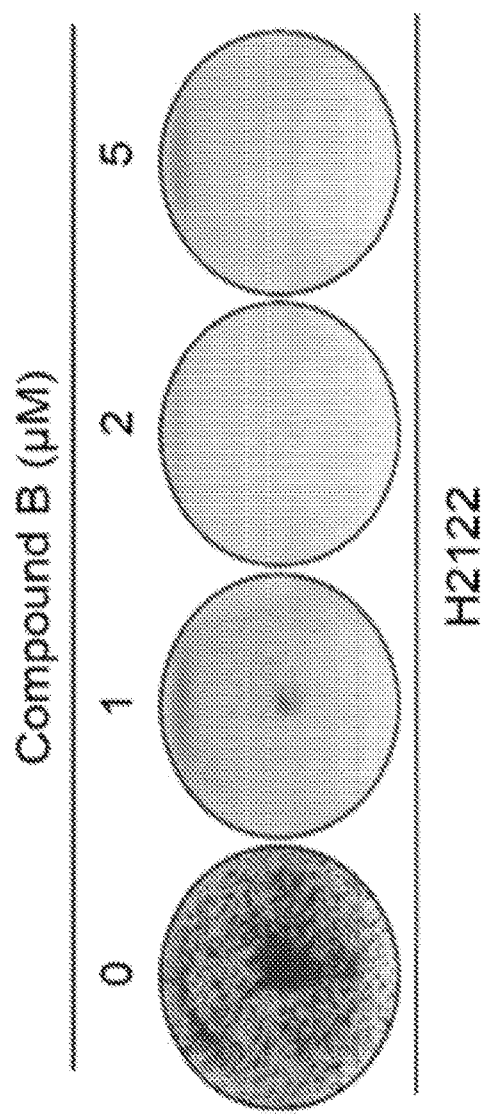
Figure 1F:
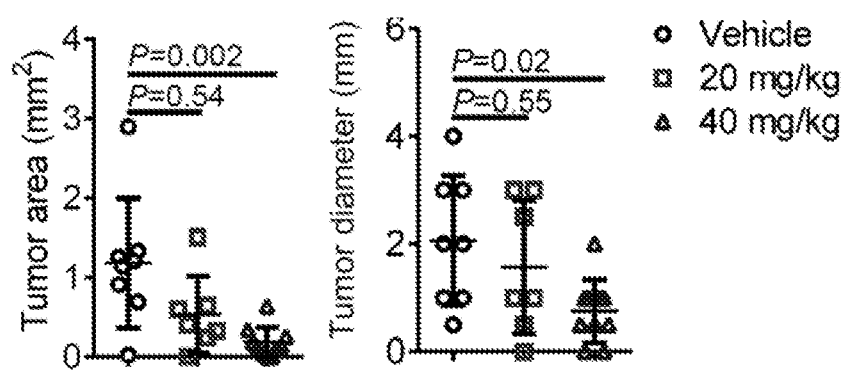

PI4KIIIβ is a target in human cancers, including lung adenocarcinoma. (FIG. 1A). PI4P concentrations in H2122 cells (dots) treated in triplicate (dots) with Compound B or vehicle dimethyl sulfoxide (DMSO). (FIG. 1B) Relative densities of PI4-kinase-amplified (red) and -diploid (black) human lung adenocarcinoma cell lines determined by WST-1 assays after 5 days of Compound B treatment. Results expressed relative to the lowest dose, which was set at 100%. (FIG. 1B, right panel) Half maximal inhibitory (IC50) concentrations of compound B determined from FIG. 1B, left panel. (FIG. 1C) Migrated and invaded H23 human lung adenocarcinoma cells in Transwell chambers were photographed (images) and counted (bar graphs) after treatment with compound B. Results expressed relative to DMSO-treated cells, which were set at 1.0. (FIG. 1C, right panel). Colonies formed by H2122 human lung cancer cells in soft agarose (FIG. 1D) and on plastic (FIG. 1E) were photographed (images) and counted (bar graphs) after 7 days of treatment with the indicated doses of compound B or vehicle DMSO (0 μM). Results expressed relative to DMSO control, which were set at 1.0. PI4-kinase inhibition leads to selective cytotoxicity for cancer cells (FIG. 1F).

FIG. 1A. Intracellular PI4P concentrations in H2122 lung cancer cells treated with compound B (PI4-kinase inhibitor) or vehicle DMSO. FIG. 1B Left panel: Relative densities of PI4KIIIβ-amplified (red) and -diploid (black) human lung adenocarcinoma cell lines by WST-1 assays after 5 days of compound B treatment. Results expressed relative to the lowest dose, which was set at 100%. Right panel: Half maximal inhibitory (IC50) concentrations of compound B determined from left panel data. FIG. 1C. Migrated and invaded H23 human lung cancer cells in Transwell chambers were photographed (images) and counted (bar graphs) after treatment with compound B. Results expressed relative to DMSO-treated cells, which were set at 1.0. (FIG. 1D-1E). Colonies formed by H2122 human lung cancer cells in soft agarose (FIG. 1D) and on plastic (FIG. 1E) were photographed (images) and counted (bar graphs) after 7 days of treatment with the indicated doses of compound B or vehicle DMSO (0 µM). Results expressed relative to DMSO control, which were set at 1.0.

PI4-kinase inhibition leads to significant cytotoxicity for cancer cells (Table 12).

TABLE 12

CC50 of cancer cells in response to treatment with PI4-kinase inhibitors

| Cancer cell line: | | Tumor type: | |
| --- | --- | --- | --- |
| | | Glioblastoma A172 | Melanoma A375 |
| Compound/CC50 (M): | Compound A | $2^{-7}$ | $6^{-7}$ |
| | Compound B | $5^{-7}$ | $7^{-6}$ |
| | Compound C | $1^{-7}$ | $4^{-6}$ |
| | Erlontinib | $1^{-4}$ | $1^{-5}$ |

FIGS. 1F and 1G. Schema of compound B treatment: Day 0, H2122 human lung cancer cell injection; day 7-27 compound B treatment; tumor imaging day 26 and necropsy day 27. (FIG. 1F) Mice subjected to micro-computed tomography after 19 days of treatment to determine tumor areas (left dot plot). Tumor diameters determined at necropsy (right dot plot). (FIG. 1G) Mice grouped on the basis of lung tumor measurements determined at necropsy, which showed a shift toward smaller tumor diameters in compound B-treated mice. No metastases were detectable following treatment with Compound B, and the sizes of the primary tumors following Compound B treatment were smaller than in those mice receiving treatment with vehicle alone.

Figure 2A:
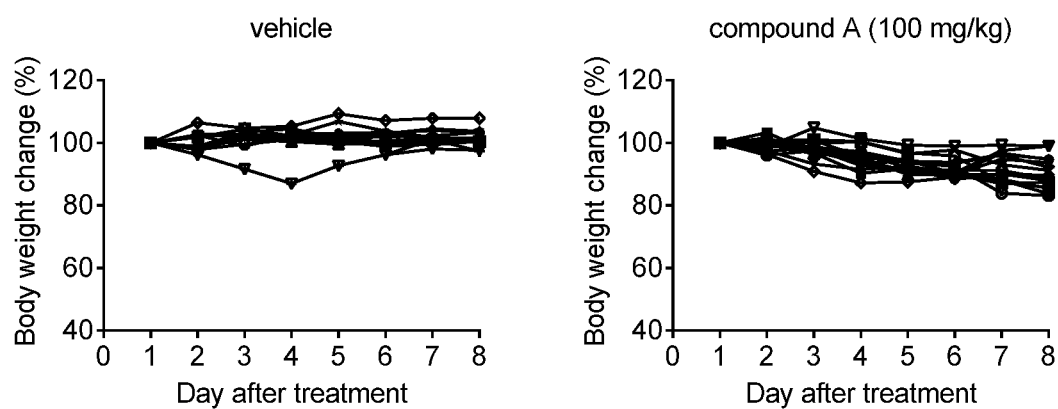
FIGS. 2A-2C. Schema of compound A treatment: Day 0, H2122 human lung cancer cell injection; day 7-15 compound A treatment; tumor imaging day 14 and necropsy day 15.
Figure 2B:
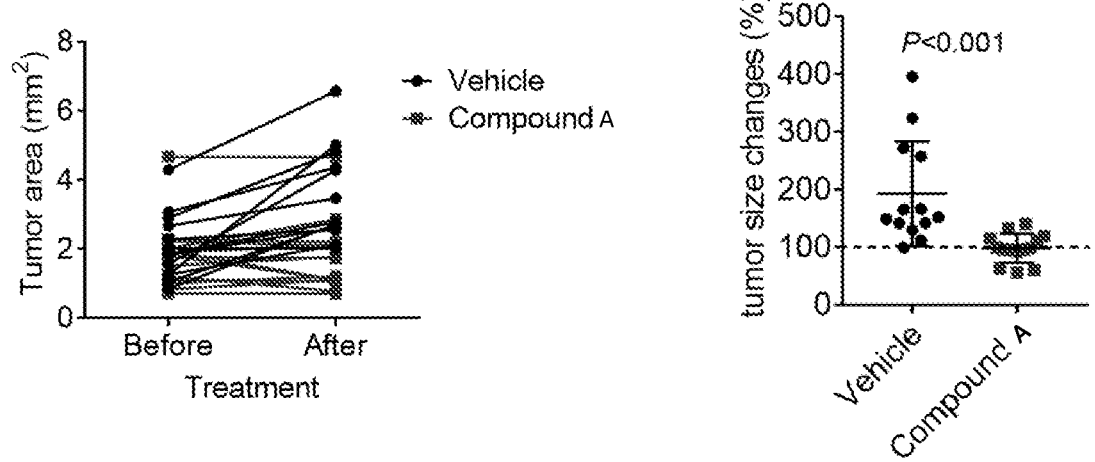
Figure 2C:
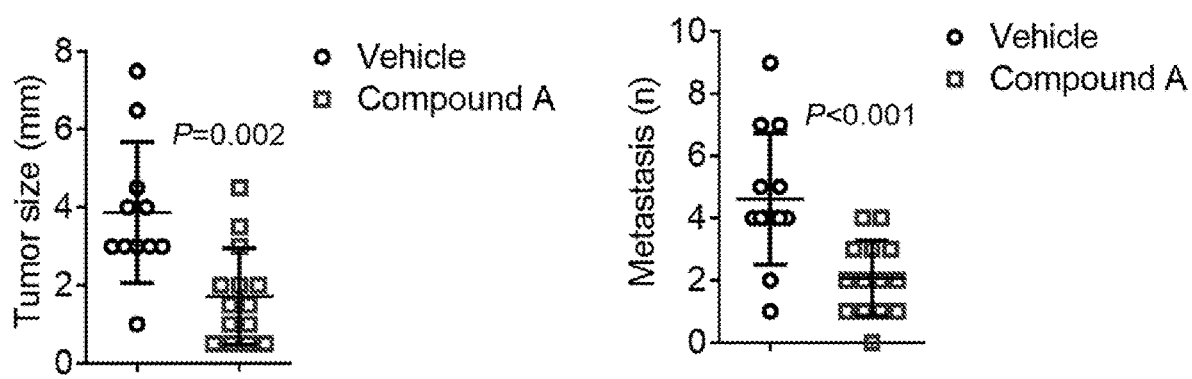

Schema of compound A treatment: Day 0, H2122 human lung cancer cell injection; day 7-15 compound A treatment; tumor imaging day 14 and necropsy day 15. (FIG. 2A) Mouse body weight changes after 8 days treatment with vehicle (left panel) or vehicle plus 100 mg/kg/twice a day compound A (right panel). (FIG. 2B) Mice subjected to micro-computed tomography before and after treatment to determine tumor areas after 7 days treatment with vehicle or vehicle plus 100 mg/kg/twice a day compound A. Left panel: tumor area as measured before and after treatment. Right panel: tumor area expressed as percent of baseline measurement. (FIG. 2C) Tumor diameters determined at necropsy (left panel), and number of tumor metastases (right panel). Whereas the primary tumors increased in size in mice receiving treatment with vehicle alone, the primary tumors in Compound A-treated mice did not (FIG. 2B). Moreover, even though this treatment was quite short, consisting of just one week, the number of metastases in Compound A-treated mice was significantly lower than in the mice treated with vehicle alone (FIG. 2C).

Figure 3:
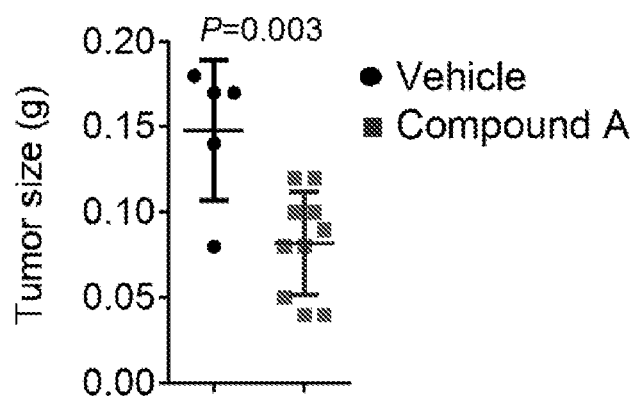
FIG. 3. Breast tumors were established by injecting human MDA-MB-468 cells into the mammary fat pads of nude mice. After the tumors were established, the mice were treated with an exemplary 5-aryl-thiazole compound (Compound A).

FIG. 3 shows breast tumors were established by injecting human MDA-MB-468 cells into the mammary fat pads of nude mice. After the tumors were established, the mice were treated with an exemplary 5-aryl-thiazole compound (Compound A).

PI4K antagonists are shown to induce apoptosis and impair metastatic properties in cancers, as well as preferentially in cancers with increased PI4K activity as a result of gene amplification (e.g. PI4K, eEF1A2) or increased expression of PI4K stimulating factors (e.g. eEF1A2). These findings have therapeutic implications spanning different cancer types.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:
1. A compound of formula (I):

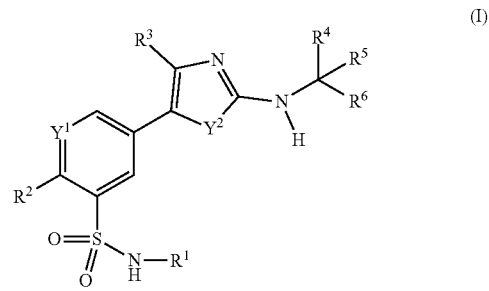

wherein:
Y$^1$ is selected from CH or N;
Y$^2$ is selected from S, O or NR$^{19}$, wherein R$^{19}$ is selected from hydrogen, alkyl, and substituted alkyl;
R$^1$ is selected from aryl, substituted aryl, heteroaryl, and substituted heteroaryl;
R$^2$ is selected from alkoxy and substituted alkoxy;

R³ is selected from hydrogen, lower alkyl and substituted lower alkyl;
R⁴ and R⁵ are both methyl; and
R⁶ is selected from aryl, substituted aryl, heteroaryl and substituted heteroaryl;
or a pharmaceutically acceptable salt thereof.

2. The compound of claim 1, wherein the R¹ is selected from B2-B9:

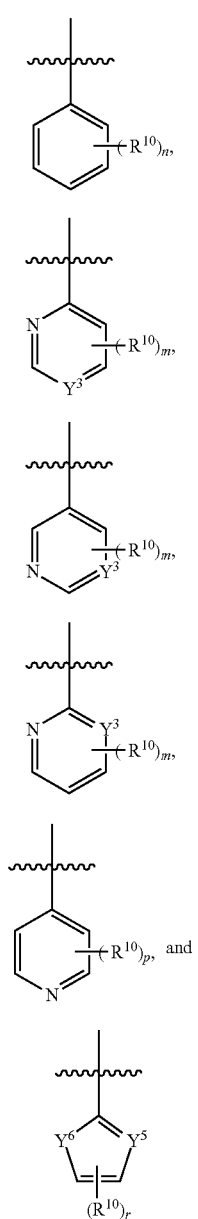

wherein:
Y³ and Y⁵ are each independently selected from N and CR¹¹, wherein R¹¹ is selected from hydrogen, R¹⁰, acyl, substituted acyl, carboxy, carboxyamide, substituted carboxyamide, sulfonyl, substituted sulfonyl, sulfonamide and substituted sulfonamide;
Y⁶ is selected from CR¹¹₂ and NR¹¹;
each R¹⁰ is selected from alkyl, substituted alkyl, hydroxy, alkoxy, substituted alkoxy, trifluoromethyl and halogen;
n is an integer from 0 to 5;
m is an integer from 0 to 3;
p is an integer from 0 to 4; and
r is an integer from 0 to 2.

3. The compound of claim 1, wherein the R⁶ is selected from:

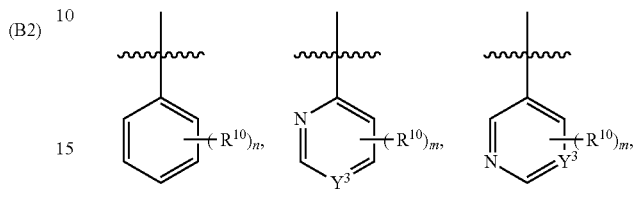

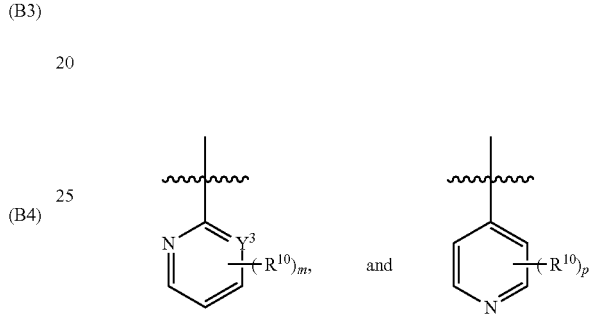

wherein:
Y³ is selected from N and CR¹¹, wherein R¹¹ is selected from hydrogen, R¹⁰, acyl, substituted acyl, carboxy, carboxyamide, substituted carboxyamide, sulfonyl, substituted sulfonyl, sulfonamide and substituted sulfonamide;
R¹⁰ is one or more optional substituents independently selected from alkyl, substituted alkyl, hydroxy, alkoxy, substituted alkoxy, trifluoromethyl and halogen;
n is an integer from 0 to 5;
m is an integer from 0 to 3; and
p is an integer from 0 to 4.

4. The compound of claim 1, wherein the compound is of one of the following formulae:

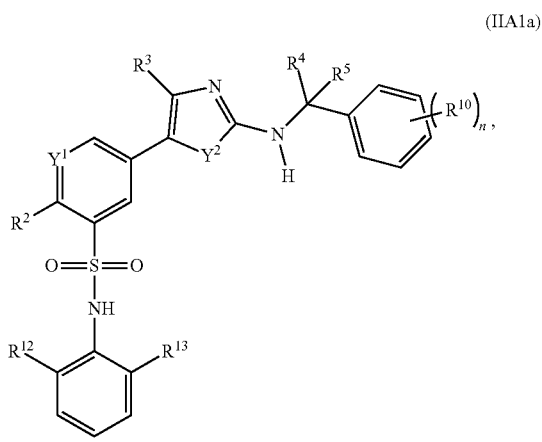

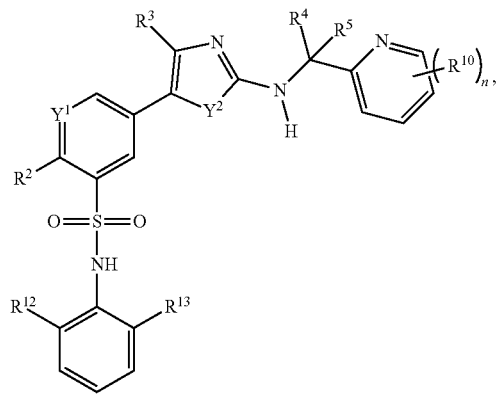
(IIA1b)
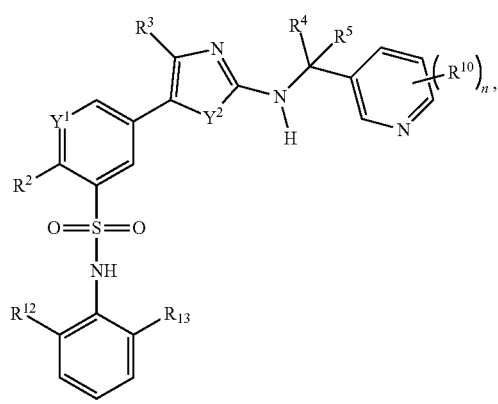
(IIA1c)
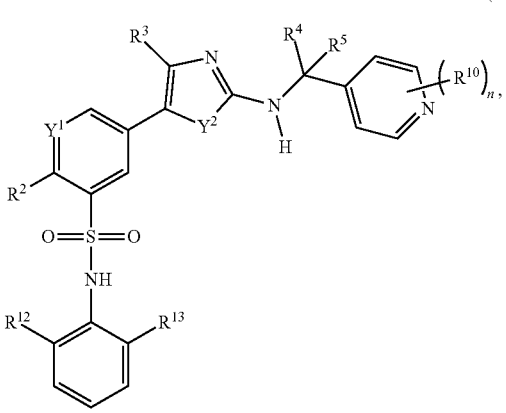
(IIA1d)
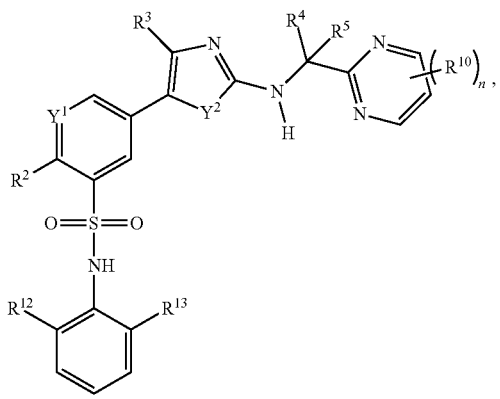
(IIA1e)
(IIA1f)
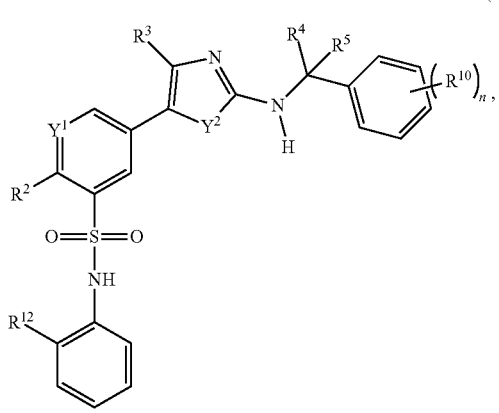
(IIA2a)

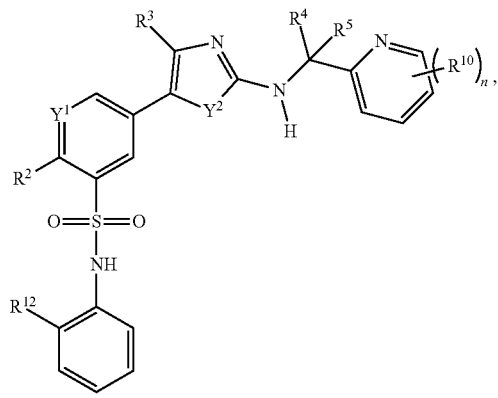
(IIA2b)
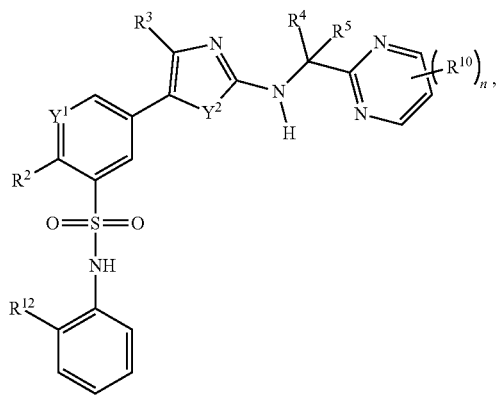
(IIA2e)
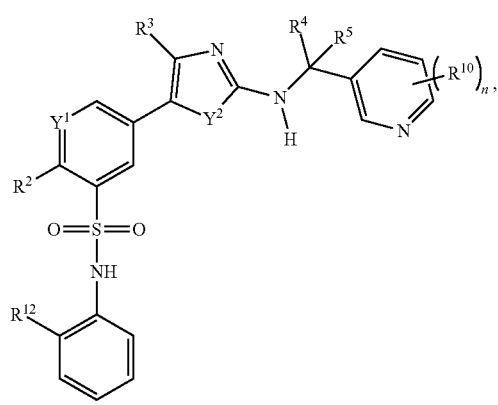
(IIA2c)
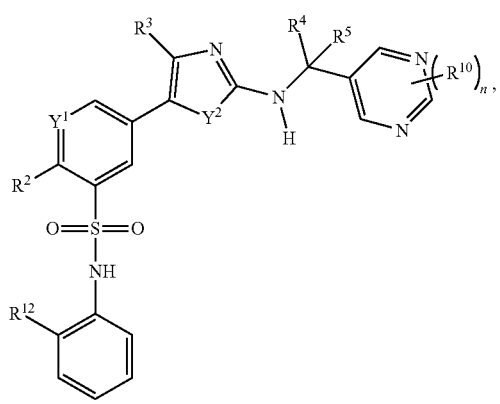
(IIA2f)
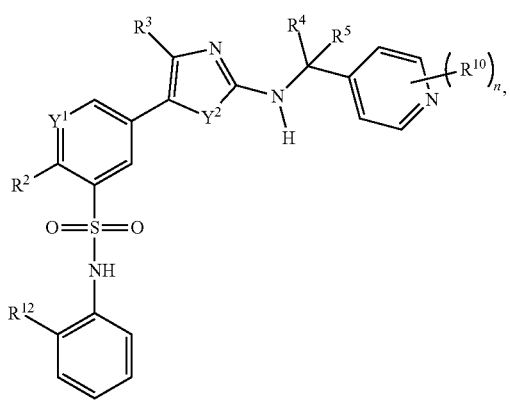
(IIA2d)
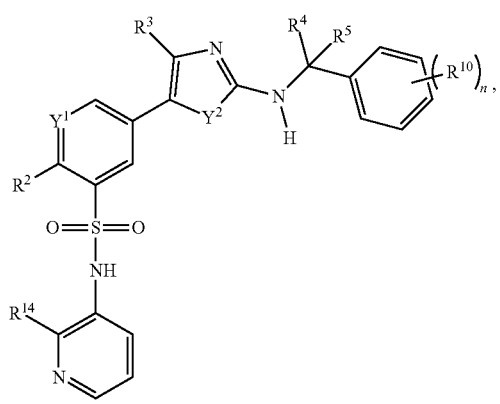
(IIC1a)

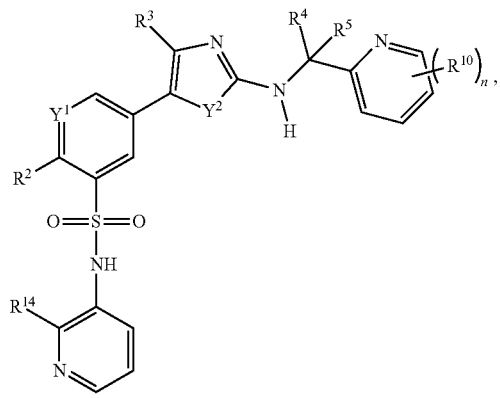
(IIC1b)
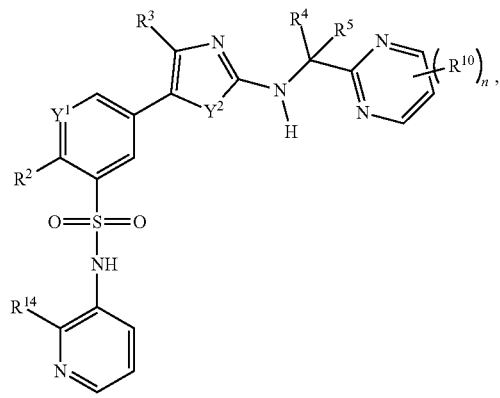
(IIC1e)
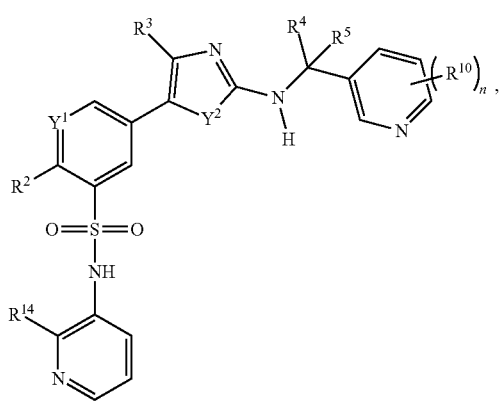
(IIC1c)
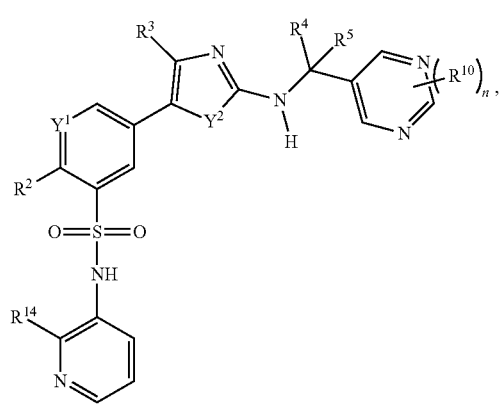
(IIC1f)
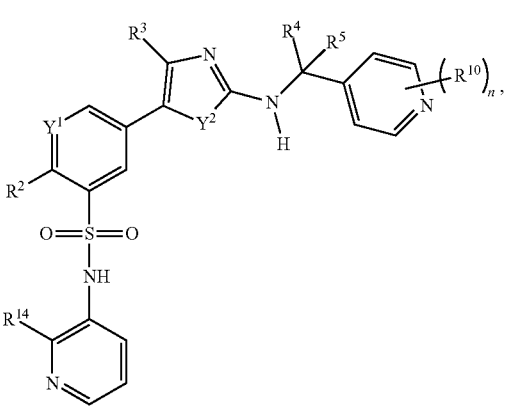
(IIC1d)
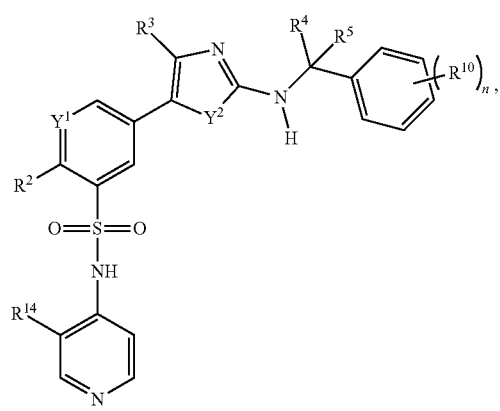
(IID1a)

(IID1b)

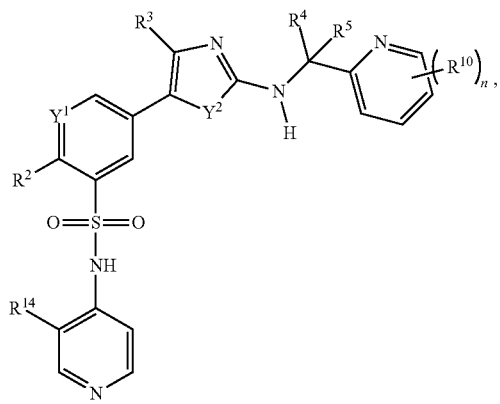

(IID1c)

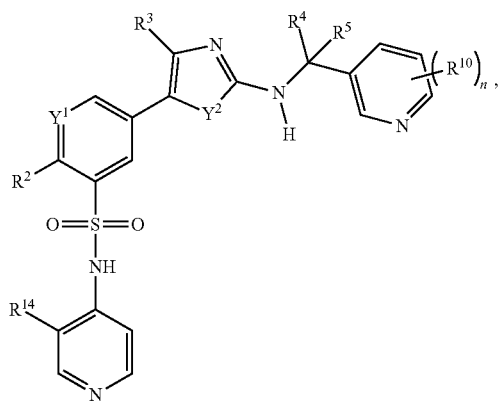

(IID1d)

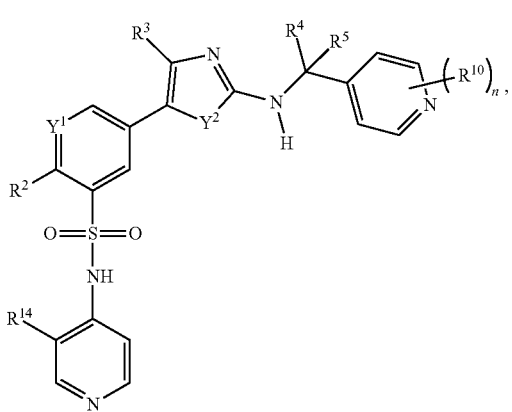

(IID1e)

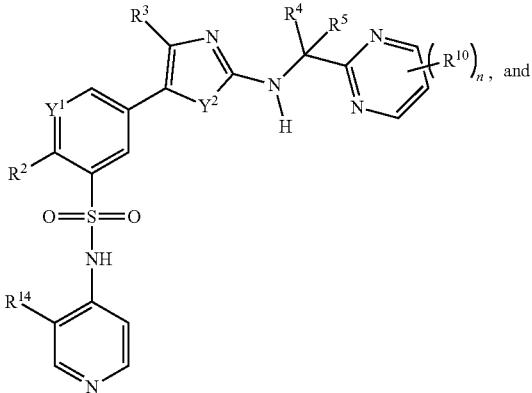

, and (IID1f)

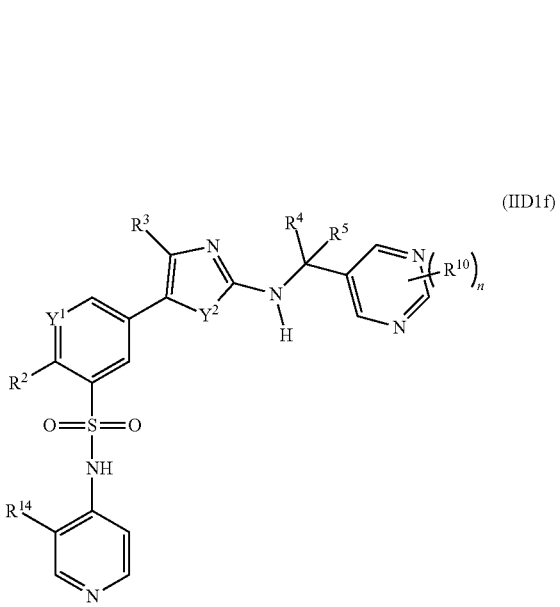

wherein $R^{10}$ is one or more optional substituents independently selected from alkyl, substituted alkyl, hydroxy, alkoxy, substituted alkoxy, trifluoromethyl and halogen;

n is an integer from 0 to 5; and $R^{12}$, $R^{13}$, and $R^{14}$ are each independently selected from alkyl, substituted alkyl, hydroxy, alkoxy, substituted alkoxy, and halogen.

5. The compound of claim 1, wherein $Y^2$ is S.

6. The compound of claim 1, wherein $R^1$ is selected from aryl, di-substituted aryl, tri-substituted aryl, tetra-substituted aryl, penta-substituted aryl, heteroaryl, and substituted heteroaryl.

7. The compound of claim 1, wherein the compound is selected from

225
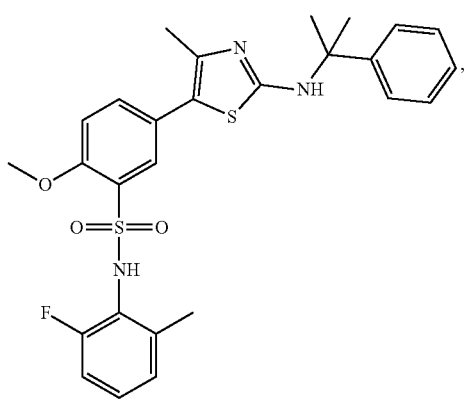
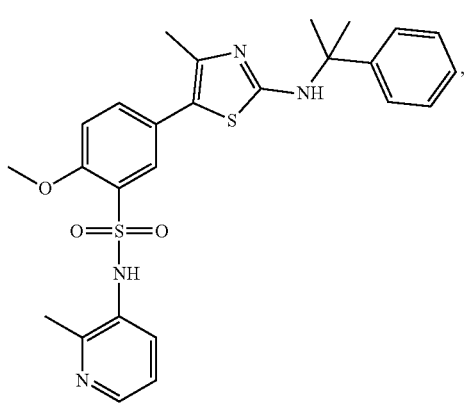
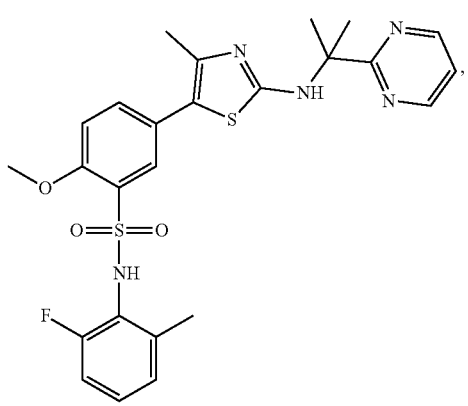
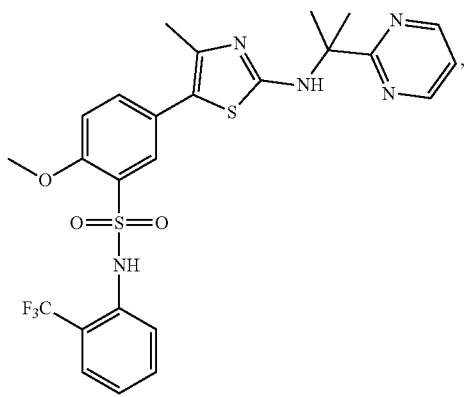
226
-continued
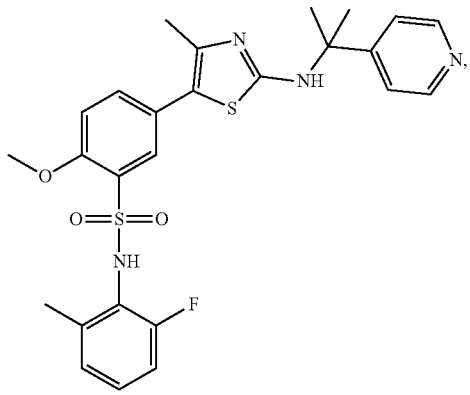
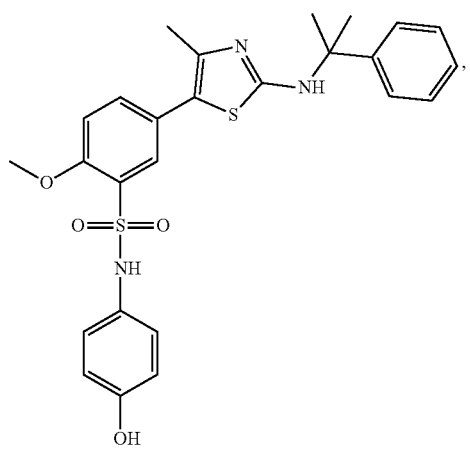
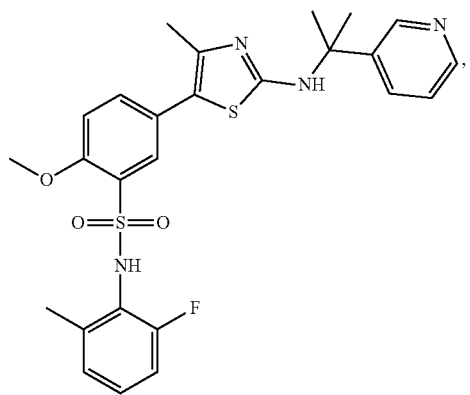
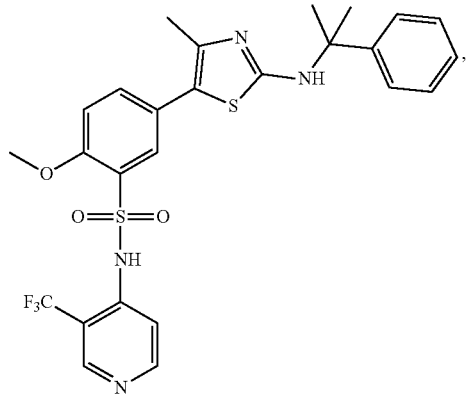

227
-continued
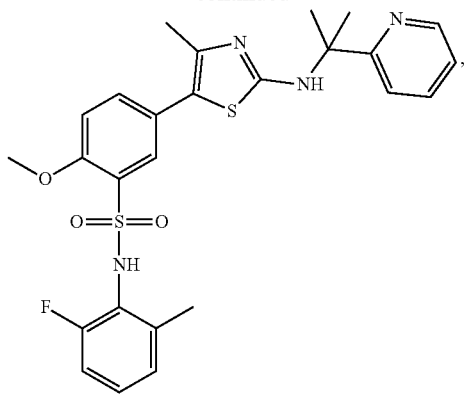
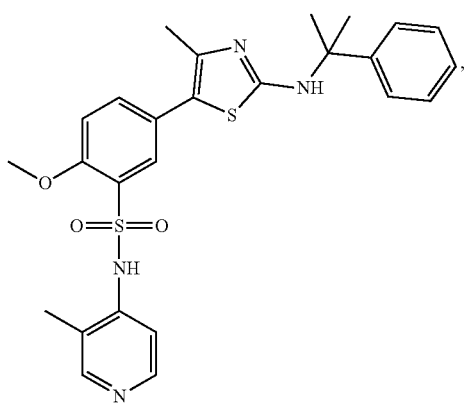
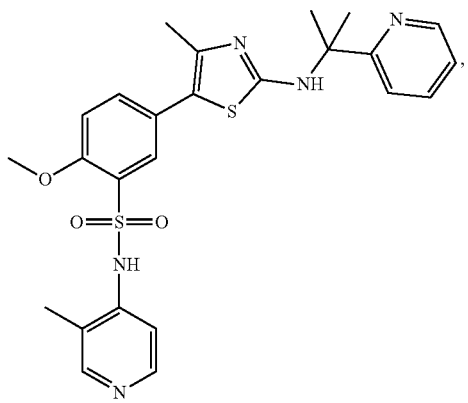
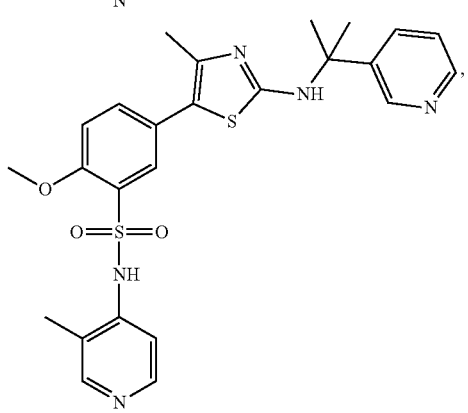
228
-continued
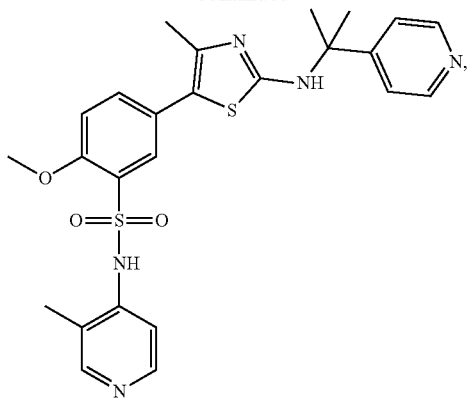
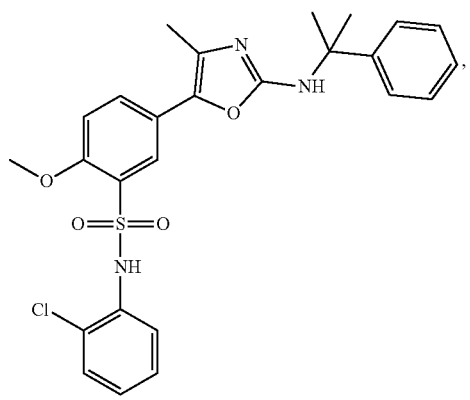
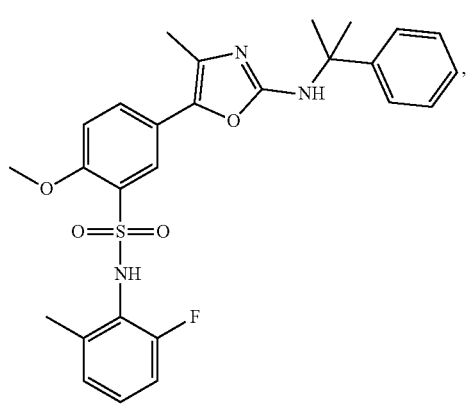

-continued

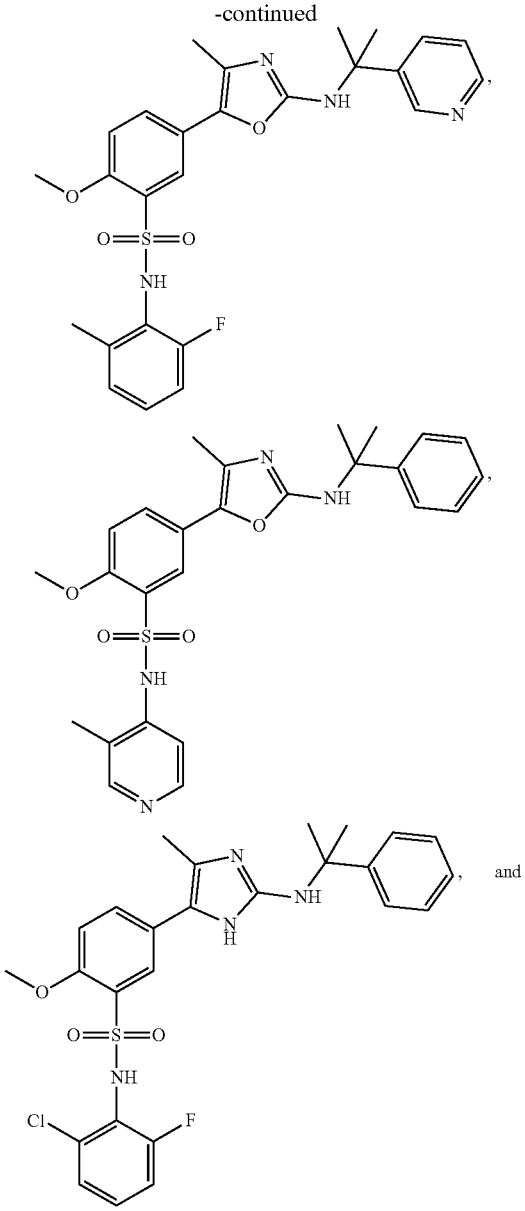

or a pharmaceutically acceptable salt thereof.

8. A pharmaceutical composition comprising:
a compound of claim 1; and
a pharmaceutically acceptable excipient.

9. A method of inhibiting a PI4-kinase, the method comprising contacting a sample comprising the PI4-kinase with a compound of claim 1.

10. The method of claim 9, wherein the PI4-kinase is a PI4-III kinase.

11. A method of treating a subject for an infective disease condition, the method comprising administering to the subject a pharmaceutical composition comprising an effective amount of a compound of claim 1 or a pharmaceutically acceptable salt thereof, wherein the infective disease condition is caused by infection of a pathogen susceptible to PI4-kinase inhibition 12. A method of treating a cancer susceptible to PI4-kinase inhibition, the method comprising:
administering to a subject with cancer a therapeutically effective amount of a compound of claim 1.

13. The method of claim 12, further comprising:
measuring the expression level or activity level of PI4KIIIβ in cancer cells of a biological sample obtained from the subject; and
determining whether the expression level or activity level of PI4KIIIβ in the cancer cells is elevated relative to one or more control cells.

14. The method of claim 12, further comprising co-administering an effective amount of an additional agent to the subject.

15. A method of inhibiting proliferation of a cancer cell susceptible to PI4-kinase inhibition, the method comprising:
contacting a cancer cell with an effective amount of a compound of claim 1.

16. An anti-cancer kit, comprising:
an effective dose of a compound of claim 1;
an effective dose of an additional anticancer agent; and
instructions for use in treating cancer.

17. The compound of claim 1, wherein the compound is:

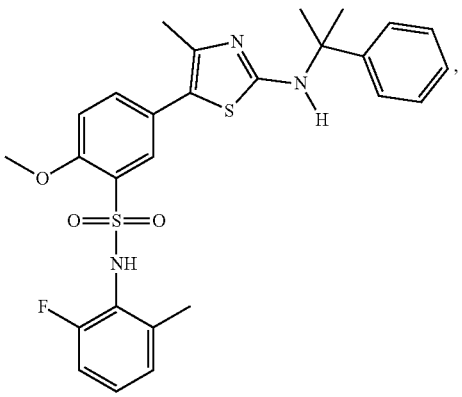 [SMILES: COc1ccc(-c2sc(NC(C)(C)c3ccccc3)nc2C)cc1S(=O)(=O)Nc1c(C)cccc1F]

or a pharmaceutically acceptable salt thereof.

18. The compound of claim 1, wherein the compound is:

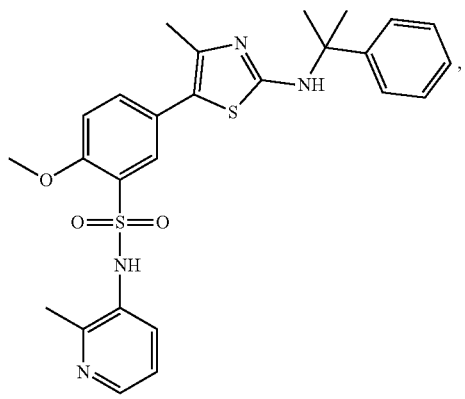 [SMILES: COc1ccc(-c2sc(NC(C)(C)c3ccccc3)nc2C)cc1S(=O)(=O)Nc1cccnc1C]

or a pharmaceutically acceptable salt thereof.

19. The compound of claim 1, wherein the compound is:

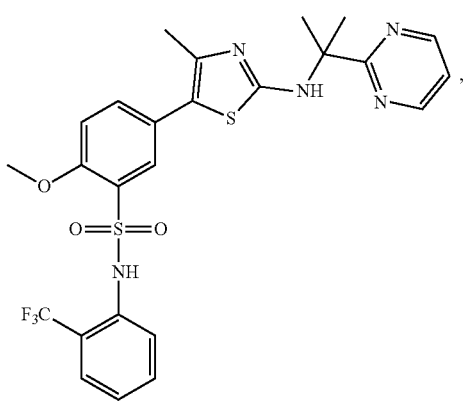 [SMILES: COc1ccc(-c2sc(NC(C)(C)c3ncccn3)nc2C)cc1S(=O)(=O)Nc1ccccc1C(F)(F)F]

or a pharmaceutically acceptable salt thereof.

20. The compound of claim 1, wherein the compound is:

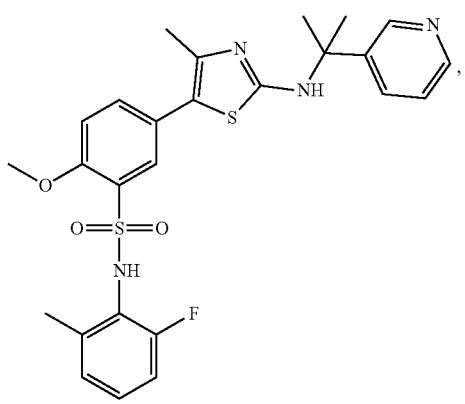 [SMILES: COc1ccc(-c2sc(NC(C)(C)c3cccnc3)nc2C)cc1S(=O)(=O)Nc1c(C)cccc1F]

or a pharmaceutically acceptable salt thereof.

21. The compound of claim 1, wherein the compound is:

or a pharmaceutically acceptable salt thereof.

* * * * *

UNITED STATES PATENT AND TRADEMARK OFFICE
CERTIFICATE OF CORRECTION

PATENT NO. : 12,415,788 B2
APPLICATION NO. : 17/439085
DATED : September 16, 2025
INVENTOR(S) : Jeffrey S. Glenn et al.

Page 1 of 1

It is certified that error appears in the above-identified patent and that said Letters Patent is hereby corrected as shown below:

In the Specification

Please replace "AT109662" with -- AI109662 -- (Column 1, Line 17).

Signed and Sealed this
Twenty-first Day of October, 2025

John A. Squires
*Director of the United States Patent and Trademark Office*